United States Patent
Bourzat et al.

(10) Patent No.: US 6,218,406 B1
(45) Date of Patent: Apr. 17, 2001

(54) FARNESYL TRANSFERASE INHIBITORS, THEIR PREPARATION, THE PHARMACEUTICAL COMPOSITIONS WHICH CONTAIN THEM AND THEIR USE IN THE PREPARATION OF MEDICAMENTS

(75) Inventors: Jean-Dominique Bourzat, Vincennes; Alain Commerçon, Vitry-sur-Seine; Norbert Dereu, Viry-Chatillon; Patrick Mailliet, Fontenay sous Bois; Fabienne Sounigo-Thompson, Paris; Jean-Paul Martin, Colombes; Marc Capet, Viry-Chatillon; Michel Cheve, Soisy sur Seine, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/346,303

(22) Filed: Jul. 2, 1999

Related U.S. Application Data

(62) Division of application No. 08/999,408, filed on Dec. 29, 1997, now Pat. No. 6,013,662.
(60) Provisional application No. 60/066,884, filed on Nov. 25, 1997.

(30) Foreign Application Priority Data

Dec. 30, 1996 (FR) .................................................. 96-16206

(51) Int. Cl.[7] ..................... A61K 31/4439; A61K 31/403
(52) U.S. Cl. .......................... 514/339; 514/323; 514/410; 514/423; 546/200; 546/276.7; 548/425
(58) Field of Search ..................... 514/423, 410, 514/323, 339; 548/425; 546/276.7, 200

(56) References Cited

U.S. PATENT DOCUMENTS 5,783,593 * 7/1998 Baker et al. .......................... 514/381

FOREIGN PATENT DOCUMENTS

| 2736641 | 1/1997 | (FR) . |
| WO/9512612 | 5/1995 | (WO) . |
| WO/9703050 | 1/1997 | (WO) . |

* cited by examiner

Primary Examiner—Laura L. Stockton
(74) Attorney, Agent, or Firm—Finnegan, Henderson, Farabow, Garrett & Dunner, L.L.P.

(57) ABSTRACT

Novel products of formula (I), their preparation, the pharmaceutical compositions which contain them and their use in the preparation of medicaments.

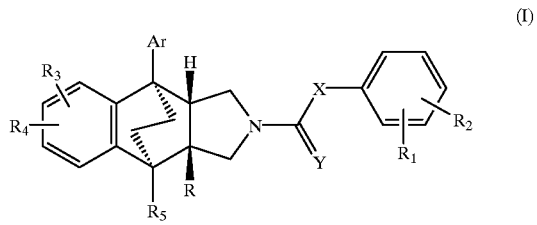

(I)

In the formula (I), the following substituents are among the preferred: Ar represents a substituted or condensed phenyl radical or a polycyclic or heterocyclic aromatic radical, R represents a radical of general formula $-(CH_2)_m-X_1-(CH_2)_n-Z$ in which $X_1$=single bond, O, S; m=0, 1; n=0, 1, 2; it being possible for the $CH_2$ radicals to be substituted; Z represents carboxyl, $COOR_6$ ($R_6$=alkyl), $CON(R_7)(R_8)$ ($R_7$= hydrogen or alkyl and $R_8$=hydrogen, hydroxyl, arylsulphonyl, heterocyclyl, optionally substituted amino, optionally substituted alkyloxy or optionally substituted alkyl), $PO(OR_9)_2$ ($R_9$=hydrogen or alkyl), an $-NH-CO-T$ (T=hydrogen or optionally substituted alkyl) radical, or else—a

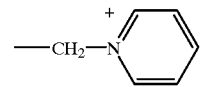

radical, $R_1$ and $R_2$=hydrogen or halogen or alkyl, alkyloxy, which is optionally substituted, alkylthio, alkyloxycarbonyl or else $R_1$ and $R_2$, at the ortho position with respect to one another, form an optionally substituted heterocycle containing 1 or 2 heteroatoms, $R_3$ and $R_4$=hydrogen or halogen or alkyl, alkenyl, alkyloxy, alkylthio, carboxyl or alkyloxycarbonyl, $R_5$=hydrogen, alkyl, alkylthio, X=O or S or $-NH-$, $-CO-$, methylene, vinyldiyl, alkene-1,1-diyl or cycloalkane-1,1-diyl, and Y=O or S, in the racemic form, as well as the optical isomers (diastereomers and enantiomers) and the salts of the product of formula (I). The compounds of formula (I) are farnesyl transferase inhibitors which exhibit notable antitumor and antileukemic properties.

2 Claims, No Drawings

FARNESYL TRANSFERASE INHIBITORS, THEIR PREPARATION, THE PHARMACEUTICAL COMPOSITIONS WHICH CONTAIN THEM AND THEIR USE IN THE PREPARATION OF MEDICAMENTS

This is a division of application Ser. No. 08/999,408, filed Dec. 29, 1997 U.S. Pat. No. 6,013,662, which claims the benefit of U.S. provisional application No. 60/066,884, filed Nov. 25, 1997, the disclosures of both of which are incorporated herein by reference.

The present invention relates to novel benzoperhydroisoindole derivatives, to their preparation, to the pharmaceutical compositions which contain them and to their use in the preparation of medicaments.

The protein farnesyl transferase is an enzyme which catalyses the transfer of the farnesyl group from farnesyl pyrophosphate (FPP) to the terminal cysteine residue of the tetrapeptide sequence CAAX of a certain number of proteins and in particular of the p21Ras protein, which expresses the ras oncogene. The ras (H-, N- or K-ras) oncogene is known to play a key role in cell signalling pathways and cell division processes. The mutation of the ras oncogene or its over expression is often associated with human cancer: the mutated p21Ras protein is found in many human cancers and in particular in more than 50% of cancers of the colon and 90% of cancers of the pancreas (Kohl et al., Science, 260, 1834–1837, 1993).

The inhibition of farnesyl transferase and consequently of the farnesylation of the p21Ras protein blocks the ability of the mutated p21Ras protein to induce cell proliferation and to transform normal cells into cancerous cells.

Moreover, it has been demonstrated that farnesyl transferase inhibitors are also active with respect to tumoral cell lines which do not express mutated or overexpressed ras, but which exhibit the mutation of an oncogene or the over expression of an oncoprotein, the signalling pathway of which uses the farnesylation of a protein, such as a normal ras (Nagasu et al., Cancer Research 55, 5310–5314, 1995; Sepp-Lorenzino et al., Cancer Research 55, 5302–5309, 1995).

The inhibitors of the protein farnesyl transferase are inhibitors of cell proliferation and consequently are antitumour and antileukaemic agents.

It has now been discovered, and this is also a subject of this invention, that the novel compounds of formula (I) presented hereinbelow possess, entirely surprisingly and unexpectedly, an inhibitory activity for the protein farnesyl transferase and prove to be notable antitumour and antileukaemic agents.

In particular, it has been discovered, according to the invention, that the biological activity of the compounds according to the invention is very markedly improved, contrary to all expectations, by the presence of specific groups (represented by Ar hereinbelow) substituted at the 9 position of the benzoperhydroisoindole skeleton.

In particular, the corresponding compounds exhibit activities which are much higher than those obtained to date with compounds having similar structures but not having these Ar substituents.

The present invention relates to the novel compounds of formula (I):

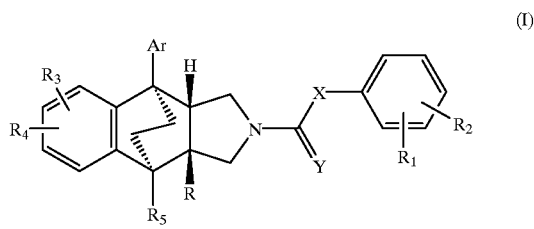

in which:
Ar represents
  a phenyl radical substituted by one or more atoms or radicals, which are identical or different and are selected from halogen atoms and the radicals: alkyl, alkenyl containing 2 to 4 carbon atoms, hydroxyl, mercapto, alkylthio, alkylsulphonyl, alkylsulphinyl, amino, alkylamino, dialkylamino, formyl, alkylcarbonyl, carboxyl, alkyloxycarbonyl, carbamoyl, alkylcarbamoyl, dialkylcarbamoyl, cyano, and alkyloxy, the alkyl portions and radicals being optionally perhalogenated, or
  a phenyl radical condensed with a 4- to 7-membered nonaromatic heterocycle containing one or more heteroatoms selected from oxygen, nitrogen and sulphur atoms, or
  a polycyclic aromatic radical, wherein the polycylic aromatic radical can contain at least one cycle that is saturated or only partially unsaturated but at least one cycle thereof must be aromatic, or
  a monocyclic 5- to 12-membered heterocyclic aromatic radical incorporating one or more heteroatoms selected from oxygen, nitrogen and sulphur atoms, the heterocyclic aromatic radical being bonded to the condensed ring via a carbon—carbon bond and optionally being substituted by one or more atoms or radicals, which are identical or different and are selected from halogen atoms and the radicals: alkyl, alkenyl containing 2 to 4 carbon atoms, hydroxyl, alkyloxy, mercapto, alkylthio, alkylsulphonyl, alkylsulphinyl, amino, alkylamino, dialkylamino, formyl, alkylcarbonyl, carboxyl, alkyloxycarbonyl, carbamoyl, alkylcarbamoyl, dialkylcarbamoyl, cyano, and trifluoromethyl,
  wherein each of the alkyl portions and radicals in the definition of Ar contains 1 to 4 carbon atoms;
R represents
  a radical of formula:

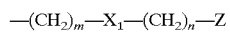
  —(CH$_2$)$_m$—X$_1$—(CH$_2$)$_n$—Z in which
    X$_1$ represents a single bond or an oxygen or sulphur atom,
    m represents an integer equal to 0 or 1, and
    n represents an integer equal to 0, 1 or 2;
  wherein one or more methylene radicals in said R radical can be substituted by a carboxyl, alkyloxycarbonyl, carbamoyl, alkylcarbamoyl, dialkylcarbamoyl, amino, alkylamino or dialkylamino radical, wherein each of the alkyl portions and radicals in the definition of R contains 1 to 4 carbon atoms;
Z represents
  a carboxyl radical, or
  a COOR$_6$ radical, in which R$_6$ represents a straight or branched alkyl radical containing 1 to 3 carbon atoms, or a radical of formula $CON(R_7)(R_8)$ in which
  $R_7$ represents a hydrogen atom or a straight or branched alkyl radical containing 1 to 6 carbon atoms, and
  $R_8$ represents
    a hydrogen atom, or
    a hydroxyl radical, or
    an arylsulphonyl radical, optionally substituted by one or more atoms or radicals, which are identical or different and are selected from halogen atoms and alkyl and alkyloxy radicals, or
    a 5- to 7-membered heterocycle incorporating one or more heteroatoms selected from nitrogen, oxygen and sulphur atoms, it being possible for said heterocycle to be bonded to the N in said $CON(R_7)(R_8)$ radical via a heteroatom, or
    an amino radical optionally substituted by one or two radicals, which are identical or different and are selected from the radicals:
      alkyl,
      carbocyclic aryl, optionally substituted by one or more radicals, which are identical or different and are selected from alkyl and alkyloxy radicals,
      5- to 7-membered heterocyclyl containing one or more heteroatoms selected from nitrogen, oxygen and sulphur atoms,
      arylcarbonyl, optionally substituted by one or more radicals, which are identical or different and are selected from alkyl and alkyloxy radicals,
  or $R_8$ represents an alkyloxy radical containing 1 to 6 straight- or branched-chain carbon atoms optionally substituted by a phenyl radical, or
    a straight or branched alkyl radical containing 1 to 6 carbon atoms, optionally substituted by at least one radical selected from amino, alkylamino, dialkylamino, hydroxyl, alkyloxy, mercapto, alkylthio, alkyloxycarbonyl, carboxyl, cyano, and optionally substituted mono- and polycyclic aromatic having from 5 to 12 ring members which may or may not incorporate one or more heteroatoms selected from oxygen, nitrogen and sulphur atoms, it being possible for the mono- and polycyclic aromatic radicals incorporating one or more nitrogen heteroatoms to be in the form of the N-oxide,
or Z represents
  a $PO(OR_9)_2$ radical in which $R_9$ represents a hydrogen atom or a straight or branched alkyl radical containing 1 to 6 carbon atoms, or
  an —NH—CO—T radical in which T represents a hydrogen atom or a straight or branched alkyl radical containing 1 to 6 carbon atoms, optionally substituted by an amino, carboxyl, alkyloxycarbonyl, hydroxyl, alkyloxy, mercapto, or alkylthio radical, or
  a

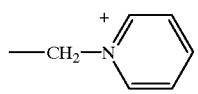

radical having an anion as a counterion,
  wherein each of the alkyl portions and radicals provided in the definition of Z, including, for example, $R_8$, which is part of Z, and that is not of a specifically defined carbon length contains 1 to 4 carbon atoms;
$R_1$ and $R_2$, which are identical or different, are selected from a hydrogen atom, a halogen atom, an alkyl radical, and an alkyloxy radical, wherein each of said radicals may optionally be substituted by a dialkylamino radical, wherein the two alkyl portions of said dialkylamino radical may form, together with the nitrogen atom to which they are attached, a saturated heterocycle containing 5 or 6 ring members, and from an alkylthio radical and an alkyloxycarbonyl radical; or alternatively, situated at the ortho position with respect to one another, $R_1$ and $R_2$, together with the ring carbon atoms to which they are attached, form a saturated or unsaturated heterocycle containing 1 or 2 heteroatoms selected from nitrogen and oxygen, optionally substituted by a halogen atom or by an alkyl or alkyloxy radical,
wherein the alkyl portions and radicals in the definition of $R_1$ and $R_2$ contain 1 to 4 carbon atoms;
$R_3$ and $R_4$, which are identical or different, are selected from a hydrogen atom, a halogen atom and a radical selected from alkyl, hydroxyl, alkyloxy, alkylcarbonyloxy, mercapto, alkylthio, alkylsulphonyl, alkylsulphinyl, amino, alkylamino, dialkylamino, alkyloxycarbonylamino, carboxyl, alkyloxycarbonyl, carbamoyl, alkylcarbamoyl, dialkylcarbamoyl, formyl, alkylcarbonyl, cyano, and trifluoromethyl,
wherein the alkyl portions and radicals in the definition of $R_3$ and $R_4$ contain 1 to 4 carbon atoms;
$R_5$ represents a hydrogen atom or an alkyl or alkylthio radical, wherein for the definition of $R_5$, the alkyl portions and radicals contain 1 to 4 carbon atoms;
X represents an oxygen or sulphur atom or one of the groups: —NH—, —CO—, methylene, alkene-1,1-diyl, or cycloalkane-1,1-diyl containing 3 to 6 carbon atoms;
and Y represents an oxygen or sulphur atom; or a pharmaceutically acceptable salt of a compound of formula (I).

In the compound of formula (I), the alkyloxy containing 1 to 4 carbon atoms that is a substituent for Ar is preferably methoxy, and the optionally perhalogenated alkyloxy substituent for Ar is preferably trifluoromethoxy. With respect to Ar, the phenyl radical condensed with a 4- to 7-membered nonaromatic heterocycle is preferably chosen from 2,3-dihydro-1,4-benzo-dioxin-6-yl or 2,3-dihydrobenzofuran-5-yl or 2,3-dihydrobenzopyran-6-yl radicals and the polycyclic aromatic radical is preferably 1- or 2-naphthyl, 5-indanyl or 1,2,3,4-tetra-hydronaphth-6-yl.

Preferably, Ar represents a 2,3-dihydro-1,4-benzodioxin-6-yl, 2,3-dihydrobenzofuran-5-yl, 2,3-dihydrobenzopyran-6-yl, 1-naphthyl, 2-naphthyl, 5-indanyl or 1,2,3,4-tetrahydronaphth-6-yl radical or a phenyl radical substituted at the 4 position, preferably by a methyl, trifluoromethyl or methoxy radical. More preferably, Ar represents a 2,3-dihydro-1,4-benzodioxin-6-yl or 2,3-dihydrobenzofuran-5-yl radical or a phenyl radical substituted at the 4 position, preferably by a methyl, trifluoromethyl or methoxy radical; in particular, the 2,3-dihydro-1,4-benzodioxin-6-yl radical or a phenyl radical substituted at the 4 position by a methyl radical, wherein the alkyl portions and radicals contain 1 to 4 carbon atoms.

The mono- or polycyclic aromatic radical having from 5 to 12 ring members that forms a substituent for the straight or branched alkyl radical containing 1 to 6 carbon atoms possibility for $R_8$ is in particular the 2- or 3- or 4-pyridyl radical, preferably 3-pyridyl or 4-pyridyl, or the N-oxide of pyridine. It is also possible for the mono- or polycyclic aromatic radical having from 5 to 12 ring members that forms a substituent for the $R_8$ straight or branched alkyl radical containing 1 to 6 carbon atoms to be (1) a phenyl radical optionally substituted by one or more halogen atoms or by one or more hydroxyl, amino or trifluoromethyl groups or by one or more alkyl or alkenyl, alkyloxy, alkylthio, alkylamino, alkylcarbonyl or $C_2$ to $C_4$ alkyloxycarbonyl, carbamoyl, alkyl-carbamoyl or dialkylcarbamoyl, the alkyl portions and radicals of which contain 1 to 8 carbon atoms, or formyl radicals, or (2) alternatively a 1- or 2-naphthyl radical.

Preferably, R represents a carboxyl radical or a —COOMe radical or alternatively a —CON($R_7$)($R_8$) radical in which, when $R_7$ represents a hydrogen atom, $R_8$ represents a methyl radical substituted by the 2-, 3-, or 4-pyridyl radical, or the N-oxide of pyridine; very advantageously, R represents a carboxyl radical; very particularly advantageously, R represents a —CON($R_7$)($R_8$) radical in which, when $R_7$ represents a hydrogen atom, $R_8$ represents a methyl radical substituted by the 3-pyridyl radical.

With respect to Z, the anion of the

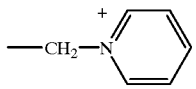

radical is preferably trifluoromethanesulphonate.

Preferably, one of the $R_1$ or $R_2$ symbols represents a hydrogen atom and the other of the symbols represents a methoxy radical, more advantageously attached at the ortho position of the phenyl ring, with all the alkyl portions and radicals in the definition of $R_1$ and $R_2$ containing 1 to 4 carbon atoms.

Preferably, either $R_3$ and $R_4$ each represent a hydrogen atom or alternatively one of the $R_3$ or $R_4$ symbols represents a hydrogen atom and the other of the $R_3$ or $R_4$ symbols represents a methoxy radical, more advantageously at the 5 position of the benzoperhydroisoindole nucleus. Very advantageously, $R_3$ and $R_4$ each represent a hydrogen atom and all the alkyl portions and radicals in the definition of $R_3$ and $R_4$ contain 1 to 4 carbon atoms.

Preferably, $R_5$ represents a hydrogen atom or a methyl radical, and very advantageously, $R_5$ represents a hydrogen atom.

Preferably, X represents a methylene or vinyldiyl group, and in a particularly advantageous way, X represents the vinyidiyl group, and preferably, Y represents an oxygen atom.

Preferably, the compound or salt of formula (I) exists in the racemic form or in the form of its optical isomers, preferably in the form of a single enantiomer. In particular, in accordance with the present invention, the inventive compounds may exist as racemates, i.e., as mixtures of equal amounts of optical isomers, i.e., equal amounts of two enantiomers, (see, e.g., Example 2 below) or equal amounts of at least four diastereomers, (see, e.g., Example 81 below, wherein an additional chiral center has been introduced by one of the substituents on a compound of formula (I)). The inventive compounds may also exist as mixtures of optical isomers in which all optical isomers are not present in equal amounts. For example, the inventive compounds may exist as mixtures of enantiomeric dextrorotatory and levorotatory isomers in which one enantiomer is present in excess relative to the other, i.e., present in an enantiomeric excess.

As used herein, "single enantiomer" is intended to mean a compound that comprises more than 50% of a single enantiomer. "Single enantiomer," therefore, means that more than 50% of the dextrorotatory enantiomer is present along with less than 50% of the levorotatory enantiomer (this can also be referred to as a single dextrorotatory enantiomer), and vice versa (this can also be referred to as a single levorotatory enantiomer).

Preferably, the single enantiomer comprises at least 75% of a single enantiomer (50% enantiomeric excess)("e.e."), more preferably at least 90% of a single enantiomer (80% e.e.), still more preferably at least 95% of a single enantiomer (90% e.e.), even more preferably at least 97.5% of a single enantiomer (95% e.e.), and most preferably at least 99% of a single enantiomer (98% e.e.).

In the preceding and succeeding definitions,
the "alkyl containing 1 to 8 carbon atoms" radicals and portions defines the methyl, ethyl, propyl, butyl, pentyl, hexyl, heptyl and octyl radicals and the corresponding iso, sec and tert isomers, the "alkyl containing 1 to 6 carbon atoms" radicals and portions defines the methyl, ethyl, propyl, butyl, pentyl and hexyl radicals and the corresponding iso, sec and tert isomers, the "alkyl containing 1 to 4 carbon atoms" radicals and portions defines the methyl, ethyl, propyl and butyl radicals and the corresponding iso, sec and tert isomers, "alkenyls containing 2 to 4 carbon atoms" defines the vinyl, allyl, propen-2-yl, buten-1-yl, buten-2-yl and buten-3-yl radicals, "alkyloxy containing 1 to 4 carbon atoms" defines the methoxy, ethoxy, propoxy and butoxy radicals, and the corresponding iso, sec and tert isomers, and "$C_2$ to $C_4$ alkyloxycarbonyl" defines the methoxycarbonyl, ethoxycarbonyl and propoxycarbonyl radicals, and the corresponding iso, sec, and tert isomers.

Preferably, the compounds according to the invention exhibit a formula (I) in which:

Ar represents a 2,3-dihydro-1,4-benzodioxin-6-yl or 2,3-dihydrobenzofuran-5-yl radical or a phenyl radical substituted at the 4 position, preferably by a methyl, trifluoromethyl or methoxy radical, R represents a carboxyl radical or a —COOMe radical or alternatively a —CON($R_7$)($R_8$) radical in which, when $R_7$ represents a hydrogen atom, $R_8$ represents a methyl radical substituted by the 3-pyridyl radical, or the N-oxide of pyridine, one of the $R_1$ or $R_2$ symbols represents a hydrogen atom and the other of the symbols represents a methoxy radical, more advantageously attached at the ortho position of the phenyl ring, either $R_3$ and $R_4$ each represent a hydrogen atom or one of the $R_3$ or $R_4$ symbols represents a hydrogen atom and the other of the $R_3$ or $R_4$ symbols represents a methoxy radical, more advantageously at the 5 position of the benzoperhydroisoindole nucleus, $R_5$ represents a hydrogen atom or a methyl radical, X represents a methylene or vinyidiyl group, and Y represents an oxygen atom;

in the racemic form or in the form of a single enantiomer as defined above, as well as their salts.

According to the invention, the compounds of formula (I) are preferably provided in the dextrorotatory form, i.e., in the form of a single dextrorotatory enantiomer. However, the single levorotatory enantiomer is also contemplated by the present invention.

A preferred group of compounds of formula (I) include those in which:

Ar represents
- a phenyl radical substituted by one or more atoms or radicals, which are identical or different, chosen from halogen atoms and alkyl, alkenyl containing 2 to 4 carbon atoms, hydroxyl, alkyloxy, mercapto, alkylthio, alkylsulphonyl or alkylsulphinyl, amino, alkylamino or dialkylamino, formyl, alkylcarbonyl, carboxyl, alkyloxycarbonyl, carbamoyl, alkylcarbamoyl or dialkylcarbamoyl, cyano or trifluoromethyl radicals, or
- a polycyclic aromatic radical, such as 1- or 2-napthyl or 5-indanyl, or
- a monocyclic 5- to 12-membered heterocyclic aromatic radical incorporating one or more heteroatoms chosen from oxygen, nitrogen and sulphur atoms, the heterocyclic aromatic radical being bonded to the condensed ring via a carbon—carbon bond, the said radical being substituted, if appropriate, by one or more atoms or radicals, which are identical or different, chosen from halogen atoms and the following radicals: alkyl, alkenyl containing 2 to 4 carbon atoms, hydroxyl, alkyloxy, mercapto, alkylthio, alkylsulphonyl or alkylsulphinyl, amino, alkylamino or dialkylamino, formyl, alkylcarbonyl, carboxyl, alkyloxycarbonyl, carbamoyl, alkylcarbamoyl or dialkylcarbamoyl, cyano or trifluoromethyl, wherein each of these alkyl radicals and portions contain 1 to 4 carbon atoms;

R represents
a radical of general formula

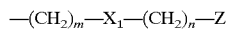

—$(CH_2)_m$—$X_1$—$(CH_2)_n$—Z in which
$X_1$ represents a single bond or an oxygen or sulphur atom,
m represents an integer equal to 0 or 1,
n represents an integer equal to 0, 1 or 2,
the methylene radicals can be substituted by a carboxyl, alkyloxycarbonyl, carbamoyl, alkylcarbamoyl, dialkylcarbamoyl, amino, alkylamino or dialkylamino radical, with all of these alkyl portions and radicals containing 1 to 4 carbon atoms;

Z represents
a carboxyl radical,
a $COOR_6$ radical, in which $R_6$ represents a straight or branched alkyl radical containing 1 to 3 carbon atoms, or
a radical of formula $CON(R_7)(R_8)$ in which
$R_7$ represents a hydrogen atom or a straight or branched alkyl radical containing 1 to 6 carbon atoms, and
$R_8$ represents
a hydrogen atom,
a hydroxyl radical,
an amino, alkylamino or dialkylamino radical with alkyl containing from 1 to 4 carbon atoms,
an alkyloxy radical containing 1 to 6 straight- or branched-chain carbon atoms optionally substituted by a phenyl radical,
a straight or branched alkyl radical containing 1 to 6 carbon atoms, preferably a methylene group, optionally substituted by an amino, alkylamino, dialkylamino, hydroxyl, alkyloxy, mercapto, alkylthio, alkyloxycarbonyl, carboxyl or cyano radical, by a mono- or polycyclic aromatic radical having from 5 to 12 ring members which may or may not incorporate one or more heteroatoms chosen from oxygen, nitrogen and sulphur atoms and, if appropriate, substituted, wherein the monocyclic aromatic radical can be a phenyl radical optionally substituted by one or more halogen atoms or by a hydroxyl, amino or trifluoromethyl group or by an alkyl or alkenyl, alkyloxy, alkylthio, alkylamino, alkylcarbonyl or $C_2$ to $C_4$ alkyloxycarbonyl, carbamoyl, alkylcarbamoyl or dialkylcarbamoyl, each alkyl portion and radical containing 1 to 8 carbon atoms, or formyl radical, or wherein the polycyclic aromatic radical can be a 1-naphthyl or 2-naphthyl radical, or Z represents
a $PO(OR_9)_2$ radical in which $R_9$ represents a hydrogen atom or a straight or branched alkyl radical containing 1 to 6 carbon atoms, or
an —NH—CO—T radical in which T represents a hydrogen atom or a straight or branched alkyl radical containing 1 to 6 carbon atoms optionally substituted by an amino, carboxyl, alkyloxycarbonyl, hydroxyl, alkyloxy, mercapto or alkylthio radical, or alternatively a

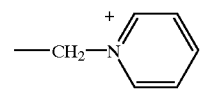

radical, having an anion as a counterion,
wherein all of the alkyl portions and radicals possessing an alkyl group provided in the definition of Z, including, for example, $R_8$, which is part of Z, contain 1 to 4 carbon atoms;

$R_1$ and $R_2$, which are identical or different, represent a hydrogen atom, a halogen atom or an alkyl radical, an alkyloxy radical optionally substituted by a dialkylamino radical, wherein the two alkyl portions of said dialkylamino radical can form, together with the nitrogen atom to which they are attached, a saturated heterocycle containing 5 or 6 ring members, or an alkylthio radical or an alkyloxycarbonyl radical; or alternatively, situated at the ortho position with respect to one another, $R_1$ and $R_2$ form a saturated or unsaturated heterocycle containing 1 or 2 heteroatoms chosen from nitrogen and oxygen, optionally substituted by a halogen atom or by an alkyl or alkyloxy radical,
with all of the alkyl portions and radicals provided in the definition of $R_1$ and $R_2$ containing 1 to 4 carbon atoms;

$R_3$ and $R_4$, which are identical or different, represent a hydrogen or halogen atom or an alkyl, hydroxyl, alkyloxy, alkylcarbonyloxy, mercapto, alkylthio, alkylsulphonyl or alkylsulphinyl, amino, alkylamino or dialkylamino, alkylcarbonyloxyamino, carboxyl, alkyloxycarbonyl, carbamoyl, alkylcarbamoyl or dialkylcarbamoyl, formyl, alkylcarbonyl, cyano or trifluoromethyl radical, with all of the alkyl portions and radicals provided in the definition of $R_3$ and $R_4$ containing 1 to 4 carbon atoms;

$R_5$ represents a hydrogen atom;

X represents an oxygen or sulphur atom or one of the groups: —NH—, —CO—, methylene, alkene-1,1-diyl, such as vinyldiyl, or cycloalkane-1,1-diyl containing 3 to 6 carbon atoms; and Y represents an oxygen or sulphur atom; in the racemic form, as well as in the form of the optical isomers, preferably in the form of a single enantiomer, as well as the salts thereof.

Another preferred group of compounds of formula (I) are those in which:

Ar represents
  a phenyl radical substituted by one or more atoms or radicals, which are identical or different, chosen from halogen atoms and alkyl, alkenyl containing 2 to 4 carbon atoms, hydroxyl, alkyloxy, mercapto, alkylthio, alkylsulphonyl or alkylsulphinyl, amino, alkylamino or dialkylamino, formyl, alkylcarbonyl, carboxyl, alkyloxycarbonyl, carbamoyl, alkylcarbamoyl or dialkylcarbamoyl, cyano or trifluoromethyl radicals, or
  a polycyclic aromatic radical, wherein all cycles are aromatic, such as 1- or 2-naphthyl or 5-indanyl, or
  a monocyclic 5- to 12-membered heterocyclic aromatic radical incorporating one or more heteroatoms chosen from oxygen, nitrogen and sulphur atoms, wherein the heterocyclic aromatic radical is bonded to the condensed ring via a carbon—carbon bond, the said radical being substituted, if appropriate, by one or more atoms or radicals, which are identical or different, chosen from halogen atoms and the following radicals: alkyl, alkenyl containing 2 to 4 carbon atoms, hydroxyl, alkyloxy, mercapto, alkylthio, alkylsulphonyl or alkylsulphinyl, amino, alkylamino or dialkylamino, formyl, alkylcarbonyl, carboxyl, alkyloxycarbonyl, carbamoyl, alkylcarbamoyl or dialkylcarbamoyl, cyano or trifluoromethyl, with all of these alkyl portions and radicals containing 1 to 4 carbon atoms;

R represents a radical of formula

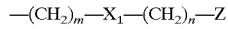

in which
  $X_1$ represents a single bond or an oxygen or sulphur atom,
  m represents an integer equal to 0 or 1,
  n represents an integer equal to 0, 1 or 2,
  the methylene radicals can be substituted by a carboxyl, alkyloxycarbonyl, carbamoyl, alkylcarbamoyl, dialkylcarbamoyl, amino, alkylamino or dialkylamino radical, with all of these alkyl portions and radicals containing 1 to 4 carbon atoms;
  Z represents
    a carboxyl radical,
    a $COOR_6$ radical, in which $R_6$ represents a straight or branched alkyl radical containing 1 to 3 carbon atoms, or
    a radical of formula $CON(R_7)(R_8)$ in which
      $R_7$ represents a hydrogen atom or a straight or branched alkyl radical containing 1 to 6 carbon atoms, and
      $R_8$ represents
        a hydrogen atom,
        a hydroxyl radical,
        an amino, alkylamino or dialkylamino radical,
        an alkyloxy radical containing 1 to 6 straight- or branched-chain carbon atoms optionally substituted by a phenyl radical,
        a straight or branched alkyl radical containing 1 to 6 carbon atoms, preferably a methylene group, optionally substituted by an amino, alkylamino, dialkylamino, hydroxyl, alkyloxy, mercapto, alkylthio, alkyloxycarbonyl, carboxyl or cyano radical, a mono- or polycyclic aromatic radical having from 5 to 12 ring members which may or may not incorporate one or more heteroatoms chosen from oxygen, nitrogen and sulphur atoms and, if appropriate, substituted, which monocyclic aromatic radical can be a phenyl radical substituted by one or more halogen atoms or by a hydroxyl, amino or trifluoromethyl group or by an alkyl, alkenyl, alkyloxy, alkylthio, alkylamino, alkylcarbonyl or $C_2$ to $C_4$ alkyloxycarbonyl, carbamoyl, alkylcarbamoyl or dialkylcarbamoyl radical, with the alkyl portions and radicals containing 1 to 8 carbon atoms, or by a formyl radical, or which polycyclic aromatic radical can be a 1-naphthyl or 2-naphthyl radical, or
  Z represents
    a $PO(OR_9)_2$ radical in which $R_9$ represents a hydrogen atom or a straight or branched alkyl radical containing 1 to 6 carbon atoms, or
    an —NH—CO—T radical in which T represents a hydrogen atom or a straight or branched alkyl radical containing 1 to 6 carbon atoms optionally substituted by an amino, carboxyl, alkyloxycarbonyl, hydroxyl, alkyloxy, mercapto or alkylthio radical, or alternatively
    a

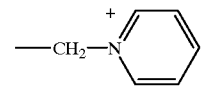

radical
    with all of the alkyl portions and radicals provided in the definition of Z, including, for example, $R_8$, which is part of Z, and that are not of a specifically defined carbon length, containing 1 to 4 carbon atoms;

$R_1$ and $R_2$, which are identical or different, represent a hydrogen atom, a halogen atom or an alkyl radical, an alkyloxy radical optionally substituted by a dialkylamino radical, wherein said two alkyl portions of said dialkylamino can form, together with the nitrogen atom to which they are attached, a saturated heterocycle containing 5 or 6 ring members, an alkylthio radical or an alkyloxycarbonyl radical, or alternatively, situated at the ortho position with respect to one another, $R_1$ and $R_2$ form a saturated or unsaturated heterocycle containing 1 or 2 heteroatoms chosen from nitrogen and oxygen, optionally substituted by a halogen atom or by an alkyl or alkyloxy radical, with all of the alkyl portions and radicals provided in the definition of $R_1$ and $R_2$ containing 1 to 4 carbon atoms;

$R_3$ and $R_4$, which are identical or different, represent a halogen atom or an alkyl, hydroxyl, alkyloxy, alkylcarbonyloxy, mercapto, alkylthio, alkylsulphonyl or alkylsulphinyl, amino, alkylamino or dialkylamino, alkylcarbonyloxyamino, carboxyl, alkyloxycarbonyl, carbamoyl, alkylcarbamoyl or dialkylcarbamoyl, formyl, alkylcarbonyl, cyano or trifluoromethyl radical, with all of the alkyl portions and radicals provided in the definition of $R_3$ and $R_4$ containing 1 to 4 carbon atoms;

$R_5$ represents a hydrogen atom;

X represents an oxygen or sulphur atom or one of the following groups: —NH—, —CO—, methylene, alkene-1,1-diyl, such as vinyldiyl, or cycloalkane-1,1-diyl containing 3 to 6 carbon atoms; and Y represents an oxygen or sulphur atom; in the racemic form, as well as in the form of the optical isomers, preferably in the form of a single enantiomer.

Mention can very particularly be made, as preferred compounds according to the present invention, of those represented by the formula (I) in which R represents a radical

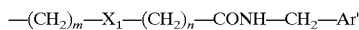

with m, n and X, being as defined above and Ar' preferably representing therein a phenyl optionally substituted by one or more radicals chosen from alkyloxy containing 1 to 4 carbon atoms and trifluoromethyl, or 1- or 2-naphthyl, 2- or 3-furyl, 2- or 3-thienyl, 2- or 3-pyrrolyl, 2- or 3-indolyl, 2- or 3- or 4-quinolyl, 1- or 3- or 4-isoquinolyl, 2- or 3-benzofuryl, 2- or 3-benzothienyl, 2- or 4- or 5-pyrimidyl, 2- or 3-pyrazinyl, 2- or 4-quinazolyl, 1-phthalazinyl, 2- or 3- or 4-naphthyridinyl, 2- or 4-imidazolyl, 2- or 4-thiazolyl or 2- or 3- or 4-pyridyl, indanyl, chromanyl or thiochromanyl radicals.

Mention may also particularly be made of the compounds of formula (I):

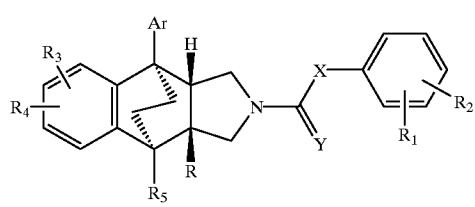

in which:

Ar represents
X a phenyl radical substituted by one or more atoms or radicals, which are identical or different and selected from halogen atoms and the radicals: alkyl, alkenyl containing 2 to 4 carbon atoms, hydroxyl, alkyloxy, mercapto, alkylthio, alkylsulphonyl, alkylsulphinyl, amino, alkylamino, dialkylamino, formyl, alkylcarbonyl, carboxyl, alkyloxycarbonyl, carbamoyl, alkylcarbamoyl, dialkylcarbamoyl, cyano, and trifluoromethyl, or a polycyclic aromatic radical, wherein all cycles are aromatic, or a 5- to 12-membered heterocyclic aromatic radical incorporating one or more heteroatoms selected from oxygen, nitrogen and sulphur atoms, said heterocyclic aromatic radical being bonded to the condensed ring via a carbon—carbon bond and optionally being substituted by one or more atoms or radicals, which are identical or different, selected from halogen atoms and the radicals: alkyl, alkenyl containing 2 to 4 carbon atoms, hydroxyl, alkyloxy, mercapto, alkylthio, alkylsulphonyl, alkylsulphinyl, amino, alkylamino, dialkylamino, formyl, alkylcarbonyl, carboxyl, alkyloxycarbonyl, carbamoyl, alkylcarbamoyl, dialkylcarbamoyl, cyano, or trifluoromethyl, wherein each of the alkyl radicals and portions contain 1 to 4 carbon atoms;

R represents
a radical of formula

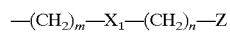

in which
$X_1$ represents a single bond or an oxygen or sulphur atom;
m represents an integer equal to 0 or 1; and
n represents an integer equal to 0, 1 or 2;
wherein one or more methylene radicals in said R radical can be substituted by a carboxyl, alkyloxycarbonyl, carbamoyl, alkylcarbamoyl, dialkylcarbamoyl, amino, alkylamino or dialkylamino radical, wherein each of the alkyl radicals and portions contains 1 to 4 carbon atoms;

Z represents
a carboxyl radical, or
a $COOR_6$ radical, in which $R_6$ represents a straight or branched alkyl radical containing 1 to 3 carbon atoms, or
a radical of formula $CON(R_7)(R_8)$ in which
$R_7$ represents a hydrogen atom or a straight or branched alkyl radical containing 1 to 6 carbon atoms, and
$R_8$ represents
a hydrogen atom, or
a hydroxyl radical, or
an amino, alkylamino or dialkylamino radical, or
an alkyloxy radical containing 1 to 6 straight- or branched-chain carbon atoms optionally substituted by a phenyl radical, or
a straight or branched alkyl radical containing 1 to 6 carbon atoms, optionally substituted by an amino, alkylamino, dialkylamino, hydroxyl, alkyloxy, mercapto, alkylthio, alkyloxycarbonyl, carboxyl, cyano radical, an optionally substituted mono- or polycyclic aromatic radical having from 5 to 12 ring members which may or may not incorporate one or more heteroatoms selected from oxygen, nitrogen and sulphur atoms, or Z represents
a $PO(OR_9)_2$ radical in which $R_9$ represents a hydrogen atom or a straight or branched alkyl radical containing 1 to 6 carbon atoms, or
an —NH—CO—T radical in which T represents a hydrogen atom or a straight or branched alkyl radical containing 1 to 6 carbon atoms optionally substituted by an amino, carboxyl, alkyloxycarbonyl, hydroxyl, alkyloxy, mercapto or alkylthio radical, or
a

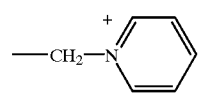

radical having an anion as a counterion, wherein each of the alkyl portions and radicals provided in the definition of Z, including, for example, $R_8$, which is part of Z, and that is not of a specifically defined carbon length, contains 1 to 4 carbon atoms;

$R_1$ and $R_2$, which are identical or different, are selected from a hydrogen atom, a halogen atom, an alkyl radical, an alkyloxy radical optionally substituted by a dialkylamino radical, wherein the two alkyl portions of said dialkylamino radical may form, with the nitrogen atom to which they are attached, a saturated heterocycle containing 5 or 6 ring members, and from an alkylthio radical and an alkyloxycarbonyl radical, or alternatively, situated at the ortho position with respect to one another, $R_1$ and $R_2$ form a saturated or unsaturated heterocycle containing 1 or 2 heteroatoms selected from nitrogen and oxygen, optionally substituted by a halogen atom or by an alkyl or alkyloxy radical, wherein each of the alkyl radicals and portions provided in the definition of $R_1$ and $R_2$ contains 1 to 4 carbon atoms;

$R_3$ and $R_4$, which are identical or different, are selected from a hydrogen atom, a halogen atom and a radical selected from alkyl, hydroxyl, alkyloxy, alkylcarbonyloxy, mercapto, alkylthio, alkylsulphonyl, alkylsulphinyl, amino, alkylamino, dialkylamino, alkylcarbonyloxyamino, carboxyl, alkyloxycarbonyl, carbamoyl, alkylcarbamoyl, dialkylcarbamoyl, formyl, alkylcarbonyl, cyano, and trifluoromethyl, wherein each of the alkyl radicals and portions provided in the definition of $R_3$ and $R_4$ contains 1 to 4 carbon atoms;

$R_5$ represents a hydrogen atom;

X represents an oxygen or sulphur atom or one of the groups: —NH—, —CO—, methylene, alkene-1,1-diyl, or cycloalkane-1,1-diyl containing 3 to 6 carbon atoms;

and Y represents an oxygen or sulphur atom; or a pharmaceutically acceptable salt thereof.

Of the foregoing compounds, those wherein Z represents a $CON(R_7)(R_8)$ radical in which $R_8$ represents an alkyl radical substituted by a phenyl radical optionally substituted by one or more halogen atoms or by one or more hydroxyl, amino or trifluoromethyl groups or by one or more alkyl, alkenyl, alkyloxy, alkylthio, alkylamino, alkylcarbonyl or $C_2$ to $C_4$ alkyloxycarbonyl, carbamoyl, alkylcarbamoyl, dialkylcarbamoyl, or formyl radicals, wherein each alkyl portion and radical contains 1 to 8 carbon atoms, or by a 1- or 2-naphthyl radical, are particularly preferred. More particularly preferred compounds amongst the foregoing are those wherein Ar is a polycyclic aromatic radical and is 1-naphthyl, 2-naphthyl or 5-indanoyl.

Compounds falling within the scope of formula (I) that are even more particularly preferred are those wherein $R_3$ and $R_4$, which are identical or different, are selected from a halogen atom and a radical selected from alkyl, hydroxyl, alkyloxy, alkylcarbonyloxy, mercapto, alkylthio, alkylsulphonyl, alkylsulphinyl, amino, alkylamino, dialkylamino, alkylcarbonyloxyamino, carboxyl, alkyloxycarbonyl, carbamoyl, alkylcarbamoyl, dialkylcarbamoyl, formyl, alkylcarbonyl, cyano, and trifluoromethyl, wherein each of the alkyl portions and radicals provided in the definition of $R_3$ and $R_4$ contains 1 to 4 carbon atoms.

Another group of preferred compounds of formula (I) are the following:

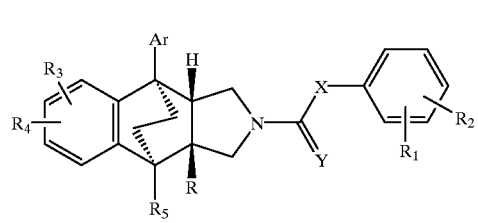

(I)

in which:

Ar represents
a phenyl radical substituted by one or more atoms or radicals, which are identical or different and are selected from halogen atoms and the radicals: alkyl, alkylthio, amino, dialkylamino, cyano, and alkyloxy, the alkyl portions and radicals being optionally perhalogenated, or a phenyl radical condensed with a 5- or 6-membered nonaromatic heterocycle containing one or more heteroatoms selected from oxygen, nitrogen and sulphur atoms, or a bicyclic aromatic radical, or a monocyclic 5-membered heterocyclic aromatic radical incorporating one or more heteroatoms selected from oxygen, nitrogen and sulphur atoms, said heterocyclic aromatic radical being bonded to the condensed ring via a carbon—carbon bond and optionally being substituted by one or more atoms or radicals, which are identical or different and are selected from halogen atoms and the radicals: alkyl, alkenyl containing 2 to 4 carbon atoms, hydroxyl, alkyloxy, mercapto, alkylthio, alkylsulphonyl, alkylsulphinyl, amino, alkylamino, dialkylamino, formyl, alkylcarbonyl, carboxyl, alkyloxycarbonyl, carbamoyl, alkylcarbamoyl, dialkylcarbamoyl, cyano, and trifluoromethyl, wherein each of the alkyl portions and radicals in the definition of Ar contains 1 to 4 carbon atoms;

R represents
a radical of formula:

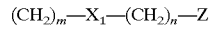

in which
$X_1$ represents a single bond,
m represents an integer equal to 0, and
n represents an integer equal to 0;

Z represents
a carboxyl radical, or
a $COOR_6$ radical, in which $R_6$ represents a straight or branched alkyl radical containing 1 to 3 carbon atoms, or
a radical of formula $CON(R_7)(R_8)$ in which
$R_7$ represents a hydrogen atom, and
$R_8$ represents
a hydrogen atom, or
a hydroxyl radical, or
an arylsulphonyl radical, optionally substituted by one or more atoms or radicals, which are identical or different and are selected from halogen atoms and alkyl and alkyloxy radicals, or
a 6-membered heterocycle incorporating one or more heteroatoms selected from nitrogen, oxygen and sulphur atoms, it being possible for said heterocycle to be bonded to the N in said $CON(R_7)(R_8)$ radical via a heteroatom, or an amino radical optionally substituted by one or two radicals, which are identical or different and are selected from the radicals:
alkyl,
carbocyclic aryl, optionally substituted by one or more radicals, which are identical or different and are selected from alkyl and alkyloxy radicals,
5- to 7-membered heterocyclyl containing one or more heteroatoms selected from nitrogen, oxygen and sulphur atoms, or
arylcarbonyl, optionally substituted by one or more radicals, which are identical or different and are selected from alkyl and alkyloxy radicals, or $R_8$ represents an alkyloxy radical containing 1 to 6 straight- or branched-chain carbon atoms optionally substituted by a phenyl radical, or a straight or branched alkyl radical containing 1 to 6 carbon atoms, optionally substituted by at least one radical selected from amino, alkylamino, dialkylamino, hydroxyl, alkyloxy, mercapto, alkylthio, alkyloxycarbonyl, carboxyl, cyano, and optionally substituted mono- and bicyclic aromatic having 5–6 and 10 ring members which may or may not incorporate one or more heteroatoms selected from oxygen, nitrogen and sulphur atoms, it being possible for said monocyclic aromatic radical incorporating one or more nitrogen heteroatoms to be in the form of the N-oxide, wherein each of the alkyl portions and radicals provided in the definition of Z, including, for example, $R_8$, which is part of Z, and that is not of a specifically defined carbon length contains 1 to 4 carbon atoms;

$R_1$ and $R_2$, which are identical or different, are selected from a hydrogen atom, a halogen atom, an alkyl radical, and an alkyloxy radical, wherein each of said radicals may optionally be substituted by a dialkylamino radical, wherein each of the alkyl radicals and portions provided in the definition of $R_1$ and $R_2$ contains 1 to 4 carbon atoms;

$R_3$ and $R_4$, which are identical or different, are selected from a hydrogen atom, a halogen atom and a radical selected from alkyl, hydroxyl, alkyloxy, alkylcarbonyloxy, mercapto, alkylthio, alkylsulphonyl, alkylsulphinyl, amino, alkylamino, dialkylamino, alkyloxycarbonylamino, carboxyl, alkyloxycarbonyl, carbamoyl, alkylcarbamoyl, dialkylcarbamoyl, formyl, alkylcarbonyl, cyano, and trifluoromethyl, wherein each of the alkyl portions and radicals provided in the definition of $R_3$ and $R_4$ contains 1 to 4 carbon atoms;

$R_5$ represents a hydrogen atom or an alkyl or alkylthio radical, wherein for the definition of $R_5$, the alkyl portions and radicals contain 1 to 4 carbon atoms;

X represents a methylene or alkene-1,1-diyl group; and Y represents an oxygen or sulphur atom; or a pharmaceutically acceptable salt of a compound of formula (I).

Another particularly preferred group of compounds of formula (I) include those:

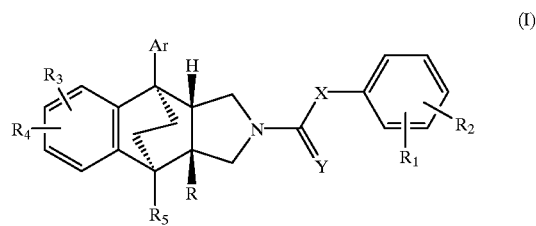

(I)

in which:
Ar represents
a phenyl radical substituted by one or more atoms or radicals, which are identical or different and are selected from halogen atoms and the radicals: alkyl, alkylthio, dialkylamino, cyano, and alkyloxy, the alkyl portions and radicals being optionally perhalogenated, or
a phenyl radical condensed with a 5 to 6-membered nonaromatic heterocycle containing one or more oxygen heteroatoms, or
a monocyclic 5-membered heterocyclic aromatic radical incorporating one or more sulphur heteroatoms, said heterocyclic aromatic radical being bonded to the condensed ring via a carbon—carbon bond and optionally being substituted by one or more atoms or radicals, which are identical or different and are selected from alkyl radicals,
wherein each of the alkyl portions and radicals in the definition of Ar contains 1 to 4 carbon atoms;

R represents
a radical of formula:

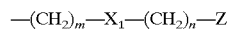

in which
$X_1$ represents a single bond,
m represents an integer equal to 0, and
n represents an integer equal to 0;

Z represents
a carboxyl radical, or
a radical of formula $CON(R_7)(R_8)$ in which
$R_7$ represents a hydrogen atom, and
$R_8$ represents
a hydroxyl radical, or
a 6-membered nonaromatic heterocycle incorporating one nitrogen heteroatom, it being possible for said heterocycle to be bonded to the N in said $CON(R_7)(R_8)$ radical via a heteroatom, or
an amino radical optionally substituted by one or two radicals, which are different and are selected from the radicals:
alkyl,
carbocyclic aryl, optionally substituted by one or more radicals, which are identical or different and are selected from alkyloxy radicals,
6-membered heterocyclyl containing one or more heteroatoms selected from nitrogen, oxygen and sulphur atoms, or $R_8$ represents a straight or branched alkyl radical containing 1 to 6 carbon atoms, optionally substituted by at least one radical selected from carboxyl and an optionally substituted monocyclic aromatic ring having from 5–6 ring members which may or may not incorporate one or more heteroatoms selected from nitrogen and sulphur atoms, wherein each of the alkyl portions and radicals provided in the definition of Z, including, for example, $R_8$, which is part of Z, and that is not of a specifically defined carbon length contains 1 to 4 carbon atoms;

$R_1$ and $R_2$, which are identical or different, are selected from a hydrogen atom, and an alkyloxy radical, wherein said radical may optionally be substituted by a dialkylamino radical, wherein each of the alkyl portions provided in the definition of $R_1$ and $R_2$ contains 1 to 4 carbon atoms;

$R_3$ and $R_4$ are selected from a hydrogen atom and an alkyloxy radical; wherein each of the alkyl portions provided in the definition of $R_3$ and $R_4$ contains 1 to 4 carbon atoms;

$R_5$ represents a hydrogen atom or an alkyl radical, wherein for the definition of $R_5$, the alkyl radicals contain 1 to 4 carbon atoms;

X represents a methylene or alkene-1,1-diyl group; and Y represents an oxygen; or a pharmaceutically acceptable salt of a compound of formula (I).

Another very particularly preferred group of the compounds of formula (I) are those:

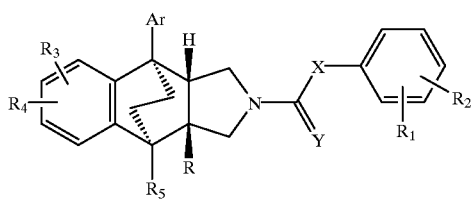

(I)

in which;

Ar represents
a phenyl radical substituted by one or more atoms or radicals, which are identical or different and are selected from halogen atoms and the radicals: alkyl, alkylthio, dialkylamino, cyano, and alkyloxy, the alkyl portions and radicals being optionally perhalogenated, or
a phenyl radical condensed with a 5 to 6-membered nonaromatic heterocycle containing one or more oxygen heteroatoms,
wherein each of the alkyl portions and radicals in the definition of Ar contains 1 to 4 carbon atoms;

R represents
a radical of formula:

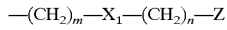

in which
$X_1$ represents a single bond,
m represents an integer equal to 0, and
n represents an integer equal to 0;

Z represents
a carboxyl radical, or
a radical of formula $CON(R_7)(R_8)$ in which
$R_7$ represents a hydrogen atom, and
$R_8$ represents
a hydroxyl radical, or
an amino radical optionally substituted by one radical, which is selected from the radicals: carbocyclic aryl, optionally substituted by one or more radicals, which are identical or different and are selected from alkyloxy radicals,
6-membered heterocyclyl containing one nitrogen heteroatom,
or $R_8$ represents a straight or branched alkyl radical containing 1 to 6 carbon atoms, optionally substituted by at least one radical selected from carboxyl and optionally substituted monocyclic aromatic ring having from 5–6 ring members which may or may not incorporate one or more nitrogen heteroatoms, wherein each of the alkyl portions and radicals provided in the definition of Z, including, for example, $R_8$, which is part of Z, and that is not of a specifically defined carbon length contains 1 to 4 carbon atoms;

$R_1$ and $R_2$, which are identical or different, are selected from a hydrogen atom and an alkyloxy radical, wherein each of the alkyl portions of said radicals contains 1 to 4 carbon atoms;

$R_3$ and $R_4$, which are identical or different, are selected from a hydrogen atom and anr alkyloxy radical, wherein each of the alkyl portions of said radicals contains 1 to 4 carbon atoms;

$R_5$ represents a hydrogen atom or an alkyl radical, wherein for the definition of $R_5$, the alkyl-radical contains 1 to 4 carbon atoms;

X represents a methylene or —C═C— group; and Y represents an oxygen; or a pharmaceutically acceptable salt of a compound of formula (I).

Mention may similarly particularly be made, as a non-limiting illustration of the claimed compounds, of the following compounds:

methyl (3aRS,4SR,9SR,9aRS)-4,9-ethano-2-[2-(2-methoxy-phenyl)propenoyl]-9-(4-methylphenyl)-2,3,3a,4,9,9a-hexahydro-1H-benzo[f]isoindole-3a-carboxylate;

(3aRS,4SR,9SR,9aRS)-4,9-ethano-2-[2-(2-methoxyphenyl)-propenoyl]-9-(4-methylphenyl)-2,3,3a,4,9,9a-hexahydro-1H-benzo[f]isoindole-3a-carboxylic acid;

(3aRS,4SR,9SR,9aRS)-4,9-ethano-2-[(2-methoxyphenyl)-acetyl]-9-(4-methylphenyl)-2,3,3a,4,9,9a-hexahydro-1H-benzo[f]isoindole-3a-carboxylic acid;

(3aRS,4SR,9SR,9aRS)-4,9-ethano-9-(4-methoxyphenyl)-2-[(2-methoxyphenyl)acetyl]-2,3,3a,4,9,9a-hexahydro-1H-benzo[f]isoindole-3a-carboxylic acid;

(3aRS,4SR,9SR,9aRS)-4,9-ethano-2-[(2-methoxyphenyl)-acetyl]-9-(4-methylsulphanylphenyl)-2,3,3a,4,9,9a-hexahydro-1H-benzo[f]isoindole-3a-carboxylic acid;

(3aRS,4SR,9SR,9aRS)-4,9-ethano-9-(4-fluorophenyl)-2-[(2-methoxyphenyl)acetyl]-2,3,3a,4,9,9a-hexahydro-1H-benzo[f]isoindole-3a-carboxylic acid;

(3aRS,4SR,9SR,9aRS)-4,9-ethano-2-[(2-methoxyphenyl)-acetyl]-9-(3-methylphenyl)-2,3,3a,4,9,9a-hexahydro-1H-benzo[f]isoindole-3a-carboxylic acid;

(3aRS,4SR,9SR,9aRS)-4,9-ethano-9-(3-methoxyphenyl)-2-[(2-methoxyphenyl)acetyl]-2,3,3a,4,9,9a-hexahydro-1H-benzo[f]isoindole-3a-carboxylic acid;

methyl (3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f]isoindole-3a-carboxylate;

(3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f]isoindole-3a-carboxylic acid;

(3aRS,4SR,9SR,9aRS)-3a-N-benzylcarbamoyl-4,9-ethano-2-[2-(2-methoxyphenyl)propenoyl]-9-(4-methylphenyl)-2,3,3a,4,9,9a-hexahydro-1H-benzo[f]isoindole;

(3aRS,4SR,9SR,9aRS)-3a-carbamoyl-4,9-ethano-2-[2-(2-methoxyphenyl)propenoyl]-9-(4-methylphenyl)-2,3,3a,4,9,9a-hexahydro-1H-benzo[f]isoindole;

benzyl (3aRS,4SR,9SR,9aRS)-4,9-ethano-2-[2-(2-methoxy-phenyl)propenoyl]-9-(4-methylphenyl)-2,3,3a,4,9,9a-hexahydro-1H-benzo[f]isoindole-3a-hydroxamate;

(3aRS,4SR,9SR,9aRS)-4,9-ethano-2-[2-(2-methoxyphenyl)-propenoyl]-9-(4-methylphenyl)-2,3,3a,4,9,9a-hexahydro-1H-benzo[f]isoindole-3a-hydroxamic acid;

in the racemic form, as well as in the form of a single enantiomer.

Mention may also be made, according to the invention, of any compound of formula (I) individually selected from:

methyl (3aRS,4SR,9SR,9aRS)-4,9-ethano-2-[2-(2-methoxy-phenyl)propenoyl]-9-(4-methylphenyl)-2,3,3a,4,9,9a-hexahydro-1H-benzo[f]isoindole-3a-carboxylate;

(3aRS,4SR,9SR,9aRS)-4,9-ethano-2-[2-(2-methoxyphenyl)-propenoyl]-9-(4-methylphenyl)-2,3,3a,4,9,9a-hexahydro-1H-benzo[f]isoindole-3a-carboxylic acid;

(3aRS,4SR,9SR,9aRS)-4,9-ethano-2-[(2-methoxyphenyl)-acetyl]-9-(4-methylphenyl)-2,3,3a,4,9,9a-hexahydro-1H-benzo[f]isoindole-3a-carboxylic acid;

(3aRS,4SR,9SR,9aRS)-4,9-ethano-9-(4-methoxyphenyl)-2-[(2-methoxyphenyl)acetyl]-2,3,3a,4,9,9a-hexahydro-1H-benzo[f]isoindole-3a-carboxylic acid;

(3aRS,4SR,9SR,9aRS)-4,9-ethano-2-[(2-methoxyphenyl)acetyl]-9-(4-methylsulphanylphenyl)-2,3,3a,4,9,9a-hexahydro-1H-benzo[f]isoindole-3a-carboxylic acid;

(3aRS,4SR,9SR,9aRS)-4,9-ethano-9-(4-fluorophenyl)-2-[(2-methoxyphenyl)acetyl]-2,3,3a,4,9,9a-hexahydro-1H-benzo[f]isoindole-3a-carboxylic acid;

(3aRS,4SR,9SR,9aRS)-4,9-ethano-2-[(2-methoxyphenyl)-acetyl]-9-(3-methylphenyl)-2,3,3a,4,9,9a-hexahydro-1H-benzo[f]isoindole-3a-carboxylic acid;

(3aRS,4SR,9SR,9aRS)-4,9-ethano-9-(3-methoxyphenyl)-2-[(2-methoxy-phenyl)acetyl]-2,3,3a,4,9,9a-hexahydro-1H-benzo[f]isoindole-3a-carboxylic acid;

methyl (3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f]isoindole-3a-carboxylaye;

(3aRS,4SR,9SR,9aRS)-9-(3,4-dimethylphenyl)-4,9-ethano-2-[(2-methoxy-phenyl)acetyl]-2,3,3a,4,9,9a-hexahydro-1H-benzo[f]isoindole-3a-carboxylic acid;

(3aRS,4SR,9SR,9aRS)-3a-N-benzylcarbamoyl-4,9-ethano-2-[2-(2-methoxy-phenyl)propenoyl]-9-(4-methylphenyl)-2,3,3a,4,9,9a-hexahydro-1H-benzo[f]isoindole;

(3aRS,4SR,9SR,9aRS)-3a-carbamoyl-4,9-ethano-2-[2-(2-methoxy-phenyl)propenoyl]-9-(4-methylphenyl)-2,3,3a,4,9,9a-hexahydro-1H-benzo[f]isoindole;

benzyl (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-hydroxamate;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-hydroxamic acid;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(3-pyridylmethyl)-carboxamide;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(4-pyridylmethyl)-carboxamide;

methyl (3aRS,4SR,9SR,9aRS)-4,9-ethano-2-[2-(2-methoxyphenyl)propenoyl]- 9-(4-methylphenyl)-2,3,3a,4,9,9a-hexahydro-1H-benzo[f]isoindole-3a-hydroxamate;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N',N'-dimethyl-carbohydrazide;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-phenylcarbohydrazide;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N',N'-pentamethylene-carbohydrazide;

(3aRS,4SR,9SR,9aRS)-4,9-ethano-2-[2-(2-methoxyphenyl)propenoyl]-9-(4-methylphenyl)-3a-phenylsulphonylaminocarbonyl-2,3,3a,4,9,9a-hexahydro-1H-benzo[f]isoindole;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(N-oxo-3-pyridyl)methylcarboxamide;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(4-methoxyphenyl)-carbohydrazide;

(3aRS,4SR,9SR,9aRS)-4,9-ethano-2-[2-(2-methoxyphenyl)propenoyl]-9-( 4-methylphenyl)-2,3,3a,4,9,9a-hexahydro-1H-benzo[f]isoindole-3a-N'-methyl-N'-phenylcarbohydrazide;

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(2-methylphenyl)carbohydrazide;

methyl (3aRS,4SR,9SR,9aRS)-9-(2,3-dihydro-1,4-benzodioxin-6-yl)-4,9-ethano-2-[2-(2-methoxyphenyl)-propenoyl]-2,3,3a,4,9,9a-hexahydro-1H-benzo[f]isoindole-3a-carboxylate;

(3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-9-(2,3-dihydro-1,4-benzodioxin-6-yl)-4,9-ethano-2-[2-methoxyphenyl)propenoyl]-2,3,3a,4,9,9a-hexahydro-1H-benzo[f]isoindole-3a-N-(3-pyridylmethyl)carboxamide;

(3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(2-thienylmethyl)carboxamide;

(3aRS,4SR,9SR,9aRS)-4,9-ethano-2-[(2-methoxyphenyl)-acetyl]-9-(3,4,5-trimethylphenyl)-2,3,3a,4,9,9a-hexahydro-1H-benzo[f]isoindole-3a-carboxylic acid;

(3aRS,4SR,9SR,9aRS)-4,9-ethano-2-[2-(2-methoxyphenyl)-propenoyl]-9-(2-methylphenyl)-2,3,3a,4,9,9a-hexahydro-1H-benzo[f]isoindole-3a-carboxylic acid;

methyl (3aRS,4SR,9SR,9aRS)-4,9-ethano-2-[2-(2-methoxyphenyl)propenoyl]-9-(4-trifluoromethylphenyl)-2,3,3a,4,9,9a-hexahydro-1H-benzo[f]isoindole-3a-carboxylate;

(3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-carboxylic acid;

(3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-N-(4-pyridylmethyl)carboxamide;

(3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-N'-benzoylcarbohydrazide;

(3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-N'-phenyl-carbohydrazide;

methyl (3aRS,4SR,9SR,9aRS)-4,9-ethano-2-[2-(2-methoxyphenyl)propenoyl]-9-(2-naphthyl)-2,3,3a,4,9,9a-hexahydro-1H-benzo[f]isoindole-3a-carboxylate;

(3aRS,4SR,9SR,9aRS)-4,9-ethano-2-[2-(2-methoxyphenyl)-propenoyl]-9-(2-naphthyl)-2,3,3a,4,9,9a-hexahydro-1H-benzo[f]isoindole-3a-carboxylic acid;

methyl (3aRS,4SR,9SR,9aRS)-4,9-ethano-2-[2-(2-methoxyphenyl)propenoyl]-9-(5-methyl-2-thienyl)-2,3,3a,4,9,9a-hexahydro-1H-benzo[f]isoindole-3a-carboxylate;

(3aRS,4SR,9SR,9aRS)-4,9-ethano-2-[2-(2-methoxyphenyl)-propenoyl]-9-(5-methyl-2-thienyl)-2,3,3a,4,9,9a-hexahydro-1H-benzo[f]isoindole-3a-carboxylic acid;

methyl (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-4,9-ethano-2-[2-(2-methoxyphenyl)propenoyl]-9-(4-chlorophenyl)-2,3,3a,4,9,9a-hexahydro-1H-benzo[f]isoindole-3a-carboxylate;

(3aRS,4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-4,9-ethano-2-[2-(2-methoxyphenyl)propenoyl]-9-(4-methoxy-3-methylphenyl)-2,3,3a,4,9,9a-hexahydro-1H-benzo[f]isoindole-3a-carboxylic acid;

methyl (3aRS,4SR,9SR,9aRS)-4,9-ethano-2-[2-(2-methoxyphenyl)propenoyl]-9-(3-indolyl)-2,3,3a,4,9,9a-hexahydro-1H-benzo[f]isoindole-3a-carboxylate;

(3aRS,4SR,9SR,9aRS)-4,9-ethano-9-(4-isopropylphenyl)-2-[(2-methoxyphenyl)acetyl]-2,3,3a,4,9,9a-hexahydro-1H-benzo[f]isoindole-3a-carboxylic acid;

(3aRS,4SR,9SR,9aRS)-4,9-ethano-9-(4-isopropylphenyl)-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-4,9-ethano-2-[2-(2-methoxyphenyl)propenoyl]-9-(3-thienyl)-2,3,3a,4,9,9a-hexahydro-1H-benzo[f]isoindole-3a-carboxylate;

methyl (3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylate;

(3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-N-(3-pyridylmethyl)-carboxamide;

methyl (3aRS,4SR,9SR,9aRS)-4,9-ethano-9-(4-fluorophenyl)-2-[2-(2-methoxyphenyl)propenoyl]-2,3,3a,4,9,9a-hexahydro-1H-benzo[f]isoindole-3a-carboxylate;

(3aRS,4SR,9SR,9aRS)-4,9-ethano-9-(4-fluorophenyl)-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-9-(4-chloro-3-fluorophenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(4-chloro-3-fluorophenyl)-4,9-ethano-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f]isoindole-3a-carboxylate;

(3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f]isoindole-3a-carboxylic acid;

methyl (3aRS,4SR,9SR,9aRS)-9-(1,3-benzodioxol-5-yl)-4,9-ethano-2-[2-(2-methoxyphenyl)propenoyl]-2,3,3a,4,9,9a-hexahydro-1H-benzo[f]isoindole-3a-carboxylate;

methyl (3aRS,4SR,9SR,9aRS)-9-(3,4-dimethylphenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(3,4-dimethylphenyl)-4,9-ethano-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylate;

(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N-(3-pyridylmethyl)carboxamide;

(3aRS,4SR,9SR,9aRS)-4,9-ethano-9-(4-methoxyphenyl)-2-[2-( 2-methoxyphenyl)propenoyl]-2,3,3a,4,9,9a-hexahydro-1H-benzo[f]isoindole-3a-N'-phenylcarbohydrazide;

(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-hydroxamic acid;

(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N'-(3-pyridyl)carbohydrazide;

(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N-(3-thienylmethyl)carboxamide;

(RS)- and (SR)-2-{(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carbonylamino}phenylacetic acids;

(3aRS,4SR,9SR,9aRS)-4,9-ethano-2-[2-(2-methoxyphenyl)propenoyl]-9-(4-trifluoromethoxyphenyl)-2,3,3a,4,9,9a-hexahydro-1H-benzo[f]isoindole-3a-carboxylic acid;

methyl (3aRS,4SR,9SR,9aRS)-9-(3-bromophenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(3-bromophenyl)-4,9-ethano-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-4,9-ethano-9-(3-fluorophenyl)-2-[2-(2-methoxyphenyl)propenoyl]-2,3,3a,4,9,9a-hexahydro-1H-benzo[f]isoindole-3a-carboxylate;

(3aRS,4SR,9SR,9aRS)-4,9-ethano-9-(3-fluorophenyl)-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-4,9-ethano-9-(3-fluorophenyl)-2-[2-(2-methoxyphenyl)propenoyl]-2,3,3a,4,9,9a-hexahydro-1H-benzo[f]isoindole-3a-N-(3-pyridylmethyl)carboxamide;

methyl (3aRS,4SR,9SR,9aRS)-9-(3-chlorophenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(3-chlorophenyl)-4,9-ethano-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-9-(3-chlorophenyl)-4,9-ethano-2-[2-(2-methoxyphenyl)propenoyl]-2,3,3a,4,9,9a-hexahydro-1H-benzo[f]isoindole-3a-N-( 3-pyridylmethyl)carboxamide;

methyl (3aRS,4SR,9SR,9aRS)-9-(3-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(3-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-9-(3-aminophenyl)-4,9-ethano-2-[2-(2-methoxyphenyl)propenoyl]-2,3,3a,4,9,9a-hexahydro-1H-benzo[f]isoindole-3a-carboxylate hydrochloride;

methyl (3aRS,4SR,9SR,9aRS)-9-(4-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-9-(4-cyanophenyl)-4,9-ethano-2-[2-(2-methoxyphenyl)propenoyl]-2,3,3a,4,9,9a-hexahydro-1H-benzo[f]isoindole-3a-carboxylic acid;

methyl (3aRS,4SR,9SR,9aRS)-9-(3-cyanophenyl)-4,9-ethano-2-[2-(2-methoxyphenyl)propenoyl]-2,3,3a,4,9,9a-hexahydro-1H-benzo[f]isoindole-3a-carboxylate;

(3aRS,4SR,9SR,9aRS)-4,9-ethano-9-(3-hydroxy-4-methoxyphenyl)-2-[2-( 2-methoxyphenyl)propenoyl]-2,3,3a,4,9,9a-hexahydro-1H-benzo[f]isoindole-3a-carboxylic acid;

methyl (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylate;

(3a RS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid;

(3aRS,4SR,9SR,9aRS)-4,9-ethano-2-[2-(2-methoxyphenyl)-propenoyl]-4-methyl-9-(4-methoxyphenyl)-2,3,3a,4,9,9a-hexahydro-1H-benzo[f]isoindole-3a-carboxylic acid;

in the racemic form or in the form of their optical isomers, preferably in the form of a single enantiomer, as well as their salts.

More preferably, mention may also be made, according to the invention, of any compound of formula (I) individually selected from:

(3aRS,4SR,9SR,9aRS)-4,9-ethano-2-[2-(2-methoxyphenyl)-propenoyl]-9-(4-methylphenyl)-2,3,3a,4,9,9a-hexahydro-1H-benzo[f]isoindole-3a-carboxylic acid;

(3aRS,4SR,9SR,9aRS)-4,9-ethano-2-[2-(2-methoxyphenyl)-propenoyl]-9-(4-methylphenyl)-2,3,3a,4,9,9a-hexahydro-1H-benzo[f]isoindole-3a-N-(3-pyridylmethyl)carboxamide;

(3aRS,4SR,9SR,9aRS)-9-(2,3-dihydro-1,4-benzodioxin-6-yl)-4,9-ethano- 2-[2-(2-methoxyphenyl)propenoyl]-2,3,3a,4,9,9a-hexahydro-1H-benzo[f]isoindole-3a-N-(3-pyridylmethyl)carboxamide;

(3aRS,4SR,9SR,9aRS)-4,9-ethano-2-[2-(2-methoxyphenyl)propenoyl]-9-(4-trifluoromethylphenyl)-2,3,3a,4,9,9a-hexahydro-1H-benzo[f]isoindole-3a-carboxylic acid;

(3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid;

(3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid;

(3aRS,4SR,9SR,9aRS)-4,9-ethano-2-[2-(2-methoxyphenyl)propenoyl]-4-methyl-9-(4- methoxyphenyl)-2,3,3a,4,9,9a-hexahydro-1H-benzo[f]
isoindole-3a-carboxylic acid;

in the racemic form or in the form of a single enantiomer, as well as their salts.

Mention may be made, as very particularly advantageous, of the single enantiomers of the compounds of formula (I) according to the invention, specifically, of any compound chosen individually from:

the dextrorotatory enantiomer of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid;

the dextrorotatory enantiomer of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(3-pyridylmethyl)carboxamide;

the levorotatory enantiomer of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(3-pyridylmethyl)carboxamide;

the dextrorotatory enantiomer of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide;

the levorotatory enantiomer of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide;

the dextrorotatory enantiomer of (3aRS,4SR,9SR,9aRS)-4,9-ethano-2-[2-(2-methoxyphenyl)propenoyl]-9-(4-tri-fluoromethylphenyl)-2,3,3a,4,9,9a-hexahydro-1H-benzo[f]isoindole-3a-carboxylic acid;

the-dextrorotatory enantiomer of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid;

the dextrorotatory enantiomer of (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid; and the dextrorotatory enantiomer of (3aRS,4SR,9SR,9aRS)-4,9-ethano-2-[2-(2-methoxyphenyl)propenoyl]-4-methyl-9-(4-methoxyphenyl)-2,3,3a,4,9,9a-hexahydro-1H-benzo[f]isoindole-3a-carboxylic acid;

in the racemic form and in the form of a single enantiomer, as well as the salts thereof.

Preferably, the single enantiomers of the invention are present in an 80% e.e., more preferably, 90% e.e., even more preferably 95% e.e., and most preferably, 98% e.e.

The inventors additionally provide hereinbelow, without implied limitation of the present invention, various operating protocols as well as reaction intermediates for use in the preparation of the compounds of formula (I). Of course, it is within the capability of a person skilled in the art to be guided by these protocols and/or intermediates in developing analogous processes or intermediates for the purpose of leading to these same compounds.

According to the invention, the claimed novel compounds of formula (I) in which:

Y represents an oxygen or sulphur atom, and

X represents one of the following groups: —CO—, methylene, alkene-1,1-diyl, such as vinyidiyl, or cycloalkane-1,1-diyl containing 3 to 6 carbon atoms, can be obtained by converting a compound of the formula (III), shown below, under conditions sufficient to obtain a compound of formula (I). The conversion can preferably be obtained by reaction of an acid of formula (II):

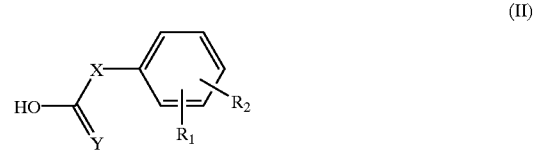

(II)

in which:

$R_1$ and $R_2$ are defined according to any disclosed embodiment of the formula (I) and X is defined as above, and Y represents an oxygen or sulphur atom, or reaction of the methyl ester of this acid or of a derivative of this acid, such as a halide or the anhydride, with a compound of formula (III):

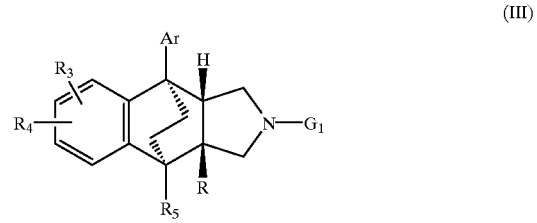

(III)

in which:

Ar, R, $R_3$, $R_4$ and $R_5$ are defined according to any disclosed embodiment of the formula (I), and $G_1$ represents a hydrogen atom (which can be obtained from a compound of formula (III) in which $G_1$ represents a protective group for an amino functional group, such as a benzyl, benzyloxycarbonyl, tert-butoxycarbonyl or vinyloxycarbonyl radical, by hydrogenolysis in the presence of a catalyst, such as palladium-on-charcoal, when $G_1$ represents a benzyl or benzyloxycarbonyl radical, or by hydrolysis in acidic medium, when $G_1$ represents a tert-butoxycarbonyl, vinyloxycarbonyl or benzyloxycarbonyl radical).

Generally, the reaction of a compound of formula (II), in the acid form, with a compound of formula (III) is carried out in an organic solvent, such as a halogenated aliphatic hydrocarbon, such as dichloromethane, in the presence of a coupling agent, such as 1-ethyl-3-[3-(dimethyl-amino)propyl]carbodiimide hydrochloride, 1,3-dicyclohexylcarbodiimide or benzotriazol-1-yloxytris-(dimethylamino)phosphonium hexafluorophosphate, and optionally of an activating agent, such as hydroxybenzotriazole, at a temperature ranging from 0° C. to the reflux temperature of the reaction mixture.

The reaction of a compound of formula (II), in the form of the methyl ester, with a compound of formula (III) is generally carried out in an organic solvent, such as dioxane or a halogenated aliphatic hydrocarbon, such as dichloromethane, at a temperature ranging from 0° C. to the reflux temperature of the reaction mixture.

The reaction of a compound of formula (iI), in the halide form, with a compound of formula (III) is generally carried out in an organic solvent, such as a halogenated aliphatic hydrocarbon, such as dichloromethane, in the presence of a base (tertiary aliphatic amine) at a temperature ranging from 0° C. to the reflux temperature of the reaction mixture.

The reaction of a compound of formula (II), in the anhydride form, with a compound of formula (III) is generally carried out in an organic solvent, such as a halogenated aliphatic hydrocarbon, such as dichloromethane, in the presence of a base (tertiary aliphatic amine, pyridine or 4-dimethylaminopyridine) at a temperature ranging from 0° C. to 50° C.

In addition, on conclusion of the reaction of (II) with (III), it is optionally possible, when R represents or contains a —$COOR_6$ or —$PO(OR_9)_2$ radical with $R_6$ and $R_9$ representing an alkyl radical,
- to saponify the product obtained, in order to obtain a compound of formula (I) in which R represents or contains a carboxyl radical, or
- to convert, by means of a nucleophilic agent, the compound obtained, in order to obtain a compound of formula (I) in which R represents or contains a —$PO_3H_2$ radical.

The saponification of a compound of formula (I) in which R represents or contains an ester of general formula —$COOR_6$ into a compound of formula (I) in which R represents or contains a carboxyl radical is generally carried out by means of an inorganic base, such as sodium hydroxide or potassium hydroxide or sodium carbonate, in an organic solvent, such as an alcohol, for example methanol or ethanol, or such as an ether, for example dioxane, at a temperature ranging from 20° C. to the reflux temperature of the solvent.

The conversion of a compound of any embodiment disclosed of the formula (I) in which R represents or contains a $PO(OR_9)_2$ radical into a compound of formula (I) in which R represents or contains a $PO_3H_2$ radical is generally carried out by reaction with a nucleophilic agent, such as a trialkylsilyl (trimethylsilyl) halide (iodide), or with a sodium or lithium halide (sodium iodide) in the presence of a trialkylhalosilane (trimethylchlorosilane, trimethylbromosilane), the reaction being carried out in a solvent, such as carbon tetrachloride or acetonitrile, at a temperature ranging from 0 to 50° C., or by heating with an alkali metal halide (sodium iodide), followed by hydrolysis.

According to the invention, the novel compounds of formula (I) in which:
Y represents an oxygen or sulphur atom, and
X represents an oxygen atom, can be obtained by the reaction of a haloformate or of a halothioformate of formula (IV):

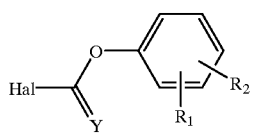

(IV)

in which:
Y represents an oxygen or sulphur atom,
$R_1$ and $R_2$ are defined as above in any disclosed embodiment of the formula (I), and
Hal represents a halogen atom, with a compound of formula (III).

The reaction of the halide of formula (IV) with the compound of formula (III) is generally carried out in organic or aqueous/organic medium, such as a dioxane/water mixture, in the presence of an inorganic base (sodium hydroxide) or organic base (triethylamine) at a temperature ranging from 0 to 50° C.

In the same way as above, when R represents or contains a —$COOR_6$ or —$PO(OR_9)_2$ radical, it is possible to saponify the product obtained, in order to obtain a compound of formula (I) in which R represents or contains a carboxyl radical, or to convert, by means of a nucleophilic agent, the product obtained into a compound of formula (I) in which R represents or contains a —$PO_3H_2$ radical.

According to the invention, the novel compounds of formula (I) in which:
Y represents an oxygen or sulphur atom, and
X represents an NH group, can be obtained by reaction of an isocyanate or of an isothiocyanate of formula (V):

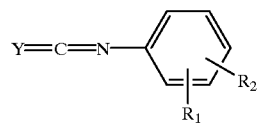

(V)

in which:
Y represents an oxygen or sulphur atom, and
$R_1$ and $R_2$ are defined according to any disclosed embodiment of the formula (I), with a compound of formula (III) as defined above.

The reaction of the compound of formula (V) with the compound of formula (III) is generally carried out in an inert organic solvent, such as tetrahydrofuran or toluene, in the presence of an activating agent, such as 4-dimethylaminopyridine or 4-pyrrolidinopyridine, at a temperature ranging from 0 to 50° C.

The reaction of a compound of formula (V) with a compound of formula (II) is optionally followed, when R represents or contains a —$COOR_6$ or —$PO(OR_9)_2$ radical in which $R_6$ or $R_9$ represent an alkyl radical, by the saponification of the product obtained, in order to obtain a compound of formula (I) in which R represents or contains a carboxyl radical, or by the conversion, by means of a nucleophilic agent, of the product obtained, in order to obtain a compound of formula (I) in which R represents or contains a —$PO_3H_2$ radical. The optional conversion of the —$COOR_6$ and $PO(OR_9)_2$ radicals respectively to carboxyl and $PO_3H_2$ radicals is carried out under the conditions described above.

According to the invention, the novel compounds of formula (I) in which:
R represents a radical of general formula

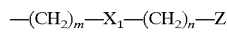

with $X_1$, m and n defined as above in any disclosed embodiment of the formula (I), and Z representing a —$COOR_6$ radical with $R_6$ representing a straight or branched alkyl radical containing 1 to 3 carbon atoms, can be obtained by esterification of a compound of formula (I) in which Z represents a carboxyl radical.

The esterification is generally carried out by means of an alcohol of general formula $R_6$—OH in which $R_6$ is defined as above, the reaction being carried out in acidic medium, or by means of an alkyl halide of general formula $R_6$—Hal in which Hal represents a halogen (iodine) atom, the reaction being carried out in alkaline medium (alkali metal or alkaline-earth metal carbonate, such as caesium carbonate), the reaction being carried out in an organic solvent, such as dimethylformamide, at a temperature ranging from 0 to 50° C.

According to the invention, the novel compounds of formula (I) in which:

R represents a radical of general formula

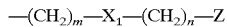

in which:

$X_1$, m and n are defined as above in any disclosed embodiment of the formula (I), and Z represents a —CON($R_7$)($R_8$) radical in which:

$R_7$ represents a hydrogen atom or a straight or branched alkyl radical containing 1 to 6 carbon atoms, and $R_8$ represents a hydrogen atom or a straight or branched alkyl radical containing 1 to 6 carbon atoms optionally substituted by an amino, alkylamino containing 1 to 4 carbon atoms, dialkylamino, wherein each alkyl portion contains 1 to 4 carbon atoms, alkyloxy, alkylthio, alkyloxycarbonyl, the alkyl portions and radicals containing 1 to 4 carbon atoms, carboxyl, cyano, phenyl optionally substituted by one or more identical or different radicals chosen from alkyloxy radicals containing 1 to 4 carbon atoms or trifluoromethyl radicals, 1- or 2-naphthyl, 2- or 3-furyl, 2- or 3-thienyl, 4- or 5-imidazolyl or 4- or 5-thiazolyl, or 2-, 3- or 4-pyridyl radical, or an indanyl or chromanyl radical, or alternatively $R_7$ represents a hydrogen atom or a straight or branched alkyl radical containing 1 to 6 carbon atoms, and $R_8$ represents a hydroxyl, amino, alkyloxy containing 1 to 6 straight- or branched-chain carbon atoms optionally substituted by a phenyl radical, alkylamino or dialkylamino, the alkyl portions of which contain 1 to 4 carbon atoms, or else preferably in which $R_7$ represents a hydrogen atom or a straight or branched alkyl radical containing 1 to 6 carbon atoms, and $R_8$ represents a hydrogen atom, a hydroxyl radical, an arylsulphonyl radical, such as phenylsulphonyl, optionally substituted by one or more atoms or radicals, which are identical or different, chosen from halogen atoms and alkyl and alkyloxy radicals, with these alkyl portions and radicals containing 1 to 4 carbon atoms, a 5- to 7-membered heterocycle incorporating one or more heteroatoms chosen from nitrogen, oxygen and sulphur atoms, it being possible for said heterocycle to be bonded via a heteroatom, an amino radical optionally substituted by one or two radicals, which are identical or different, chosen from the following radicals:

alkyl containing 1 to 4 carbon atoms, carbocyclic aryl, such as phenyl, optionally substituted by one or more radicals, which are identical or different, chosen from alkyl or alkyloxy radicals, with the alkyl portions and radicals containing 1 to 4 carbon atoms, 5- to 7-membered heterocyclyl containing one or more heteroatoms chosen from nitrogen, oxygen and sulphur atoms, arylcarbonyl, such as benzoyl, optionally substituted by one or more radicals, which are identical or different, chosen from alkyl or alkyloxy radicals with the alkyl portions and radicals containing 1 to 4 carbon atoms, an alkyloxy radical containing 1 to 6 straight- or branched-chain carbon atoms optionally substituted by a phenyl radical, a straight or branched alkyl radical containing 1 to 6 carbon atoms, such as methyl, optionally substituted by an amino, alkylamino, dialkylamino, hydroxyl, alkyloxy, mercapto, alkylthio, alkyloxycarbonyl, carboxyl or cyano radical, or by an optionally substituted mono- or polycyclic aromatic radical having from 5 to 12 ring members which may or may not incorporate one or more heteroatoms chosen from oxygen, nitrogen and sulphur atoms, it being possible for the said aromatic radical to be, in particular, the 2- or 3- or 4-pyridyl radical, preferably 3-pyridyl or 4-pyridyl, or the N-oxide of pyridine, or it also being possible for the said aromatic radical to be a phenyl radical optionally substituted by one or more halogen atoms or by one or more hydroxyl, amino or trifluoromethyl groups or by one or more alkyl, alkenyl, alkyloxy, alkylthio, alkylamino, alkylcarbonyl or $C_2$ to $C_4$ alkyloxycarbonyl, carbamoyl, alkylcarbamoyl or dialkylcarbamoyl, the alkyl portions and radicals thereof containing 1 to 8 carbon atoms, or formyl radicals, or alternatively said aromatic radical can be a 1- or 2-naphthyl radical, preferably, $R_7$ represents a hydrogen atom and $R_8$ represents a methyl radical substituted by the 3-pyridyl radical, can be obtained by reaction of a product of general formula:

in which $R_7$ and $R_8$ are defined as above, with a compound of formula (I) in which Z represents a carboxyl radical.

It is particularly advantageous:

either first to react oxalyl chloride with a compound of formula (I), in which R represents a carboxyl radical, in solution in dichloromethane, in order to form the acid chloride as an intermediate, and then to react the compound of general formula HN($R_7$)($R_8$), optionally in the presence of a base, such as triethylamine, or directly to react the compound of general formula HN($R_7$)($R_8$) with a compound of formula (I) in which R represents a carboxyl radical, in an organic solvent, such as an alcohol (ethanol) or a halogenated solvent, such as dichloromethane, in the presence of a coupling agent, such as N,N'-carbonyldiimidazole, 1,1-dicyclohexylcarbodiimide, 1-ethyl-3-[3-(dimethylamino)propyl]carbodiimide or benzotriazol-1-yloxytris(dimethylamino)phosphonium hexafluorophosphate, at a temperature ranging from 0 to 50° C.

When at least one of the $R_7$ and $R_8$ symbols is substituted by an amino radical, it is particularly advantageous to protect it by a protective group, such as a tert-butoxycarbonyl, benzyloxycarbonyl or benzyl radical, prior to the coupling of the amine of general formula $HN(R_7)(R_8)$ to the appropriate acid and then to replace the protective group by a hydrogen atom, for example by hydrogenolysis by means of hydrogen in the presence of a catalyst, such as palladium-on-charcoal, when it represents a benzyl or benzyloxycarbonyl radical, or by hydrolysis in acidic medium, when it represents a tert-butoxycarbonyl or benzyloxycarbonyl radical.

When at least one of the $R_7$ and $R_8$ symbols is substituted by a carboxyl radical, it is particularly advantageous to protect it by a protective group, such as an alkyl radical optionally substituted by a phenyl radical, such as the benzyl radical, prior to the coupling of the amine of general formula $HN(R_7)(R_8)$ to the appropriate acid and then to replace the protective group by a hydrogen atom, for example by hydrogenolysis by means of hydrogen in the presence of a catalyst, such as palladium-on-charcoal, or by saponification under the conditions described above.

When, in a compound of formula (I), $R_7$ represents a hydrogen atom or an alkyl radical containing 1 to 6 carbon atoms and $R_8$ represents an alkyloxy radical substituted by a phenyl radical, the replacement of the alkyloxy radical, substituted by a phenyl radical, by a hydroxyl radical, carried out:
  either by hydrogenolysis in the presence of a catalyst, such as palladium-on-charcoal,
  or by treatment with aluminium chloride in the presence of anisole in an organic solvent, such as nitromethane, at a temperature ranging from −20° C. to room temperature, when the alkyl radical substituted by a phenyl radical is a benzyl radical,
    makes it possible to obtain a compound of formula (I) in which $R_7$ represents a hydrogen atom or an alkyl radical containing 1 to 4 carbon atoms and $R_8$ represents a hydroxyl radical.

According to the invention, novel compounds of formula (I) in which:
R represents a radical of general formula:

—NHCO—T in which T represents a hydrogen atom or an alkyl radical (1 to 6 carbon atoms) optionally substituted by an amino, carboxyl, alkyloxycarbonyl, hydroxyl, alkyloxy, mercapto or alkylthio radical,
can be obtained by reaction of an acid of general formula:

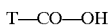
T—CO—OH in which T is defined as above,
with a compound of formula (VI):

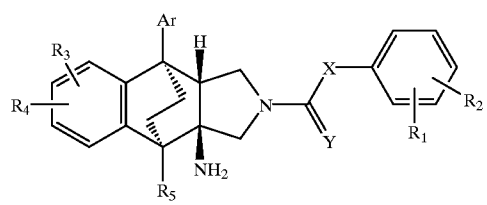

(VI)

in which:
Ar, $R_1$, $R_2$, $R_3$, $R_4$, $R_5$, X and Y are defined according to any disclosed embodiment of the formula (I).

The reaction of the acid of general formula T—CO—OH, in the acid form, with a compound of formula (VI) is generally carried out in an organic solvent, such as a halogenated aliphatic hydrocarbon, such as dichloromethane, in the presence of a coupling agent, such as 1-ethyl-3-[3-(dimethylamino)propyl]carbodiimide hydrochloride, 1,1-dicyclohexylcarbodiimide or benzotriazol-1-oxytris(dimethylamino)phosphonium hexafluorophosphate, optionally in the presence of an activating agent, such as hydroxybenzotriazole, at a temperature ranging from 0 to 50° C.

The reaction of the acid of general formula T—CO—OH, in the halide form, when T is other than a hydrogen atom, with the compound of formula (VI) is generally carried out in an organic solvent, such as a halogenated aliphatic hydrocarbon, such as dichloromethane, in the presence of a base (tertiary aliphatic amine) at a temperature ranging from 0 to 50° C.

The reaction of the acid of general formula T—CO—OH, in the anhydride form, with the compound of formula (VI) is generally carried out in an organic solvent, such as a halogenated aliphatic hydrocarbon, such as dichloromethane, in the presence of a base (tertiary aliphatic amine, pyridine or 4-dimethylaminopyridine) at a temperature ranging from 0 to 50° C.

The reaction of a compound T—CO—OH with a compound (VI) can optionally be followed by replacement of the protected ester functional groups or amine functional groups carried by T by carboxyl or amino radicals respectively, under the conditions described above.

When T is substituted by an amino radical, it is particularly advantageous to protect it by a protective group, such as a benzyloxycarbonyl or tert-butoxycarbonyl radical, prior to the coupling of the acid of general formula T—CO—OH to the appropriate amine and then to replace the protective group by a hydrogen atom, for example by hydrogenolysis by means of hydrogen in the presence of a catalyst, such as palladium-on-charcoal, or by hydrolysis in acidic medium.

When T is substituted by a carboxyl radical, it is particularly advantageous to protect it by a protective group, such as a methyl, ethyl or benzyl radical, prior to the coupling of the acid of general formula T—CO—OH to the appropriate amine and then to replace the protective group by a hydrogen atom, for example by hydrogenolysis by means of hydrogen in the presence of a catalyst, such as palladium-on-charcoal, or by saponification under the conditions described above.

According to the invention, the novel compound of formula (I) in which: R represents a radical of general formula

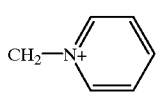

wherein the radical has an anion as a counterion, can be obtained by reaction of an excess of pyridine and of a strong acid or of a derivative of this acid with a compound of formula (VII):

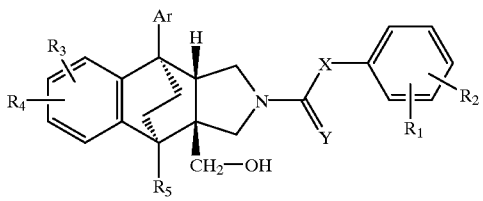

(VII)

in which Ar, $R_1$, $R_2$, $R_3$, $R_4$, $R_5$, X and Y are defined according to any disclosed embodiment of the formula (I).

The strong acid is preferably trifluoromethanesulphonic acid, optionally in the presence of trifluoromethanesulphonic anhydride.

According to the invention, the novel compounds of formula (I) in which Y represents a sulphur atom can be obtained by thionation of a compound of formula (I) in which Y represents an oxygen atom.

The thionation is generally carried out under the usual conditions by means of phosphorus pentasulphide, the reaction being carried out in an organic solvent, such as tetrahydrofuran, at a temperature ranging from 0 to 50° C.

According to the invention, the compounds of formula (I) in which one of the $R_1$ or $R_2$ symbols represents an alkylcarbonyloxy radical can be obtained by acylation of a compound of formula (I) in which one of the $R_1$ or $R_2$ symbols represents a hydroxyl radical by means of an aliphatic acid or of a derivative of this acid, such as a halide or the anhydride, under the usual esterification conditions.

As regards the intermediates described above, operating protocols and compounds useful in obtaining them are also provided hereinbelow.

Conventionally, the compounds of formula (III) in which R represents a carboxyl radical or a radical of general formula $COOR_6$ can be obtained by the action of trifluoromethanesulphonic acid on a product of general formula (VIII):

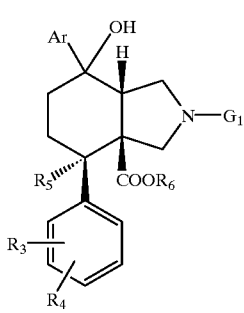

(VIII)

in which:
Ar, $R_3$, $R_4$ and $R_5$ are defined as in any disclosed embodiment of the formula (I),
$G_1$ represents a protective group, preferably a benzyl radical, and
$R_6$ represents an alkyl radical containing 1 to 3 carbon atoms, followed by replacement of the $G_1$ group by a hydrogen atom:
 either by hydrogenolysis under the conditions described above, then, optionally, depending on the situation, by replacement of the hydrogen atom by a tert-butoxycarbonyl radical, by reaction with tert-butoxycarbonyl anhydride in an organic solvent, or by a benzy.oxycarbonyl radical, by reaction by benzyloxycarbonyl chloride in an organic solvent,
 or by reaction with an alkyl chloroformate, such as vinyl chloroformate or ethyl chloroformate or 2-chloroethyl chloroformate or 2,2,2-trichloroethyl chloroformate, in an organic solvent, such as dichloromethane, at a temperature ranging from 0° C. to room temperature, followed by acid hydrolysis of the intermediate carbamate formed, generally using a 1 to 6M aqueous hydrochloric acid solution, optionally in an organic solvent, such as an alcohol, for example methanol or ethanol, or an ether, for example tetrahydrofuran or dioxane.

The intramolecular cyclization of Friedel-Crafts type of a compound of formula (VIII) to a compound of formula (III) can generally be carried out by the action of an excess, from 3 to 15 molar equivalents, of a strong acid, such as trifluoromethanesulphonic acid, optionally in the presence of trifluoromethanesulphonic anhydride as a catalytic amount or optionally added as successive additions, the reaction being carried out in an organic solvent, such as dichloromethane, at a temperature ranging from 0° C. to the reflux temperature, for a few minutes to several days. It is also possible to carry out the intramolecular cyclization of Friedel-Crafts type by the action of a Lewis acid, such as aluminium chloride or titanium tetrachloride or boron trifluoride, optionally in the form of a complex with diethyl ether, in an organic solvent, such as dichloromethane or nitromethane or nitrobenzene.

This reaction can optionally be followed by saponification of the product obtained and optionally followed, depending on the situation, by replacement of the benzyl radical by a hydrogen atom.

A compound of formula (VIII) can be obtained, for its part, conventionally by reaction of an organomagnesium derivative of general formula Ar—Mg—X, in which Ar is defined as above and X represents a halogen atom, or of an organolithium derivative of general formula Ar—Li, in which Ar is defined as above, with a compound of formula (IX):

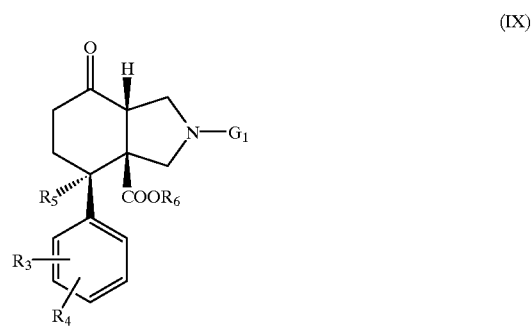

(IX)

in which $R_3$, $R_4$, and $R_5$ are defined as in any disclosed embodiment of the formula (I) and $R_6$ and $G_1$ are defined as in formula (VIII) above, under the usual conditions.

The reaction of an arylmagnesium derivative, obtained conventionally and optionally in the presence of anhydrous cerium(III) chloride under the conditions described by Imamoto (Tetrahedron Lett., 1985, p. 4763), with the ketone derivative of general formula (IX) is generally carried out in an organic solvent, such as diethyl ether or tetrahydrofuran, the reaction being carried out at a temperature ranging from 0° C. to the reflux temperature of the reaction mixture from a few minutes to 24 hours. However, it has been found to be particularly advantageous to carry out the reaction in toluene, optionally as a mixture with diethyl ether or tetrahydrofuran.

The reaction of an aryllithium derivative, obtained conventionally, with the ketone derivative of formula (IX) is generally carried out in an organic solvent, such as diethyl ether or tetrahydrofuran, the reaction being carried out at a temperature ranging from −78° to −20° C. for a few minutes to 4 hours. However, it has been found to be particularly advantageous to carry out the reaction in toluene, optionally as a mixture with diethyl ether or tetrahydrofuran.

Advantageously, a preparation process has been developed, in the context of the present invention, which makes it possible to obtain the compounds of formula (III) from compounds of formula (IX) via the formation of a stable and characterizable intermediate of formula (XV) characterized by the presence of an arylethylene functional group at the 7 position.

More specifically, the compounds of formula (III):

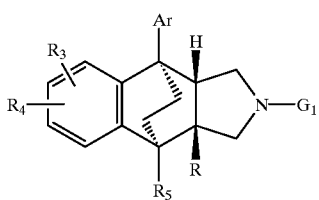

(III)

in which $R_3$, $R_4$, $R_5$, Ar and R are as defined in any disclosed embodiment of the formula (I) and $G_1$ represents a protective group, preferably a benzyl radical, can be obtained from compounds of formula (IX) in the racemic form or in the form of optical isomers, preferably in the form of a single enantiomer:

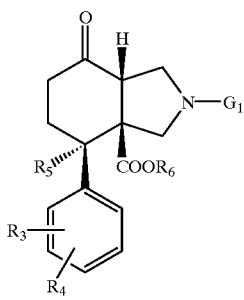

(IX)

in which $R_3$, $R_4$, and $R_5$ are as defined in any disclosed embodiment of the formula (I) and $R_6$ and $G_1$ are as defined above in formula (VIII), via the formation of an intermediate of formula (XV):

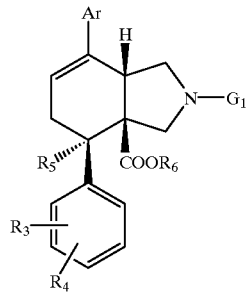

(XV)

in which $R_3$, $R_4$, $R_5$, $R_6$, and Ar are as defined in any disclosed embodiment of the formula (I) and $G_1$ is as defined above in formula (VIII).

The operating protocol developed successively involves:
  either the condensation, at the 7 position, of a ketone derivative of formula (IX) with hydrazine, to result in a hydrazone, followed by reaction with iodine to result, according to the Barton reaction (J. Chem. Soc., 1962, p. 470), in an iodoethylene derivative; followed by a palladium coupling reaction with an arylboronic acid, the Suzuki reaction (Tetrahedron Lett., 1979, p. 3437), the disclosure of which is specifically incorporated herein by reference, of general formula Ar—B(OH)$_2$ or optionally with the trimeric anhydride of arylboronic acid, in which Ar is defined as above, or with an arylstannane, the Stille reaction (Angew. Chem. Int. Ed. Engl., 1986, p. 508), the disclosure of which is specifically incorporated herein by reference, of general formula Ar—SnMe$_3$ in which Ar is defined as above, in order to result in this arylethylene intermediate of formula (XV), the conversion of which by intramolecular cyclization of Friedel-Crafts type results in the expected compound (III),
  or the reaction of a ketone derivative of formula (IX) with trifluoromethanesulphonic anhydride, in order to result in an enol triflate at the 7 position (Org. Synth., 1990, p. 116); followed by a palladium coupling reaction with an arylboronic acid, the Suzuki reaction (Tetrahedron Lett., 1979, p. 3437), of general formula Ar—B(OH)$_2$ in which Ar is defined as above, or with an arylstannane, the Stille reaction (Angew. Chem. Int. Ed. Engl., 1986, p. 508), of general formula Ar—SnMe$_3$ in which Ar is defined as above, in order to result in this arylethylene intermediate of formula (XV), the conversion of which by intramolecular cyclization of Friedel-Crafts type results in the expected compound (III).

The ketone derivative of formula (IX) is generally treated with an excess of hydrazine hydrate, from 3 to 20 molar equivalents, at reflux in a solvent, such as ethanol, from a few minutes to a few hours. The hydrazone thus obtained is then stirred with an excess of iodine, in the presence of an aliphatic tertiary amine, such as triethylamine, at a temperature in the region of 20° C. for a few hours in order to result in an iodoethylene derivative.

The ketone derivative of formula (IX) is generally treated:
  either with trifluoromethanesulphonic anhydride in the presence of an organic base, such as 2,6-di-tert-butyl-4-methylpyridine, in an organic solvent, such as dichloromethane, at a temperature in the region of room temperature for a few hours, according to Stang (Synthesis, 1980, p. 283), or with a bis(trifluoromethylsulphonyl)amide, such as N,N-bis(trifluorosulphonyl)aniline, according to Mac-Murry (Tetrahedron Lett., 1983, p. 979), or 2-[N,N-bis (trifluorosulphonyl)amino]pyridine, according to Comins (Tetrahedron Lett., 1992, p. 979), in the presence of a base, such as lithium diisopropylamide, in an organic solvent, such as dichloromethane or 1,2-dimethoxyethane, in order to result in an enol triflate.

The coupling between the iodoethylene derivative or the enol triflate obtained above and an arylboronic acid obtained conventionally and optionally isolated in the trimeric anhydride form is generally carried out by stirring in a two-phase system composed of an organic solvent, preferably a mixture of toluene and methanol, and of a basic aqueous solution, preferably a 2N sodium carbonate solution, in the presence of a catalytic amount of palladium(0) derivative, preferably tetrakis(triphenylphosphine)palladium, at a temperature in the region of the reflux temperature for a few hours, in order to result in the arylethylene compound of formula (XV).

The coupling between the iodoethylene derivative or the enol triflate obtained above with an arylstannane obtained conventionally is generally carried out by stirring in a polar aprotic organic solvent, preferably dimethylformamide or N-methylpyrrolidone, in the presence of a catalytic amount of palladium(0) derivative, preferably tetrakis (triphenylphosphine)palladium, at a temperature ranging from 50° to 100° C. for a few hours, in order to result in the arylethylene compound of formula (XV).

The intramolecular cyclization of Friedel-Crafts type of the compound of formula (XV) to the product of formula (III) is generally carried out under the conditions described above for the intramolecular cyclization of the products of formula (VIII).

Advantageously, a second preparation process has additionally been developed, in the context of the present invention, which makes it possible to obtain the compounds of formula (III) as defined above from the compounds of formula (IX) via the formation of the intermediate of formula (XV), which can optionally be isolated. This second process is very particularly advantageous when the aryl radical Ar represents a phenyl nucleus substituted, at the para or meta-para or meta-para-meta positions, by electron-donating groups or a heterocyclic radical which is naturally rich in electrons or a heterocyclic radical suitably substituted by electron-donating groups. This second process includes directly reacting, according to tandem intermolecular and then intramolecular cyclization reactions of Friedel-Crafts type, an aromatic or heterocyclic hydrocarbon Ar—H with a compound of formula (IX) in an organic solvent in the presence of an excess of strong acid, such as trifluoromethanesulphonic acid, or optionally of a Lewis acid, such as aluminium chloride.

The procedure developed includes condensing the product of formula (IX) with an excess of trifluoromethanesulphonic acid (from 5 to 20 molar equivalents) in an organic solvent, such as dichloromethane, at a temperature in the region of room temperature, for a few hours to several days. According to the number of molar equivalents in the concentration of trifluoromethanesulphonic acid, as well as the nature of the Ar radical and of the substituents which it carries, this reaction results either directly in the compounds of formula (III) or in the compounds of formula (XV) as intermediates, which are then cyclized as described above to compounds of formula (III).

In addition, the compounds of formula (I) or (III) can be obtained by functionalization of the substituents of the aromatic ring Ar of the corresponding compounds of formula (I) or (III), by application or adaptation of the known methods for standard functionalizations, such as, and without implied limitation: functional substitution reactions (for example the replacement of a halogen atom by a cyano group by a palladium coupling), dealkylation reactions (for example by $BBr_3$) or alkylation reactions (in particular alkylation/cyclization reactions by the action of $BBr_2$).

Another subject of the present invention relates to these compounds of formula (XV):

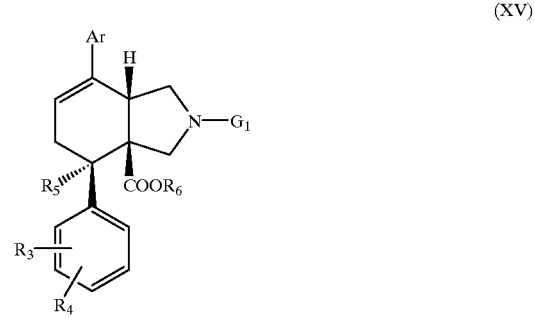

(XV)

in which $R_3$, $R_4$, $R_5$ and Ar are as defined in any disclosed embodiment of the formula (I), $G_1$ represents a protective group, preferably a benzyl radical, and $R_6$ represents an alkyl radical containing 1 to 3 carbon atoms, in the racemic form, and in the form of their optical isomers, and preferably in the form of a single enantiomer.

The compounds of formula (IX) in which $R_3$, $R_4$, $R_5$, $R_6$ and Ar are as defined in any disclosed embodiment of the formula (I) and $G_1$ represents a protective group, preferably a benzyl radical, can be obtained by reaction of an N-trialkylsilylmethyl-N-(alkyloxy-methyl)amine carrying a protective group for the amine functional group, such as a benzyl radical, for example N-trimethylsilylmethyl-N-(n-butoxymethyl)benzylamine, which can be prepared under the conditions described in Chem. Pharm. Bull., 276 (1985), with a cyclohexenone derivative of formula (X):

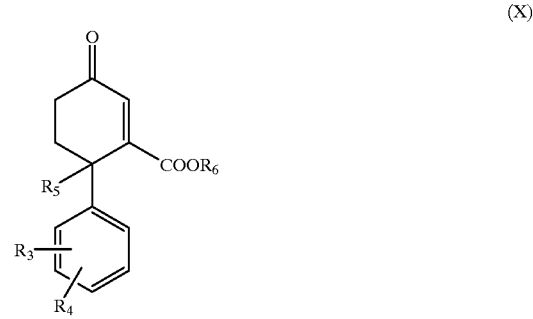

(X)

in which $R_3$, $R_4$, and $R_5$ are as defined in any disclosed embodiment of the formula (I) and $R_6$ is as defined above in formula (VIII).

The reaction is generally carried out in an organic solvent, such as a halogenated aliphatic hydrocarbon, for example dichloromethane, in the presence of a strong acid, such as trifluoroacetic acid, at a temperature ranging from 0° C. to the reflux temperature of the reaction mixture.

Compounds of formula (IX) in the racemic form can be obtained from compounds of formula (X) in the racemic form, and compounds of formula (IX) in the form of a single enantiomer, as defined herein, can be obtained from the isomeric forms of compounds of formula (X'):

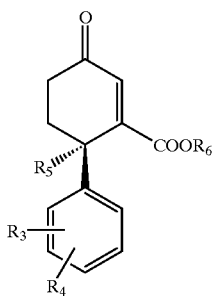

in which $R_3$, $R_4$, $R_5$ and $R_6$ are defined as above in formula (X), and preferably, $R_3$, $R_4$, and $R_5$ are hydrogen.

In practicing this particular process, it is understood that the further steps of the process described hereabove and hereafter remain the same, and can be conducted in the same way on either the racemic mixtures or the single enantiomer of the compounds, when starting from (X') in the form of a single enantiomer.

A single enantiomer, as defined herein, of the compounds of formula (X') can be obtained from compounds of formula (X) in the following manner: the separation of a single enantiomer of the compounds of formula (X') can be performed starting from compounds of formula (X) in racemic form, preferably by enzymatic splitting. Advantageously, it has been discovered that enantioselective resolution can be achieved by means of an enantioselective enzymatic reaction. It is preferable to use enzymes allowing for the separation of an enantiomer of formula (X') in the desired isomeric form, e.g. dextrorotatory, from the enantiomer in the other isomeric form or their derivatives, i.e. levorotatory. Preferably, it has been discovered that enzymatic resolution can be achieved according to the following reaction, producing the isomer forms as drawn hereafter or their respective enantiomer forms:

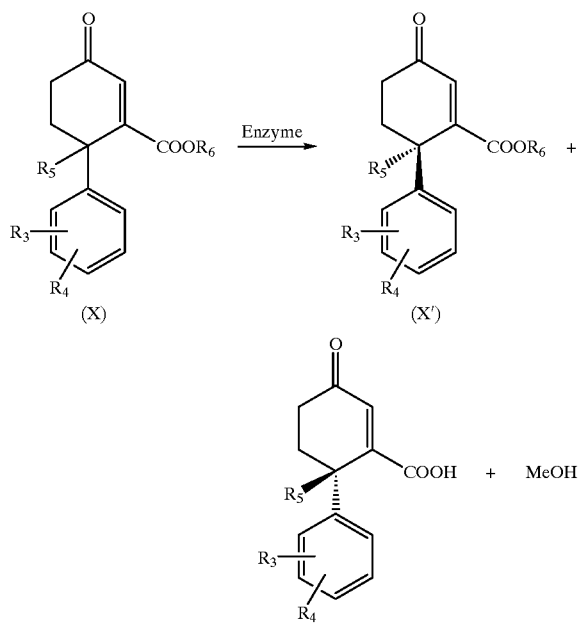

in which $R_3$, $R_4$, $R_5$ and $R_6$ are defined as above in formula (X).

More preferably, it has been discovered that the enzyme "Lipase L2" can achieve the reaction leading to compounds of formula (X') in the isomer form as drawn above, which leads to the dextrorotatory form of compounds of formula (I) according to the invention. The reaction by "Lipase L2" (commercially available as Chirazyme L2) can be conducted in the conditions described in Example X (described below as part of Example 1).

The products of formula (X) can be obtained by esterification of 3-oxo-6-phenylcyclohex-1-ene-1-carboxylic acids, in which $R_3$, $R_4$ and $R_5$ are defined as above in formula (X), by means of an aliphatic alcohol containing 1 to 3 carbon atoms, in the presence of an inorganic base, such as hydrochloric acid or sulphuric acid, at a temperature ranging from 0° C. to the reflux temperature of the reaction mixture, or by means of an alkyl halide (iodide), in the presence of an organic base, such as 1,8-diazabicyclo[5.4.0]undec-7-ene, or an inorganic base, such as caesium carbonate, the reaction being carried out in a solvent chosen from tetrahydrofuran, dimethylformamide, acetone or dioxane. 3-Oxo-6-phenylcyclohex-1-ene-1-carboxylic acids, in which $R_3$, $R_4$ and $R_5$ are defined as above in formula (X), can be obtained from 1-hydroxy-3-oxo-6-phenylcyclohexane-1-carboxylic acids, in which $R_3$, $R_4$ and $R_5$ are defined as above in formula (X), either by thermal dehydration, by heating at a temperature in the region of 190° C. (according to J. Org. Chem., 1971, p. 3707) or by heating in refluxing toluene in the presence of p-toluenesulphonic acid, or by reacting with an inorganic base, such as sodium hydroxide, at a temperature ranging from 0 to 50° C.

1-Hydroxy-3-oxo-6-phenylcyclohexane-1-carboxylic acids, in which $R_3$, $R_4$ and $R_5$ are defined as above in formula (X), can be obtained by reaction of phenylpyruvic acids, or optionally of the corresponding esters, more particularly in the case where $R_5$ does not represent a hydrogen atom, the phenyl nucleus of which is optionally substituted by substituents defined by $R_3$ and $R_4$ as in formula (X), with methyl vinyl ketone, the reaction generally being carried out in aqueous/alcoholic medium, such as a methanol/water mixture, in the presence of an inorganic base, such as sodium hydroxide (according to J. Org. Chem., 1971, 3707).

Phenylpyruvic acids, the phenyl nucleus of which is optionally substituted by substituents defined by $R_3$ and $R_4$ as in formula (X), can be obtained, more particularly in the case where $R_5$ represents a hydrogen atom, either by hydrolysis of the corresponding α-acetamidocinnamic acids, by heating in hydrochloric acid, according to Org. Synth., 1943, p. 519, or by hydrolysis of the corresponding benzalhydantoins, by heating in 20% sodium hydroxide solution, according to Org. Synth. Coll. Vol. V, p. 627.

α-Acetamidocinnamic acids, the phenyl nucleus of which is optionally substituted by substituents defined by $R_3$ and $R_4$ as in formula (X), can be obtained, from the corresponding benzaldehydes according to Org. Synth., 1939, p. 1, by reaction with N-acetylglycine in refluxing acetic anhydride in the presence of sodium acetate. The intermediate azlactones thus obtained are then hydrolysed to α-acetamidocinnamic acids by heating at reflux in aqueous acetone.

Benzalhydantoins, the phenyl nucleus of which is optionally substituted by substituents defined by $R_3$ and $R_4$ as in formula (X), can be obtained by heating the corresponding benzaldehydes, according to Org. Synth. Coll. Vol. V, p. 267, with hydantoin in the presence of an organic base, such as piperidine, at a temperature in the region of 130° C.

Phenylpyruvates, the phenyl nucleus of which is optionally substituted by substituents defined by $R_3$ and $R_4$ as in formula (X), can be obtained, more particularly in the case where $R_5$ does not represent a hydrogen atom but an alkyl or alkylthio radical, from 2-phenylalkanoic acids, the phenyl nucleus of which is optionally substituted by substituents defined by $R_3$ and $R_4$, by reaction of the corresponding dianion, generally obtained by reaction of an organic base, such as n-butyllithium, with the acid, with ethyl oxalate at a temperature in the region of −70° C., followed by decarboxylation, the reaction being carried out under the conditions described in Tetrahedron Lett., 1981, 2439–42.

The compounds of formula (III):

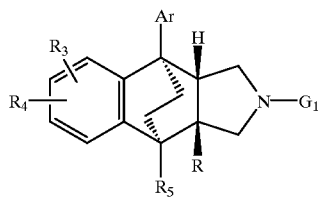

(III)

in which R represents a radical

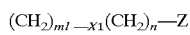

in which:

m is equal to 0, $X_1$ represents a bond, n is equal to 0, and

Z represents a —$COOR_6$ or —$CON(R_7)(R_8)$ radical, wherein $R_6$, $R_7$, and $R_8$, which are all part of Z, are defined as in any disclosed embodiment of the formula (I), can be obtained from a compound of formula (VIII), in which R represents a carboxyl radical, by esterification and amidation under the conditions described above, followed by cyclization by the action of trifluoromethanesulphonic acid under the conditions described above.

The compounds of formula (III) in which R represents a radical

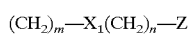

in which:

m is equal to 1, $X_1$ represents a bond, n is equal to 0, and

Z represents a —$COOR_6$, —$CON(R_7)(R_8)$ or $PO(OR_9)_2$ radical, wherein $R_6$, $R_7$, $R_8$, and $R_9$, which are all part of Z, are defined as in any disclosed embodiment of the formula (I), can be obtained from a compound of formula (XI):

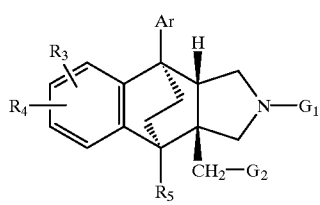

(XI)

in which Ar, $R_3$, $R_4$ and R are defined as in any disclosed embodiment of the formula (I), $G_1$ represents a protective group for the amine functional group (such as benzyl, benzyloxycarbonyl or tert-butoxycarbonyl) and $G_2$ represents a leaving group, such as a trifluoromethylsulphonyloxy radical.

More particularly, in order to obtain a compound of formula (III) in which R represents a radical

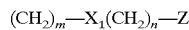

in which:

m is equal to 1, $X_1$ represents a bond, n is equal to 0, and

Z represents a carboxyl, —$COOR_6$, in which $R_6$ represents an alkyl radical, or —$CON(R_7)(R_8)$ radical, wherein $R_7$, and $R_8$, which are both part of Z, are defined as in any disclosed embodiment of the formula (I), it is particularly advantageous to use the corresponding nitrile as an intermediate, which nitrile can be obtained by reaction of an alkali metal cyanide with the compound of formula (XI), the reaction being carried out in a polar organic solvent, such as dimethyl sulphoxide, at a temperature ranging from 0 to 50° C., which nitrile is hydrolysed to the corresponding acid, which can then be esterified or amidated under the usual conditions.

More particularly, in order to obtain a compound of formula (III) in which R represents a radical

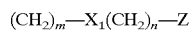

in which:

m is equal to 1, $X_1$ represents a bond, n is equal to 0, and

Z represents a —$PO(OR_9)_2$ radical, wherein $R_9$, which is part of Z, is defined as in any disclosed embodiment of the formula (I), it is particularly advantageous to react a trialkyl phosphite with a compound of formula (XI) and then, optionally, to convert the phosphonate obtained to the corresponding phosphonic acid.

The compounds of formula (III)

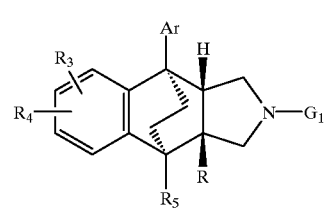

(III)

in which:

R represents a $(CH_2)_m$—$X_1$—$(CH_2)_n$—Z radical with m equal to 1, $X_1$ representing an oxygen or sulphur atom, n equal to 1 or 2 and Z representing a carboxyl, —$COOR_6$, in which $R_6$ represents an alkyl radical, or —$CON(R_7)(R_8)$ radical wherein $R_7$ and $R_8$, which are both part of Z, are defined as in any disclosed embodiment of the formula (I), and $G_1$ represents a protective group for the amine functional group can be obtained by reaction of an ester or of an amide of general formula:

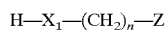

in which $X_1$, n and Z are defined as in any disclosed embodiment of the formula (I) with a compound of formula (XI), the reaction being carried out in an anhydrous organic solvent, such as dioxane, in the presence of an alkali metal hydride, such as sodium hydride, optionally followed, depending on the situation, by saponification of the compound of formula (III) thus obtained.

The compounds of formula (III) in which:

m is equal to 1, $X_1$ represents a bond, n is equal to 1, with it being possible for the methylene group to be substituted by a carboxyl or alkyloxycarbonyl or carbamoyl or alkylcarbamoyl or dialkylcarbamoyl radical, $G_1$ represents a protective group for the amine functional group, and Z represents a carboxyl, —$COOR_6$, in which $R_6$ represents an alkyl radical, or —$CON(R_7)(R_8)$ radical, wherein $R_7$ and $R_8$, which are both part of Z, are defined as in any disclosed embodiment of the formula (I), can be obtained by reaction of a malonic acid, anionized beforehand, or of a malonic acid derivative, preferably a diester, with a compound of formula (XI), the reaction being carried out in an anhydrous organic solvent, such as dioxane, in the presence of an alkali metal hydride, such as sodium hydride, at a temperature ranging from 0° C. to the reflux temperature of the reaction mixture, followed, depending on the situation, by saponification, esterification, amidation or decarboxylation of a compound of formula (III) thus obtained.

The compounds of formula (III) in which:

R represents an —NH—CO—T radical in which T is defined as above can be obtained by amidation of a compound of formula (III) in which:

$R_3$ is defined as above, $G_1$ represents a protective group of the amine functional group and R represents an amino radical by means of an acid of general formula T—CO—OH in which T is defined as above, under the conditions described above for the amidation of a compound of formula (VI).

The compounds of formula (III) in which R represents an amino radical or the compounds of formula (VI) can be obtained according to the methods which make it possible to convert a carboxyl radical to an amino radical without affecting the remainder of the molecule.

The carboxyl functional group of a compound of formula (III) or (I) is generally converted to the amino radical via an isocyanate which can be obtained by pyrolysis of the acid azide, which can itself be obtained by reaction of an alkali metal azide with the corresponding acid halide. The intermediate isocyanate thus obtained is conventionally condensed with benzyl alcohol and then the benzyl carbamate obtained is converted to the amino radical, either by hydrogenolysis or by acid hydrolysis under the conditions described above.

The compounds of formula (III) in which R represents

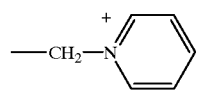

radical can be obtained by reaction of pyridine and of a strong acid or of a derivative of this acid with a compound of formula (XII):

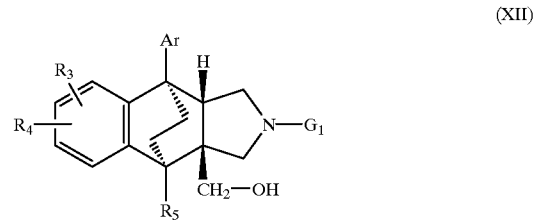

(XII)

in which Ar, $R_3$, $R_4$ and $R_5$ are defined as in any disclosed embodiment of the formula (I) and $G_1$ represents a protective group for the amine functional group.

The compounds of formula (VII) or of formula (XII) can be obtained respectively by reduction of a compound of formula (I) or of a compound of formula (III) in which R represents a radical of general formula —$COOR_6$ in which $R_6$ preferably represents an alkyl radical containing 1 to 3 carbon atoms.

The reduction is generally carried out by means of a lithium aluminium hydride, the reaction being carried out in an organic solvent, such as an ether, for example tetrahydrofuran, at a temperature ranging from 0 to 50° C.

According to the invention, the compounds of formula (I), in which Ar, $R_1$, $R_2$, $R_3$, $R_4$, $R_5$, X and Y are defined as in any disclosed embodiment of the formula (I) and R represents a $COOR_6$ radical in which $R_6$ is defined as above in formula (VIII), can also be obtained from a compound of formula (IX) in which $R_3$, $R_4$, $R_5$ and $R_6$ are defined as in this paragraph and $G_1$ represents a hydrogen atom.

According to the invention, the compound of formula (IX):

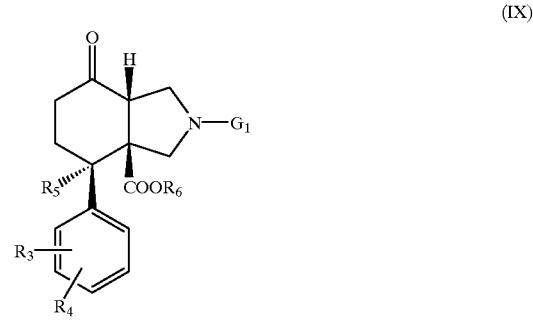

(IX)

in which $G_1$ represents a hydrogen atom, is obtained from a compound of formula (IX), in which $G_1$ represents a protective group for the amino functional group, under the conditions described above for the preparation of a compound of formula (III) in which $G_1$ represents a hydrogen atom.

The compound of formula (IX) in which $G_1$ represents a hydrogen atom is converted to a compound of formula (XIII):

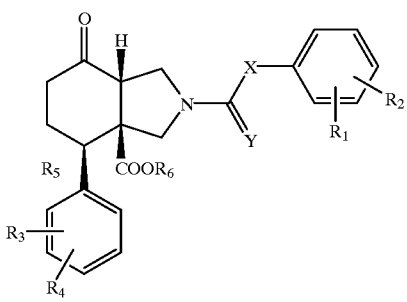

(XIII)

in which $R_1$, $R_2$, $R_3$, $R_4$, $R_5$, and X and Y are defined as in any disclosed embodiment of the formula (I) and $R_6$ is as defined in formula (VIII), the reaction being carried out, depending on the meanings of X and Y, in the following way:

- the compounds of formula (XIII), in which Y represents an oxygen or sulphur atom and X represents a —CO—, methylene, vinyidiyl, alkene-1,1-diyl or cycloalkane-1,1-diyl group, can be obtained by reaction of an acid of formula (II) or of its chloride or of its anhydride with a compound of formula (IX) in which $G_1$ represents a hydrogen atom, the reaction being carried out under the conditions described above for the reaction of a compound of formula (II) with a compound of formula (III) in which $G_1$ represents a hydrogen atom,
- the compounds of formula (XIII), in which Y represents an oxygen or sulphur atom and X represents an oxygen atom, can be obtained by reaction of a haloformate or of a halothioformate of formula (IV) with a compound of formula (IX) in which $G_1$ represents a hydrogen atom, the reaction being carried out under the conditions described above for the reaction of a compound of formula (IV) with a compound of formula (III) in which $G_1$ represents a hydrogen atom,
- the compounds of formula (XIII), in which Y represents an oxygen or sulphur atom and X represents an NH group, can be obtained by reaction of an isocyanate or of an isothiocyanate of formula (V) with a compound of formula (IX) in which G, represents a hydrogen atom, the reaction being carried out under the conditions described above for the reaction of a compound of formula (V) with a compound of formula (III) in which $G_1$ represents a hydrogen atom.

The compound of formula (XIII) is converted to a compound of formula (XIV):

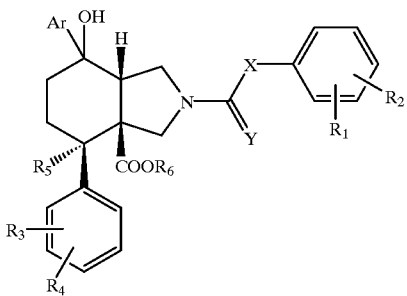

(XIV)

which Ar, $R_1$, $R_2$, $R_3$, $R_4$, $R_5$, and X and Y are defined as in any disclosed embodiment of the formula (I) and $R_6$ is as defined in formula (VIII), by reaction of a metallic derivative of general formula Ar—Mg—X or Ar—Li, in which X represents a halogen atom, with a compound of formula (XIII), the reaction being carried out under the conditions described above for the reaction of an organomagnesium or organolithium derivative of general formula Ar—Mg—X or Ar—Li with a compound of formula (IX).

The compound of formula (XIV) is converted to the compound of formula (I), in which Ar, $R_1$, $R_2$, $R_3$, $R_4$, $R_5$, $R_6$, X and Y are defined as in the preceding paragraph, by the action of trifluoromethanesulphonic acid or of a Lewis acid on the compound of formula (XIV), the reaction being carried out under the conditions described above for the action of trifluoromethanesulphonic acid or of a Lewis acid on a compound of formula (VIII).

The reaction of an aromatic hydrocarbon or of an aromatic heterocycle Ar—H, as defined above, in the presence of trifluoromethanesulphonic acid or of a Lewis acid, with a compound of formula (XIII), in which $R_1$, $R_2$, $R_3$, $R_4$, $R_5$, $R_6$, X and Y are defined as in the preceding paragraph, results in a compound of formula (I) in which Ar is defined as above and R represents a $COOR_6$ radical in which $R_6$ represents an alkyl radical containing 1 to 3 carbon atoms.

According to the invention, the compounds of formula (I) in which:

Ar, $R_1$, $R_2$, $R_3$, $R_4$, $R_5$, X and Y are defined as in any disclosed embodiment of the formula (I), and R represents a radical

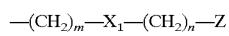

in which m, n, $X_1$ and Z are defined as in any disclosed embodiment of the formula (I), can also be prepared from a compound of formula (VII) under the conditions described above for the preparation of the compounds of formula (III) from a compound of formula (XI), after replacement of the hydroxyl radical of the compound of formula (VII) by a leaving group, such as a trifluoromethanesulphonyloxy radical.

The reaction mixtures obtained by the various processes described above are treated according to conventional physical methods (evaporation, extraction, distillation, chromatography, crystallization, for example) or conventional chemical methods (formation of salts, for example).

The compounds of formula (I) can optionally be converted into addition salts with an inorganic or organic acid by the action of such an acid in an organic solvent, such as an alcohol, a ketone, an ether or a chlorinated solvent. These salts also form part of the invention.

The single enantiomers, i.e., the dextrorotatory and/or levorotatory enantiomers of the compounds of formula (I) can be obtained according to the usual separation methods from the corresponding racemic product or can preferably be obtained by enzymatic splitting of compounds of formula (X) as described above. The separation can be carried out by high performance liquid phase chromatography using a chiral stationary phase of modified Pirkle type, elution being carried out with a suitable solvent.

Use may be made, as chiral stationary phase, of a phase in which the chiral selector, which is preferably 3,5-dinitrophenylalanine, is kept at a distance from the silica by an aminoalkyl arm containing 3 to 14 carbon atoms attached to the amine functional groups of an aminopropyl silica, the free silanol functional groups of which are blocked by trialkylsilyl radicals.

This chiral phase may be defined by the following structure:

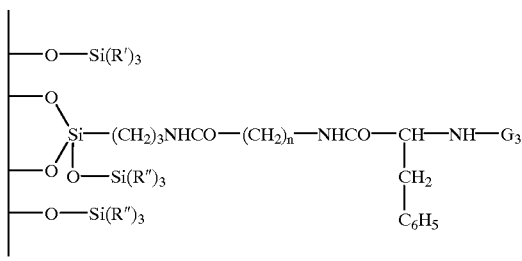

in which the R' symbols, which are identical or different, and the R" symbols, which are identical or different, represent alkyl radicals containing 1 to 10 carbon atoms, $G_3$ represents an electron-withdrawing group and n represents an integer from 3 to 13 inclusive, the porosity of which is in the region of 100 Å.

The chiral phase can be prepared by reaction of an aminopropyl silica with the anhydride of an aminoalkanoic acid containing 4 to 14 carbon atoms, the amine functional group of which is protected by a protective group, such as the tert-butoxycarbonyl radical, followed by blocking a part of the silanol functional groups by $Si(R')_3$ radicals as defined above, then, after removal of the protective groups for the amine functional group, by amidation by means of an amino acid of general formula:

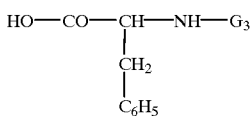

in which $G_3$ is defined as above, and finally blocking of the residual silanol functional groups by $Si(R")_3$ radicals as defined above.

Generally, the reaction of the anhydride of a protected aminoalkanoic acid with the aminopropyl silica is carried out in an anhydrous organic solvent, such as dimethylformamide, at a temperature in the region of 20° C.

Blocking of the silanol functional groups by $—Si(R'_3)$ groups as defined above is carried out by reaction of a halotrialkylsilane with the aminopropyl silica, which has been grafted by aminoalkanoyl residues, in an organic solvent, such as methylene chloride, in the presence of a basic agent, such as pyridine.

Removal of the protective groups from the aminoalkanoyl residues is generally carried out, when the protective group is a tert-butoxycarbonyl radical, by the action of trifluoroacetic acid in an organic solvent, such as methylene chloride.

Amidation by means of phenylalanine in which the amine functional group is protected is carried out in the presence of a coupling agent, such as N-ethoxycarbonyl-2-ethoxy-1,2-dihydroquinoline, in an anhydrous organic solvent, such as dimethylformamide.

Blocking the residual silanol functional groups by —Si (R")_3 radicals as defined above is generally carried out by means of trialkylsilylimidazole in an organic solvent, such as methylene chloride.

The aminopropyl silica can be prepared by reaction of aminopropyltriethoxysilane with a silica in which the porosity is in the region of 100 Å in the presence of imidazole in an anhydrous organic solvent, such as an aromatic hydrocarbon, for example toluene.

As shown in the examples below, the novel compounds of formula (I), which inhibit farnesyl transferase and the farnesylation of the Ras protein, exhibit notable antitumour and antileukaemic properties.

Another subject of the present invention is any pharmaceutical composition containing at least one compound of formula (I) or a salt thereof in combination with one or more pharmaceutically acceptable carriers. As used herein, carrier includes any acceptable diluent or adjuvant, whether inert or biologically active.

The novel compounds of formula (I) can be provided in the form of non-toxic and pharmaceutically acceptable salts. These non-toxic salts comprise salts with inorganic acids (hydrochloric, sulfuric, hydrobromic, phosphoric, nitric) or with organic acids (acetic, propionic, succinic, maleic, hydroxymaleic, benzoic, fumaric, methanesulphonic, trifluoroacetic or oxalic acids) or with inorganic bases (sodium hydroxide, potassium hydroxide, lithium hydroxide, calcium hydroxide) or organic bases (tertiary amines, such as triethylamine, piperidine, benzylamine), depending on the nature of the compounds of formula (I).

The present invention also relates to the use of the compounds of formula (I) according to the invention for inhibiting the protein farnesyl transferase. The compounds of formula (I) or the salts thereof can be administered in effective amounts, which can readily be determined by one skilled in the light in view of the disclosure herein, for the purpose of effecting said inhibition or for any other purpose disclosed herein. In one embodiment, the compounds of formula (I) or salts thereof can be used in the preparation of pharmaceutical compositions useful in inhibiting the protein farnesyl transferase and more particularly in inhibiting farnesylation of the ras oncogene.

In particular, the present invention relates to the use of the compounds of formula (I) or salts thereof according to the invention for treating diseases related to cell proliferation. In one embodiment, the compounds of formula (I) or salts thereof can be used in in the preparation of pharmaceutical compositions useful in the treatment of diseases related to cell proliferations by inhibition of farnesyl transferase and in particular in the treatment of diseases related to cell proliferations overexpressing any one of the H-Ras, N-Ras or K-Ras oncoproteins or exhibiting a mutation of any one of the corresponding ras oncogenes.

The invention relates in particular to the use of the compounds of formula (I) according to the invention in the preparation of pharmaceutical compositions useful in the treatment of diseases related to cell proliferations, malignant or benign, of cells of various tissues and/or organs, comprising muscle, bone or connective tissues, the skin, the brain, the lungs, the sexual organs, the lymphatic or renal systems, mammary or blood cells, the liver, the digestive system, the colon, the pancreas and the thyroid or adrenal glands, and including the following pathologies: psoriasis, restenosis, solid tumours, Kaposi's sarcoma, carcinomas, cholangiocarcinoma, choriocarcinoma, neuroblastoma, Wilms' tumour, Hodgkin's disease, melanomas, teratocarcinomas, gliomas, multiple myelomas, chronic lymphocytic leukaemias, acute or chronic granulocytic lymphomas, and cancers, such as cancers of the pancreas, colon, lung, ovary, breast, brain, prostate, liver, stomach, bladder or testicles.

The invention very particularly relates to the use of the compounds of formula (I) according to the invention, preferably the compound described in Example 3, i.e., the single dextrorotatory enantiomer of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]-isoindole-3a-carboxylic acid or salt thereof, in the preparation of pharmaceutical compositions useful in the treatment of cancers, such as cancers of the pancreas, colon, lung, ovary, breast, brain, prostate, liver, stomach, bladder or testicles, and more advantageously cancer of the colon and pancreas, in particular of the colon.

Advantageously, the single dextrorotatory enantiomer of (3aRS,4SR,9SR,9aRS)-4,9-ethano-2-[2-(2-methoxyphenyl) propenoyl]-9-(4-methylphenyl)-2,3,3a,4,9,9a-hexahydro-1H-benzo[f]-isoindole-3a-carboxylic acid or salt thereof, is administered in an effective amount for the particular purpose and in a purity such that the single dextrorotatory enantiomer is present relative to the levorotatory enantiomer in at least an 80% enantiomeric excess, preferably in at least a 90% enantiomeric excess, more preferably in at least a 95% enantiomeric excess, and still more preferably, in at least a 98% enantiomeric excess.

This treatment can in particular be carried out by inhibition of tumor growth, in particular by inhibition of the protein farnesyl transferase, or alternatively by inhibition of the growth of tumours expressing the activated ras oncogene.

Compounds according to the invention can also be useful for the preparation of pharmaceutical compositions for the treatment and/or prophylaxis of diseases associated with cell signal transduction pathways, operating through farnesyl transferase, or their effects or symptoms.

Advantageously, compounds according to the invention can be used for the preparation of pharmaceutical compositions for the treatment and/or prophylaxis of diseases associated with cell signal transduction pathways, operating through Ras. Consequently, compounds according to the invention can be used for the treatment and/or prophylaxis of graft rejection, e.g., allograft (O'Donnel et al., 1995, Kidney International, vol. 48, suppl. 52, p.S.29–33).

Compounds according to the invention can also be useful for the preparation of pharmaceutical compositions for inhibiting angiogenesis and thereby affecting the growth of tumors (J. Rak et al., Cancer Research, 55, 4575–4580, 1995), such anti-angiogenesis properties could also be useful in the treament of certain forms of blindness related to retinal vascularization. Advantageously, compounds according to the invention can be used for the preparation of pharmaceutical compositions for the treatment and/or prophylaxsis of: diseases associated with aberrations in apoptosis, including cancers, such as described above, hepatatite delta virus and associated virus (J. S. Glenn et al., Science 256, 1331–1333, 1992); and viral infections including, but not limited to, herpesvirus, poxvirus, Epstein-Barr virus, Sindbis virus and adenovirus; inflammatory and/or auto-immune diseases, such as rheumatoid arthritis, inflammatory bowel diseases, interstitial pulmonary oedema, myocardial infarction, cystic fibrosis, systemic lupus erythematosus as Kaposi disease, immune mediated glomerulonephritis, autoimmune diabetes mellitus; bone diseases, for example, regulation of bone metabolism, such as in the treatment of Paget's disease, hypercalcaemia, bone metastases or osteoporosis; diseases associated with high cholesterol levels, such as hypercholesterolaemia, hyperlipidaemia, nephrotic hyperlipidaemia or atherosclerosis (Massy et al., Lancet, 347, 102–103, 1996); cardiovascular diseases, such as arteriosclerosis or other arterial injuries, or restenosis following angioplasty or vascular surgery; neurodegenerative disorders, including, but not limited to, Parkinson's disease, Alzheimer's disease, AIDS-related dementia, amyotrophic lateral sclerosis, retinitis pigmentosa, spinal muscular atrophy and cerebellar degeneration; and the following diseases: AIDS, polycystic kidney disease (D. L. Schaffner et al., American Journal of Pathology, 142, 1051–1060, 1993), neurofibromatosis, pulmonary fibrosis, arthritis, psoriasis, glomerulonephritis, hypertrophic scar formation, endotoxic shock; and myelodysplastic syndromes, aplastic anemia, ischemic injury associated myocardial infarctions, stroke, reperfusion injury, arrhythmia, toxin-induced or alcohol-induced liver diseases, hematological diseases, such as chronic anemia and aplastic anemia, degenerative diseases of the musculoskeletal system (such as arthritis), cystic fibrosis, multiple sclerosis, kidney diseases, and cancer pain.

The therapeutic treatment may also be carried out conjointly with other therapeutic treatments including antineoplastic medicaments, monoclonal antibodies, immunological therapies or radio therapies or biological-response modifiers. The response modifiers include, without implied limitation, lymphokines and cytokines such as interleukins, interferons ($\alpha$, $\beta$ or $\delta$) and TNF. Other chemotherapeutic agents which are useful in the treatment of disorders due to abnormal cell proliferation include, without implied limitation, alkylating agents such as nitrogen mustards, for instance mechlorethamine, cyclophosphamide, melphatan and chlorambucil, alkyl sulptronates such as busulphan, nitrosoureas such as carmustine, lomusine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products such as vinca alkaloids, for instance vinblastine, vincristine and vendesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for example cisplatin, substituted ureas such as hydroxyurea, methylhydrazine derivatives such as procarbazine, adrenocorticoid suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethyl-stilboestrol and ethinyloestradiol, antioestrogens such as tamoxifen, and androgens such as testosterone propionate and fluoxymesterone.

Another subject of the present invention is any combination of a compound of formula (I) with one or more compatible and pharmacologically active compounds and/or a radiotherapy treatment, in order to obtain a therapeutic, preferably a synergistic, effect, the said compounds preferably being active principles known for their inhibitory activity with respect to cell proliferation and particularly for their activity in the treatment of cancer; they may preferably be anti-proliferative compounds acting, at any one of the stages of the ras oncogene signalling pathway, as an inhibitor of protein-tyrosine kinase, or another inhibitor of farnesyl transferase, or an inhibitor of HMG-Co-reductase, or the cytotoxic compounds commonly used in the treatment of cancer. In preferred embodiments, a synergistic therapeutic effect is observed by such combinations.

The compounds according to the invention can be used to prevent or delay the appearance or the reappearance of pathological conditions or to treat these pathological conditions.

The compounds according to the invention can be administered orally, parenterally, intraperitoneally or rectally, preferably orally.

The compositions for oral administration comprise tablets, pills, powders or granules. In these compositions, the active product according to the invention is mixed with one or more inert diluents, such as sucrose, lactose or starch. These compositions can comprise substances other than diluents, for example a lubricant such as magnesium stearate.

As liquid compositions for oral administration, solutions, suspensions, syrups, elixirs and pharmaceutically acceptable emulsions, containing inert diluents such as water or liquid paraffin, may be used. These compositions can also comprise substances other than diluents, for example wetting, sweetening or flavouring products.

The compositions according to the invention for parenteral administration can be suspensions, emulsions or aqueous or non-aqueous sterile solutions. As solvent or vehicle, propylene glycol, a polyethylene glycol, vegetable oils, especially olive oil, or injectable organic esters, for example ethyl oleate, may be employed. These compositions can also contain adjuvants, especially wetting, emulsifying and dispersing agents. The sterilization may be carried out in several ways, for example using a bacteriological filter, by incorporating sterilizing agents in the composition or by heating. They may also be prepared in the form of sterile solid compositions which can be dissolved at the time of use in sterile water or any other sterile injectable medium.

The compositions for rectal administration are suppositories which can contain, besides the active product, excipients such as cocoa butter.

The doses used for implementing the methods according to the invention are those which permit a prophylactic treatment or a maximum therapeutic response and can be determined in accordance with the ordinary skill in the art. The doses vary according to the administration form, the particular product selected and the features specific to the subject to be treated. In general, the doses are those which are therapeutically effective in the treatment of disorders due to an abnormal cell proliferation and in particular a cytostatic treatment. The products according to the invention can be administered as often and as long as necessary to obtain the desired therapeutic effect.

The doses are generally, in man, from 0.1 to 10,000 mg/kg per day, preferably from 100 to 2000 mg/kg per day, preferably by the oral route. It is understood that, in order to choose the most appropriate dosage, account should be taken of the administration route, the weight of the patient, his general state of health, his age and all the factors which can influence the effectiveness of the treatment.

Generally, the doctor will determine the appropriate posology according to the age, weight and all the other factors specific to the subject to be treated.

Compositions according to the invention are illustrated in Example 105.

The following examples provide no limitation to the invention, rather they illustrate the present invention.

EXAMPLE 1

Preparation of methyl (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylate Stage A 358 g (2.52 mol) of methyl iodide and 361 g (2.38 mol) of 1,8-diazabicyclo[5.4.0]undec-7-ene were successively added to a solution of 428 g (1.98 mol) of (RS)-3-oxo-6-phenylcyclohex-1-ene-1-carboxylic acid, which was obtained according to J. Org. Chem., 1971, 36, 3707, in 4.5 cm$^3$ of acetone and then the reaction mixture was brought to reflux for five hours. The acetone was subsequently distilled off and then the residue was stirred with 2.5 dm$^3$ of water. After cooling to 10° C., the precipitate formed was filtered off, washed with ice-cold water and then dried at 30° C. 423 g (93%) of methyl (RS)-3-oxo-6-phenylcyclohex-1-ene-1-carboxylate were thus obtained in the form of a yellow powder, the characteristics of which were as follows:

melting point=66° C.

N.M.R. spectrum (300 MHz, CDCl$_3$, δ in ppm): 2.1–2.4 (mt, 4H, H at 4 and at 5), 3.72 (s, 3H, CH$_3$), 4.25 (dt, 1H, H at 6), 6.88 (s, 1H, H at 2), 7.2–7.52 (mt, 5H, aromatic protons).

Stage X (optionally performed after Stage A and before Stage B)

Preparation of methyl 3-oxo-6-phenyl-cyclohex-1-ene carboxylate in resolved enantiomeric form: 202 g of methyl 3-oxo-6-phenyl-cyclohex-1-ene carboxylate in racemic form was dissolved under vigorous stirring in 7.75 dm$^3$ of cyclohexane at 30° C. and insoluble particles were removed by decantation (Solution 1). 513.6 g of K$_2$HPO$_4$ were dissolved in 29.43 dm$^3$ of demineralized water in a 50 dm$^3$ stirred vessel (Solution 2). Solution 2 was adjusted to pH 7.2 with 85% (w/w) H$_3$PO$_4$, heated to 30° C. and mixed with solution 1. 2.8 dm$^3$ of a Candida antartica <<fraction B>> lipase solution (e.g., Chirazyme® L2, sol. purchased from Boehringer Mannheim) was then added to the reactor. The reaction was carried out under strong agitation at 30° C. The enantioselective resolution was followed by chiral HPLC column: Chiralpak® AD from Daicel Chemical Industries Ltd., mobile phase: heptane/ethanol 90/10 (V/V), UV detection: 220 nm, flow rate: 1 mL/mn. After 342 hours, the emulsioned organic phase (Solution 3) was separated from the aqueous phase by decantation. 7.75 dm$^3$ of cyclohexane and 1.25 dm$^3$ of ethanol was mixed with solution 3. 15.5 dm$^3$ of the light phase was separated from the heavy phase containing 2.4 dm$^3$ of water and ethanol. The light phase was concentrated and dried under vacuum at 40° C. leading to 53.5 g of a yellow solid: methyl 3-oxo-6-phenyl-cyclohex-1-ene carboxylate in resolved enantiomeric form at 93% enantiomeric excess.

Retention time on HPLC (column: Chiralpak® AD from Daicel Chemical Industries Ltd., mobile phase: heptane/ethanol 90/10 (V/V), UV detection: 220 nm, flow-rate: 1 mL/mn):

Retention time methyl 3-oxo-6-phenyl-cyclohex-1-ene carboxylate in resolved enantiomeric form: 8.4 min.

Stage B

A solution of 170 g (0.77 mol) of methyl (RS)-3-oxo-6-phenylcyclohex-1-ene-1-carboxylate (or appropriate amounts of methyl 3-oxo-6-phenyl-cyclohex-1-ene carboxylate in resolved enantiomeric form and other materials described hereinafter in Stage B if Stage X was performed) and of 0.9 cm$^3$ of trifluoroacetic acid in 880 cm$^3$ of dichloromethane was brought to reflux. 256.3 g (0.913 mol) of N-n-butoxymethyl-N-(trimethylsilyl)methyl]benzylamine, which was obtained according to Chem. Pharm. Bull., 1985, 276, were then added over 15 minutes at reflux. The reaction mixture was then cooled to 20° C. After addition of 20 cm$^3$ of a saturated aqueous sodium hydrogencarbonate solution, the organic phase was separated by settling, washed with water and then stirred with 900 g of silica (63–200 mesh) for 30 minutes. The silica was filtered off and then washed with 1.5 cm$^3$ of dichloromethane. After concentrating the solvent under reduced pressure, 270 g of a brown oil were then obtained, which oil was taken up in 800 cm$^3$ of cyclohexane and 770 cm$^3$ of a normal aqueous methanesulphonic acid solution. After separation by settling, the organic phase was washed with two times 200 cm$^3$ of water. The combined aqueous phases were washed with two times 200 cm³ of cyclohexane, then neutralized by addition of sodium hydrogencarbonate and extracted with 400 cm³ and then two times 200 cm³ of ethyl acetate. The combined organic phases were then washed with a half-saturated sodium chloride solution, dried over sodium sulphate and then concentrated under reduced pressure. 248 g (90%) of methyl (3aRS,4SR,7aRS)-2-benzyl-7-oxo-4-phenyloctahydroisoindole-3a-carboxylate were then obtained in the form of an orange-coloured oil, the characteristics of which were as follows:

N.M.R. spectrum (300 MHz, $CDCl_3$, δ in ppm): 2.4–2.65 (mt, 4H, H at 5 and at 6), 2.85 (2 dt, 2H, H at 1), 3.02 (2 dt, 2H, H at 3), 3.2 (2 dt, 1H, H at 4), 3.35 (mt, 1H, H at 7a), 3.5 (2 dt, 2H, benzyl H), 7–7.3 (mt, 10H, aromatic protons).

Stage C 5.1 cm³ of 4-bromotoluene and 1 g of magnesium turnings in 100 cm³ of diethyl ether were heated at reflux for one hour. 100 cm³ of toluene were added and the mixture was heated to 60° C. under a stream of nitrogen. After cooling to a temperature in the region of 5° C., a solution of 10 g of methyl (3aRS,4SR,7aRS)-2-benzyl-7-oxo-4-phenyloctahydroisoindole-3a-carboxylate in 80 cm³ of toluene was added. The reaction mixture was stirred for one hour at a temperature in the region of 20° C. and then hydrolysed with 100 cm³ of a saturated aqueous ammonium chloride solution. The aqueous phase was separated by settling and extracted with two times 75 cm³ of ethyl acetate. The organic phases were combined, washed successively with 100 cm³ of distilled water and 100 cm³ of a saturated aqueous sodium chloride solution, dried over magnesium sulphate and concentrated under reduced pressure. After purification by flash chromatography on silica gel (230–400 mesh), elution was carried out with a cyclohexane/ethyl acetate (80/20 by volume) mixture, 9 g of methyl (3aRS,4SR,7RS,7aRS)-2-benzyl-7-hydroxy-7-(4-methylphenyl)-4-phenyloctahydroisoindole-3a-carboxylate were obtained in the form of a white solid, the characteristics of which were as follows:

melting point=164° C.

$^1$H N.M.R. spectrum (250 MHz, $CDCl_3$, δ in ppm): 1.84 and 2.60 (d mt and mt, J=12.5 Hz, each 1H, $CH_2$ at 5), from 2.05 to 2.20 (mt, 2H, 1H of the $CH_2$ at 1 and 1H of the $CH_2$ at 6), 2.32 (s, 3H, $ArCH_3$), 2.40 and 2.95 (2d, J=10.5 Hz, each 1H, $CH_2$ at 3), 2.45 (mt, 1H, the other H of the $CH_2$ at 6), 2.64 (mt, 1H, the other H of the $CH_2$ at 1), 2.85 (mt, 1H, H at 7a), 3.32 (s, 3H, $COOCH_3$), 3.40 and 3.70 (2d, J=1.25 Hz, each 1H, $NCH_2Ar$), 3.50 (dd, J=12.5 and 3 Hz, 1H, H at 4), 6.68 (s, 1H, OH at 7), from 7.00 to 7.50 (mt, 10H, aromatic H at 4 and aromatic H of the benzyl), 7.12 and 7.40 (2d, J=8 Hz, each 2H, H at the ortho and meta positions of the aromatic at 7).

Stage D

A mixture of 29 cm³ of trifluoromethane-sulphonic acid and of 100 cm³ of dichloromethane was added dropwise to a solution of 20 g of methyl (3aRS,4SR,7RS,7aRS)-2-benzyl-7-hydroxy-7-(4-methyl-phenyl)-4-phenyloctahydroisoindole-3a-carboxylate in 200 cm³ of dichloromethane maintained at a temperature in the region of 0° C. The reaction mixture was stirred for 30 minutes at a temperature in the region of 0° C. and 2 hours at a temperature in the region of 20° C. and was then cooled to a temperature in the region of 0° C. 50 cm³ of distilled water were then added and then the pH of the aqueous phase was brought to between 8 and 9 by addition of a 4N aqueous sodium hydroxide solution. The organic phase was separated by settling, washed successively with 100 cm³ of distilled water and 100 cm³ of a saturated aqueous sodium chloride solution, dried over magnesium sulphate and concentrated under reduced pressure. After recrystallization from isopropanol, 18.2 g of methyl (3aRS,4SR,9RS,9aRS)-2-benzyl-4,9-ethano-(4-methylphenyl)-2,3,3a,4,9,9a-hexahydro-1H-benzo[f]isoindole-3a-carboxylate were thus obtained in the form of a white solid, the characteristics of which were as follows:

melting point=158° C.

$^1$H N.M.R. spectrum (300 MHz, $CDCl_3$, δ in ppm): 1.61, 1.90 and 2.67 (3 mts, respectively 1H, 1H and 2H, $CH_2CH_2$), from 2.50 to 2.60 (mt, 2H, 1H of the $CH_2$ at 1 and 1H of the $CH_2$ at 3), 2.57 (s, 3H, $ArCH_3$), 2.95 (d, J=10 Hz, the other H of the $CH_2$ at 1), 3.37 (d, J=10 Hz, the other H of the $CH_2$ at 3), 3.44 (broad d, J=10 Hz, 1H, H at 9a), 3.54 and 3.85 (2d, J=12.5 Hz, each 1H, $NCH_2Ar$), 3.57 (broad s, 1H, H at 4), 3.72 (s, 3H, $COOCH_3$), 6.70 (broad d, J=7.5 Hz, 1H, H at 8), from 7.10 to 7.60 (mt, 12H, H at 5, H at 6, H at 7, H at the ortho and meta positions of the aromatic at 9 and aromatic H of the benzyl).

Stage E 18 g of methyl (3aRS,4SR,9RS,9aRS)-2-benzyl-4,9-ethano-9-(4-methylphenyl)-2,3,3a,4,9,9a-hexahydro-1H-benzo[f]isoindole-3a-carboxylate, in solution in 250 cm³ of methanol, were reduced by 7.8 g of ammonium formate in the presence of 2 g of 10% (w/w) palladium-on-charcoal by heating at reflux for two hours. After cooling, the catalyst was separated by filtration and rinsed with three times 50 cm³ of methanol and the filtrate was concentrated under reduced pressure. The residue was dissolved in 200 cm³ of ethyl acetate and the organic phase was washed successively with 100 cm³ of a saturated aqueous sodium hydrogen carbonate solution, 100 cm³ of distilled water and 100 cm³ of a saturated aqueous sodium chloride solution, dried over magnesium sulphate and concentrated under reduced pressure. By stirring in 100 cm³ of pentane, the oil obtained crystallized. By filtration, 13.2 g of methyl (3aRS,4SR,9SR,9aRS)-4,9-ethano-9-(4-methylphenyl)-2,3,3a,4,9,9a-hexahydro-1H-benzo[f]isoindole-3a-carboxylate were obtained in the form of a white solid, the characteristics of which were as follows:

melting point=118° C.

$^1$H N.M.R. spectrum (250 MHz, $CDCl_3$, δ in ppm): 1.56, 1.78 and 2.24 (3 mts, respectively 1H, 1H and 2H, $CH_2CH_2$), 2.42 (s, 3H, $ArCH_3$), 2.79 and 2.96 (2 dd, respectively J=12.5 and 5.5 Hz and J=1.25 and 8 Hz, each 1H, $CH_2$ at 1), 3.10 and 3.39 (2 d, J=12.5 Hz, each 1H, $CH_2$ at 3), 3.30 (mt, 1H, H at 9a), 3.51 (broad s, 1H, H at 4), 3.60 (s, 3H, $COOCH_3$), 6.56 (broad d, J=7.5 Hz, 1H, H at 8), from 6.95 to 7.45 (mt, 7H, H at 5, H at 6, H at 7 and H at the ortho and meta positions of the aromatic at 9).

Stage F 36.6 g of (2-methoxyphenyl)acetic acid, in suspension in 110 cm³ of bis(dimethylamino)methane, were cooled to a temperature in the region of 0° C. 110 cm³ of acetic anhydride were added dropwise, the temperature of the reaction mixture not exceeding 40° C. The reaction mixture was stirred for 24 hours at a temperature in the region of 20° C. and then cooled to a temperature in the region of 0° C. 500 cm³ of distilled water were then added and stirring was continued for 2 hours at a temperature in the region of 0° C. The solid which had appeared was separated by filtration, washed with three times 100 cm³ of distilled water and dried under reduced pressure at 40° C. 23 g of 2-(2-methoxyphenyl)propenoic acid were thus obtained in the form of a cream solid, the characteristics of which were as follows:

melting point=145° C.

¹H N.M.R. spectrum (200 MHz, d6-DMSO, δ in ppm): 3.74 (s, 3H, ArOCH₃), 5.71 and 6.15 (2d, J=0.5 Hz, each 1H, =CH₂), from 6,90 to 7.50 (mt, 4H, aromatic H), from 11.5 to 13.5 (very broad unresolved peak, 1H, COOH).

Stage G

A solution of 3.05 cm³ of oxalyl chloride in 150 cm³ of dichloromethane was added dropwise to a solution of 6.31 g of 2-(2-methoxyphenyl)propenoic acid in 150 cm³ of dichloromethane containing 5 drops of N,N-dimethylformamide. The reaction mixture was stirred for a further two hours at a temperature in the region of 20° C., then cooled to a temperature in the region of 0° C. and run dropwise into a solution of 12.3 g of methyl (3aRS,4SR,9RS,9aRS)-4,9-ethano-9-(4-methylphenyl)-2,3,3a,4,9,9a-hexahydro-1H-benzo[f]isoindole-3a-carboxylate in 250 cm³ of dichloromethane and 10 cm³ of triethylamine, the temperature was maintained in the region of 0° C. The reaction mixture was stirred for a further one hour at a temperature in the region of 0° C., then for one hour at a temperature in the region of 20° C. and poured into 200 cm³ of distilled water. The organic phase was separated by settling, washed with two times 200 cm³ of distilled water and then 200 cm³ of a saturated aqueous sodium chloride solution, dried over magnesium sulphate and concentrated under reduced pressure. After purification by flash chromatography on silica gel (230–400 mesh), elution was carried out with a cyclohexane/ethyl acetate (70/30 by volume) mixture, 14.9 g of methyl (3aRS,4SR,9RS,9aRS)-4,9-ethano-2-[2-(2-methoxyphenyl)propenoyl]- 9-(4-methylphenyl)-2,3,3a,4,9,9a-hexahydro-1H-benzo[f]isoindole-3a-carboxylate were obtained in the form of a white solid, the characteristics of which were as follows:

melting point=152° C.

¹H N.M.R. spectrum (250 MHz, d6-DMSO, at a temperature of 383 K, δ in ppm): 1.44, 1.68 and from 2.00 to 2.30 (3 mts, respectively 1H, 1H and 2H, CH₂CH₂), 2.40 (s, 3H, ArCH₃), from 3.35 to 3.50 (mt, 3H, CH₂ at 1 and H at 9a), 3.46 (mt, 1H, H at 4), 3.55 (s, 3H, COOCH₃), 3.60 and 4.10 (2d, J=12.5 Hz, each 1H, CH₂ at 3), 3.73 (s, 3H, ArOCH₃), 5.54 and 5.70 (2s, each 1H, =CH₂), 6.46 (broad d, J=7.5 Hz, 1H, H at 8), from 6.90 to 7.40 (mt, 11H, H at 5, H at 6, H at 7, H at the ortho and meta positions of the aromatic at 9 and aromatic H at the ortho, meta and para positions with respect to the OCH₃).

EXAMPLE 2

Preparation of (3aRS,4SR,9RS,9aRS)-4,9-ethano-2-[2-(2-methoxyphenyl)propenoyl]-9-(4-methylphenyl)-2,3,3a,4,9,9a-hexahydro-1H-benzo[f] isoindole-3a-carboxylic Acid 14.7 g of methyl (3aRS,4SR,9RS,9aRS)-4,9-ethano-2-[2-(2-methoxyphenyl)propenoyl-9-(4-methylphenyl)-2,3,3a,4,9,9a-hexahydro-1H-benzo[f]isoindole-3a-carboxylate were heated at reflux for six hours in 400 cm³ of ethanol in the presence of 43.5 cm³ of a normal aqueous sodium hydroxide solution. The reaction mixture was subsequently concentrated under reduced pressure and the resiude dissolved in 250 cm³ of distilled water. The aqueous phase was washed with three times 200 cm³ of diethyl ether and then acidified with a 4N aqueous hydrochloric acid solution to a pH in the region of 2. The crystals which appeared were separated off by filtration, washed with three times 400 cm³ of distilled water and then 200 cm³ of petroleum ether and dried under reduced pressure at 40° C. 12.6 g of (3aRS,4SR,9RS,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid were thus obtained in the form of a white solid, the characteristics of which were as follows:

melting point=142° C.

¹H N.M.R. spectrum (400 MHz, d6-DMSO, at a temperature of 413 K, δ in ppm): 1.42, 1.65, 2.00 and 2.15 (4 mts, each 1H, CH₂CH₂), 2.40 (s, 3H, ArCH₃), from 3.20 to 3.40 (mt, 3H, CH₂ at 1 and H at 9a), 3.55 (mt, 1H, H at 4), 3.60 and 4.06 (2d, J=12.5 Hz, each 1H, CH₂ at 3), 3.68 (s, 3H, OCH₃), 5.53 and 5.70 (2 s, each 1H, =CH₂), 6.45 (broad d, J=7.5 Hz, 1H, H at 8), 6.95 (broad t, J=7.5 Hz, 1H, aromatic H at the para position with respect to the OCH₃), 7.03 (broad d, J=7.5 Hz, 1H, aromatic H at the ortho position with respect to the OCH₃), from 6.90 to 7.30 (mt, 9H, H at 5, H at 6, H at 7 and aromatic H at the meta positions with respect to the OCH₃ and aromatic H at the ortho and meta positions of the aromatic at 9).

EXAMPLE 3

Isolation of the dextrorotatory enantiomer of (3aRS,4SR,9RS,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid 500 mg of (3aRS,4SR,9RS,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid were resolved on a chiral silica column, carrying (3,5-dinitrobenzoyl)-S-phenylalanine grafts, elution was carried out with a mixture of dichloromethane, of isopropanol and of n-heptane (85/10/5 by volume). On collecting the second fraction eluted (retention time 60 minutes), 220 mg of the dextrorotatory enantiomer were obtained after concentrating under reduced pressure, the characteristics of which enantiomer were as follows:

melting point=225° C.

mass spectrum (EI): M/Z=493 (M⁺) and 449 (M⁺—CO₂);

optical rotation: $[\alpha]_{365}^{20}$=+63.3+/−1.0° (c=0.5, methanol).

The chiral silica was prepared in the following way:

948 g of aminopropyl silica (100 Å, 10 μm, NH₂; Macherey-Nagel) were suspended in 3 dm³ of N,N-dimethylformamide in a 6-dm³ three-necked flask. 180 g of the anhydride of N-(tert-butoxycarbonyl)-11-aminoundecanoic acid were added and the reaction mixture was stirred for 18 hours at a temperature in the region of 20° C. The silica was separated by filtration and washed successively with 2 times 2500 cm³ of dichloromethane and then 2 times 2500 cm³ of N,N-dimethylformamide. The silica, thus washed, was resuspended in 3 liters of N,N-dimethylformamide and 180 g of the anhydride of N-(tert-butoxycarbonyl)-11-aminoundecanoic acid were added and then the reaction mixture was stirred for 18 hours at a temperature in the region of 20° C. The silica was separated by filtration, washed successively with 2 times 2500 cm³ of dichloromethane, 2 times 2500 cm³ of tetrahydrofuran, 2 times 2500 cm³ of methanol and 2 times 2500 cm³ of diethyl ether and then dried under reduced pressure at a temperature in the region of 20° C. 971 g of silica, denoted by the term "BOC-C₁₁–C₃-silica", were thus obtained in the form of a white powder, the structure of which was confirmed by the infrared spectrum and the elemental analysis (found) of which was: C %=9.85, H %=2.05, N, %=1.05.

971 g of "BOC-C₁₁–C₃-silica" silica were suspended in 2500 cm³ of dichloromethane and 470 g of imidazole in a 6-dm³ three-necked flask. 850 cm³ of dimethyloctylchlorosilane were added dropwise and the reaction mixture was stirred for 16 hours at a temperature in the region of 20° C. The solid obtained was separated by filtration and washed successively with 2 times 2500 cm³ of dichloromethane, two times 2500 cm³ of methanol, 2 times 2500 cm³ of tetrahydrofuran, 2 times 2500 cm³ of dichloromethane and 2 times 2500 cm³ of diethyl ether and then dried under reduced pressure at a temperature in the region of 20° C. 1179 g of silica, denoted by the term "BOC-$C_{11}$–$C_3$-silica-O—Si($CH_3$)$_2$($CH_2$)$_7$$CH_3$", were thus obtained in the form of a white powder, the structure of which was confirmed by the infrared spectrum and the elemental analysis (found) of which was: C %=13.9, H %=2.83, N %=1.16.

1178 g of "BOC-$C_{11}$–$C_3$-silica-O—Si($CH_3$)$_2$($CH_2$)$_7$$CH_3$" silica were suspended in 2500 cm³ of a 5% by volume solution of trifluoroacetic acid in dichloromethane in a 6-dm³ three-necked flask. The reaction mixture was stirred at 20° C. The silica was separated by filtration and washed successively with 2 times 2500 cm³ of dichloromethane, 2 times 2500 cm³ of a dichloromethane/diisopropylethylamine (70/30 by volume) mixture, 2500 cm³ of dichloromethane, 2 times 2500 cm³ of tetrahydrofuran, 2 times 2000 cm³ of methanol and 2 times 2000 cm³ of diethyl ether and then dried under reduced pressure at a temperature in the region of 50° C. 1080.5 g of silica, denoted by the term "$C_{11}$–$C_3$-silica-O—Si($CH_3$)$_2$($CH_2$)$_7$$CH_3$"; were thus obtained in the form of a white powder, the structure of which was confirmed by the infrared spectrum and the elemental analysis (found) of which was: C %=12.6, H %=2.44, N %=1.05.

1080 g of "$C_{11}$–$C_3$-(silica)-O—Si($CH_3$)$_2$($CH_2$)$_7$$CH_3$" silica were suspended in 2500 cm³ of N,N-dimethylformamide, which had been dried over 4 Å molecular sieve, in a 6-dm³, three-necked, round-bottomed flask. 108 g of N-(3,5-dinitrobenzoyl)-L-phenylalanine and 75 g of N-ethoxycarbonyl-2-ethoxy-1,2-dihydroquinoline were added. The reaction mixture was stirred overnight. The silica was separated by filtration on sintered glass and was then washed with 2 times 2500 cm³ of dichloromethane, 2 times 2500 cm³ of tetrahydrofuran, 2500 cm³ of N,N-dimethylformamide and 2500 cm³ of dichloromethane. The silica, thus washed, was resuspended in 2500 cm³ of N,N-dimethylformamide. 108 g of N-(3,5-dinitrobenzoyl)-L-phenylalanine and 75 g of N-ethoxycarbonyl-2-ethoxy-1,2-dihydroquinoline were successively added and the reaction mixture was then stirred overnight at 20° C. The silica was separated by filtration on sintered glass and was washed successively with 2 times 2500 cm³ of dichloromethane, 2 times 2500 cm³ of tetrahydrofuran, 2 times 2500 cm³ of methanol and 2 times 2500 cm³ of diethyl ether. After drying at 60° C. under reduced pressure (2.7 kPa), 1093.6 g of silica, denoted by the term "DNB-L-Phe-$C_{11}$–$C_3$(silica)-O—Si($CH_3$)$_2$($CH_2$)$_7$$CH_3$", were obtained in the form of a pale yellow powder, the structure of which was confirmed by its infrared spectrum and the elemental analysis (found) of which was: C %=14.5, H %=2.4, N %=1.68.

519 g of "DNB-L-Phe-$C_{11}$–$C_3$(silica)-O—Si($CH_3$)$_2$($CH_2$)$_7$$CH_3$" silica were suspended in 3000 cm³ of N,N-dimethylformamide, dried over 4 Å molecular sieve, in a 4-dm³, three-necked, round-bottomed flask. 450 cm³ of trimethylsilylimidazole were added over 15 minutes and the reaction mixture was then stirred overnight. The silica was separated by filtration and was washed successively with 2 times 1500 cm³ of tetrahydrofuran, 2 times 1500 cm³ of methanol, 2 times 1500 cm³ of acetone and 2 times 1500 cm³ of dichloromethane. After drying at a temperature of 60° C. under reduced pressure (2.7 kPa), 519 g of silica, denoted by the term "DNB-L-Phe-$C_{11}$–$C_3$(silica)-[O—Si($CH_3$)$_2$($CH_2$)$_7$$CH_3$]—[O—Si($CH_3$)$_3$]", were obtained of a pale yellow powder, the structure of which was confirmed by its infrared spectrum and the elemental analysis (found) of which was: C, %=15.3, H, %=1.8, N, %=2.6.

The anhydride of N-(tert-butoxycarbonyl)-11-aminoundecanoic acid was prepared in the following way:

30.1 g of N-(tert-butoxycarbonyl)-11-aminoundecanoic acid were dissolved in 480 cm³ of ethyl acetate. This solution was cooled to 5° C. and then, while maintaining it at this temperature, a solution of 10.63 g of 1,3-dicyclohexylcarbodiimide in 120 cm³ of ethyl acetate was added over 10 minutes. The reaction mixture was stirred for 1 hour at 5° C. and then for 16 hours at a temperature in the region of 20° C. The precipitate formed was separated by filtration and washed with 30 cm³ of ethyl acetate. The filtrate was concentrated to dryness under reduced pressure (2.7 kPa) at 30° C. The solid obtained was dried at 20° C. under reduced pressure (2.7 kPa). 31 g of the anhydride of N-(tert-butoxycarbonyl)-11-aminoundecanoic acid were thus obtained, with a yield in the region of 100%.

N-(tert-Butoxycarbonyl)-11-aminoundecanoic acid was prepared according to J. Org. Chem., 41, 1350 (1976).

EXAMPLE 4

Isolation of the laevorotatory enantiomer of (3aRS, 4SR,9RS,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid 500 mg of (3aRS,4SR,9RS,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid were resolved on a chiral silica column, carrying (3,5-dinitrobenzoyl)-S-phenylalanine grafts, elution was carried out with a dichloromethane/isopropanol/n-heptane (85/10/5 by volume) mixture. Upon collecting the first fraction eluted (retention time 47 minutes), 240 mg of the laevorotatory enantiomer were obtained after concentrating under reduced pressure, the characteristics of which enantiomer were as follows:

melting point=225° C.

mass spectrum (EI): M/Z=493 (M⁺) and 449 (M⁺—$CO_2$);

optical rotation: $[\alpha]_{365}^{20}$=−76.0+/−1.2° (c=0.5, methanol).

EXAMPLE 5

Preparation of (3aRS,4SR,9SR,9aRS)-4,9-ethano-2-[(2-methoxyphenyl)acetyl]-9-(4-methylphenyl)-2,3,3a,4,9,9a-hexahydro-1H-benzo[f]isoindole-3a-carboxylic Acid Stage A 362 mg (2.17 mmol) of 2-methoxyphenylacetic acid, 456 mg (2.38 mmol) of 1-ethyl-3-[3-(dimethyl-amino)propyl] carbodiimide and 59 mg (0.43 mmol) of N-hydroxybenzotriazole hydrate were successively added to a solution of 755 mg (2.17 mmol) of methyl (3aRS,4SR, 9RS,9aRS)-4,9-ethano-9-(4-methylphenyl)-2,3,3a,4,9,9a-hexahydro-1H-benzo[f]isoindole-3a-carboxylate, obtained in Stage E of Example 1, in 20 cm³ of dichloromethane. After stirring overnight at room temperature, 15 cm³ of dichloromethane were added, washing was carried out with two times 15 cm³ of water, drying was carried out over magnesium sulphate and the solvent was evaporated under reduced pressure. After purification by flash chromatography on silica gel (230–400 mesh), elution was carried out with a cyclohexane/ethyl acetate (90/10 by volume) mixture, 820 mg (76%) of methyl (3aRS,4SR,9SR,9aRS)-4,9-ethano-2-[(2-methoxyphenyl)-acetyl]-9-(4-methylphenyl)-2,3,3a,4,9,9a-hexahydro-1H-benzo[f]isoindole-3a-carboxylate were obtained, after concentrating the solvent under reduced pressure, in the form of a white powder, the characteristics of which were as follows:

melting point=189° C.

mass spectrum (EI): M/Z=495 (M$^+$).

Stage B

By carrying out the reaction as in Example 2, but from 819 mg (1.65 mmol) of methyl (3aRS,4SR,9SR,9aRS)-4,9-ethano-2-[(2-methoxyphenyl)-acetyl]-9-(4-methylphenyl)-2,3,3a,4,9,9a-hexahydro-1H-benzo[f]isoindole-3a-carboxylate at reflux for 18 hours in 17 cm$^3$ of a normal aqueous sodium hydroxide solution and 17 cm$^3$ of methanol, 720 mg (74%) of (3aRS,4SR,9SR,9aRS)-4,9-ethano-2-[(2-methoxyphenyl)acetyl]-9-(4-methylphenyl)-2,3,3a,4,9,9a-hexahydro-1H-benzo[f]isoindole-3a-carboxylic acid were obtained, after recrystallization from 25 cm$^3$ of diisopropyl ether, in the form of a white powder, the characteristics of which were as follows:

melting point=182° C.

$^1$H N.M.R. spectrum (400 MHz, d6-DMSO, at a temperature of 423 K, δ in ppm): 1.40, 1.64, 1.95 and 2.10 (4 mts, each 1H, CH$_2$CH$_2$), 2.41 (s, 3H, ArCH$_3$), from 3.30 to 3.65 (mt, 6H, CH$_2$ at 1, NCOCH$_2$Ar, 1H of the CH$_2$ at 3 and H at 9a), 3.48 (mt, 1H, H at 4), 3.75 (s, 3H, OCH$_3$), 4.18 (d, J=12.5 HJz, 1H, the other H of the CH$_2$ at 3), 6.46 (broad d, J=7.5 Hz, 1H, H at 8), 6.90 (broad t, J=7.5 Hz, 1H, aromatic H in the para position with respect to the OCH$_3$), 6.96 (broad d, J=7.5 Hz, 1H, aromatic H in the ortho position with respect to the OCH$_3$), from 7.00 to 7.35 (mt, 5H, H at 5, H at 6, H at 7 and aromatic H at the meta position with respect to the OCH$_3$), 7.30 (limit AB, 4H, aromatic H at the ortho and meta positions of the aromatic at 9).

EXAMPLE 6

Preparation of (3aRS,4SR,9SR,9aRS)-4,9-ethano-9-(4-methoxyphenyl)-2-[(2-methoxyphenyl)acetyl]-2,3,3a,4,9,9a-hexahydro-1H-benzo[f]isoindole-3a-carboxylic Acid Stage A 2.07 cm$^3$ (16.5 mmol) of 4-bromoanisole and 402 mg (16.5 mmol) of magnesium turnings in 20 cm$^3$ of diethyl ether were heated at reflux under an argon atmosphere for three hours. After cooling to 0° C., 1.36 g (5.5 mmol) of anhydrous cerium chloride were added and then a solution of 2 g (5.5 mmol) of methyl (3a RS,4SR,7a RS)-2-benzyl-7-oxo-4-phenyloctahydro-isoindole-3a-carboxylate, obtained in Stage B of Example 1, in 5 cm$^3$ of dry diethyl ether was run in dropwise at a temperature in the region of 5° C. and under an argon atmosphere. The reaction mixture was stirred for one hour at a temperature in the region of 0° C. and then overnight at room temperature. After cooling to 0° C., the reaction mixture was hydrolysed by 15 cm$^3$ of a saturated aqueous ammonium chloride solution. The aqueous phase was separated by settling and extracted with two times 50 cm$^3$ of ethyl acetate. The organic phases were combined, washed successively with 25 cm$^3$ of distilled water and 25 cm$^3$ of a saturated aqueous sodium chloride solution, dried over magnesium sulphate and concentrated under reduced pressure. After purification by flash chromatography on silica gel (230–400 mesh), elution was carried out with a cyclohexane/ethyl acetate (60/40 by volume) mixture, 1.345 g (51%) of methyl (3aRS,4SR,7RS,7aRS)-2-benzyl-7-hydroxy-7-(4-methoxyphenyl)-4-phenyloctahydroisoindole-3a-carboxylate were obtained in the form of a white solid, the characteristic of which was as follows:

melting point=136° C.

Stage B

By carrying out the reaction as in Stage D of Example 1, but from 1.343 g (2.85 mmol) of methyl (3aRS,4SR,7RS,7aRS)-2-benzyl-7-hydroxy-7-(4-methoxyphenyl)-4-phenyloctahydroisoindole-3a-carboxylate and from 4.56 cm$^3$ of trifluoromethanesulphonic acid in 65 cm$^3$ of dichloromethane for 30 minutes at a temperature in the region of 0° C. and then overnight at room temperature, 863 mg (67%) of methyl (3aRS,4SR,9SR,9aRS)-2-benzyl-4,9-ethano-9-(4-methoxyphenyl)-2,3,3a,4,9,9a-hexahydro-1H-benzo[f]isoindole-3a-carboxylate were obtained, after purification by flash chromatography on silica gel (230–400 mesh), elution was carried out with a cyclohexane/ethyl acetate (90/10 by volume) mixture, in the form of a white solid, the characteristic of which was as follows:

melting point=127° C.

Stage C

By carrying out the reaction as in Stage E of Example 1, but from 839 mg (1.85 mmol) of methyl (3aRS,4SR,9SR,9aRS)-2-benzyl-4,9-ethano-9-(4-methoxyphenyl)-2,3,3a,4,9,9a-hexahydro-1H-benzo[f]isoindole-3a-carboxylate and from 0.35 g (5.5 mmol) of ammonium formate in the presence of 0.27 g of 10% (w/w) palladium-on-charcoal in 20 cm$^3$ of methanol, heating being carried out at reflux for 3 hours, 559 mg (83%) of methyl (3aRs,4SR,9SR,9aRS)-4,9-ethano-9-(4-methoxyphenyl)-2,3,3a,4,9,9a-hexahydro-1H-benzo[f]isoindole-3a-carboxylate were obtained, after stirring the foam obtained in 30 cm$^3$ of pentane, in the form of a white solid, the characteristic of which was as follows:

melting point=112° C.

Stage D

By carrying out the reaction as in Stage A of Example 5, but from 548 mg (1.51 mmol) of methyl (3aRs,4SR,9SR,9aRS)-4,9-ethano-9-(4-methoxyphenyl)-2,3,3a,4,9,9a-hexahydro-1H-benzo[f]isoindole-3a-carboxylate, from 251 mg (1.51 mmol) of 2-methoxyphenylacetic acid, from 318 mg (1.66 mmol) of 1-ethyl-3-[3-(dimethylamino)propyl]carbodiimide and from 41 mg (0.3 mmol) of N-hydroxybenzotriazole hydrate in 15 cm$^3$ of dichloromethane, 575 mg (75%) of methyl (3aRS,4SR,9SR,9aRS)-4,9-ethano-9-(4-methoxyphenyl)-2-[(2-methoxyphenyl)acetyl]-2,3,3a,4,9,9a-hexahydro-1H-benzo[f]isoindole-3a-carboxylate were obtained, after purification by flash chromatography on silica gel (230–400 mesh), elution was carried out with a cyclohexane/ethyl acetate (90/10 by volume) mixture, in the form of a white powder, the characteristics of which were as follows:

melting point=169° C.

mass spectrum (EI): M/Z=511 (M$^+$).

Stage E

By carrying out the reaction as in Example 2, but from 566 mg (1.1 mmol) of methyl (3aRS,4SR,9SR,9aRS)-4,9-ethano-9-(4-methoxyphenyl)-2-[(2-methoxyphenyl)acetyl]-2,3,3a,4,9,9a-hexahydro-1H-benzo[f]isoindole-3a-carboxylate at reflux for eighteen hours in 11.5 cm$^3$ of a normal aqueous sodium hydroxide solution and 7.5 cm$^3$ of methanol, 385 mg (70%) of (3aRS,4SR,9SR,9aRS)-4,9-ethano-9-(4-methoxyphenyl)-2-[(2-methoxyphenyl)acetyl]-2,3,3a,4,9,9a-hexahydro-1H-benzo[f]isoindole-3a-carboxylic acid were obtained, after recrystallization from 10 cm$^3$ of diisopropyl ether, in the form of a white powder, the characteristics of which were as follows:

melting point=163° C.

$^1$H N.M.R. spectrum (400 MHz, d6-DMSO, at a temperature of 393 K, δ in ppm): 1.36, 1.61, 1.90 and 2.07 (4 mts, each 1H, CH$_2$CH$_2$), from 3.30 to 3.65 (mt, 6H, CH$_2$ at 1, NCOCH$_2$Ar, 1H of the CH$_2$ at 3 and H at 9a), 3.46 (mt, 1H, H at 4), 3.73 (broad s, 3H, OCH$_3$), 3.80 (s, 3H, OCH$_3$ of the aromatic at 9), 4.15 (d, J=12.5 Hz, 1H, the other H of the CH$_2$ at 3), 6.45 (broad d, J=7.5 Hz, 1H, H at 8), 6.90 (broad t, J=7.5 Hz, 1H, aromatic H at the para position with respect to OCH$_3$), 6.96 (broad d, J=7.5 Hz, 1H, aromatic H at the ortho position with respect to the OCH$_3$), 7.06 (d, J=8 Hz, 2H, aromatic H at the ortho positions with respect to the OCH$_3$ for the aromatic at 9), from 7.00 to 7.30 (mt, 5H, H at 5, H at 6, H at 7 and aromatic H at the meta positions with respect to the OCH$_3$),7.30 (d, J=8 Hz, 2H, aromatic H at the meta positions with respect to the OCH$_3$ for the aromatic at 9).

EXAMPLE 7

Preparation of (3aRS,4SR,9SR,9aRS)-4,9-ethano-2-[(2-methoxyphenyl)acetyl]-9-(4-methylsulphanylphenyl)-2,3,3a,4,9,9a-hexahydro-1H-benzo[f]isoindole-3a-carboxylic Acid Stage A By carrying out the reaction as in Stage A of Example 6, but from 1.34 g (6.6 mmol) of 4-bromothioanisole and 161 mg (6.6 mmol) of magnesium turnings at reflux for three hours in 4 cm$^3$ of diethyl ether and then, successively, from 543 mg (2.2 mmol) of anhydrous cerium chloride and from a solution of 800 mg (2.2 mmol) of methyl (3aRS,4SR,7aRS)-2-benzyl-7-oxo-4-phenyloctahydroisoindole-3a-carboxylate, obtained in Stage B of Example 1, in 2 cm$^3$ of diethyl ether, 679 g (63%) of methyl (3aRS,4SR,7RS,7aRS)-2-benzyl-7-hydroxy-7-(4-methylsulphanylphenyl)-4-phenyloctahydroisoindole-3a-carboxylate were obtained, after purification by flash chromatography on silica gel (230–400 mesh), elution was carried out with cyclohexane and then with a cyclohexane/ethyl acetate (80/20 by volume) mixture, in the form of a white solid, the characteristic of which was as follows:

melting point=124–6° C.

Stage B

By carrying out the reaction as in Stage D of Example 1, but from 676 mg (1.39 mmol) of methyl (3aRS,4SR,7RS,7aRS)-2-benzyl-7-hydroxy-7-(4-methylsulphanylphenyl)-4-phenyloctahydroisoindole-3a-carboxylate and from 2.22 cm$^3$ of trifluoromethanesulphonic acid in 34 cm$^3$ of dichloromethane for thirty minutes at a temperature in the region of 0° C. and then seventy hours at room temperature, 366 mg (56%) of methyl (3aRS,4SR,9SR,9aRS)-2-benzyl-4,9-ethano-9-(4-methylsulphanylphenyl)-2,3,3a,4,9,9a-hexahydro-1H-benzo[f]isoindole-3a-carboxylate were obtained, after purification by flash chromatography on silica gel (230–400 mesh), elution was carried out with cyclohexane and then with a cyclohexane/ethyl acetate (90/10 by volume) mixture, in the form of a white solid, the characteristic of which was as follows:

melting point=105–7° C.

Stage C

A solution of 246 mg (0.52 mmol) of methyl (3aRS,4SR,9SR,9aRS)-2-benzyl-4,9-ethano-9-(4-methylsulphanylphenyl)-2,3,3a,4,9,9a-hexahydro-1H-benzo[f]isoindole-3a-carboxylate in 10 cm$^3$ of dichloromethane was cooled to 0° C. under an argon atmosphere. 115 mg (0.79 mmol) of 2-chloroethyl chloroformate were then added and then the reaction mixture was stirred overnight at room temperature. After concentrating the solvent under reduced pressure, the residue was heated at reflux for four hours in 10 cm$^3$ of methanol containing 1.5 cm$^3$ of a 1M solution of hydrochloric acid in methanol. The crystals formed were filtered off, washed with two times 1 cm$^3$ of ice-cold methanol and then neutralized by stirring in 10 cm$^3$ of a decinormal solution of sodium hydroxide. After extracting with dichloromethane and concentrating to dryness, 145 mg (62%) of methyl (3aRS,4SR,9SR,9aRS)-4,9-ethano-9-(4-methylsulphanylphenyl)-2,3,3a,4,9,9a-hexahydro-1H-benzo[f]isoindole-3a-carboxylate were obtained in the form of a white foam, the characteristic of which was as follows:

melting point=90–4° C.

Stage D

By carrying out the reaction as in Stage A of Example 5, but from 145 mg (0.38 mmol) of methyl (3aRS,4SR,9SR,9aRS)-4,9-ethano-9-(4-methylsulphanylphenyl)-2,3,3a,4,9,9a-hexahydro-1H-benzo[f]isoindole-3a-carboxylate, from 64 mg (0.38 mmol) of 2-methoxyphenylacetic acid, from 91 mg (0.42 mmol) of 1-ethyl-3-[3-(dimethylamino)propyl]carbodiimide hydrochloride and from 10 mg (0.076 mmol) of N-hydroxybenzotriazole hydrate in 5 cm$^3$ of dichloromethane, 182 mg (90%) of methyl (3aRS,4SR,9SR,9aRS)-4,9-ethano-2-[(2-methoxyphenyl)acetyl]-9-(4-methylsulphanylphenyl)-2,3,3a,4,9,9a-hexahydro-1H-benzo[f]isoindole-3a-carboxylate were obtained, after purification by flash chromatography on silica gel (230–400 mesh), elution was carried out with cyclohexane/ethyl acetate (80/20, then 70/30, by volume) mixtures, in the form of a white powder, the characteristics of which were as follows:

melting point=137° C.

mass spectrum (EI): M/Z=527 (M$^+$).

Stage E

By carrying out the reaction as in Example 2, but from 180 mg (0.34 mmol) of methyl (3aRS,4SR,9SR,9aRS)-4,9-ethano-2-[(2-methoxyphenyl)acetyl]-9-(4-methylsulphanylphenyl)-2,3,3a,4,9,9a-hexahydro-1H-benzo[f]isoindole-3a-carboxylate at reflux for eighteen hours in 3.7 cm$^3$ of a normal aqueous sodium hydroxide solution and 3.7 cm$^3$ of methanol, 144 mg (81%) of (3aRS,4SR,9SR,9aRS)-4,9-ethano-2-[(2-methoxyphenyl)acetyl]-9-(4-methylsulphanylphenyl)-2,3,3a,4,9,9a-hexahydro-1H-benzo[f]isoindole-3a-carboxylic acid were obtained, after recrystallization from 5 cm$^3$ of diisopropyl ether, in the form of a white powder, the characteristics of which were as follows:

melting point=145° C.

$^1$H N.M.R. spectrum (250 MHz, d6-DMSO, at a temperature of 393 K, δ in ppm): 1.40, 1.63, 1.92 and 2.10 (4 mts, each 1H, CH$_2$CH$_2$), 2.59 (s, 3H, SCH$_3$), from 3.30 to 3.70 (mt, 6H, CH$_2$ at 1, NCOCH$_2$Ar, 1H of the CH$_2$ at 3 and H at 9a), 3.50 (mt, 1H, H at 4), 3.73 (broad s, 3H, OCH$_3$), 4.18 (d, J=12.5 Hz, 1H, the other H of the CH$_2$ at 3), 6.48 (broad d, J=7.5 Hz, 1H, H at 8), 6.92 (broad t, J=7.5 Hz, 1H, aromatic H at the para position with respect to OCH$_3$), 7.00 (broad d, J=7.5 Hz, 1H, aromatic H at the ortho position with respect to the OCH$_3$), from 7.05 to 7.35 (mt, 5H, H at 5, H at 6, H at 7 and aromatic H at the meta positions with respect to the OCH$_3$), 7.35 and 7.45 (2 broad d, J=8 Hz, each 2H, aromatic H at the ortho and meta positions of the aromatic at 9).

EXAMPLE 8

Preparation of (3aRS,4SR,9SR,9aRS)-4,9-ethano-9-(4-fluorophenyl)-2-[(2-methoxyphenyl)acetyl]-2,3,3a,4,9,9a-hexahydro-1H-benzo[f]isoindole-3a-carboxylic Acid Stage A By carrying out the reaction as in Stage A of Example 6, from 6.1 cm³ of a 1M solution of 4-fluorophenylmagnesium bromide in diethyl ether and then, successively, from 1.36 g (5.5 mmol) of anhydrous cerium chloride and from a solution of 2 g (5.5 mmol) of methyl (3aRs,4SR,7aRS)-2-benzyl-7-oxo-4-phenyloctahydroisoindole-3a-carboxylate, obtained in Stage B of Example 1, in 20 cm³ of diethyl ether, 507 g (20%) of methyl (3aRS,4SR,7RS,7aRS)-2-benzyl-7-(4-fluorophenyl)-7-hydroxy-4-phenyloctahydroisoindole-3a-carboxylate were obtained, after purification by flash chromatography on silica gel (230–400 mesh), elution was carried out with cyclohexane and then with a cyclohexane/ethyl acetate (60/40 by volume) mixture, in the form of a white solid, the characteristic of which was as follows:
melting point=163° C.

Stage B

By carrying out the reaction as in Stage D of Example 1, from 433 mg (0.94 mmol) of methyl (3aRS,4SR,7RS,7aRS)-2-benzyl-7-(4-fluorophenyl)-7-hydroxy-4-phenyloctahydroisoindole-3a-carboxylate and from 1.51 cm³ of trifluoromethanesulphonic acid in 20 cm³ of dichloromethane for thirty minutes at a temperature in the region of 0° C. and then 70 hours at room temperature, 360 mg (86%) of methyl (3aRS,4SR,9SR,9aRS)-2-benzyl-4,9-ethano-9-(4-fluorophenyl)-2,3,3a,4,9,9a-hexahydro-1H-benzo[f]isoindole-3a-carboxylate were obtained, after purification by flash chromatography on silica gel (230–400 mesh), elution was carried out with cyclohexane and then with a cyclohexane/ethyl acetate (90/10 by volume) mixture, in the form of a white solid, the characteristic of which was as follows:
melting point=157° C.

Stage C

By carrying out the reaction as in Stage E of Example 1, but from 358 mg (0.81 mmol) of methyl (3aRS,4SR,9SR,9aRS)-2-benzyl-4,9-ethano-9-(4-fluorophenyl)-2,3,3a,4,9,9a-hexahydro-1H-benzo[f]isoindole-3a-carboxylate and from 153 mg (2.43 mmol) of ammonium formate in the presence of 120 mg of 10% (w/w) palladium-on-charcoal in 20 cm³ of methanol, heating being carried out at reflux for 3 hours, 236 mg (83%) of methyl (3aRS,4SR,9SR,9aRS)-4,9-ethano-9-(4-fluorophenyl)-2,3,3a,4,9,9a-hexahydro-1H-benzo[f]isoindole-3a-carboxylate were obtained, after stirring the foam obtained in 15 cm³ of pentane, in the form of a white solid, the characteristic of which was as follows:
melting point=163° C.

Stage D

By carrying out the reaction as in Stage A of Example 5, from 235 mg (0.67 mmol) of methyl (3aRS,4SR,9SR,9aRS)-4,9-ethano-9-(4-fluorophenyl)-2,3,3a,4,9,9a-hexahydro-1H-benzo[f]isoindole-3a-carboxylate, from 112 mg (0.67 mmol) of 2-methoxyphenylacetic acid, from 142 mg (0.74 mmol) of 1-ethyl-3-[3-(dimethylamino)propyl]carbodiimide hydrochloride and from 19 mg (0.076 mmol) of N-hydroxybenzotriazole hydrate in 10 cm³ of dichloromethane, 230 mg (68%) of methyl (3aRS,4SR,9SR,9aRS)-4,9-ethano-9-(4-fluorophenyl)-2-[(2-methoxyphenyl)acetyl]-2,3,3a,4,9,9a-hexahydro-1H-benzo[f]isoindole-3a-carboxylate were obtained, after purification by flash chromatography on silica gel (230–400 mesh), elution was carried out with cyclohexane/ethyl acetate (90/10, then 80/20, by volume) mixtures, in the form of a white powder, the characteristics of which were as follows:
melting point=216° C.
mass spectrum (EI): M/Z=499 (M⁺).

Stage E

By carrying out the reaction as in Example 2, but from 228 mg (0.45 mmol) of methyl (3aRS,4SR,9SR,9aRS)-4,9-ethano-9-(4-fluorophenyl)-2-[( 2-methoxyphenyl)acetyl]-2,3,3a,4,9,9a-hexahydro-1H-benzo[f]isoindole-3a-carboxylate at reflux for eighteen hours in 4.7 cm³ of a normal aqueous sodium hydroxide solution and 5 cm³ of methanol, 171 mg (77%) of (3aRS,4SR,9SR,9aRS)-4,9-ethano-9-(4-fluorophenyl)-2-[(2-methoxyphenyl)acetyl]-2,3,3a,4,9,9a-hexahydro-1H-benzo[f]isoindole-3a-carboxylic acid were obtained, after recrystallization from 5 cm³ of diisopropyl ether, in the form of a white powder, the characteristics of which were as follows:
melting point=250° C.
¹H N.M.R. spectrum (400 MHz, d6-DMSO, at a temperature of 423 K, δ in ppm): 1.40, 1.64, 1.95 and 2.10 (4 mts, each 1H, CH₂CH₂), 2.41 (s, 3H, ArCH₃), from 3.30 to 3.65 (mt, 6H, CH₂ at 1, NCOCH₂Ar, 1H of the CH₂ at 3 and H at 9a), 3.48 (mt, 1H, H at 4), 3.75 (s, 3H, OCH₃), 4.18 (d, J=12.5 Hz, 1H, the other H of the CH₂ at 3), 6.46 (broad d, J=7.5 Hz, 1H, H at 8), 6.90 (broad t, J=7.5 Hz, 1H, aromatic H at the para position with respect to the OCH₃), 6.96 (broad d, J=7.5 Hz, 1H, aromatic H at the ortho position with respect to the OCH₃), from 7.00 to 7.35 (mt, 5H, H at 5, H at 6, H at 7 and aromatic H at the meta positions with respect to the OCH₃), 7.30 (limit AB, 4H, aromatic H at the ortho and meta positions of the aromatic at 9).

EXAMPLE 9

Preparation of (3aRS,4SR,9SR,9aRS)-4,9-ethano-2-[(2-methoxyphenyl)acetyl]-9-(3-methylphenyl)-2,3,3a,4,9,9a-hexahydro-1H-benzo[f]isoindole-3a-carboxylic Acid Stage A By carrying out the reaction as in Stage A of Example 6, but from 2.42 cm³ of a 1M solution of meta-tolylmagnesium bromide in tetrahydrofuran and then, successively, from 543 mg (2.2 mmol) of anhydrous cerium chloride and from a solution of 800 mg (2.2 mmol) of methyl (3aRS,4SR,7aRS)-2-benzyl-7-oxo-4-phenyloctahydroisoindole-3a-carboxylate, obtained in Stage B of Example 1, in 10 cm³ of diethyl ether, 505 mg (50%) of methyl (3aRS,4SR,7Rs,7aRS)-2-benzyl-7-hydroxy-7-(3-methylphenyl)-4-phenyloctahydroisoindole-3a-carboxylate were obtained, after purification by flash chromatography on silica gel (230–400 mesh), elution being carried out with cyclohexane and then with a cyclohexanelethyl acetate (80/20 by volume) mixture, in the form of a white solid, the characteristic of which was as follows:
melting point=117–9° C.

Stage B

By carrying out the reaction as in Stage D according to Example 1, but from 669 mg (1.47 mmol) of methyl (3aRS,4SR,7RS,7aRS)-2-benzyl-7-hydroxy-7-(3-methylphenyl)-4-phenyloctahydroisoindole-3a-carboxylate and from 2.35 cm³ of trifluoromethanesulphonic acid in 33 cm³ of dichloromethane for thirty minutes at a temperature in the region of 0° C. and then forty-eight hours at room temperature, 582 mg (90%) of methyl (3aRS,4SR,9SR,9aRS)-2-benzyl-4,9-ethano-9-(3-methylphenyl)-2,3,3a,4,9,9a-hexahydro-1H-benzo[f]isoindole-3a-carboxylate were obtained, after purification by flash chromatography on silica gel (230–400 mesh), elution being carried out with cyclohexane and then with a cyclohexane/ethyl acetate (90/10 by volume) mixture, in the form of a white solid, the characteristic of which was as follows:

melting point=113–5° C.

Stage C

By carrying out the reaction as in Stage E of Example 1, but from 578 mg (1.27 mmol) of methyl (3aRS,4SR,9SR, 9aRS)-2-benzyl-4,9-ethano-9-(3-methylphenyl)-2,3,3a,4,9, 9a-hexahydro-1H-benzo[f]isoindole-3a-carboxylate and from 241 mg (3.82 mmol) of ammonium formate in the presence of 185 mg of 10% (w/w) palladium-on-charcoal in 20 cm³ of methanol, heating being carried out at reflux for 3 hours, 412 mg (93%) of methyl (3aRS,4SR,9SR,9aRS)-4,9-ethano-9-(3-methylphenyl)-2,3,3a,4,9,9a-hexahydro-1H-benzo[f]-isoindole-3a-carboxylate were obtained, after stirring the foam obtained in 10 cm³ of pentane, in the form of a white solid, the characteristic of which was as follows:

melting point=103° C.

Stage D

By carrying out the reaction as in Stage A of Example 6, but from 409 mg (1.18 mmol) of methyl (3aRS,4SR,9SR, 9aRS)-4,9-ethano-9-(3-methylphenyl)-2,3,3a,4,9,9a-hexahydro-1H-benzo[f]isoindole-3a-carboxylate, from 196 mg (1.18 mmol) of 2-methoxy-phenylacetic acid, from 248 mg (1.29 mmol) of 1-ethyl-3-[3-(dimethylamino)propyl] carbodiimide hydrochloride and from 32 mg (0.076 mmol) of N-hydroxybenzotriazole hydrate in 12 cm³ of dichloromethane, 509 mg (86%) of methyl (3aRS,4SR,9SR, 9aRS)-4,9-ethano-2-[(2-methoxyphenyl)-acetyl]-9-(3-methylphenyl)-2,3,3a,4,9,9a-hexahydro-1H-benzo[f] isoindole-3a-carboxylate were obtained, after purification by flash chromatography on silica gel (230–400 mesh), elution being carried out with cyclohexane and then with a cyclohexane/ethyl acetate (90/10 by volume) mixture, in the form of a white powder, the characteristics of which were as follows:

melting point=132° C.

mass spectrum (EI): M/Z=495 (M⁺).

Stage E

By carrying out the reaction as in Example 2, but from 506 mg (1.02 mmol) of methyl (3aRS,4SR,9SR,9aRS)-4,9-ethano-2-[(2-methoxyphenyl)-acetyl]-9-(3-methylphenyl)-2,3,3a,4,9,9a-hexahydro-1H-benzo[f]isoindole-3a-carboxylate at reflux for eighteen hours in 10.3 cm³ of a normal aqueous sodium hydroxide solution and 7 cm³ of methanol, 424 mg (87%) of (3aRS,4SR,9SR,9aRS)- 4,9-ethano-2-[(2-methoxyphenyl)acetyl]-9-(3-methylphenyl)-2, 3,3a,4,9,9a-hexahydro-1H-benzo[f]isoindole-3a-carboxylic acid were obtained, after recrystallization from 5 cm³ of diisopropyl ether, in the form of a white powder, the characteristics of which were as follows:

melting point=138° C.

¹H N.M.R. spectrum (250 MHz, d6-DMSO, at a temperature of 393 K, δ in ppm): 1.40, 1.66, 1.95 and 2.10 (4 mts, each 1H, CH₂CH₂), 2.43 (s, 3H, ArCH₃), from 3.30 to 3.65 (mt, 6H, CH₂ at 1, NCOCH₂Ar, 1H of the CH₂ at 3 and H at 9a), 3.48 (mt, 1H, H at 4), 3.73 (broad s, 3H, OCH₃), 4.18 (d, J=12.5 Hz, 1H, the other H of the CH₂ at 3), 6.45 (broad d, J=7.5 Hz, 1H, H at 8), 6.92 (broad t, J=7.5 Hz, 1H, aromatic H at the para position with respect to the OCH₃), 6.98 (broad d, J=7.5 Hz, 1H, aromatic H at the ortho position with respect to the OCH₃), from 7.00 to 7.35 (mt, 8H, H at 5, H at 6, H at 7, aromatic H at the meta position with respect to the OCH₃ and aromatic H at the ortho and para positions with respect to the CH₃ for the aromatic at 9), 7.40 (t, J=8 Hz, 1H, aromatic H at the meta position with respect to the CH₃ for the aromatic at 9).

EXAMPLE 10

Preparation of (3aRS,4SR,9SR,9aRS)-4,9-ethano-9-(3-methoxyphenyl)-2-[(2-methoxyphenyl)acetyl]-2, 3,3a,4,9,9a-hexahydro-1H-benzo[f]isoindole-3a-carboxylic Acid Stage A By carrying out the reaction as in Stage A of Example 6, but from 1.56 cm³ (12.4 mmol) of 3-bromoanisole and from 302 mg (12.4 mmol) of magnesium turnings at reflux for one hour in 5 cm³ of dry diethyl ether, followed successively by 1.02 g (4.13 mmol) of anhydrous cerium chloride and by a solution of 1.5 g (4.13 mmol) of methyl (3aRS,4SR,7aRS)-2-benzyl-7-oxo-4-phenyloctahydroisoindole-3a-carboxylate, obtained in Stage B of Example 1, in 8 cm³ of diethyl ether, 945 mg (48%) of methyl (3aRS,4SR,7RS, 7aRS)-2-benzyl-7-hydroxy-7-(3-methoxyphenyl)-4-phenyloctahydroisoindole-3a-carboxylate were obtained, after purification by flash chromatography on silica gel (230–400 mesh), elution being carried out with cyclohexane and then with a cyclohexane/ethyl acetate (80/20 by volume) mixture, in the form of a white solid, the characteristic of which was as follows:

melting point=118° C.

Stage B

By carrying out the reaction as in Stage D of Example 1, but from 941 mg (1.99 mmol) of methyl (3aRS,4SR,7RS, 7aRS)-2-benzyl-7-hydroxy-7-( 3-methoxyphenyl)-4-phenyloctahydroisoindole-3a-carboxylate and from 3.19 cm³ of trifluoromethanesulphonic acid in 45 cm³ of dichloromethane for 30 minutes at a temperature in the region of 0° C. and then forty-eight hours at room temperature, 755 mg (83%) of methyl (3aRS,4SR,9RS,9aRS)-2-benzyl-4,9-ethano-9-(3-methoxyphenyl)-2,3,3a,4,9,9a-hexahydro-1H-benzo[f]isoindole-3a-carboxylate were obtained, after purification by flash chromatography on silica gel (230–400 mesh), elution being carried out with cyclohexane and then with a cyclohexane/ethyl acetate (90/10 by volume) mixture, in the form of a white solid, the characteristic of which was as follows:

melting point=117° C.

Stage C

By carrying out the reaction as in Stage E of Example 1, but from 747 mg (1.65 mmol) of methyl (3aRS,4SR,9RS, 9aRS)-2-benzyl-4,9-ethano-9-(3-methoxyphenyl)-2,3,3a,4, 9,9a-hexahydro-1H-benzo[f]isoindole-3a-carboxylate and from 311 mg (4.94 mmol) of ammonium formate in the presence of 240 mg of 10% (w/w) palladium-on-charcoal in 18 cm³ of methanol, heating being carried out at reflux for three hours, 501 mg (83%) of methyl (3aRS,4SR,9RS, 9aRS)-4,9-ethano-9-(3-methoxyphenyl)-2,3,3a,4,9,9a-hexahydro-1H-benzo[f]-isoindole-3a-carboxylate were obtained, after stirring the foam obtained in 10 cm³ of pentane, in the form of a white solid, the characteristic of which was as follows:

melting point=96–8° C.

Stage D

By carrying out the reaction as in Stage A of Example 5, but from 500 mg (1.38 mmol) of methyl (3aRS,4SR,9RS, 9aRS)-4,9-ethano-9-(3-methoxyphenyl)-2,3,3a,4,9,9a-hexahydro-1H-benzo[f]isoindole-3a-carboxylate, from 229 mg (1.38 mmol) of 2-methoxy-phenylacetic acid, from 291 mg (1.52 mmol) of 1-ethyl-3-[3-(dimethylamino)propyl] carbodiimide hydrochloride and from 37 mg (0.27 mmol) of N-hydroxybenzotriazole hydrate in 14 cm³ of dichloromethane, 451 mg (64%) of methyl (3aRS,4SR,9RS, 9aRS)-4,9-ethano-9-(3-methoxyphenyl)-2-[(2-methoxyphenyl)acetyl]-2,3,3a,4,9,9a-hexahydro-1H-benzo

[f]isoindole-3a-carboxylate were obtained, after purification by flash chromatography on silica gel (230–400 mesh), elution being carried out with cyclohexane and then with a cyclohexane/ethyl acetate (80/20 by volume) mixture, in the form of a white powder, the characteristics of which were as follows:

melting point=128° C.

mass spectrum (EI): M/Z=511 (M$^+$).

Stage E

By carrying out the reaction as in Example 2, from 450 mg (0.88 mmol) of methyl (3aRS,4SR,9RS,9aRS)-4,9-ethano-9-(3-methoxyphenyl)-2-[(2-methoxyphenyl)acetyl]-2,3,3a,4,9,9a-hexahydro-1H-benzo[f]isoindole-3a-carboxylate at reflux for 18 hours in 4.7 cm$^3$ of a normal aqueous sodium hydroxide solution and 5 cm$^3$ of methanol, 391 mg (89%) of (3aRS,4SR,9SR,9aRS)- 4,9-ethano-9-(3-methoxyphenyl)-2-[(2-methoxyphenyl)acetyl]-2,3,3a,4,9,9a-hexahydro-1H-benzo[f]isoindole-3a-carboxylic acid were obtained, after recrystallization from 10 cm$^3$ of diisopropyl ether, in the form of a white powder, the characteristics of which were as follows:

melting point=135° C.

$^1$H N.M.R. spectrum (250 MHz, d6-DMSO, at a temperature of 393 K, δ in ppm): 1.40, 1.63, 1.94 and 2.10 (4 mts, each 1H, CH$_2$CH$_2$), from 3.35 to 3.70 (mt, 6H, CH$_2$ at 1, NCOCH$_2$Ar, 1H of the CH$_2$ at 3 and H at 9a), 3.50 (mt, 1H, H at 4), 3.73 (broad s, 3H, OCH$_3$), 3.87 (s, 3H, OCH$_3$ of the aromatic at 9), 4.18 (d, J=12.5 Hz, 1H, the other H of the CH$_2$ at 3), 6.48 (broad d, J=7.5 Hz, 1H, H at 8), from 6.85 to 7.35 (mt, 10H, H at 5, H at 6, H at 7, aromatic H at the ortho, meta and para position with respect to the OCH$_3$ and aromatic H at the ortho and para positions with respect to the OCH$_3$ for the aromatic at 9), 7.43 (t, J=8 Hz, 1H, aromatic H at the meta position with respect to the OCH$_3$ for the aromatic at 9).

EXAMPLE 11

Preparation of Methyl (3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f] isoindole-3a-carboxylate Stage A 2.3 cm$^3$ of 4-bromo-ortho-xylene and 0.42 g of magnesium turnings in a mixture of 20 cm$^3$ of diethyl ether and 20 cm$^3$ of tetrahydrofuran were heated at reflux for one hour. After cooling to a temperature in the region of −7° C., a solution of 3.11 g of methyl (3aRS,4SR,7aRS)-2-benzyl-7-oxo-4-phenyloctahydroisoindole-3a-carboxylate in 20 cm$^3$ of diethyl ether was added over 25 minutes. The reaction mixture was stirred for four hours at a temperature in the region of 25° C. and then hydrolysed by 50 cm$^3$ of a saturated aqueous ammonium chloride solution. The aqueous phase was separated by settling and extracted with 25 cm$^3$ of ethyl acetate. The organic phases were combined, dried over magnesium sulphate and concentrated under reduced pressure. After purification by flash chromatography on silica gel (230–400 mesh), elution being carried out with a cyclohexane/ethyl acetate (80/20 by volume) mixture, 1.995 9 of methyl (3aRS,4SR,7RS,7aRS)-2-benzyl-7-hydroxy-7-(3,4-dimethylphenyl)-4-phenyl-octahydroisoindole-3a-carboxylate were obtained, the characteristic of which compound, used as it was in the following stage, was as follows:

mass spectrum (EI): M/Z=469 (M$^+$) and 410 (M$^+$—CO$_2$).

Stage B

By carrying out the reaction as in Stage D of Example 1, but starting from 1.99 g of the mixture obtained in the preceding stage, in solution in 100 cm$^3$ of dichloromethane, maintained at a temperature in the region of −5° C., and from 3.7 cm$^3$ of trifluoromethane-sulphonic acid, stirring being carried out for 72 hours at a temperature in the region of 25° C., 1.63 g of methyl (3aRS,4SR,9RS,9aRS)-2-benzyl-9-(3,4-dimethylphenyl)-4,9-ethano-2,3,3a,4,9,9a-hexahydro-1H-benzo[f]isoindole-3a-carboxylate were obtained in the form of a brown oil, the characteristic of which compound, used as it was in the following stage, was as follows:

mass spectrum (EI): M/Z=451 (M$^+$).

Stage C

By carrying out the reaction as in Stage E of Example 1, but starting from 1.63 g of methyl (3aRS,4SR,9RS,9aRS)-2-benzyl-9-(3,4-dimethylphenyl)-4,9-ethano-2,3,3a,4,9,9a-hexahydro-1H-benzo[f]isoindole-3a-carboxylate in 40 cm$^3$ of methanol and from 0.68 g of ammonium formate in the presence of 0.41 g of 10% (w/w) palladium-on-charcoal, heating being carried out at reflux for two hours, 0.79 g of methyl (3aRS,4SR,9RS,9aRS)-9-(3,4-dimethylphenyl)-4,9-ethano-2,3,3a,4,9,9a-hexahydro-1H-benzo[f]isoindole-3a-carboxylate was obtained in the form of a white solid, the characteristic of which was as follows:

mass spectrum (EI): M/Z=361 (M$^+$).

Stage D

By carrying out the reaction as in Stage A of Example 5, but from 0.79 g of methyl (3aRS,4SR,9RS,9aRS)-9-(3,4-dimethylphenyl)-4,9-ethano-2,3,3a,4,9,9a-hexahydro-1H-benzo[f]isoindole-3a-carboxylate, from 0.44 g of 2-methoxyphenylacetic acid, from 0.5 g of 1-ethyl-3-[3-(dimethylamino)propyl]carbo-diimide hydrochloride and from 0.35 g of N-hydroxybenzotriazole hydrate in 35 cm$^3$ of dichloromethane, 0.7 g of methyl (3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f]isoindole-3a-carboxylate was obtained, after purification by flash chromatography on 37 g of silica gel (230–400 mesh), elution being carried out with pure dichloromethane and then with a dichloromethane/ethanol (99/1 by volume) mixture, in the form of a foam which was recrystallized in the following way: this foam was dissolved in 5 cm$^3$ of absolute ethanol, water was added until the solution became cloudy and then the mixture was cooled for one hour at a temperature in the region of 0° C. 0.61 g of methyl (3aRS, 4SR,9SR,9aRS)-9-(3,4-dimethylphenyl)-4,9-ethano-2-[(2-methoxyphenyl)acetyl]-2,3,3a,4,9,9a-hexahydro-1H-benzo [f]isoindole-3a-carboxylate was thus obtained in the form of a yellow powder, the characteristics of which were as follows:

melting point=88° C.;

mass spectrum (EI): M/Z=509 (M$^+$).

EXAMPLE 12

Preparation of (3aRS,4SR,9SR,9aRS)-9-(3,4-dimethyl-phenyl)-4,9-ethano-2-[(2-methoxyphenyl)acetyl]-2,3,3a,4,9,9a-hexahydro-1H-benzo[f] isoindole-3a-carboxylic Acid By carrying out the reaction as in Example 2, from 637 mg of methyl (3aRS,4SR,9SR,9aRS)-9-(3,4-dimethylphenyl)-4,9-ethano-2-[( 2-methoxyphenyl)acetyl]-2,3,3a,4,9,9a-hexahydro-1H-benzo[f]isoindole-3a-carboxylate at reflux for 18 hours in 1.9 cm$^3$ of a normal aqueous sodium hydroxide solution and 60 cm$^3$ of ethanol, 176 mg of (3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f]isoindole-3a-carboxylic acid were obtained, after recrystallization from 5 cm$^3$ of diisopropyl ether, in the form of a white powder, the characteristics of which were as follows:

melting point=257° C.

mass spectrum (EI): M/Z=495 (M$^+$) and 451 (M$^+$—CO$_2$).

EXAMPLE 13

Preparation of (3aRS,4SR, 9SR,9aRS)-3a-N-benzylcarbamoyl-4,9-ethano-2-[2-(2-methoxyphenyl)propenoyl]-9-(4-methylphenyl)-2,3,3a,4,9,9a-hexahydro-1H-benzo[f]isoindole A solution of 0.19 cm$^3$ of oxalyl chloride in 5 cm$^3$ of dichloromethane was added dropwise to a solution of 1 g of (3aRS,4SR,9RS,9aRS)-4,9-ethano-2-[2-(2-methoxyphenyl) propenoyl]-9-(4-methylphenyl)-2,3,3a,4,9,9a-hexahydro-1H-benzo[f]isoindole-3a-carboxylic acid in 10 cm$^3$ of dichloromethane containing 1 drop of N,N-dimethylformamide. The reaction mixture was stirred for a further 2 hours at a temperature in the region of 20° C., then cooled to a temperature in the region of 0° C. and run dropwise into a solution of 0.22 cm$^3$ of benzylamine in 10 cm$^3$ of dichloromethane and 0.57 cm$^3$ of triethylamine, the temperature being maintained in the region of 0° C. The reaction mixture was stirred for a further 15 minutes at a temperature in the region of 0° C. and then for two hours at a temperature in the region of 20° C., and poured into 50 cm$^3$ of distilled water. The organic phase was separated by settling, washed with 50 cm$^3$ of distilled water and then 50 cm$^3$ of a saturated aqueous sodium chloride solution, dried over magnesium sulphate and concentrated under reduced pressure. After purification by flash chromatography on silica gel (230–400 mesh), elution being carried out with a cyclohexane/ethyl acetate (50/50 by volume) mixture, 0.8 g of (3aRS,4SR,9SR,9aRS)-3a-N-benzylcarbamoyl-4,9-ethano-2-[2-(2-methoxyphenyl)propenoyl]-9-(4-methylphenyl)-2,3,3a,4,9,9a-hexahydro-1H-benzo[f] isoindole was obtained in the form of a white solid, the characteristics of which were as follows:

melting point=227° C.

$^1$H N.M.R. spectrum (300 MHz, d6-DMSO, at a temperature of 413 K, δ in ppm): 1.40, 1.64, 2.02 and 2.15 (4 mts, each 1H, CH$_2$CH$_2$), 2.39 (s, 3H, ArCH$_3$), 3.31 and 3.40 (respectively mt and d (broad), J=13 Hz, each 1H, CH$_2$ at 1), 3.50 and 4.20 (respectively d and d (broad), J=13 Hz, each 1H, CH$_2$ at 3), 3.59 (mt, 1H, H at 9a), 3.61 (broad s, 1H, H at 4), 3.71 (s, 3H, ArOCH$_3$), 4.22 (limit AB, 2H, CH$_2$NAr), 5.52 and 5.67 (2s, each 1H, =CH$_2$), 6.44 (broad d, J=7.5 Hz, 1H, H at 8), 6.95 (broad t, J=7.5 Hz, 1H, aromatic H at the para position with respect to the OCH$_3$), 7.01 (broad d, J=7.5 Hz, 1H, aromatic H at the ortho position with respect to the OCH$_3$), from 6.95 to 7.35 (mt, 14H, H at 5, H at 6, H at 7, aromatic H at the meta positions with respect to the OCH$_3$, H at the ortho and meta positions of the aromatic at 9 and aromatic H of the benzyl), 7.75 (unresolved peak, 1H, CONH).

EXAMPLE 14

Preparation of benzyl (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-hydroxamate By carrying out the reaction as in Example 13, but from 2.49 g of (3aRS,4SR,9RS,9aRS)-4,9-ethano-2-[2-(2-methoxyphenyl)propenoyl]-9-(4-methylphenyl)-2,3,3a,4,9, 9a-hexahydro-1H-benzo[f]isoindole-3a-carboxylic acid in 20 cm$^3$ of dichloromethane containing 2 drops of N,N-dimethylformamide, from a solution of 0.48 cm$^3$ of oxalyl chloride in 5 cm$^3$ of dichloromethane and from a solution of 0.8 g of O-benzylhydroxylamine hydrochloride in a mixture of 2.1 cm$^3$ of triethylamine and of 20 cm$^3$ of dichloromethane, 2.4 g of benzyl (3aRS,4SR,9SR,9aRS)-4, 9-ethano-2-[2-(2-methoxyphenyl)propenoyl]-9-(4-methylphenyl)-2,3,3a,4,9,9a-hexahydro-1H-benzo[f] isoindole-3a-hydroxamate were obtained in the form of a white solid, the characteristics of which were as follows:

melting point=227° C.

$^1$H N.M.R. spectrum (300 MHz, d6-DMSO, at a temperature of 413 K, δ in ppm): 1.38, 1.61, 1.98 and 2.10 (4 mts, each 1H, CH$_2$CH$_2$), 2.39 (s, 3H, ArCH$_3$), 3.26 and 3.38 (respectively dd and d (very broad), J=13 and 9 Hz and J=13 Hz, each 1H, CH$_2$ at 1), 3.46 and 4.14 (respectively d and d (broad), J=13 Hz, each 1H, CH$_2$ at 3), 3.50 (mt, 1H, H at 4), 3.52 (dt, J=9 and 3 Hz, 1H, H at 9a), 3.72 (s, 3H, ArOCH$_3$), 4.63 and 4.70 (2 d, J=11 Hz, each 1H, OCH$_2$Ar), 5.52 and 5.68 (respectively s and s (broad), each 1H, =CH$_2$), 6.44 (broad d, J=7.5 Hz, 1H, H at 8), 6.95 (broad t, J=7.5 Hz, 1H, aromatic H at the para position with respect to the OCH$_3$), from 7.00 to 7.40 (mt, 15H, H at 5, H at 6, H at 7, aromatic H at the meta and ortho positions with respect to the OCH$_3$, H at the ortho and meta positions of the aromatic at 9 and aromatic H of the benzyl), 10.83 (unresolved peak, 1H, CONH).

EXAMPLE 15

Preparation of (3aRS,4SR,9SR,9aRS)-3a-carbamoyl-4,9-ethano-2-[2-(2-methoxyphenyl) propenoyl]-9-(4-methylphenyl)-2,3,3a,4,9,9a-hexahydro-1H-benzo[f]isoindole A solution of 0.24 cm$^3$ of oxalyl chloride in 5 cm$^3$ of dichloromethane was added dropwise to a solution of 1.24 g of (3aRS,4SR,9SR,9aRS)-4,9-ethano-2-[2-(2-methoxyphenyl)propenoyl]-9-(4-methylphenyl)-2,3,3a,4,9, 9a-hexahydro-1H-benzo[f]isoindole-3a-carboxylic acid in 10 cm$^3$ of dichloromethane containing 1 drop of N,N-dimethylformamide. The reaction mixture was stirred for a further two hours at a temperature in the region of 20° C. and then concentrated under reduced pressure. The residue was dissolved in 10 cm$^3$ of dioxane and run dropwise into 10 cm$^3$ of a 2.5N aqueous ammonia solution, the temperature being maintained in the region of 0° C. The reaction mixture was stirred for a further one hour at a temperature in the region of 0° C. and then filtered. The precipitate was washed successively with three times 50 cm$^3$ of distilled water and 50 cm$^3$ of diisopropyl ether and then dried under reduced pressure at a temperature in the region of 40° C. 0.85 g of (3aRS,4SR,9SR,9aRS)-3a-carbamoyl-4,9-ethano-2-[2-(2-methoxyphenyl)propenoyl]-9-(4-methylphenyl)-2,3,3a,4,9, 9a-hexahydro-1H-benzo[f]isoindole was thus obtained, after recrystallization from methanol, in the form of a white solid, the characteristics of which were as follows:

melting point: >260° C.

$^1$H N.M.R. spectrum (300 MHz, d6-DMSO, at a temperature of 413 K, δ in ppm): 1.38, 1.60, 1.98 and 2.12 (4 mts, each 1H, CH$_2$CH$_2$), 2.39 (s, 3H, ArCH$_3$), 3.26 and 3.36 (respectively dd and d (very broad), J=13 and 9 Hz and J=13 Hz, each 1H, CH$_2$ at 1), 3.48 and 4.16 (respective d and d (broad), J=13 Hz, each 1H, CH$_2$ at 3), 3.50 (dt, J=9 and 3 Hz, 1H, H at 9a), 3.56 (mt, 1H, H at 4), 3.72 (s, 3H, ArOCH$_3$), 5.52 and 5.68 (respectively s and s (broad), each 1H, =CH$_2$), 6.42 (broad d, J=7.5 Hz, 1H, H at 8), 6.70

(unresolved peak, 2H, CONH$_2$), 6.95 (broad t, J=7.5 Hz, 1H, aromatic H at the para position with respect to the OCH$_3$), 7.03 (broad d, J=7.5 Hz, 1H, aromatic H at the ortho position with respect to OCH$_3$); from 7.00 to 7.40 (mt, 9H, H at 5, H at 6, H at 7, aromatic H at the meta positions with respect to the OCH$_3$ and H at the ortho and meta positions of the aromatic at 9).

EXAMPLE 16

Preparation of (3aRS,4SR,9SR,9aRS)-4,9-ethano-2-[2-(2-methoxyphenyl)propenyl]-9-(4-methylphenyl)-2,3,3a,4,9,9a-hexahydro-1H-benzo[f]isoindole-3a-hydroxamic Acid 0.61 cm$^3$ of anisole and then 0.72 g of aluminium chloride were added to a solution of 1.3 g of benzyl (3aRS,4SR,9SR, 9aRS)-4,9-ethano-2-[2-(2-methoxyphenyl)propenyl]-9-(4-methylphenyl)-2,3,3a,4,9,9a-hexahydro-1H-benzo[f]isoindole-3a-hydroxamate in a mixture of 10 cm$^3$ of nitromethane and 10 cm$^3$ of dichloromethane cooled to a temperature in the region of −15° C. The reaction mixture was stirred for one hour at a temperature in the region of 20° C. and then concentrated under reduced pressure. The residue was taken up in 50 cm$^3$ of a normal aqueous hydrochloric acid solution and extracted with two times 50 cm$^3$ of dichloromethane. The extracts were combined, washed successively with 50 cm$^3$ of distilled water and 50 cm$^3$ of a saturated aqueous sodium chloride solution, dried over magnesium sulphate and concentrated under reduced pressure. The residue was purified by flash chromatography on silica gel (230–400 mesh), elution being carried out with a dichloromethanelmethanol (90/10 by volume) mixture. 0.75 g of (3aRS,4SR,9SR,9aRS)-4,9-ethano-2-[2-(2-methoxyphenyl)propenyl]-9-( 4-methylphenyl)-2,3,3a,4,9, 9a-hexahydro-1H-benzo[f]isoindole-3a-hydroxamic acid was thus obtained, after recrystallization from acetonitrile, in the form of a cream solid, the characteristics of which were as follows:

melting point=252° C.

$^1$H N.M.R. spectrum (300 MHz, (CD$_3$)$_2$SO, at a temperature of 413 K, δ in ppm): 1.36, 1.60, 1.98 and 2.08 (4 mts, each 1H, CH$_2$CH$_2$), 2.39 (s, 3H, ArCH$_3$), 3.26 and from 3.30 to 3.45 (respectively dd and mt, J=13 and 9 Hz, each 1H, CH$_2$ at 1), 3.43 and 4.12 (respectively d and d (broad), J=13 Hz, each 1H, CH$_2$ at 3), 3.50 (dt, J=9 and 3 Hz, 1H, H at 9a), 3.56 (mt, 1H, H at 4), 3.72 (s, 3H, ArOCH$_3$), 5.52 and 5.68 (respectively s and s (broad), each 1H, =CH$_2$), 6.42 (broad d, J=7.5 Hz, 1H, H at 8), 6.95 (broad t, J=7.5 Hz, 1H, aromatic H at the para position with respect to the OCH$_3$), 7.03 (broad d, J=7.5 Hz, 1H, aromatic H at the ortho position with respect to the OCH$_3$), from 7.00 to 7.40 (mt, 9H, H at 5, H at 6, H at 7, aromatic H at the meta positions with respect to the OCH$_3$ and H at the ortho and meta positions of the aromatic at 9). At room temperature, the signals were observed corresponding to the exchangeables: 8.70 (unresolved peak, 1H, CONH), 10.65 (unresolved peak, 1H, OH).

EXAMPLE 17

Preparation of (3aRS,4SR,9SR,9aRS)-4,9-ethano-2-[2-(2-methoxyphenyl)propenyl]-9-(4-methylphenyl)-2,3,3a,4,9,9a-hexahydro-1H-benzo[f]isoindole-3a-N-(3-pyridylmethyl)carboxamide A solution of 0.24 cm$^3$ of oxalyl chloride in 5 cm$^3$ of dichloromethane was added dropwise to a solution of 1.24 g of (3aRS,4SR,9SR,9aRS)-4,9-ethano-2-[2-(2-methoxyphenyl)propenoyl]-9-(4-methylphenyl)-2,3,3a,4,9, 9a-hexahydro-1H-benzo[f]isoindole-3a-carboxylic acid in 10 cm$^3$ of dichloromethane and one drop of N,N-dimethylformamide. The reaction mixture was stirred for two hours at a temperature in the region of 20° C., then cooled to a temperature in the region of 0° C. and run onto a solution of 0.26 cm$^3$ of 3-(aminomethyl)pyridine and of 0.7 cm$^3$ of triethylamine in 10 cm$^3$ of dichloromethane cooled to a temperature in the region of 0° C. The reaction mixture was stirred at a temperature in the region of 0° C. for fifteen minutes and then in the region of 20° C. for two hours, and then run into 100 cm$^3$ of distilled water. The aqueous phase was separated by settling and extracted with two times 50 cm$^3$ of dichloromethane. The organic phases were combined, washed with 50 cm$^3$ of distilled water and then 50 cm$^3$ of a saturated aqueous sodium chloride solution, dried over magnesium sulphate and concentrated under reduced pressure. After purification by flash chromatography on silica gel (230–400 mesh), elution being carried out with a dichloromethane/methanol (95/5 by volume) mixture, and crystallization by reflux in isopropanol, 1.0 g of (3aRS, 4SR,9SR,9aRS)-4,9-ethano-2-[2-(2-methoxyphenyl) propenoyl]-9-(4-methylphenyl)-2,3,3a,4,9,9a-hexahydro-1H-benzo[f]isoindole-3a-N-(3-pyridylmethyl)carboxamide was obtained, the characteristics of which compound were as follows:

melting point: 234° C.

$^1$H N.M.R. spectrum (250 MHz, (CD$_3$)$_2$SO, at a temperature of 393 K, δ in ppm): 1.40, 1.62 and from 1.90 to 2.20 (3 mts, respectively 1H, 1H and 2H, CH$_2$CH$_2$), 2.39 (s, 3H, ArCH$_3$), from 3.20 to 3.40 (limit AB, 2H, CH$_2$ at 1), 3.44 (d, J=12.5 Hz, 1H, 1H of the CH$_2$ at 3), from 3.55 to 3.65 (mt, 2H, CH at 4 and CH at 9a), 3.68 (s, 3H, ArOCH$_3$), from 4.10 to 4.35 (mt, 3H, the other H of the CH$_2$ at 3 and NCH$_2$Ar), 5.51 and 5.68 (2 s, each 1H, =CH$_2$), 6.42 (broad d, J=7.5 Hz, 1H, H at 8), from 6.90 to 7.50 (mt, 13H, H at 5, H at 6, H at 7, aromatic H of the 2-methoxyphenyl, aromatic H of the 4-methylphenyl, H at 4 of the pyridyl and H at 5 of the pyridyl), 8.05 (unresolved peak, 1H, CONH), 8.39 (broad s, 1H, H at 2 of the pyridyl), 8.44 (broad d, J=5 Hz, 1H, H at 6 of the pyridyl).

EXAMPLE 18

Isolation of the Dextrorotatory Enantiomer of (3aRS,4SR,9SR,9aRS)-4,9-ethano-2-[2-(2-methoxyphenyl)propenoyl]-9-(4-methylphenyl)-2,3, 3a,4,9,9a-hexahydro-1H-benzo[f]isoindole-3a-N-(3-pyridylmethyl)carboxamide 12 g of (3aRS,4SR,9SR,9aRS)-4,9-ethano-2-[2-(2-methoxyphenyl)-propenoyl]-9-(4-methylphenyl)-2,3,3a,4,9, 9a-hexahydro-1H-benzo[f]isoindole-3a-N-(3-pyridylmethyl)carboxamide, obtained in Example 17, were resolved, in 12 injections of 1 g, on a Whelk 01 (SS) chiral silica column, elution being carried out with an n-heptane/ dichloromethane/propanol (50/50/2 by volume) mixture. On collecting the first fraction eluted (retention time 42 min), 4.78 g of the dextrorotatory enantiomer of (3aRS,4SR,9SR, 9aRS)-4,9-ethano-2-[2-(2-methoxyphenyl)propenoyl]-9-(4-methylphenyl)-2,3,3a,4,9,9a-hexahydro-1H-benzo[f] isoindole-3a-N-(3-pyridylmethyl)carboxamide were obtained, after concentrating the solvent under reduced pressure, the characteristics of this product were as follows:

melting point=210° C.

mass spectrum (EI): M/Z=583 (M⁺);

optical rotation: $[\alpha]_{365}^{20}$=+104.6+/−1.6° (c=0.5, methanol).

EXAMPLE 19

Isolation of the Levorotatory Enantiomer of (3aRS, 4SR,9SR,9aRS)-4,9-ethano-2-[2-(2-methoxyphenyl) propenoyl]-9-(4-methylphenyl)-2,3,3a,4,9,9a-hexahydro-1H-benzo[f]isoindole-3a-N-(3-pyridylmethyl)carboxamide 12 g of (3aRS,4SR,9SR,9aRS)-4,9-ethano-2-[2-(2-methoxyphenyl)-propenoyl]-9-(4-methylphenyl)-2,3,3a,4,9,9a-hexahydro-1H-benzo[f]isoindole-3a-N-(3-pyridylmethyl)carboxamide, obtained in Example 17, were resolved, in 12 injections of 1 g, on a Whelk 01 (SS) chiral silica column, elution being carried out with an n-heptane/dichloromethane/propanol (50/50/2 by volume) mixture. On collecting the second fraction eluted (retention time 65 min), 4.86 g of the levorotatory enantiomer of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(3-pyridylmethyl)carboxamide were obtained, after concentrating the solvent under reduced pressure, the characteristics of this product were as follows:

melting point=210° C.

mass spectrum (EI): M/Z=583 (M⁺);

optical rotation: $[\alpha]_{365}^{20}$=+102.2+/−1.5° (c=0.5, methanol).

EXAMPLE 20

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(4-pyridylmethyl)carboxamide By carrying out the reaction as in Example 17, but from 1.24 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid, from one drop of N,N-dimethylformamide, from 0.24 cm³ of oxalyl chloride, from 0.26 cm³ of 4-(aminomethyl) pyridine and from 0.7 cm³ of triethylamine, 0.7 g of (3aRS,4SR,9SR,9aRS)-4,9-ethano-2-[2-(2-methoxyphenyl) propenoyl]-9-(4-methylphenyl)-2,3,3a,4,9,9a-hexahydro-1H-benzo[f]isoindole-3a-N-(4-pyridylmethyl)carboxamide was obtained, after crystallization from a mixture of equal volumes of isopropanol and of diisopropyl ether, the characteristic of which product was as follows:

melting point=202° C.

EXAMPLE 21

Preparation of Methyl (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-hydroxamate A solution of 0.24 cm³ of oxalyl chloride in 5 cm³ of dichloromethane was added dropwise to a solution of 1.24 g of (3aRS,4SR,9SR,9aRS)-4,9-ethano-2-[2-(2-methoxyphenyl)propenoyl]-9-(4-methylphenyl)-2,3,3a,4,9, 9a-hexahydro-1H-benzo[f]isoindole-3a-carboxylic acid in 10 cm³ of dichloromethane and one drop of N,N-dimethylformamide. The reaction mixture was stirred for two hours at a temperature in the region of 20° C. and then run onto a solution of 0.21 g of O-methylhydroxylamine hydrochloride in a mixture of 1.05 cm³ of triethylamine and of 10 cm³ of dichloromethane cooled to a temperature in the region of 0° C. The reaction mixture was stirred at a temperature in the region of 0° C. for thirty minutes and then at a temperature in the region of 20° C. for one hour, and then run into 50 cm³ of distilled water. The organic phase was separated by settling, washed with two times 50 cm³ of distilled water, two times 20 cm³ of a normal aqueous sodium hydroxide solution, 50 cm³ of distilled water and 50 cm³ of a saturated aqueous sodium chloride solution, dried over magnesium sulphate and concentrated under reduced pressure. After recrystallization from 20 cm³ of refluxing isopropanol, 0.95 g of methyl (3aRS,4SR,9SR,9aRS)-4,9-ethano-2-[2-(2-methoxyphenyl)propenoyl]-9-(4-methylphenyl)-2,3,3a,4,9,9a-hexahydro- 1H-benzo[f] isoindole-3a-hydroxamate was obtained, the characteristics of which product were as follows:

melting point=256° C.

¹H N.M.R. spectrum (250 MHz, (CD₃)₂SO, at a temperature of 383 K, δ in ppm): 1.38, 1.62 and 1.90 to 2.20 (3 mts, respectively 1H, 1H and 2H, CH₂CH₂), 2.40 (s, 3H, ArCH₃), from 3.15 to 3.45 (respectively dd and mt, J=12 and 9 Hz, 2H, CH₂ at 1), from 3.30 to 3.60 (mt, 3H, CH at 9a, CH at 4 and 1H of the CH₂ at 3), 3.48 (s, 3H, NOCH₃); 3.71 (s, 3H, ArOCH₃), 4.14 (broad d, J=12.5 Hz, 1H, the other H of the CH₂ at 3), 5.52 and 5.69 (2 s, each 1H, =CH₂), 6.43 (broad d, J=7.5 Hz, 1H, H at 8), from 6.90 to 7.40 (mt, 11H, H at 5, H at 6, H at 7 and aromatic H of the 2-methoxyphenyl and aromatic H of the 4-methylphenyl).

EXAMPLE 22

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N',N'-dimethylcarbohydrazide A solution of 0.24 cm³ of oxalyl chloride in 5 cm³ of dichloromethane was added dropwise to a solution of 1.24 g of (3aRS,4SR,9SR,9aRS)-4,9-ethano-2-[2-(2-methoxyphenyl)propenoyl]-9-(4-methylphenyl)-2,3,3a,4,9, 9a-hexahydro-1H-benzo[f]isoindole-3a-carboxylic acid in 10 cm³ of dichloromethane and one drop of N,N-dimethylformamide. The reaction mixture was stirred for two hours at a temperature in the region of 20° C. and then run onto a solution of 0.2 cm³ of N,N-dimethylhydrazine and of 0.7 cm³ of triethylamine in 10 cm³ of dichloromethane cooled to a temperature in the region of 0° C. The reaction mixture was stirred at a temperature in the region of 0° C. for thirty minutes and then at a temperature in the region of 20° C. for one hour and then run into 50 cm³ of distilled water. The organic phase was separated by settling, washed with 50 cm³ of distilled water, two times 25 cm³ of a normal aqueous sodium hydroxide solution, 50 cm³ of distilled water and 50 cm³ of a saturated aqueous sodium chloride solution, dried over magnesium sulphate and concentrated under reduced pressure. After purification by flash chromatography on silica gel (230–400 mesh), elution being carried out with a dichloromethane/methanol (97.5/2.5 by volume) mixture, and recrystallization from 50 cm³ of an isopropanol/diisopropyl ether (1/9 by volume) mixture, 0.95 g of (3aRS,4SR,9SR,9aRS)-4,9-ethano-2-[2-(2-methoxyphenyl)propenoyl]-9-(4-methylphenyl)-2,3,3a,4,9, 9a-hexahydro-1H-benzo[f]isoindole-3a-N',N'-dimethylcarbohydrazide was obtained, the characteristics of which compound were as follows:

melting point: 230° C.

¹H N.M.R. spectrum (250 MHz, $(CD_3)_2SO$, at a temperature of 383 K, δ in ppm): 1.38, 1.60 and from 1.90 to 2.20 (3 mts, respectively 1H, 1H and 2H, $CH_2CH_2$), 2.40 (s, 3H, $ArCH_3$), 2.47 (s, 6H, $N(CH_3)_2$), 3.21 and 3.35 (resp and mt, J=12 and 9 Hz, each 1H, $CH_2$ at 1), 3.40 and 4.19 (respectively d and d (broad), J 13 Hz, each 1H, $CH_2$ at 3), from 3.50 to 3.65 (mt, 2H, CH at 9a and CH at 4), 3.71 (s, 3H, $ArOCH_3$), 5.51 and 5.69 (2 s, each 1H, =$CH_2$), 6.42 (broad d, J=7.5 Hz, 1H, H at 8), from 6.90 to 7.40 (mt, 11H, H at 5, H at 6, H at 7, aromatic H of the 2-methoxyphenyl and aromatic H of the 4-methylphenyl), 8.41 (unresolved peak, 1H, CONH).

EXAMPLE 23

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-phenylcarbohydrazide By carrying out the reaction as in Example 22, but from 0.5 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid, from one drop of N,N-dimethylformamide, from 0.095 cm³ of oxalyl chloride, from 0.098 cm³ of N-phenylhydrazine and from 0.28 cm³ of triethylamine, 0.22 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-phenylcarbohydrazide was obtained, after crystallization from 10 cm³ of diisopropyl ether, the characteristics of which compound were as follows:

melting point: 220° C.

EXAMPLE 24

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N',N'-pentamethylenecarbohydrazide By carrying out the reaction as in Example 22, but from 0.5 g of (3aRS,4SR,9SR,9aRS)-4,9-ethano-2-[2-(2-methoxyphenyl)propenoyl]-9-( 4-methylphenyl)-2,3,3a,4,9,9a-hexahydro-1H-benzo[f]isoindole-3a-carboxylic acid, from one drop of N,N-dimethylformamide, from 0.095 cm³ of oxalyl chloride, from 0.095 cm³ of 1-aminopiperidine and from 0.28 cm³ of triethylamine, 0.06 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N',N'-pentamethylenecarbohydrazide was obtained, after purification by flash chromatography on silica gel (230–400 mesh), elution being carried out with ethyl acetate, and after crystallization from diisopropyl ether, the characteristics of which compound were as follows:

melting point: 220° C.

EXAMPLE 25

Preparation of (3aRS,4SR,9SR,9aRS)-4,9-ethano-2-[2-(2-methoxyphenyl)propenoyl]-9-(4-methylphenyl)-3a-phenylsulphonylaminocarbonyl-2,3,3a,4,9,9a-hexahydro-1H-benzo[f]isoindole A solution of 0.096 cm³ of oxalyl chloride in 0.5 cm³ of dichloromethane was added dropwise to a solution of 0.5 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid in 5 cm³ of dichloromethane and one drop of N,N-dimethyiformamide. The reaction mixture was stirred for two hours at a temperature in the region of 20° C. and then run into a mixture of 0.12 g of a 60% suspension of sodium hydride in petroleum jelly and 0.31 g of benzenesulphonamide in 5 cm³ of N,N-dimethylformamide. The reaction mixture was stirred at a temperature in the region of 20° C. for three days. 10 cm³ of distilled water are subsequently added and the mixture was extracted with two times 20 cm³ of dichloromethane. The organic extracts were combined, washed with 20 cm³ of distilled water and then 20 cm³ of a saturated aqueous sodium chloride solution, dried over magnesium sulphate and concentrated under reduced pressure. After purification by flash chromatography on silica gel (230–400 mesh), elution being carried out with a dichloromethane/methanol (98/2 by volume) mixture, and crystallization from diisopropyl ether, 0.005 g of (3aRS,4SR,9SR,9aRS)-4,9-ethano-2-[2-(2-methoxyphenyl)propenoyl]-9-(4-methylphenyl)-3a-phenylsulphonylaminocarbonyl-2,3,3a,4,9,9a-hexahydro-1H-benzo[f]isoindole was obtained, the characteristics of which compound were as follows:

melting point: approximately 166° C.

¹H N.M.R. spectrum (400 MHz, $(CD_3)_2SO$, at a temperature of 393 K, δ in ppm): 1.35, 1.58, 1.97 and 2.09 (4 mts, each 1H, $CH_2CH_2$), 2.39 (s, 3H, $ArCH_3$), 3.20 and 3.31 (respectively dd and d (broad), J=12.5 and 9 Hz and J=12.5 Hz, each 1H, $CH_2$ at 1), from 3.40 to 3.50 (mt, 1H, CH at 9a), 3.45 and 4.14 (respectively dd and d (broad), J=13 Hz, each 1H, $CH_2$ at 3), 3.59 (mt, 1H, CH at 4), 3.66 (s, 3H, $ArOCH_3$), 5.45 and 5.65 (2 s, each 1H, =$CH_2$), 6.35 (mt, 1H, H at 8), from 6.85 to 7.60 (mt, 14H, H at 5, H at 6, H at 7, aromatic H of the 2-methoxyphenyl, aromatic H of the 4-methylphenyl, aromatic H at the meta positions of the phenylsulphonyl and aromatic H at the para position of the phenylsulphonyl), 7.77 (d, J=8 Hz, 2H, aromatic H at the ortho positions of the phenylsulphonyl), 8.00 (broad s, 1H, CONH).

EXAMPLE 26

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(N-oxo-3-pyridylmethylcarboxamide 0.20 g of sodium carbonate and 6 cm³ of distilled water were added to a solution of 0.29 g of (3aRS,4SR,9SR,9aRS)-4,9-ethano-2-[2-( 2-methoxyphenyl)propenoyl]-9-(4-methylphenyl)-2,3,3a,4,9,9a-hexahydro-1H-benzo[f]isoindole-3a-N-(3-pyridylmethyl)carboxamide in 8 cm³ of chloroform. The mixture was cooled to a temperature in the region of 0° C. and 0.11 g of meta-chloroperbenzoic acid was added. The reaction mixture was stirred for one hour at 2° C. and then for twenty-two hours at a temperature in the region of 20° C. 0.22 g of meta-chloroperbenzoic acid was again added and the mixture was stirred for four hours at a temperature in the region of 20° C. and then diluted with 10 cm³ of dichloromethane. The organic phase was separated by settling, washed with three times 5 cm³ of a 10% aqueous sodium sulphite solution, three times 5 cm³ of a saturated aqueous sodium hydrogencarbonate solution and 5 cm³ of distilled water, dried over magnesium sulphate and concentrated under reduced pressure. The residue was purified by recrystallization from 8 cm³ of isopropyl acetate to give 0.25 g of (3aRS,4SR,9SR,9aRS)-4,9-ethano-2-[2-(2-methoxyphenyl)-propenoyl]-9-(4-methylphenyl)-2,3,3a,4,9, 9a-hexahydro-1H-benzo[f]isoindole-3a-N-(N-oxo-3-pyridyl)methylcarboxamide, the characteristics of which were as follows:

melting point=250° C.

$^1$H N.M.R. spectrum (250 MHz, (CD$_3$)$_2$SO, at a temperature of 383 K, δ in ppm): 1.40, 1.62 and from 1.90 to 2.25 (3 mts, respectively 1H, 1H and 2H, CH$_2$CH$_2$), 2.40 (s, 3H, ArCH$_3$), from 3.20 to 3.50 (limit AB, 2H, CH$_2$ at 1), 3.44 (d, J=12.5 Hz, $_1$H, 1H of the CH$_2$ at 3), from 3.50 to 3.65 (mt, 1H, CH at 9a), 3.57 (mt, 1H, CH at 4), 3.70 (s, 3H, ArOCH$_3$), from 4.00 to 4.30 (mt, 3H, the other H of the CH$_2$ at 3 and NCH$_2$Ar), 5.51 and 5.68 (2 s, each 1H, =CH$_2$), 6.41 (broad d, J=7.5 Hz, 1H, H at 8), from 6.90 to 7.40 (mt, 13H, H at 5, H at 6, H at 7, aromatic H of the 2-methoxyphenyl, H at 4 of the N-oxopyridyl, H at 5 of the N-oxopyridyl and aromatic H of the 4-methylphenyl), 8.00 (broad s, 1H, H at 2 of the N-oxopyridyl), 8.05 (broad d, J=5 Hz, 1H, H at 6 of the N-oxopyridyl), 8.11 (broad t, J=5 Hz, 1H, CONH).

EXAMPLE 27

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(4-methoxyphenyl)carbohydrazide 0.21 g of 4-methoxyphenylhydrazine hydrochloride, 0.23 g of 1-ethyl-3-[3-(dimethylamino)propyl]carbodiimide hydrochloride, 0.08 g of N-1-hydroxybenzotriazole hydrate and 0.17 cm$^3$ of triethylamine were successively added to a solution of 0.49 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid in 10 cm$^3$ of dichloromethane. The reaction mixture was stirred for twenty hours at a temperature in the region of 20° C. and then diluted with 15 cm$^3$ of dichloromethane. The organic phase was washed with three times 10 cm$^3$ of distilled water, dried over magnesium sulphate in the presence of 3S charcoal and concentrated under reduced pressure. By crystallization from 10 cm$^3$ of isopropyl acetate, 0.36 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(4-methoxyphenyl)carbohydrazide was obtained, the characteristics of which were as follows:

melting point=180° C.

$^1$H N.M.R. spectrum (250 MHz, (CD$_3$)$_2$SO, at a temperature of 383 K, δ in ppm): 1.40, 1.62 and from 1.90 to 2.25 (3 mts, respectively 1H, 1H and 2H, CH$_2$CH$_2$), 2.38 (s, 3H, ArCH$_3$), 3.25 (dd, J=12 and 9 Hz, 1H, 1H of the CH$_2$at 1), 3.39 (broad d, J=12 Hz, 1H, the other H of the CH$_2$ at 1), 3.48 and 4.22 (respectively d and d (broad), J=12.5 Hz, each 1H, CH$_2$ at 3), 3.56 (mt, 1H, CH at 9a), from 3.60 to 3.75 (mt, 1H, CH at 4), 3.68 (s, 6H, the 2 ArOCH$_3$), 5.52 and 5.69 (2 s, each 1H, =CH$_2$), 6.42 (broad d, J=7.5 Hz, 1H, H at 8), 6.56 and 6.69 (2 d, J=8 Hz, each 2H, aromatic H at the ortho and meta positions with respect to the OCH$_3$), 6.80 (broad s,1H, ArNH), from 6.90 to 7.40 (mt, 11H, H at 5, H at 6, H at 7, aromatic H of the 2-methoxyphenyl and aromatic H of the 4-methylphenyl), 9, 46 (broad s, 1H:—CONH).

EXAMPLE 28

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-methyl-N'-phenylcarbohydrazide By carrying out the reaction as in Example 27, but from 0.49 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid, 0.14 cm$^3$ of N-methyl-N-phenylhydrazine, 0.23 g of 1-ethyl-3-[3-(dimethylamino)propyl]carbodiimide hydrochloride, 80 mg of N-1-hydroxybenzotriazole hydrate and 0.17 cm$^3$ of triethylamine, 0.22 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-methyl-N'-phenylcarbohydrazide was obtained, after crystallization from 5 cm$^3$ of isopropanol, the characteristic of which compound was as follows:

melting point=240° C.

EXAMPLE 29

Preparation of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(2-methylphenyl)carbohydrazide By carrying out the reaction as in Example 27, but from 0.4 g of (3aRS,4SR,9SR,9aRS)-4,9-ethano-2-[2-(2-methoxyphenyl)propenoyl]- 9-(4-methylphenyl)-2,3,3a,4,9,9a-hexahydro-1H-benzo[f]isoindole-3a-carboxylic acid, 0.16 g of N-(2-methylphenyl)hydrazine, 0.19 g of 1-ethyl-3-[3-(dimethylamino)propyl]carbodiimide hydrochloride, 60 mg of N-1-hydroxybenzotriazole hydrate and 0.14 cm$^3$ of triethylamine, 0.28 g of (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(2-methylphenyl)carbohydrazide was obtained, after crystallization from 7.5 cm$^3$ of isopropyl acetate, the characteristic of which compound was as follows:

melting point=235° C.

EXAMPLE 30

Isolation of the dextrorotatory enantiomer of (3aRS,4SR,9SR,9aRS)-4,9-ethano-2-[2-(2-methoxyphenyl)acetyl]-9-(4-methylphenyl)-2,3,3a,4,9,9a-hexahydro-1H-benzo[f]isoindole-3a-carboxylic Acid (3aRS,4SR,9SR,9aRS)-4,9-Ethano-2-[2-(2-methoxyphenyl)acetyl]-9-(4-methylphenyl)-2,3,3a,4,9,9a-hexahydro-1H-benzo[f]isoindole-3a-carboxylic acid, obtained in Example 5, was resolved, on a chiral silica column carrying N-(3,5-dinitrobenzoyl)-(S)-phenylalanine grafts, by carrying out the resolution as in Example 3. On collecting the second fraction eluted by a mixture of dichloromethane, of isopropanol and of n-heptane (85/10/5 by volume), 70 mg of the dextrorotatory enantiomer of (3aRS,4SR,9SR,9aRS)-4,9-ethano-2-[2-(2-methoxyphenyl)acetyl]-9-(4-methylphenyl)-2,3,3a,4,9,9a-hexahydro-1H-benzo[f]isoindole-3a-carboxylic acid were obtained, after concentrating under reduced pressure, the characteristics of which compound were as follows:

melting point=205° C.;

mass spectrum (EI): M/Z=481 (M$^+$);

optical rotation: $[\alpha]_{365}^{20}$=+59.5+/−0.9° (c=0.5, methanol).

EXAMPLE 31

Preparation of methyl (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-carboxylate Stage A 7.1 cm$^3$ of 1,4-benzodioxane were added, under an argon atmosphere, to a solution of 6.3 g of methyl (3aRS,4SR,7aRS)-2-benzyl-7-oxo-4-phenyloctahydroisoindole-3a-carboxylate in 60 cm$^3$ of dichloromethane stabilized over amylene; this solution was cooled by a bath of ice-cold water and 10.7 cm$^3$ of 99% trifluoromethanesulphonic acid were run in over 5 minutes. After stirring in the cold bath, the temperature was allowed to rise to a temperature in the region of 20° C. and reaction was allowed to take place at this temperature for twenty-one hours, under an argon atmosphere. 200 cm$^3$ of distilled water were then run in, followed by 300 cm$^3$ of ethyl acetate. The organic phase was separated by settling and washed successively three times with 180 cm$^3$ of a 1N aqueous sodium hydroxide solution and then 240 cm$^3$ of a saturated aqueous sodium chloride solution, and then dried over magnesium sulphate. After filtration, the organic phase was evaporated under reduced pressure to give 10.8 g of an oil. This oil was purified by flash chromatography on an 8-cm diameter column containing 430 g of silica gel (230–400 mesh), elution being carried out successively with 1 dm$^3$ of the cyclohexane/ethyl acetate (98/2 by volume) mixture, then 2 dm$^3$ of the cyclohexane/ethyl acetate (95/5 by volume) mixture and then the cyclohexane/ethyl acetate (90/10 by volume) mixture, 50-cm$^3$ fractions were collected. After concentrating the solvent under reduced pressure, 5.41 g of impure methyl (3aRS,4SR,9SR,9aRS)-2-benzyl-9-(2,3-dihydro-1,4-benzodioxin-6-yl)-4,9-ethano-2,3,3a,4,9,9a-hexahydro-1H-benzo[f]isoindole-3a-carboxylate were obtained in the form of a white foam, which can be used as was in the following stage, the characteristics of which compound were as follows:

mass spectrum (EI): M/Z=481 (M$^+$).

$^1$H N.M.R. spectrum (300 MHz, CDCl$_3$, δ in ppm): 1.45, 1.65 and from 2.40 to 2.55 (3 mts, respectively 1H, 1H and 2H, CH$_2$CH$_2$), 2.31 and 3.20 (2 d, J=10 Hz, each 1H, CH$_2$ at 3), from 2.35 to 2.45 (mt, 1H, 1H of the CH$_2$ at 1), 2.81 (d, J=10 Hz, 1H, the other H of the CH$_2$ at 1), from 3.00 to 3.20 (mt, 1H, CH at 9a), from 3.30 to 3.45 and 3.71 (respectively mt and d (broad), J=13 Hz, each 1H, NCH$_2$Ar), 3.39 (broad s, 1H, CH at 4), 3.55 (s, 3H, COOCH$_3$), 4.31 (s, 4H, OCH$_2$CH$_2$O), 6.63 (broad d, J=7.5 Hz, 1H, H at 8), from 6.85 to 7.40 (mt, 11H, H at 5, H at 6, H at 7, aromatic H of the benzyl and aromatic H of the 1,4-benzodioxanyl).

Stage B

By carrying out the reaction as in Example 1, Stage E, starting from 5.4 g of methyl (3aRS,4SR,9SR,9aRS)-2-benzyl-9-(2,3-dihydro-1,4-benzodioxin-6-yl)-4,9-ethano-2,3,3a,4,9,9a-hexahydro-1H-benzo[f]isoindole-3a-carboxylate, from 2.16 g of ammonium formate and from 1.35 g of 10% (w/w) palladium hydroxide-on-charcoal in 80 cm$^3$ of refluxing methanol for five hours, 4 g of impure methyl (3aRS,4SR,9SR,9aRS)-9-(2,3-dihydro-1,4-benzodioxin-6-yl)-4,9-ethano-2,3,3a,4,9,9a-hexahydro-1H-benzo[f]isoindole-3a-carboxylate were obtained in the form of an off-white foam, which was used in the following stage, the characteristic of which compound was as follows:

mass spectrum (DCI):M/Z=392 (M+H$^+$).

Stage C

By carrying out the reaction as in Example 1, Stage G, starting from a solution of 0.275 g of 2-(2-methoxyphenyl) propenoic acid in 5 cm$^3$ of dichloromethane containing 4 drops of N,N-dimethylformamide, a solution of 0.2 cm$^3$ of oxalyl chloride in 7 cm$^3$ of dichloromethane was added dropwise. The reaction mixture was stirred for a further two hours at a temperature in the region of 20° C. and then cooled to a temperature in the region of 0° C.; the introduction was then carried out, over twenty minutes, of a solution of 0.73 g of impure methyl (3aRS,4SR,9SR,9aRS)-9-(2,3-dihydro-1,4-benzodioxin-6-yl)-4,9-ethano-2,3,3a,4,9,9a-hexahydro-1H-benzo[f]isoindole-3a-carboxylate in 15 cm$^3$ of dichloromethane, followed by 0.4 cm$^3$ of triethylamine. The reaction mixture was stirred at the same temperature for one hour and 100 cm$^3$ of distilled water were run in; dilution was carried out with dichloromethane, so as to bring the organic phase to approximately 200 cm$^3$. The pH was brought to 11 by running in 10 cm$^3$ of a 32% aqueous ammonia solution, the aqueous phase was separated by settling and then the organic phase was washed with successively 100 cm$^3$ of a 1N aqueous hydrochloric acid solution, then 100 cm$^3$ of distilled water and then 100 cm$^3$ of a saturated aqueous sodium chloride solution. After drying over magnesium sulphate, the organic phase was evaporated to give 0.75 g of an oil, which was purified by flash chromatography on silica gel (230–400 mesh), elution being carried out with a mixture of cyclohexane and ethyl acetate (60/40 by volume), 10-cm$^3$ fractions were collected. The fractions containing the good product (140 to 650 cm$^3$) were combined and evaporated without going to dryness to give an oil, which was taken up in diisopropyl ether; 465 mg of methyl (3aRS,4SR,9SR,9aRS)-9-(2,3-dihydro-1,4-benzodioxin-6-yl)-4,9-ethano-2-[2(2-methoxyphenyl) propenoyl]-2,3,3a,4,9,9a-hexahydro-1H-benzo[f]isoindole-3a-carboxylate were thus obtained in the form of a white powder, the characteristics of which were as follows:

melting point=184° C.;

mass spectrum (EI): M/Z=551 (M$^+$).

$^1$H N.M.R. spectrum (400 MHz, (CD$_3$)$_2$SO, at a temperature of 403 K, δ in ppm): 1.40, 1.58, 1.96 and 2.12 (4 mts, each 1H, CH$_2$CH$_2$), from 3.25 to 3.45 (mt, 3H, CH$_2$ at 1 and CH at 9a), 3.42 (mt, 1H, CH at 4), 3.52 (s, 3H, COOCH$_3$), 3.60 and 4.06 (respectively d and d (broad), J=13 Hz, each 1H, CH$_2$ at 3), 3.73 (s, 3H, ArOCH$_3$), 4.31 (s, 4H, OCH$_2$CH$_2$O), 5.54 and 5.68 (2 s, each 1H, =CH$_2$), 6.51 (broad d, J=7.5 Hz, 1H, H at 8), from 6.75 to 7.35 (mt, 10H, H at 5, H at 6, H at 7, aromatic H of the 2-methoxyphenyl and aromatic H of the 1,4-benzodioxanyl).

EXAMPLE 32

Preparation of (3aRS,4SR,9SR,9aRS)-9-(2,3-dihydro-1,4-benzodioxin-6-yl)-4,9-ethano-2-[2-(2-methoxyphenyl)-propenoyl]-2,3,3a,4,9,9a-hexahydro-1H-benzo[f]isoindole-3a-carboxylic Acid By carrying out the reaction as in Example 2, but from 5.43 g of methyl (3aRS,4SR,9SR,9aRS)-9-(2,3-dihydro-1,4-benzodioxin-6-yl)-4,9-ethano-2-[2-(2-methoxyphenyl) propenoyl]-2,3,3a,4,9,9a-hexahydro-1H-benzo[f]isoindole-3a-carboxylate, obtained in the preceding example, and from 40 cm$^3$ of a normal aqueous sodium hydroxide solution in 150 cm$^3$ of refluxing dioxane for sixteen hours, then addition of 50 cm$^3$ of a normal aqueous sodium hydroxide solution, at reflux for four hours, and then 3.5 cm$^3$ of a 10N aqueous sodium hydroxide solution, at reflux for sixteen hours, 3.76 g of a beige-coloured solid were obtained after taking up in diisopropyl ether. By dissolving in 50 cm$^3$ of absolute ethanol and then diluting with 12.5 cm$^3$ of distilled water, 2.64 g of (3aRS,4SR,9SR,9aRS)-9-(2,3-dihydro-1,4- benzodioxin-6-yl)-4,9-ethano-2-[2-(2-methoxyphenyl)
propenoyl]-2,3,3a,4,9,9a-hexahydro-1H-benzo[f]isoindole-
3a-carboxylic acid were obtained in the form of a white
powder, the characteristics of which were as follows:

melting point=78° C.;

mass spectrum (EI): M/Z=537 (M+).

$^1$H N.M.R. spectrum (250 MHz, $(CD_3)_2SO$, at a temperature of 383 K, δ in ppm): 1.38, 1.57, 1.94 and 2.11 (4 mts, each 1H, $CH_2CH_2$), from 3.20 to 3.45 (mt, 3H, $CH_2$ at 1 and CH at 9a), 3.42 (mt, 1H, CH at 4), 3.59 and 4.06 (respectively d and d (broad), J=13 Hz, each 1H, $CH_2$ at 3), 3.73 (s, 3H, $ArOCH_3$), 4.31 (s, 4H, $OCH_2CH_2O$), 5.54 and 5.69 (2 s, each 1H, =$CH_2$), 6.50 (broad d, J=7.5 Hz, 1H, H at 8), from 6.75 to 7.40 (mt, 10H, H at 5, H at 6, H at 7, aromatic H of the 2-methoxyphenyl and aromatic H of the 1,4-benzodioxanyl).

EXAMPLE 33

Preparation of (3aRS,4SR,9SR,9aRS)-9-(2,3-
dihydro-1,4-benzodioxin-6-yl)-4,9-ethano-2-[2-(2-
methoxyphenyl)propenoyl]-2,3,3a,4,9,9a-hexahydro-
1H-benzo[f]isoindole-3a-N-(3-pyridylmethyl)
carboxamide By carrying out the reaction as in Example 13, and by starting from 0.5 g of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-carboxylic acid, from 0.24 cm³ of oxalyl chloride and from 0.5 cm³ of N,N-dimethylformamide, in 20 cm³ of dichloromethane, for 2 hours, then evaporation to dryness, taken up in 20 cm³ of dichloromethane and addition of 0.09 cm³ of 3-aminomethylpyridine and of 0.26 cm³ of triethylamine in 15 cm³ of dichloromethane; then, after stirring for eighteen hours at a temperature in the region of 20° C., successively running in 50 cm³ of distilled water and 40 cm³ of a normal aqueous sodium hydroxide solution; dilution with 200 cm³ of dichloromethane; separation by settling and washing of the organic phase with two times 100 cm³ of a normal aqueous hydrochloric acid solution, then 200 cm³ of a saturated aqueous sodium chloride solution and finally drying over magnesium sulphate, 0.38 g of a green-yellow foam was obtained, which foam was recrystallized from diisopropyl ether to produce 249 mg of a yellow solid, which was then purified on a Merck 60F254 preparative silica plate, elution being carried out with the dichloromethane/methanol (90/10 by volume) mixture. An orange-coloured oil was thus obtained which, taken up in diisopropyl ether, gave 165 mg of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide in the form of a white powder, the characteristics of which were as follows:

melting point=228° C.;

mass spectrum (EI): M/Z=627 (M+).

$^1$H N.M.R. spectrum (250 MHz, $(CD_3)_2SO$, at a temperature of 373 K, δ in ppm): 1.38, 1.56, 1.93 and 2.10 (4 mts, each 1H, $CH_2CH_2$), from 3.20 to 3.55 (mt, 3H, $CH_2$ at 1 and CH at 9a), 3.43 (d, J=12.5 Hz, 1H, 1H of the $CH_2$ at 3), 3.57 (broad s, 1H, CH at 4), 3.71 (s, 3H, $ArOCH_3$), from 4.05 to 4.30 (mt, 3H, the other H of the $CH_2$ at 3 and $NCH_2Ar$), 4.31 (s, 4H, $OCH_2CH_2O$), 5.52 and 5.70 (2s, each 1H, =$CH_2$), 6.48 (mt, 1H, H at 8), from 6.75 to 7.45 (mt, 12H, H at 5, H at 7, aromatic H of the 2-methoxyphenyl, aromatic H of the 1,4-benzodioxanyl, H at 4 of the pyridyl and H at 5 of the pyridyl), 8.10 (mt, 1H, CONH), 8.38 (broad s, 1H, H at 2 of the pyridyl), 8.45 (broad d, J=5 Hz, 1H, H at 6 of the pyridyl).

EXAMPLE 34

Isolation of the dextrorotatory enantiomer of
(3aRS,4SR,9SR,9aRS)-9-(2,3-dihydro-1,4-
benzodioxin-6-yl)-4,9-ethano-2-[2-(2-
methoxyphenyl)propenoyl]-2,3,3a,4,9,9a-hexahydro-
1H-benzo[f]isoindole-3a-N-(3-pyridylmethyl)
carboxamide By carrying out the reaction as in Example 18, but from 17 g of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide, in 10 successive injections, on a Whelk 01 (SS) chiral silica column, elution being carried out with an n-heptane/ethanol/triethylamine (70/30/0.05 by volume) mixture and the first product eluted (retention time=45 min) being isolated, 8.4 g of the dextrorotatory enantiomer of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide were obtained, after concentrating the solvent under reduced pressure, in the form of a white powder, the characteristics of which were as follows:

mass spectrum (EI): M/Z=627 (M+);

optical rotation: $[\alpha]_{365}^{20}$=+103.2+/−1.5° (c=0.5, methanol).

EXAMPLE 35

Isolation of the levorotatory enantiomer of (3aRS,
4SR,9SR,9aRS)-9-(2,3-dihydro-1,4-benzodioxin-6-
yl)-4,9-ethano-2-[2-(2-methoxyphenyl)propenoyl]-2,
3,3a,4,9,9a-hexahydro-1H-benzo[f]isoindole-3a-N-
(3-pyridylmethyl)carboxamide By carrying out the reaction as in Example 19, but from 17 g of (3aRS,4SR,9SR,9aRS)-9-(2,3-dihydro-1,4-benzodioxin-6-yl)-4,9-ethano-2-[2-methoxyphenyl)propenoyl]-2,3,3a,4,9,9a-hexahydro-1H-benzo[f]isoindole-3a-N-(3-pyridylmethyl)carboxamide, in 10 successive injections, on a Whelk 01 (SS) chiral silica column, elution being carried out with a mixture of n-heptane, of ethanol and of triethylamine (70/30/0.05 by volume) and the second product eluted (retention time=67 min) being isolated, 6.6 g of the levorotatory enantiomer of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide were obtained, after concentrating the solvent under reduced pressure, in the form of a white powder, the characteristics of which were as follows:

mass spectrum (EI): M/Z=627 (M+);

optical rotation: $[\alpha]_{365}^{20}$=−102+/−1.5° (c=0.5, methanol).

EXAMPLE 36

Preparation of (3aRS,4SR,9SR,9aRS)-9-(2,3-
dihydro-1,4-benzodioxin-6-yl)-4,9-ethano-2-[2-(2-
methoxyphenyl)propenoyl]-2,3,3a,4,9,9a-hexahydro-
1H-benzo[f]isoindole-3a-N-(2-thienylmethyl)
carboxamide By carrying out the reaction as in Example 33, and by starting from 0.5 g of (3aRS,4SR,9SR,9aRS)-9-(2,3- dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-carboxylic acid, from 0.24 cm³ of oxalyl chloride, from 0.1 cm³ of N,N-dimethylformamide, in 20 cm³ of dichloromethane, and then from 0.1 cm³ of 2-(aminomethyl)thiophene and from 0.26 cm³ of triethylamine in 15 cm³ of dichloromethane, 29 mg of (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(2-thienylmethyl)carboxamide were obtained, after lyophilization, in the form of a powder, the characteristics of which were as follows:

melting point=134° C.;

mass spectrum (EI): M/Z=632 (M⁺).

EXAMPLE 37

Preparation of (3aRS,4SR,9SR,9aRS)-4,9-ethano-2-[(2-methoxyphenyl)acetyl]-9-(3,4,5-trimethylphenyl)-2,3,3a,4,9,9a-hexahydro-1H-benzo[f]isoindole-3a-carboxylic Acid Stage A The reaction was carried out as in Example 31, Stage A, starting from 3.49 g of methyl (3aRS,4SR,7aRS)-2-[(2-methoxyphenyl)acetyl]-7-oxo-4-phenyloctahydroisoindole-3a-carboxylate in 40 cm³ of dichloromethane stabilized over amylene, from 3.34 cm³ of 1,2,3-trimethylbenzene and from 5.1 cm³ of trifluoromethanesulphonic acid; after stirring for eighteen hours at a temperature in the region of 20° C., 2.8 cm³ of trifluoromethanesulphonic anhydride were added and the reaction mixture was stirred for a further 18 hours. 263 mg of methyl (3aRS,4SR,9SR,9aRS)-4,9-ethano-2-[(2-methoxyphenyl)acetyl]-9-(3,4,5-trimethylphenyl)-2,3,3a,4,9,9a-hexahydro-1H-benzo[f]isoindole-3a-carboxylate were thus obtained in the form of a white powder, the characteristics of which were as follows:

melting point=159° C.;

mass spectrum (EI): M/Z=523 (M⁺).

Stage B

By carrying out the reaction as in Example 2, from 192 mg of methyl (3aRS,4SR,9SR,9aRS)-4,9-ethano-2-[(2-methoxyphenyl)acetyl]-9-( 3,4,5-trimethylphenyl)-2,3,3a,4,9,9a-hexahydro-1H-benzo[f]isoindole-3a-carboxylate at reflux for eighteen hours in 0.55 cm³ of 1N aqueous sodium hydroxide solution and 20 cm³ of ethanol, 69.3 mg of (3aRS,4SR,9SR,9aRS)-4,9-ethano-2-[(2-methoxyphenyl)acetyl]-9-(3,4,5-trimethylphenyl)-2,3,3a,4,9,9a-hexahydro-1H-benzo[f]isoindole-3a-carboxylic acid were obtained, after recrystallization from 5 cm³ of diisopropyl ether, in the form of a white powder, the characteristics of which were as follows:

melting point=>260° C.;

mass spectrum (EI): M/Z=509 (M⁺).

EXAMPLE 38

Preparation of (3aRS,4SR,9SR,9aRS)-4,9-ethano-2-[2-(2-methoxyphenyl)propenoyl]-9-(2-methylphenyl)-2,3,3a,4,9,9a-hexahydro-1H-benzo[f]isoindole-3a-carboxylic Acid Stage A By carrying out the reaction as in Stage C of Example 1, but from 1.33 cm³ of 2-bromotoluene, from 0.27 g of magnesium turnings and from 2 g of methyl (3aRS,4SR,7aRS)-2-benzyl-7-oxo-4-phenyloctahydroisoindole-3a-carboxylate, 2.2 g of methyl (3aRS,4SR,7RS,7aRS)-2-benzyl-7-hydroxy-7-(2-methylphenyl)-4-phenyloctahydroisoindole-3a-carboxylate were obtained, after purification by flash chromatography on silica gel (230–400 mesh), elution being carried out with a cyclohexane/ethyl acetate (90/10 by volume) mixture, in the form of a pale-yellow foam, was used in the subsequent syntheses.

Stage B

A mixture of 3.2 cm³ of trifluoromethanesulphonic acid and of 3 cm³ of dichloromethane was added dropwise to a solution of 2.2 g of methyl (3aRS,4SR,7RS,7aRS)-2-benzyl-7-hydroxy-7-(2-methylphenyl)-4-phenyloctahydroisoindole-3a-carboxylate in 20 cm³ of dichloromethane maintained at a temperature in the region of 0° C. The reaction mixture was stirred for thirty minutes at a temperature in the region of 0° C. and twenty hours at a temperature in the region of 20° C. and then cooled to a temperature in the region of 0° C. The pH was then brought to 8 by addition of a normal aqueous sodium hydroxide solution. The aqueous phase was separated by settling and extracted with three times 50 cm³ of dichloromethane. The organic phases were combined, washed with three times 100 cm³ of distilled water and 100 cm³ of a saturated aqueous sodium chloride solution, dried over magnesium sulphate and concentrated under reduced pressure. 1.9 g of methyl (3aRS,4SR)-2-benzyl-7-(2-methylphenyl)-4-phenyl-1,3,3a,4,5,6-hexahydroisoindole-3a-carboxylate were thus obtained in the form of an oil, and used in the subsequent syntheses, the characteristics of which were as follows:

¹H N.M.R. spectrum (250 MHz, CDCl₃ with addition of a few drops of d4-CD₃COOD, δ in ppm): 1.90 (mt, 1H, 1H of the CH₂ at 5), 2.17 (s, 3H, ArCH₃), from 2.40 to 2.55 (mt, 2H, the other H of the CH₂ at 5 and 1H of the CH₂ at 6), 2.66 (mt, 1H, the other H of the CH₂ at 6), 3.08 (dd, J=11 and 2.5 Hz, 1H, CH at 4), 3.32 (mt, 1H, 1H of the CH₂ at 1), 3.63 (s, 3H, COOCH₃), from 3.60 to 3.70 (mt, 1H, 1H of the CH₃ at 3), 3.75 (d, J=11.5 Hz, the other H of the CH₂ at 1), 3.92 (d, J=10 Hz, the other H of the CH₂ at 3), 3.98 and 4.32 (2 d, J=11 Hz, each 1H, NCH₂Ar), from 6.90 to 7.40 (mt, 14H, aromatic H of the phenyl, aromatic H of the benzyl and aromatic H of the 2-methylphenyl).

Stage C

A mixture of 5.8 cm³ of trifluoromethanesulphonic acid and of 5 cm³ of dichloromethane was added dropwise to a solution of 1.9 g of methyl (3aRS,4SR,9SR,9aRS)-2-benzyl-7-(2-methylphenyl)-4-phenyl-1,3,3a,4,5,6-hexahydroisoindole-3a-carboxylate in 50 cm³ of dichloromethane maintained at a temperature in the region of 0° C. The reaction mixture was stirred for one hour at a temperature in the region of 0° C. and ninety-six hours at a temperature in the region of 20° C. and then cooled to a temperature in the region of 0° C. The pH was then brought to 8 by addition of a normal aqueous sodium hydroxide solution. The organic phase was separated by settling, washed with 100 cm³ of distilled water and 100 cm³ of a saturated aqueous sodium chloride solution, dried over magnesium sulphate and concentrated under reduced pressure. The residue was purified by flash chromatography on silica gel (230–400 mesh), elution being carried out with a cyclohexane/ethyl acetate (95/5 by volume) mixture. 0.85 g of methyl (3aRS,4SR,9SR,9aRS)-2-benzyl-4,9-ethano-9-(2-methylphenyl)-2,3,3a,4,9,9a-hexahydro-1H-benzo[f]isoindole-3a-carboxylate was obtained in the form of an oil, and used in the subsequent syntheses.

Stage D

By carrying out the reaction as in Stage E of Example 1, but from 0.85 g of methyl (3aRS,4SR,9SR,9aRS)-2-benzyl-4,9-ethano-9-(2-methylphenyl)-2,3,3a,4,9,9a-hexahydro- 1H-benzo[f]isoindole-3a-carboxylate, from 0.37 g of ammonium formate and from 0.15 g of 10% (w/w) palladium-on-charcoal, 0.6 g of methyl (3aRS,4SR,9SR,9aRS)-4,9-ethano-9-(2-methylphenyl)-2,3,3a,4,9,9a-hexahydro-1H-benzo[f]isoindole-3a-carboxylate was obtained, after flash chromatography on silica gel (230–400 mesh), elution being carried out with a cyclohexane/ethyl acetate (70/30 by volume) mixture, in the form of a colourless oil, and was used in the subsequent syntheses.

Stage E

By carrying out the reaction as in Stage G of Example 1, but from 0.6 g of methyl (3aRS,4SR,9SR,9aRS)-4,9-ethano-9-(2-methylphenyl)-2,3,3a,4,9,9a-hexahydro-1H-benzo[f]isoindole-3a-carboxylate, from 0.31 g of 2-(2-methoxyphenyl)propenoic acid and from 0.15 cm³ of oxalyl chloride, 0.51 g of methyl (3aRS,4SR,9SR,9aRS)-4,9-ethano-2-[2-(2-methoxyphenyl)propenoyl]-9-(2-methylphenyl)-2,3,3a,4,9,9a-hexahydro-1H-benzo[f]isoindole-3a-carboxylate was obtained, after purification by flash chromatography on silica gel (230–400 mesh), elution being carried out with a cyclohexane/ethyl acetate (70/30 by volume) mixture, in the form of an off-white foam, and used in the subsequent syntheses.

Stage F

By carrying out the reaction as in Example 2, but from 0.51 g of methyl (3aRS,4SR,9SR,9aRS)-4,9-ethano-2-[2-(2-methoxyphenyl)propenoyl]-9-(2-methylphenyl)-2,3,3a,4,9,9a-hexahydro-1H-benzo[f]isoindole-3a-carboxylate in 1.5 cm³ of a normal aqueous sodium hydroxide solution and 15 cm³ of ethanol, 0.22 g of (3aRS,4SR,9SR,9aRS)-4,9-ethano-2-[2-(2-methoxyphenyl)propenoyl]-9-(2-methylphenyl)-2,3,3a,4,9,9a-hexahydro-1H-benzo[f]isoindole-3a-carboxylic acid was obtained, after recrystallization from isopropanol, the characteristic of which compound was as follows:

melting point: above 260° C.

$^1$H N.M.R. spectrum (250 MHz, (CD$_3$)$_2$SO, at a temperature of 393 K, δ in ppm): from 1.15 to 1.50 and from 2.05 to 2.35 (2 mts, each 2H, CH$_2$CH$_2$), 2.25 (s, 3H, ArCH$_3$), 3.13 (dd, J=12 and 9 Hz, 1H, 1H of the CH$_2$ at 1), 3.31 (broad d, J=12 Hz, 1H, the other H of the CH$_2$ at 1), 3.44 (mt, 1H, CH at 4), 3.60 and 4.05 (respectively d and d (broad), J=12.5 Hz, each 1H, CH$_2$ at 3), 3.75 (s, 3H, ArOCH$_3$), 5.54 and 5.69 (2 s, each 1H, =CH$_2$), 6.62 (broad d, J=7.5 Hz, 1H, H at 8), from 6.90 to 7.45 (mt, 11H, H at 5, H at 6, H at 7, aromatic H of the 2-methoxyphenyl and aromatic H of the 2-methylphenyl).

EXAMPLE 39

Preparation of methyl (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylate Stage A 0.8 g of magnesium turnings was added to a solution of 7.2 g of 4-(trifluoromethyl)bromobenzene in 40 cm³ of dry diethyl ether. The reaction mixture was spontaneously brought to reflux for ten minutes and was then heated at reflux for twenty minutes. The reaction mixture was subsequently cooled and a solution of 5.6 g of methyl (3aRS,4SR,7aRS)-2-benzyl-7-oxo-4-phenyloctahydroisoindole-3a-carboxylate in 40 cm³ of dry diethyl ether was added over fifteen minutes at a temperature in the region of 10° C. The reaction mixture was stirred for ten minutes at a temperature in the region of 10° C. and then poured into 150 cm³ of a saturated aqueous ammonium chloride solution. The aqueous phase was separated by settling and extracted with three times 75 cm³ of diethyl ether. The organic phases were combined, washed successively with three times 75 cm³ of distilled water, dried over magnesium sulphate in the presence of 3S charcoal and concentrated under reduced pressure. After crystallization from 25 cm³ of pentane, 5.2 g of methyl (3aRS,4SR,7RS,7aRS)-2-benzyl-7-hydroxy-7-[4-(trifluoromethyl)phenyl]-4-phenyloctahydroisoindole-3a-carboxylate were obtained in the form of a beige solid, the characteristic of which was as follows:

melting point=164° C.

Stage B 4 g of methyl (3aRS,4SR,7RS,7aRS)-2-benzyl-7-hydroxy-7-[4-(trifluoromethyl)phenyl]-4-phenyloctahydroisoindole-3a-carboxylate were added to 20 cm³ of trifluoromethanesulphonic acid cooled to a temperature in the region of 0° C. The reaction mixture was stirred for 3 hours at a temperature in the region of 20° C. and then cooled to a temperature in the region of 10° C. 50 cm³ of distilled water were then added and then the pH of the aqueous phase was brought to between 8 and 9 by addition of a 30% aqueous sodium hydroxide solution, the temperature always being maintained in the region of 10 to 15° C. with a bath containing an ethanol/dry ice mixture. The aqueous phase was separated by settling and extracted with three times 75 cm³ of ethyl acetate. The organic extracts were combined, washed with three times 75 cm³ of distilled water, dried over magnesium sulphate in the presence of 3S charcoal and concentrated under reduced pressure. 3.4 g of methyl (3aRS,4SR,9SR,9aRS)-2-benzyl-4,9-ethano-9-[4-(trifluoromethyl)phenyl]-2,3,3a,4,9,9a-hexahydro-1H-benzo[f]isoindole-3a-carboxylate were thus obtained in two crops, after crystallization from petroleum ether, in the form of a white solid, the characteristic of which was as follows:

melting point: 132° C.

Stage C

By carrying out the reaction as in Stage E of Example 1, but from 3.4 g of methyl (3aRS,4SR,9SR,9aRS)-2-benzyl-4,9-ethano-9-[4-(trifluoromethyl)phenyl]-2,3,3a,4,9,9a-hexahydro-1H-benzo[f]isoindole-3a-carboxylate, from 1.3 g of ammonium formate and from 0.4 g of 10% (w/w) palladium-on-charcoal, 2.2 g of methyl (3aRS,4SR,9SR,9aRS)-4,9-ethano-9-[4-(trifluoromethyl)phenyl]-2,3,3a,4,9,9a-hexahydro-1H-benzo[f]isoindole-3a-carboxylate were obtained in the form of a white solid, a characteristic of which was as follows:

melting point=172° C.

Stage D

By carrying out the reaction as in Stage G of Example 1, but from 1.4 g of methyl (3aRS,4SR,9SR,9aRS)-4,9-ethano-9-[4-(trifluoromethyl)phenyl]-2,3,3a,4,9,9a-hexahydro-1H-benzo[f]isoindole-3a-carboxylate, from 0.62 g of 2-(2-methoxyphenyl)propenoic acid, from 0.94 cm³ of triethylamine and from 0.3 cm³ of oxalyl chloride, 1.3 g of methyl (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylate were obtained, after purification by flash chromatography on silica gel (230–400 mesh), elution being carried out with a cyclohexane/ethyl acetate (50/50 by volume) mixture, and crystallization from diisopropyl ether, the characteristics of which compound were as follows:

melting point=163° C.

$^1$H N.M.R. spectrum (250 MHz, (CD$_3$)$_2$SO, at a temperature of 373 K, δ in ppm): 1.45, 1.72 and from 1.95 to 2.25 (3 mts, respectively 1H, 1H and 2H, CH$_2$CH$_2$), from 3.20 to 3.45 (mt, 3H, CH$_2$ at 1 and CH at 9a), 3.48 (mt, 1H, CH at 4), 3.55 (s, 3H, COOCH$_3$), 3.61 and 4.11 (respectively d and d (broad), J=12.5 Hz, each 1H, CH₂ at 3), 3.70 (s, 3H, ArOCH₃), 5.55 and 5.68 (2 s, each 1H, =CH₂), 6.36 (broad d, J=7.5 Hz, 1H, H at 8), from 6.90 to 7.40 (mt, 7H, H at 5, H at 6, H at 7 and aromatic H of the 2-methoxyphenyl), 7.59 and 7.83 (2 broad d, J=8 Hz, each 2H, aromatic H of the 4-trifluoromethylphenyl).

EXAMPLE 40

Preparation of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic Acid By carrying out the reaction as in Example 2, but from 1.1 g of methyl (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylate, from 9.8 cm³ of a normal aqueous sodium hydroxide solution and 20 cm³ of methanol, 0.65 g of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic acid was obtained, after crystallization from diisopropyl ether, base/acid passage and recrystallization from 8 cm³ of isopropyl acetate, the characteristic of which compound was as follows:

melting point=153° C.

EXAMPLE 41

Isolation of the dextrorotatory enantiomer of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic Acid 11 g of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic acid, obtained in Example 40, were resolved on a chiral silica column carrying N-(3,5-dinitrobenzoyl)-(R)-phenylalanine grafts, in 4 successive injections and by eluting with a mixture of n-heptane, of dichloromethane and of ethanol (50/50/1 by volume). On collecting the first fractions eluted (retention time 31 min), 5 g of the dextrorotatory enantiomer of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic acid were obtained, after concentrating under reduced pressure, in the form of a white powder, the characteristics of which were as follows:

melting point=228° C.;

mass spectrum (EI): M/Z=547 (M⁺);

optical rotation: $[\alpha]_{365}^{20}$=+63.1+/−1.2° (c=0.5, methanol).

The chiral stationary phase carrying N-(3,5-dinitrobenzoyl)-(R)-phenylalanine grafts was prepared according to the synthesis described in Example 3, by replacing N-(3,5-dinitrobenzoyl)-(S)-phenylalanine by N-(3,5-dinitrobenzoyl)-(R)-phenylalanine.

EXAMPLE 42

Preparation of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-N-(3-pyridylmethyl)carboxamide 0.24 cm³ of 3-(aminomethyl)pyridine, 0.46 g of 1-ethyl-3-[3-(dimethylamino)propyl]carbodiimide hydrochloride and 0.16 g of N-1-hydroxybenzotriazole hydrate were successively added to a solution of 1.1 g of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic acid in 20 cm³ of dichloromethane. The reaction mixture was stirred for forty-eight hours at a temperature in the region of 20° C. The organic phase was washed with three times 10 cm³ of distilled water, dried over magnesium sulphate and concentrated under reduced pressure. After recrystallizing from 15 cm³ of isopropanol, 0.95 g of (3aRS,4SR,9SR,9aRS)-4,9-ethano-2-[2-(2-methoxyphenyl)propenoyl]-9-(4-(trifluoromethyl)phenyl]-2,3,3a,4,9,9a-hexahydro-1H-benzo[f]isoindole-3a-N-(3-pyridylmethyl)carboxamide was obtained, the characteristic of which was as follows:

melting point=214° C.

EXAMPLE 43

Preparation of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-N'-benzoylcarbohydrazide 0.16 g of benzoylhydrazine, 0.23 g of 1-ethyl-3-[3-(dimethylamino)propyl]carbodiimide hydrochloride and 81 mg of N-1-hydroxybenzotriazole hydrate were successively added to a solution of 0.55 g of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic acid in 10 cm³ of dichloromethane. The reaction mixture was stirred for twenty hours at a temperature in the region of 20° C. and then filtered through sintered glass. The precipitate was washed successively with three times 1.5 cm³ of dichloromethane and then three times 2.5 cm³ of distilled water. 0.34 g of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-N'-benzoylcarbohydrazide was thus obtained, the characteristics of which were as follows:

melting point=275° C.

¹H N.M.R. spectrum (250 MHz, (CD₃)₂SO, at a temperature of 383 K, δ in ppm): 1.44, 1.70, 2.01 and 2.18 (4 mts, each 1H, CH₂CH₂), from 3.20 to 3.40 (limit AB, 2H, CH₂ at 1), from 3.55 to 3.85 (mt, 3H, 1H of the CH₂ at 3, CH at 9a and CH at 4), 3.72 (s, 3H, ArOCH₃), 4.36 (broad d, J=12.5 Hz, 1H, the other H of the CH₂ at 3), 5.57 and 5.70 (2 s, each 1H, =CH₂), 6.34 (broad d, J=7.5 Hz, 1H, H at 8), from 6.85 to 7.60 (mt, 10H, H at 5, H at 6, H at 7, aromatic H at the meta positions of the benzoylcarbohydrazide, aromatic H at the para position of the benzoylcarbohydrazide and aromatic H of the 2-methoxyphenyl), 7.60 and 7.85 (2d, J=8 Hz, each 2H, aromatic H of the 4-trifluoromethylphenyl), 7.81 (d, J=8 Hz, 2H, aromatic H at the ortho positions of the benzoylcarbohydrazide), 9.66 and 9.91 (2 broad s, each 1H, CONHNHCO).

EXAMPLE 44

Preparation of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-N'-phenylcarbohydrazide 0.12 cm³ of phenylhydrazine, 0.23 g of 1-ethyl-3-[3-(dimethylamino)propyl]carbodiimide hydrochloride and 81 mg of N-1-hydroxybenzotriazole hydrate were successively added to a solution of 0.55 g of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-carboxylic acid in 10 cm³ of dichloromethane. The reaction mixture was stirred for twenty hours at a temperature in the region of 20° C. The reaction mixture was diluted with 15 cm³ of dichloromethane, washed with three times 10 cm³ of distilled water, dried over magnesium sulphate in the presence of 3S charcoal and concentrated under reduced pressure. After recrystallizing from 10 cm³ of isopropanol, 0.21 g of (3aRS,4SR,9SR,9aRS)-4,9-ethano-2-[2-(2-methoxyphenyl)propenoyl]-9-[4-(trifluoromethyl)phenyl]-2,3,3a,4,9,9a-hexahydro-1H-benzo[f]isoindole-3a-N'-phenylcarbohydrazide was obtained, the characteristics of which compound were as follows:

melting point: 226° C.

¹H N.M.R. spectrum (250 MHz, (CD₃)₂SO, at a temperature of 383 K, δ in ppm): 1.44, 1.69 and from 1.95 to 2.25 (3 mts, respectively 1H, 1H and 2H, CH₂CH₂), from 3.20 to 3.45 (limit AB, 2H, CH₂ at 1), 3.52 and 4.26 (respectively d and d (broad), J=12.5 Hz, each 1H, CH₂ at 3), 3.63 (mt, 1H, CH at 9a), 3.69 (s, 3H, ArOCH₃), 3.75 (mt, 1H, CH at 4), 5.55 and 5.68 (2 s, each 1H, =CH₂), 6.35 (broad d, J=7.5 Hz, 1H, H at 8), 6.60 (d, J=7.5 Hz, 2H, aromatic H at the ortho positions of the phenylcarbohydrazide), 6.70 (t, J=7.5 Hz, 1H, aromatic H at the para position of the phenylcarbohydrazide), from 6.90 to 7.45 (mt, 10H, H at 5, H at 6, H at 7, aromatic H at the meta positions of the phenylcarbohydrazide, aromatic H of the 2-methoxyphenyl and ArNH), 7.61 and 7.82 (2d, J=8 Hz, each 2H, aromatic H of the 4-trifluoromethylphenyl), 9.52 (broad s, 1H, CONH).

EXAMPLE 45

Preparation of methyl (3aRS,4SR,9SR,9aRS)-4,9-ethano-2-[2-(2-methoxyphenyl)propenoyl]-9-(2-naphthyl)-2,3,3a,4,9,9a-hexahydro-1H-benzo[f]isoindole-3a-carboxylate Stage A 21.4 g of hydrazine hydrate were added to a solution of 40 g of methyl 2-benzyl-7-oxo-4-phenyloctahydroisoindole-3a-carboxylate, obtained in Stage B of Example 1, in 300 cm³ of ethanol and then the reaction mixture was brought to reflux for two hours thirty minutes. After concentrating the solvent under reduced pressure, the residue was taken up in water and extracted with dichloromethane. The organic phase was separated by settling, washed with water and dried over magnesium sulphate. After concentrating under reduced pressure, 38.73 g (93%) of methyl (3aRs,4SR,7aRS)-2-benzyl-7-hydrazono-4-phenyloctahydroisoindole-3a-carboxylate were obtained in the form of a brown oil, the characteristics of which were as follows:

mass spectrum (EI): M/Z=377 (M⁺);
IR spectrum (in solution in dichloromethane):

| 3400 cm⁻¹ | ν NH |
| 3080, 3060, 3045, 3030 cm⁻¹ | ν CH, aromatic |
| 2950, 2800 cm⁻¹ | ν CH, aliphatic |
| 2730 cm⁻¹ | ν CH, N(CH₂)₃ |
| 1720 cm⁻¹ | ν C=O, methyl ester |
| 1605, 1495, 1455, 1435 cm⁻¹ | respiration of the aromatic nuclei |
| 1435 cm⁻¹ | δₛ CH₃, methyl ester |
| 1220 cm⁻¹ | ν O—C=O, methyl ester |

Stage B 52.07 g of iodine, in solution in 250 cm³ of tetrahydrofuran, were added dropwise to a solution of 37.75 g of methyl (3aRS,4SR,7aRS)-2-benzyl-7-hydrazono-4-phenyloctahydroisoindole-3a-carboxylate in 200 cm³ of tetrahydrofuran and 43 cm³ of triethylamine. Stirring was maintained at room temperature for one hour after the end of the addition. 1 dm³ of water and 1 dm³ of ethyl acetate were then added. The organic phase was separated by settling, washed successively with a saturated sodium hydrosulphite solution and then with a saturated sodium chloride solution, and dried over magnesium sulphate. After concentrating the solvent under reduced pressure, the residue was purified by flash chromatography on silica gel (230–400 mesh), elution being carried out with a mixture of cyclohexane and of ethyl acetate (95/5 by volume). 22.25 g (47%) of methyl (3aRS,4SR,7aRS)-2-benzyl-7-iodo-4-phenyl-2,3,3a,4,5,7a-hexahydro-1H-isoindole-3a-carboxylate were thus obtained in the form of a yellow pasty solid, the characteristics of which were as follows:

mass spectrum (EI): M/Z=473 (M⁺);
IR spectrum (in solution in carbon tetrachloride):

| 3080, 3060, 3030 cm⁻¹ | ν CH, aromatic |
| 2925, 2800 cm⁻¹ | V CH, aliphatic |
| 2730 cm⁻¹ | ν CH, N(CH₂)₃ |
| 1730 cm⁻¹ | ν C=O, methyl ester |
| 1600, 1495, 1455, 1435 cm⁻¹ | respiration of the aromatic nuclei |
| 1435 cm⁻¹ | δₛ CH₃, methyl ester |
| 1210 cm⁻¹ | ν O—C=O, methyl ester |
| 700 cm⁻¹ | γ CH, aromatic |

Stage C 240 mg of tetrakis(triphenylphosphine)palladium and then a solution of 0.69 g of 2-naphthylboronic acid, isolated in the trimer anhydride form, in 20 cm³ of methanol were added to a solution of 2 g of methyl (3aRS,4SR,7aRS)-2-benzyl-7-iodo-4-phenyl-2,3,3a,4,5,7a-hexahydro-1H-isoindole-3a-carboxylate in 40 cm³ of toluene. 45 cm³ of a 2N aqueous sodium carbonate solution were added dropwise and the reaction mixture is brought to reflux for four hours. After cooling, 80 cm³ of water and 60 cm³ of ethyl acetate were added. The organic phase was separated by settling, washing with water to neutrality and dried over magnesium sulphate. After concentrating the solvent under reduced pressure, the residue was purified by flash chromatography on silica gel (230–400 mesh), elution being carried out with a mixture of cyclohexane and of ethyl acetate (90/10 by volume). 1.33 g (67%) of methyl (3aRS,4SR,7aRS)-2-benzyl-7-(2-naphthyl)-4-phenyl-2,3,3a,4,5,7a-hexahydro-1H-isoindole-3a-carboxylate were thus obtained in the form of a white foam, the characteristic of which was as follows:

mass spectrum (EI): M/Z=473 (M⁺).

Stage D

By carrying out the reaction as in Stage C of Example 38, but from 1.66 g of methyl (3aRS,4SR,7aRS)-2-benzyl-7-(2-naphthyl)-4-phenyl-2,3,3a,4,5,7a-hexahydro-1H-isoindole-3a-carboxylate and from 1.9 cm³ of trifluoromethanesulphonic acid in solution in 20 cm³ of dry dichloromethane for four hours at room temperature, 1.22 g (51%) of a white foam were isolated after purification by flash chromatography on silica gel (230–400 mesh), elution being carried out with a mixture of cyclohexane and of ethyl acetate (95/5 by volume), the white foam mainly containing (approximately 90% by NMR quantitative determination) methyl (3aRS,4SR,9SR,9aRS)-2-benzyl-4,9-ethano-9-(2-naphthyl)-2,3,3a,4,9,9a-hexahydro-1H-benzo[f]isoindole-3a-carboxylate, which foam, was used in the continuation of the synthesis, had the following characteristics:

¹H N.M.R. spectrum (300 MHz, CDCl₃, δ in ppm): from 1.40 to 2.00 and 2.52 (2 mts, each 2H, CH₂CH₂), from 2.20 to 2.40 (mt, 2H, 1H of the CH$_2$ at 1 and 1H of the CH$_2$ at 3), 2.68 (broad d, J=10 Hz, 1H, the other H of the CH$_2$ at 1), 3.21 (broad d, J=10 Hz, the other H of the CH$_2$ at 3), 3.31 and 3.67 (d, J=12.5 Hz, 2H, NCH$_2$Ar), 3.36 (mt, 1H, CH at 9a), 3.45 (broad s, 1H, CH at 4), 3.58 (s, 3H, COOCH$_3$), 6.61 (broad d, J=7.5 Hz, 1H, H at 8), from 6.91 to 8.00 (mt, 15H, H at 5, H at 6, H at 7, aromatic H of the naphthyl and aromatic H of the benzyl).

Stage E 1.2 g of methyl (3aRS,4SR,9SR,9aRS)-2-benzyl-4,9-ethano-9-(2-naphthyl)-2,3,3a,4,9,9a-hexahydro-1H-benzo[f]isoindole-3a-carboxylate, in solution in 50 cm$^3$ of methanol and 2 cm$^3$ of a 2M solution of hydrochloric acid in methanol, were stirred, in the presence of 115 mg of 10% (w/w) palladium-on-charcoal, for five hours at 50° C. under hydrogen at atmospheric pressure. After filtering off the catalyst, the solvent was concentrated under reduced pressure. 0.96 g (91%) of methyl (3aRS,4SR,9SR,9aRS)-4,9-ethano-9-(2-naphthyl)-2,3,3a,4,9,9a-hexahydro-1H-benzo[f]isoindole-3a-carboxylate hydrochloride was thus obtained in the form of a beige powder, the characteristics of which were as follows:

melting point>260° C.;
mass spectrum (EI): M/Z=383 (M$^+$).

Stage F

By carrying out the reaction as in Stage G of Example 1, but from 0.96 g of methyl (3aRS,4SR,9SR,9aRS)-4,9-ethano-9-(2-naphthyl)-2,3,3a,4,9,9a-hexahydro-1H-benzo[f]isoindole-3a-carboxylate hydrochloride, from 0.41 g of 2-(2-methoxyphenyl)propenoic acid, from 0.2 cm$^3$ of oxalyl chloride and from 0.64 cm$^3$ of triethylamine in solution in 60 cm$^3$ of dichloromethane for twenty hours at room temperature, 1.15 g (78%) of methyl (3aRS,4SR,9SR,9aRS)-4,9-ethano-2-[2-(2-methoxyphenyl)propenoyl]-9-(2-naphthyl)-2,3,3a,4,9,9a-hexahydro-1H-benzo[f]isoindole-3a-carboxylate were obtained, after purification on silica gel (230–400 mesh), elution being carried out with a mixture of cyclohexane and of ethyl acetate (70/30 by volume), in the form of a white powder, the characteristics of which were as follows:

melting point=140–2° C.;
mass spectrum (EI): M/Z=473 (M$^+$).

EXAMPLE 46

Preparation of the sodium salt of (3aRS,4SR,9SR,9aRS)-4,9-ethano-2-[2-(2-methoxyphenyl)propenoyl]-9-(2-naphthyl)-2,3,3a,4,9,9a-hexahydro-1H-benzo[f]isoindole-3a-carboxylic Acid By carrying out the reaction as in Example 2, but from 1.15 g of methyl (3aRS,4SR,9SR,9aRS)-4,9-ethano-2-[2-(2-methoxyphenyl)propenoyl]-9-(2-naphthyl)-2,3,3a,4,9,9a-hexahydro-1H-benzo[f]isoindole-3a-carboxylate at reflux for five hours in 6.3 cm$^3$ of a normal aqueous sodium hydroxide solution and 40 cm$^3$ of ethanol, 50 mg (4.8%) of the sodium salt of (3aRS,4SR,9SR,9aRS)-4,9-ethano-2-[2-(2-methoxyphenyl)propenoyl]-9-(2-naphthyl)-2,3,3a,4,9,9a-hexahydro-1H-benzo[f]isoindole-3a-carboxylic acid were obtained, after purification by flash chromatography on silica gel (230–400 mesh), elution was carried out with a mixture of dichloromethane and of methanol (95/5 by volume), and then by high performance liquid chromatography on C18 Waters grafted silica, elution was carried out with a mixture of water and of acetonitrile (70/30 by volume), in the form of a white solid, the characteristics of which were as follows:

melting point>260° C.;
mass spectrum (EI): M/Z=529 (M$^+$).

EXAMPLE 47

Preparation of methyl (3aRS,4SR,9SR,9aRS)-4,9-ethano-2-[2-(2-methoxyphenyl)propenoyl]-9-(5-methyl-2-thienyl)-2,3,3a,4,9,9a-hexahydro-1H-benzo[f]isoindole-3a-carboxylate Stage A By carrying out the reaction as in Stage A of Example 31, but from 2 g of methyl (3aRS,4SR,9SR,9aRS)-2-benzyl-7-oxo-4-phenyloctahydroisoindole-3a-carboxylate, from 0.8 cm$^3$ of 2-methylthiophene and from 3 cm$^3$ of trifluoromethanesulphonic acid in 30 cm$^3$ of dichloromethane for five hours at room temperature, 0.49 g of methyl (3aRS,4SR,9SR,9aRS)-2-benzyl-4,9-ethano-9-(5-methyl-2-thienyl)-2,3,3a,4,9,9a-hexahydro-1H-benzo[f]isoindole-3a-carboxylate was obtained, after purification on silica gel (230–400 mesh), elution was carried out with mixtures of cyclohexane and ethyl acetate (95/5, then 90/10, by volume), in the form of a white powder, the characteristics of which were as follows:

$^1$H N.M.R. spectrum (300 MHz, CDCl$_3$, δ in ppm): 1.14, 1.66 and from 2.35 to 2.55 (3 mts, respectively 1H, 1H and 2H, CH$_2$CH$_2$), 2.29 and 3.18 (d, J=10 Hz, each 1H, CH$_2$ at 3), from 2.35 to 2.55 and 3.00 (respectively mt and d, J=10 Hz, each 1H, CH$_2$ at 1), 2.52 (s, 3H, ArCH$_3$), 3.10 (broad d, J=8 Hz, 1H, CH at 9a), from 3.30 to 3.40 (mt, 2H, H at 4 and 1H of the NCH$_2$Ar), 3.54 (s, 3H, COOCH$_3$), 3.74 (d, J=12.5 Hz, 1H, the other H of the NCH$_2$Ar), 6.71 (mt, 1H, H at 8), 6.71 and 6.74 (respectively mt and d, J=4 Hz, each 1H, aromatic H of the thienyl), from 6.95 to 7.45 (mt, 8H, H at 5, H at 6, H at 7 and aromatic H of the benzyl).

Stage B

A solution of 0.48 g of methyl (3aRS,4SR,9SR,9aRS)-2-benzyl-4,9-ethano-9-(5-methyl-2-thienyl)-2,3,3a,4,9,9a-hexahydro-1H-benzo[f]isoindole-3a-carboxylate and of 0.17 cm$^3$ of vinyl chloroformate in 5 cm$^3$ of dichloromethane was stirred at room temperature for eighteen hours. After concentrating the solvent under reduced pressure, the residue was purified by flash chromatography on silica gel, elution was carried out with a mixture of cyclohexane and of ethyl acetate (85/15 by volume), to give 0.37 g of a foam, which was redissolved in 7 cm$^3$ of methanol. 1.65 cm$^3$ of a normal aqueous hydrochloric acid solution were then added and the mixture was brought to reflux for three hours. After concentrating the solvent, the residue was recrystallized from a mixture of isopropanol and of isopropyl ether (50/50 by volume). 0.3 g (70%) of methyl (3aRS,4SR,9SR,9aRS)-4,9-ethano-9-(5-methyl-2-thienyl)-2,3,3a,4,9,9a-hexahydro-1H-benzo[f]isoindole-3a-carboxylate hydrochloride was then obtained in the form of a pale-green solid, the characteristics of which were as follows:

melting point=226–30° C.;
mass spectrum (EI): M/Z=353 (M$^+$).

Stage C

By carrying out the reaction as in Stage G of Example 1, but from 0.58 g of methyl (3aRS,4SR,9SR,9aRS)-4,9-ethano-9-(5-methyl-2-thienyl)-2,3,3a,4,9,9a-hexahydro-1H-benzo[f]isoindole-3a-carboxylate hydrochloride, from 0.27 g of 2-(2-methoxyphenyl)propenoic acid, from 0.13 cm$^3$ of oxalyl chloride and from 0.42 cm$^3$ of triethylamine in solution in 35 cm$^3$ of dichloromethane for twenty hours at room temperature, 0.53 g (69%) of methyl (3aRS,4SR,9SR,9aRS)-4,9-ethano-2-[2-(2-methoxyphenyl)propenoyl]-9-(5-methyl-2-thienyl)-2,3,3a,4,9,9a-hexahydro-1H-benzo[f]isoindole-3a-carboxylate was obtained, after purification on silica gel (230–400 mesh), elution was carried out with mixtures of cyclohexane and of ethyl acetate (80/20, then 60/40, by volume), in the form of a light-beige powder, the characteristics of which were as follows:
melting point=112–5° C.;
mass spectrum (EI): M/Z=513 (M$^+$).

EXAMPLE 48

Preparation of (3aRS,4SR,9SR,9aRS)-4,9-ethano-2-[2-(2-methoxyphenyl)propenoyl]-9-(5-methyl-2-thienyl)-2,3,3a,4,9,9a-hexahydro-1H-benzo[f]isoindole-3a-carboxylic Acid By carrying out the reaction as in Example 2, but from 0.45 g of methyl (3aRS,4SR,9SR,9aRS)-4,9-ethano-2-[2-(2-methoxyphenyl)propenoyl]-9-(5-methyl-2-thienyl)-2,3,3a,4,9,9a-hexahydro-1H-benzo[f]isoindole-3a-carboxylate at reflux for five hours in 2.6 cm$^3$ of a normal aqueous sodium hydroxide solution and 15 cm$^3$ of ethanol, 285 mg of (3aRS,4SR,9SR,9aRS)-4,9-ethano-2-[2-(2-methoxyphenyl)propenoyl]-9-(5-methyl-2-thienyl)-2,3,3a,4,9,9a-hexahydro-1H-benzo[f]isoindole-3a-carboxylic acid were obtained, after purification by recrystallization from diisopropyl ether, in the form of a light-beige solid, the characteristics of which were as follows:
melting point=164–6° C.;
mass spectrum (EI): M/Z=499 (M$^+$).

EXAMPLE 49

Preparation of methyl (3aRS,4SR,9SR,9aRS)-9-(4-bromophenyl)-4,9-ethano-2-[2-(2-methoxyphenyl)-propenoyl]-2,3,3a,4,9,9a-hexahydro-1H-benzo[f]isoindole-3a-carboxylate Stage A By carrying out the reaction as in Stage C of Example 45, but from 1 g of methyl (3aRS,4SR,7aRS)-2-benzyl-7-iodo-4-phenyl-2,3,3a,4,5,7a-hexahydro-1H-isoindole-3a-carboxylate in 20 cm$^3$ of toluene, from 120 mg of tetrakis(triphenylphosphine)palladium, from 0.46 g of 4-bromophenylboronic acid in 10 cm$^3$ of methanol and from 15 cm$^3$ of a 2N aqueous sodium carbonate solution at reflux for eighteen hours, 0.77 g (73%) of methyl (3aRS,4SR,7aRS)-2-benzyl-7-(4-bromophenyl)-4-phenyl-2,3,3a,4,5,7a-hexahydro-1H-isoindole-3a-carboxylate was obtained, after purification by flash chromatography on silica gel (230–400 mesh), elution was carried out with a mixture of cyclohexane and of ethyl acetate (90/10 by volume), in the form of a white foam, the characteristic of which was as follows:
mass spectrum (EI): M/Z=502 (M$^+$). ps Stage B By carrying out the reaction as in Stage C of Example 38, but from 0.77 g of methyl (3aRS,4SR,7aRS)-2-benzyl-7-(4-bromophenyl)-4-phenyl-2,3,3a,4,5,7a-hexahydro-1H-isoindole-3a-carboxylate and from 1.18 cm$^3$ of trifluoromethanesulphonic acid in 20 cm$^3$ of dichloromethane for eighteen hours at room temperature, 0.71 g (92%) of methyl (3aRS,4SR,9SR,9aRS)-2-benzyl-9-(4-bromophenyl)-4,9-ethano-2,3,3a,4,9,9a-hexahydro-1H-benzo[f]isoindole-3a-carboxylate was obtained in the form of a beige powder, used as was in the continuation of the synthesis, the characteristic of which was as follows:
mass spectrum (EI): M/Z=502 (M$^+$).

Stage C

By carrying out the reaction as in Stage B of Example 47, but from 0.71 g of methyl (3aRS,4SR,9SR,9aRS)-2-benzyl-9-(4-bromophenyl)-4,9-ethano-2,3,3a,4,9,9a-hexahydro-1H-benzo[f]isoindole-3a-carboxylate and from 0.4 cm$^3$ of vinyl chloroformate for seventy-two hours at room temperature in 20 cm$^3$ of dichloromethane, and by then taking the concentrate up in 40 cm$^3$ of methanol and 5 cm$^3$ of a 6M solution of hydrochloric acid in dioxane at reflux for three hours, 0.45 g (77%) of methyl (3aRS,4SR,9SR,9aRS)-9-(4-bromophenyl)-4,9-ethano-2,3,3a,4,9,9a-hexahydro-1H-benzo[f]isoindole-3a-carboxylate hydrochloride was obtained, after crystallizing from diisopropyl ether, in the form of white crystals, the characteristic of which was as follows:
mass spectrum (EI): M/Z=412 (M$^+$).

Stage D

By carrying out the reaction as in Stage G of Example 1, but from 0.45 g of methyl (3aRS,4SR,9SR,9aRS)-9-(4-bromophenyl)-4,9-ethano-2,3,3a,4,9,9a-hexahydro-1H-benzo[f]isoindole-3a-carboxylate hydrochloride, from 0.21 g of 2-(2-methoxyphenyl)propenoic acid, from 0.10 cm$^3$ of oxalyl chloride and from 0.33 cm$^3$ of triethylamine in solution in 30 cm$^3$ of dichloromethane for twenty hours at room temperature, 0.25 g (40%) of methyl (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylate was obtained, after purification on silica gel (230–400 mesh), elution was carried out with a mixture of cyclohexane and ethyl acetate (70/30 by volume), in the form of a light-beige powder, the characteristics of which were as follows:
melting point=190–2° C.;
mass spectrum (EI): M/Z=572 (M$^+$).

EXAMPLE 50

Preparation of (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylic Acid By carrying out the reaction as in Example 2, but from 0.19 g of methyl (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylate at reflux for three hours in 0.44 cm$^3$ of a normal aqueous sodium hydroxide solution and 10 cm$^3$ of ethanol, 120 mg (66%) of (3aRS,4SR,9SR,9aRS)-9-(4-bromophenyl)-4,9-ethano-2-[2-(2-methoxyphenyl)propenoyl]-2,3,3a,4,9,9a-hexahydro- 1H-benzo[f]isoindole-3a-carboxylic acid were obtained, after purification by recrystallizing from diisopropyl ether, in the form of a white solid, the characteristics of which were as follows:
melting point=169° C.;
mass spectrum (EI): M/Z=558 (M$^+$).

EXAMPLE 51

Preparation of (3aRS,4SR,9SR,9aRS)-9-(3,4-dichlorophenyl)-4,9-ethano-2-[2-(2-methoxyphenyl)-propenoyl]-2,3,3a,4,9,9a-hexahydro-1H-benzo[f]isoindole-3a-carboxylic Acid Stage A By carrying out the reaction as in Stage A of Example 39, but from 3.6 g of 3,4-dichloro-bromobenzene, from 0.4 g of magnesium turnings in 20 cm$^3$ of diethyl ether and from 2.9 g of methyl (3aRS,4SR,7aRS)-2-benzyl-7-oxo-4-phenyloctahydroisoindole-3a-carboxylate in 20 cm$^3$ of diethyl ether, 1.8 g of methyl (3aRS,4SR,7RS,7aRS)-2-benzyl-7-(3,4-dichlorophenyl)-7-hydroxy-4-phenyloctahydroisoindole-3a-carboxylate were obtained, after recrystallization from 35 cm³ of isopropanol, in the form of a white solid, the characteristic of which was as follows:

melting point=144° C.

Crystallization by diisopropyl ether of the filtrate, brought to dryness, made it possible to obtain an additional 0.6 g. The purification of this second filtrate by flash chromatography on silica gel (230–400 mesh), elution being carried out with a cyclohexane/ethyl acetate (80/20 by volume) mixture, made it possible to obtain, after crystallization from diisopropyl ether, an additional 0.25 g.

Stage B

By carrying out the reaction as in Stage D of Example 1, but from 1.2 g of methyl (3aRS,4SR,7RS,7aRS)-2-benzyl-7-(3,4-dichlorophenyl)-7-hydroxy-4-phenyl-1,3,3a,4,5,6-hexahydroisoindole-3a-carboxylate, from 3 cm³ of trifluoromethanesulphonic acid and from 45 cm³ of dichloromethane, 1.1 g of methyl (3aRS,4SR,9SR,9aRS)-2-benzyl-9-(3,4-dichlorophenyl)-4,9-ethano-2,3,3a,4,9,9a-hexahydro-1H-benzo[f]isoindole-3a-carboxylate were obtained in the form of a white foam, used as was in the subsequent syntheses.

Stage C 0.18 cm³ of vinyl chloroformate was added to a solution of 0.7 g of methyl hexahydro-1H-benzo[f]isoindole-3a-carboxylate in 7.5 cm³ of dichloromethane. The reaction mixture was stirred for twenty hours at a temperature in the region of 20° C. and then concentrated under reduced pressure. The residue was diluted with 7.5 cm³ of methanol. 14 cm³ of a normal solution of hydrogen chloride gas in diethyl ether were added to this solution. The reaction mixture was stirred for twenty hours at a temperature in the region of 20° C. and then concentrated under reduced pressure. The residue was taken up in a mixture of 25 cm³ of dichloromethane and 20 cm³ of a saturated aqueous sodium hydrogencarbonate solution. The aqueous phase was separated by settling and extracted with two times 15 cm³ of diethyl ether. The organic phases were combined, washed with three times 15 cm³ of distilled water, dried over magnesium sulphate and concentrated under reduced pressure. After flash chromatography on silica gel (230–400 mesh), elution was carried out with a cyclohexane/ethyl acetate (80/20 by volume) mixture, and crystallization from 5 cm³ of diisopropyl ether, 0.21 g of methyl (3aRS,4SR,9SR,9aRS)-9-(3,4-dichlorophenyl)-4,9-ethano-2,3,3a,4,9,9a-hexahydro-1H-benzo[f]isoindole-3a-carboxylate was thus obtained in the form of a white solid, the characteristic of which was as follows:

melting point=185° C.

Stage D

By carrying out the reaction as in Stage G of Example 1, but from 0.2 g of methyl (3aRS,4SR,9SR,9aRS)-9-(3,4-dichlorophenyl)-4,9-ethano-2,3,3a,4,9,9a-hexahydro-1H-benzo[f]isoindole-3a-carboxylate, from 0.1 g of 2-(2-methoxyphenyl)propenoic acid, from 0.04 cm³ of oxalyl chloride and from 0.14 cm³ of triethylamine, 0.19 g of methyl (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylate was obtained, after crystallization from diisopropyl ether, in the form of a white solid, the characteristic of which was as follows:

melting point=150° C.

Stage E

By carrying out the reaction as in Example 2, but from 0.16 g of methyl a (3aRS,4SR,9SR,9aRS)-9-(3,4-dichlorophenyl)-4,9-ethano-2-[2-(2-methoxyphenyl) propenoyl]-2,3,3a,4,9,9a-hexahydro-1H-benzo[f]isoindole-3a-carboxylate, from 1.4 cm³ of a normal aqueous sodium hydroxide solution and from 3 cm³ of methanol, 0.1 g of (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylic acid was obtained, after recrystallization from 2.5 cm³ of isopropyl acetate, the characteristic of which was as follows:

melting point=168° C.

EXAMPLE 52

Preparation of methyl (3aRS,4SR,9SR,9aRS)-9-(4-chlorophenyl)-4,9-ethano-2-[2-(2-methoxyphenyl)-propenoyl]-2,3,3a,4,9,9a-hexahydro-1H-benzo[f] isoindole-3a-carboxylate Stage A By carrying out the reaction as in Stage C of Example 1, but from 9.58 g of 4-chlorobromobenzene, from 1.2 g of magnesium turnings and from 9.1 g of methyl (3aRS,4SR,7aRS)-2-benzyl-7-oxo-4-phenyloctahydroisoindole-3a-carboxylate, 7.9 g of methyl (3aRS,4SR,7RS,7aRS)-2-benzyl-7-(4-chlorophenyl)-7-hydroxy-4-phenyloctahydroisoindole-3a-carboxylate were obtained, after recrystallization from 25 cm³ of isopropanol, in the form of a white solid, the characteristic of which was as follows:

melting point=189° C.

Stage B

By carrying out the reaction as in Stage D of Example 1, but from 7.5 g of methyl (3aRS,4SR,7RS,7aRS)-2-benzyl-7-(4-chlorophenyl)-7-hydroxy-4-phenyloctahydroisoindole-3a-carboxylate, from 25 cm³ of trifluoromethanesulphonic acid and from 80 cm³ of dichloromethane, 6.35 g of methyl (3aRS,4SR,9SR,9aRS)-2-benzyl-9-(4-chlorophenyl)-4,9-ethano-2,3,3a,4,9,9a-hexahydro-1H-benzo[f]isoindole-3a-carboxylate were obtained, after crystallization from 100 cm³ of isopropanol, in the form of a white solid, the characteristic of which was as follows:

melting point=142° C.

Stage C

By carrying out the reaction as in Stage C of Example 51, but from 2.29 g of methyl (3aRS,4SR,9SR,9aRS)-2-benzyl-9-(4-chlorophenyl)-4,9-ethano-2,3,3a,4,9,9a-hexahydro-1H-benzo[f]isoindole-3a-carboxylate and from 0.98 cm³ of vinyl chloroformate in 7.5 cm³ of dichloromethane, and by then treating the intermediate, diluted in 25 cm³ of methanol, with 8.5 cm³ of a hexanormal solution of hydrogen chloride gas in dioxane, 0.8 g of methyl (3aRS,4SR,9SR,9aRS)-9-( 4-chlorophenyl)-4,9-ethano-2,3,3a,4,9,9a-hexahydro-1H-benzo[f]isoindole-3a-carboxylate was obtained, after flash chromatography on silica gel (230–400 mesh), elution was carried out with a dichloromethane/methanol (98/2 by volume) mixture, in the form of a light-coloured foam, used as was in the subsequent syntheses.

Stage D

By carrying out the reaction as in Stage G of Example 1, but from 0.75 g of methyl (3aRS,4SR,9SR,9aRS)-9-(4-chlorophenyl)-4,9-ethano-2,3,3a,4,9,9a-hexahydro-1H-benzo[f]isoindole-3a-carboxylate, from 0.36 g of 2-(2-methoxyphenyl)propenoic acid, from 0.17 cm³ of oxalyl chloride and from 0.57 cm³ of triethylamine, 0.8 g of methyl (3aRS,4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylate was obtained, the characteristic of which was as follows:

melting point=90° C.

EXAMPLE 53

Preparation of (3aRS,4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylic Acid By carrying out the reaction as in Example 2, but from 0.7 g of methyl (3aRS,4SR,9SR,9aRS)-9-(4-chlorophenyl)-4,9-ethano-2-[2-( 2-methoxyphenyl)propenoyl]-2,3,3a,4,9,9a-hexahydro-1H-benzo[f]isoindole-3a-carboxylate, from 2 cm³ of a normal aqueous sodium hydroxide solution and from 30 cm³ of ethanol, 0.45 g of (3aRS,4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylic acid was obtained, after flash chromatography on silica gel (230–400 mesh), elution was carried out with a dichloromethane/methanol (98/2 by volume) mixture, the characteristic of which was as follows:

melting point: approximately 160° C.

EXAMPLE 54

Preparation of (3aRS,4SR,9SR,9aRS)-4,9-ethano-2-[2-(2-methoxyphenyl)propenoyl]-9-(4-methoxy-3-methylphenyl)-2,3,3a,4,9,9a-hexahydro-1H-benzo[f]isoindole-3a-carboxylic Acid Stage A By carrying out the reaction as in Stage A of Example 31, but from 2 g of methyl (3aRS,4SR,7aRS)-2-benzyl-7-oxo-4-phenyloctahydroisoindole-3a-carboxylate, from 2 g of 2-methylanisole and from 2.9 cm³ of trifluoromethanesulphonic acid in 30 cm³ of dichloromethane, 2.3 g of methyl (3aRS,4SR,9SR,9aRS)-2-benzyl-4,9-ethano-9-(4-methoxy-3-methylphenyl)-2,3,3a,4,9,9a-hexahydro-1H-benzo[f]isoindole-3a-carboxylate were obtained, after purification by flash chromatography on silica gel (230–400 mesh), elution being carried out with a cyclohexane/ethyl acetate (90/10 by volume) mixture, in the form of an off-white foam, used as was in the subsequent syntheses.

Stage B

By carrying out the reaction as in Stage E of Example 1, but from 2.3 g of methyl (3aRS,4SR,9SR,9aRS)-2-benzyl-4,9-ethano-9-(4-methoxy-3-methylphenyl)-2,3,3a,4,9,9a-hexahydro-1H-benzo[f]isoindole-3a-carboxylate, from 0.93 g of ammonium formate and from 0.5 g of 10% (w/w) palladium-on-charcoal, 0.5 g of methyl (3aRS,4SR,9SR,9aRS)-4,9-ethano-9-(4-methoxy-3-methylphenyl)-2,3,3a,4,9,9a-hexahydro-1H-benzo[f]isoindole-3a-carboxylate was obtained, after flash chromatography on silica gel (230–400 mesh), elution being carried out with a dichloromethane/methanol (99/1 by volume) mixture, and recrystallization from 20 cm³ of isopropanol, in the form of a white solid, the characteristic of which was as follows:

melting point=123° C.

Stage C

By carrying out the reaction as in Stage G of Example 1, but from 1.1 g of methyl (3aRS,4SR,9SR,9aRS)-4,9-ethano-9-(4-methoxy-3-methylphenyl)-2,3,3a,4,9,9a-hexahydro-1H-benzo[f]isoindole-3a-carboxylate, from 0.52 g of 2-(2-methoxyphenyl)propenoic acid, from 0.25 cm³ of oxalyl chloride and from 0.82 cm³ of triethylamine, 0.85 g of methyl (3aRS,4SR,9SR,9aRS)-4,9-ethano-2-[2-(2-methoxyphenyl)propenoyl]-9-(4-methoxy-3-methylphenyl)-2,3,3a,4,9,9a-hexahydro- 1H-benzo[f]isoindole-3a-carboxylate was obtained, after purification by flash chromatography on silica gel (230–400 mesh), elution being carried out with a dichloromethane/methanol (99/1 by volume) mixture, and recrystallization from 5 cm³ of isopropanol, the characteristic of which compound was as follows:

melting point=125° C.

Stage D

By carrying out the reaction as in Example 2, but from 0.8 g of methyl (3aRS,4SR,9SR,9aRS)-4,9-ethano-2-[2-(2-methoxyphenyl)propenoyl]-9-(4-methoxy-3-methylphenyl)-2,3,3a,4,9,9a-hexahydro-1H-benzo[f]isoindole-3a-carboxylate, from 2.25 cm³ of a normal aqueous sodium hydroxide solution and from 40 cm³ of ethanol, 0.45 g of (3aRS,4SR,9SR,9aRS)-4,9-ethano-2-[2-(2-methoxyphenyl)propenoyl]-9-(4-methoxy-3-methylphenyl)-2,3,3a,4,9,9a-hexahydro-1H-benzo[f]isoindole-3a-carboxylic acid was obtained, after flash chromatography on silica gel (230–400 mesh), elution being carried out with a dichloromethane/methanol (97.5/2.5 by volume) mixture, in the form of an amorphous white solid.

mass spectrum (EI): M/Z=523 (M⁺).

EXAMPLE 55

Preparation of methyl (3aRS,4SR,9SR,9aRS)-4,9-ethano-2-[2-(2-methoxyphenyl)propenoyl]-9-(3-indolyl)-2,3,3a,4,9,9a-hexahydro-1H-benzo[f]isoindole-3a-carboxylate Stage A By carrying out the reaction as in Stage A of Example 31, but from 3.63 g of methyl (3aRS,4SR,7aRS)-2-benzyl-7-oxo-4-phenyloctahydroisoindole-3a-carboxylate, from 3.85 g of 1-phenylsulphonylindole and from 5.3 cm³ of trifluoromethanesulphonic acid in 30 cm³ of dichloromethane, 2.1 g of a crude product were obtained, after purification by flash chromatography on silica gel (230–400 mesh), elution being carried out with a cyclohexane/ethyl acetate (80/20 by volume) mixture, which crude product was combined with a second batch originating from an experiment carried out with respect to the same amounts. The purification of this mixture by flash chromatography on silica gel (230–400 mesh), elution being carried out with a cyclohexane/ethyl acetate (95/5 by volume) mixture, provided 1 g of methyl (3aRS,4SR,9SR,9aRS)-2-benzyl-4,9-ethano-9-(3-indolyl)-2,3,3a,4,9,9a-hexahydro-1H-benzo[f]isoindole-3a-carboxylate in the form of an off-white foam, used as was in the subsequent syntheses, the characteristics of which were as follows:

¹H N.M.R. spectrum (300 MHz, CDCl₃, δ in ppm): from 1.30 to 1.60 and 2.55 (2 mts, each 2H, CH₂CH₂), 2.11 and 2.65 (respectively dd and d, J=10 and 9 Hz and J=10 Hz, each 1H, CH₂ at 1), 2.31 and 3.21 (2d, J=10 Hz, each 1H, CH₂ at 3), 3.37 and 3.51 (2 d, J=12.5 Hz, each 1H, NCH₂Ar), 3.42 (broad s, 1H, CH at 4), from 3.50 to 3.70 (mt, 1H, CH at 9a), 3.59 (s, 3H, COOCH₃), 6.81 (broad d, J=7.5 Hz, 1H, H at 8), from 6.90 to 7.60 (mt, 13H, H at 5, H at 6, H at 7, aromatic H of the indole and aromatic H of the benzyl), 8.11 (broad s, 1H, NH).

Stage B

By carrying out the reaction as in Stage C of Example 51, but from 1 g of methyl (3aRS,4SR,9SR,9aRS)-2-benzyl-4,9-ethano-9-(3-indolyl)-2,3,3a,4,9,9a-hexahydro-1H-benzo[f]isoindole-3a-carboxylate and from 0.285 cm³ of vinyl chloroformate in 20 cm³ of dichloromethane, and by then treating the intermediate, dissolved in 20 cm³ of methanol, with 21.4 cm³ of a normal solution of hydrogen chloride gas in diethyl ether, 0.3 g of methyl (3aRS,4SR,9SR,9aRS)-4,9-ethano-9-(3-indolyl)-2,3,3a,4,9,9a-hexahydro-1H-benzo[f]isoindole-3a-carboxylate was obtained, after flash chromatography on silica gel (230–400 mesh), elution being carried out with a dichloromethane/methanol (97.5/2.5 by volume) mixture, in the form of an orange-coloured foam, used as was in the subsequent syntheses.

Stage C

By carrying out the reaction as in Stage G of Example 1 but from 0.3 g of methyl (3aRS,4SR,9SR,9aRS)-4,9-ethano-9-(3-indolyl)-2,3,3a,4,9,9a-hexahydro-1H-benzo[f]isoindole-3a-carboxylate, from 0.145 g of 2-(2-methoxyphenyl)propenoic acid and from 0.07 cm³ of oxalyl chloride, 0.16 g of methyl (3aRS,4SR,9SR,9aRS)-4,9-ethano-2-[2-(2-methoxyphenyl)propenoyl]-9-(3-indolyl)-2,3,3a,4,9,9a-hexahydro-1H-benzo[f]isoindole-3a-carboxylate was obtained, after purification by flash chromatography on silica gel (230–400 mesh), elution being carried out with a cyclohexane/ethyl acetate (50/50 by volume) mixture, and crystallization from diisopropyl ether, the characteristics of which compound were as follows:

mass spectrum (EI): M/Z=532 (M⁺).

¹H N.M.R. spectrum (250 MHz, (CD₃)₂SO, at a temperature of 383 K, $\delta_6$ in ppm): 1.46 and 2.16 (2 mts, each 2H, CH₂CH₂), from 3.30 to 3.80 (mt, 4H, CH₂ at 1, CH at 9a and 1H of the CH₂ at 3), 3.47 (mt, 1H, CH at 4), 3.57 (s, 3H, COOCH₃), 3.71 (s, 3H, ArOCH₃), 4.10 (broad d, J=12.5 Hz, 1H, the other H of the CH₂ at 3), 5.52 and 5.67 (2 s, each 1H, =CH₂), 6.65 (broad d, J=7.5 Hz, 1H, H at 8), from 6.90 to 7.88 (mt, 12H, H at 5, H at 6, H at 7, aromatic H of the indole and aromatic H of the 2-methoxyphenyl).

EXAMPLE 56

Preparation of (3aRS,4SR,9SR,9aRS)-4,9-ethano-9-(4-isopropylphenyl)-2-[(2-methoxyphenyl)acetyl]-2,3,3a,4,9,9a-hexahydro-1H-benzo[f]isoindole-3a-carboxylic Acid Stage A By carrying out the reaction as in Stage A of Example 1, but from 6 g of methyl (3aRS,4SR,7aRS)-2-benzyl-7-oxo-4-phenyloctahydroisoindole-3a-carboxylate in 60 cm³ of dry diethyl ether and from a solution of 4-isopropylphenyl magnesium bromide, prepared at the time of use from 4 g of 4-bromoisopropylbenzene and 0.52 g of magnesium turnings in 7 cm³ of dry diethyl ether, for eighteen hours at room temperature, 3.3 g (41%) of methyl (3aRS,4SR,7RS,7aRS)-2-benzyl-7-(4-isopropylphenyl)-7-hydroxy-4-phenyloctahydroisoindole-3a-carboxylate were obtained, after purification by flash chromatography on silica gel (230–400 mesh), elution being carried out with a gradient of mixtures of cyclohexane and of ethyl acetate (from 98/2 to 80/20 by volume), in the form of a yellow oil, the characteristic of which was as follows:

mass spectrum (EI): M/Z=483 (M⁺).

Stage B

By carrying out the reaction as in Stage D of Example 1, but from 1.7 g of methyl (3aRS,4SR,7RS,7aRS)-2-benzyl-7-(4-isopropylphenyl)-7-hydroxy-4-phenyloctahydroisoindole-3a-carboxylate and from 2.3 cm³ of trifluoromethanesulphonic acid in 22 cm³ of dichloromethane for three hours at room temperature, 1.44 g (90%) of methyl (3aRS,4SR,9SR,9aRS)-2-benzyl-4,9-ethano-9-(4-isopropylphenyl)-2,3,3a,4,9,9a-hexahydro-1H-benzo[f]isoindole-3a-carboxylate were obtained in the form of a brown viscous oil, used as was in the continuation of the synthesis, the characteristic of which was as follows:

mass spectrum (EI): M/Z=465 (M⁺).

Stage C

By carrying out the reaction as in Stage C of Example 45, but from 1.4 g (3 mmol) of methyl (3aRS,4SR,9SR,9aRS)-2-benzyl-4,9-ethano-9-(4-isopropylphenyl)-2,3,3a,4,9,9a-hexahydro-1H-benzo[f]isoindole-3a-carboxylate and from 140 mg of 10% (w/w) palladium-on-charcoal in 125 cm³ of methanol and 3.3 cm³ of a normal aqueous hydrochloric acid solution for four hours at room temperature under hydrogen at atmospheric pressure, 1.03 g (86%) of methyl (3aRS,4SR,9SR,9aRS)-4,9-ethano-9-(4-isopropylphenyl)-2,3,3a,4,9,9a-hexahydro-1H-benzo[f]isoindole-3a-carboxylate hydrochloride were obtained, after crystallization from diisopropyl ether, in the form of a beige powder, the characteristic of which was as follows:

mass spectrum (EI): M/Z=375 (M⁺).

Stage D

By carrying out the reaction as in Stage A of Example 5, but from 500 mg of methyl (3aRS,4SR,9SR,9aRS)-4,9-ethano-9-(4-isopropylphenyl)-2,3,3a,4,9,9a-hexahydro-1H-benzo[f]isoindole-3a-carboxylate hydrochloride, from 240 mg of 2-methoxyphenylacetic acid, from 280 mg of 1-ethyl-3-[3-(dimethylamino)propyl]carbodiimide hydrochloride, from 16 mg of N-1-hydroxybenzotriazole hydrate and from 0.2 cm³ of triethylamine in 55 cm³ of dichloromethane, 460 mg (76%) of methyl (3aRS,4SR,9SR,9aRS)-4,9-ethano-9-(4-isopropylphenyl)-2-[2-(methoxyphenyl)acetyl]-2,3,3a,4,9,9a-hexahydro-1H-benzo[f]isoindole-3a-carboxylate were obtained, after purification by flash chromatography on silica gel (240–400 mesh), elution being carried out with a cyclohexane/ethyl acetate (70/30 by volume) mixture, in the form of a white powder, the characteristics of which were as follows:

melting point=85–7° C.;

mass spectrum (EI): M/Z=523 (M⁺).

Stage E

By carrying out the reaction as in Example 2, but from 0.379 g of methyl (3aRS,4SR,9SR,9aRS)-4,9-ethano-9-(4-isopropylphenyl)-2-[2-(methoxyphenyl)acetyl]-2,3,3a,4,9,9a-hexahydro-1H-benzo[f]isoindole-3a-carboxylate at reflux for three hours in 0.85 cm³ of a normal aqueous sodium hydroxide solution and 15 cm³ of ethanol, 170 mg (47%) of (3aRS,4SR,9SR,9aRS)-4,9-ethano-9-(4-isopropylphenyl)-2-[(2-methoxyphenyl)acetyl]-2,3,3a,4,9,9a-hexahydro-1H-benzo[f]isoindole-3a-carboxylic acid were obtained, after purification by stirring in ethyl acetate in the presence of silica gel (230–400 mesh) and then recrystallization from pentane, in the form of a white solid, the characteristics of which were as follows:

melting point=135–6° C.;

mass spectrum (EI): M/Z=509 (M⁺).

EXAMPLE 57

Preparation of (3aRS,4SR,9SR,9aRS)-4,9-ethano-9-(4-isopropylphenyl)-2-[2-(2-methoxyphenyl)propenoyl]-2,3,3a,4,9,9a-hexahydro-1H-benzo[f]isoindole-3a-carboxylic Acid By carrying out the reaction as in Stage G of Example 1, but from 0.53 g of methyl (3aRS,4SR,9SR,9aRS)-4,9-ethano-9-(4-isopropylphenyl)-2,3,3a,4,9,9a-hexahydro-1H-benzo[f]isoindole-3a-carboxylate hydrochloride, obtained in Stage C of Example 56, from 0.25 g of 2-(2-methoxyphenyl)propenoic acid, from 0.12 cm³ of oxalyl chloride and from 0.4 cm³ of triethylamine in solution of 30 cm³ of dichloromethane for twenty hours at room temperature, 0.375 g (54%) of methyl (3aRS,4SR,9SR,9aRS)-4,9-ethano-9-(4-isopropylphenyl)-2-[2-(2-methoxyphenyl)propenoyl]-2,3,3a,4,9,9a-hexahydro-1H-benzo[f]isoindole-3a-carboxylate was obtained, after purification on silica gel (230–400 mesh), elution being carried out with a gradient of mixtures of cyclohexane and of ethyl acetate (from 98/2 to 70/30 by volume), in the form of a white powder, the characteristics of which were as follows:

melting point=98–100° C.;

mass spectrum (EI): M/Z=535 (M$^+$).

By carrying out the reaction as in Example 2, but from 0.32 g of methyl (3aRS,4SR,9SR,9aRS)-4,9-ethano-9-(4-isopropylphenyl)-2-[2-(2-methoxyphenyl)propenoyl]-2,3,3a,4,9,9a-hexahydro-1H-benzo[f]isoindole-3a-carboxylate at reflux for two hours in 0.71 cm$^3$ of a normal aqueous sodium hydroxide solution and 15 cm$^3$ of ethanol, 190 mg (59%) of (3aRS,4SR,9SR,9aRS)-4,9-ethano-9-(4-isopropylphenyl)-2-[2-(2-methoxyphenyl)propenoyl]-2,3,3a,4,9,9a-hexahydro-1H-benzo[f]isoindole-3a-carboxylic acid were obtained, after purification by stirring in ethyl acetate in the presence of silica gel (230–400 mesh) and then recrystallization from pentane, in the form of a white solid, the characteristics of which were as follows:

melting point=168–70° C.;

mass spectrum (EI): M/Z=521 (M$^+$).

EXAMPLE 58

Preparation of (3aRS,4SR,9SR,9aRS)-4,9-ethano-2-[2-(2-methoxyphenyl)propenoyl]-9-(3-thienyl)-2,3,3a,4,9,9a-hexahydro-1H-benzo[f]isoindole-3a-carboxylic Acid Stage A By carrying out the reaction as in Stage C of Example 45, but from 1.2 g of methyl (3aRS,4SR,7aRS)-2-benzyl-7-iodo-4-phenyl-2,3,3a,4,5,7a-hexahydro-1H-isoindole-3a-carboxylate in 30 cm$^3$ of toluene, from 150 mg of tetrakis (triphenylphosphine)palladium, from 0.35 g of 3-thienylboronic acid in 15 cm$^3$ of methanol and from 28 cm$^3$ of a 2N aqueous sodium carbonate solution at reflux for three hours, 0.99 g (93%) of methyl (3aRS,4SR,7aRS)-2-benzyl- 4-phenyl-7-(3-thienyl)-2,3,3a,4,5,7a-hexahydro-1H-isoindole-3a-carboxylate was obtained, after purification by flash chromatography on silica gel (230–400 mesh), elution being carried out with a mixture of cyclohexane and ethyl acetate (85/15 by volume), in the form of a yellow oil, the characteristic of which was as follows:

mass spectrum (EI): M/Z=429 (M$^+$).

Stage B

By carrying out the reaction as in Stage C of Example 38, but from 1.1 g of methyl (3aRS,4SR,7aRS)-2-benzyl-4-phenyl-7-(3-thienyl)-2,3,3a,4,5,7a-hexahydro-1H-isoindole-3a-carboxylate and from 1.4 cm$^3$ of trifluoromethanesulphonic acid in 15 cm$^3$ of dichloromethane for eighteen hours at room temperature, 0.62 g (56%) of methyl (3aRS,4SR,9SR,9aRS)-2-benzyl-4,9-ethano-9-(3-thienyl)-2,3,3a,4,9,9a-hexahydro-1H-benzo[f]isoindole-3a-carboxylate was obtained in the form of a beige powder, used as was in the continuation of the synthesis, the characteristic of which was as follows:

mass spectrum (EI): M/Z=429 (M$^+$).

Stage C

By carrying out the reaction as in Stage B of Example 47, but from 0.62 g of methyl (3aRS,4SR,9SR,9aRS)-2-benzyl-4,9-ethano-9-(3-thienyl)-2,3,3a,4,9,9a-hexahydro-1H-benzo[f]isoindole-3a-carboxylate and from 0.19 cm$^3$ of vinyl chloroformate for seventy-two hours at room temperature in 10 cm$^3$ of dichloromethane, and by then taking the concentrate up in 20 cm$^3$ of methanol and 2.7 cm$^3$ of a 5M solution of hydrochloric acid in isopropanol at reflux for two hours, 0.48 g (89%) of methyl (3aRS,4SR,9SR,9aRS)-4,9-ethano-9-(3-thienyl)-2,3,3a,4,9,9a-hexahydro-1H-benzo[f]isoindole-3a-carboxylate hydrochloride was obtained, after crystallization from diisopropyl ether, in the form of a white solid, the characteristic of which was as follows:

mass spectrum (EI): M/Z=339 (M$^+$).

Stage D

By carrying out the reaction as in Stage G of Example 1, but from 0.48 g of methyl (3aRS,4SR,9SR,9aRS)-4,9-ethano-9-(3-thienyl)-2,3,3a,4,9,9a-hexahydro-1H-benzo[f]isoindole-3a-carboxylate hydrochloride, from 0.27 g of 2-(2-methoxyphenyl)propenoic acid, from 0.12 cm$^3$ of oxalyl chloride and from 0.36 cm$^3$ of triethylamine in solution of 35 cm$^3$ of dichloromethane for twenty hours at room temperature, 0.40 g (63%) of methyl (3aRS,4SR,9SR,9aRS)-4,9-ethano-2-[2-(2-methoxyphenyl)propenoyl]-9-(3-thienyl)-2,3,3a,4,9,9a-hexahydro-1H-benzo[f]isoindole-3a-carboxylate was obtained, after purification by flash chromatography on silica gel (230–400 mesh), elution being carried out with a mixture of cyclohexane and of ethyl acetate (60/40 by volume), followed by recrystallization from diisopropyl ether, in the form of a white solid, the characteristics of which were as follows:

melting point=174° C.;

mass spectrum (EI): M/Z=499 (M$^+$).

Stage E

By carrying out the reaction as in Example 2, but from 0.35 g of methyl (3aRS,4SR,9SR,9aRS)-4,9-ethano-2-[2-(2-methoxyphenyl)propenoyl]-9-(3-thienyl)-2,3,3a,4,9,9a-hexahydro-1H-benzo[f]isoindole-3a-carboxylate at reflux for three hours in 2.1 cm$^3$ of a normal aqueous sodium hydroxide solution and 12 cm$^3$ of ethanol, 340 mg (88%) of (3aRS,4SR,9SR,9aRS)-4,9-ethano-2-[2-(2-methoxyphenyl)propenoyl]-9-(3-thienyl)-2,3,3a,4,9,9a-hexahydro-1H-benzo[f]isoindole-3a-carboxylic acid were obtained, after purification by recrystallization from petroleum ether (40–65° C.), in the form of a white solid, the characteristics of which were as follows:

melting point=170° C.;

mass spectrum (EI): M/Z=485 (M$^+$).

EXAMPLE 59

Preparation of methyl (3aRS,4SR,9SR,9aRS)-4,9-ethano-9-(4-ethylphenyl)-2-[2-(2-methoxyphenyl) propenoyl]-2,3,3a,4,9,9a-hexahydro-1H-benzo[f] isoindole-3a-carboxylate Stage A By carrying out the reaction as in Stage C of Example 45, but from 1.35 g of methyl (3aRS,4SR,7aRS)-2-benzyl-7-iodo-4-phenyl-2,3,3a,4,5,7a-hexahydro-1H-isoindole-3a-carboxylate in 20 cm$^3$ of toluene, from 340 mg of tetrakis (triphenylphosphine)palladium, from 0.38 g of trimer anhydride of 4-ethylphenylboronic acid in 10 cm$^3$ of methanol and from 15 cm$^3$ of a 2N aqueous sodium carbonate solution at reflux for eighteen hours, 0.92 g (72%) of methyl (3aRS,4SR,7aRS)-2-benzyl-7-(4-ethylphenyl)-4-phenyl-2,3,3a,4,5,7a-hexahydro-1H-isoindole-3a-carboxylate was obtained, after purification by flash chromatography on silica gel (230–400 mesh), elution being carried out with a mixture of cyclohexane and of ethyl acetate (90/10 by volume), in the form of a viscous yellow oil, the characteristic of which was as follows:

mass spectrum (EI): M/Z=451 (M$^+$).

Stage B

By carrying out the reaction as in Stage C of Example 38, but from 0.92 g of methyl (3aRS,4SR,7aRS)-2-benzyl-7-(4-ethylphenyl)-4-phenyl-2,3,3a,4,5,7a-hexahydro-1H-isoindole-3a-carboxylate and from 1.18 cm$^3$ of trifluoromethanesulphonic acid in 18 cm$^3$ of dichloromethane for six hours at room temperature, 0.68 g (74%) of methyl (3aRS,4SR,9SR,9aRS)-2-benzyl-4,9-ethano-9-(4-ethylphenyl)-2,3,3a,4,9,9a-hexahydro-1H-benzo[f]isoindole-3a-carboxylate was obtained, after purification by flash chromatography on silica gel (230–400 mesh), elution being carried out with a mixture of cyclohexane and of ethyl acetate (95/5 by volume), in the form of a viscous yellow oil, the characteristic of which was as follows:

mass spectrum (EI): M/Z=451 (M$^+$).

Stage C

By carrying out the reaction as in Stage E of Example 1, but from 0.68 g of methyl (3aRS,4SR,9SR,9aRS)-2-benzyl-4,9-ethano-9-(4-ethylphenyl)-2,3,3a,4,9,9a-hexahydro-1H-benzo[f]isoindole-3a-carboxylate and from 0.27 g of ammonium formate in 40 cm$^3$ of methanol in the presence of 200 mg of 3% (w/w) palladium-on-charcoal at reflux for four hours, 0.47 g (87%) of methyl (3aRS,4SR,9SR,9aRS)-4,9-ethano-9-(4-ethylphenyl)-2,3,3a,4,9,9a-hexahydro-1H-benzo[f]isoindole-3a-carboxylate was obtained in the form of a yellow pasty solid, the characteristic of which was as follows:

mass spectrum (EI): M/Z=461 (M$^+$).

Stage D

By carrying out the reaction as in Stage A of Example 5, but from 0.47 g of methyl (3aRS,4SR,9SR,9aRS)-4,9-ethano-9-(4-ethylphenyl)-2,3,3a,4,9,9a-hexahydro-1H-benzo[f]isoindole-3a-carboxylate, from 0.23 g of 2-(2-methoxyphenyl)-propenoic acid, from 0.3 g of 1-ethyl-3-[3-(dimethylamino)propyl]carbodiimide hydrochloride and from 20 mg of N-1-hydroxybenzotriazole hydrate in 30 cm$^3$ of dichloromethane for six hours at room temperature, 0.26 g (38%) of methyl (3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylate was obtained, after purification by flash chromatography on silica gel (230–400 mesh), elution was carried out with a mixture of cyclohexane and of ethyl acetate (70/30 by volume), in the form of a white powder, the characteristics of which were as follows:

melting point=90–2° C.;
mass spectrum (EI): M/Z=521 (M$^+$).

EXAMPLE 60

Preparation of (3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylic Acid By carrying out the reaction as in Example 2, but starting from 0.18 g of methyl (3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylate at reflux for three hours in 0.43 cm$^3$ of a normal aqueous sodium hydroxide solution and 10 cm$^3$ of methanol, 59 mg (34%) of (3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylic acid were obtained, after purification by recrystallization from petroleum ether, in the form of a white solid, the characteristics of which were as follows:

melting point=141° C.;
mass spectrum (EI): M/Z=507 (M$^+$).

EXAMPLE 61

Preparation of methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate Stage A By carrying out the reaction as in Example 31, Stage A, but starting from 2.5 g of methyl (3aRS,4SR,7aRS)-2-benzyl-7-oxo-4-phenyloctahydroisoindole-3a-carboxylate in 250 cm$^3$ of dichloromethane, from 2.4 cm$^3$ of 2,3-dihydrobenzofuran and from 4.25 cm$^3$ of trifluoromethanesulphonic acid; after stirring for 18 hours at a temperature in the region of 20° C., 1.56 g of methyl (3aRS,4SR,9SR,9aRS)-2-benzyl-9-(2,3-dihydrobenzofuran-5-yl)-4,9-ethano-2,3,3a,4,9,9a-hexahydro-1H-benzo[f]isoindole-3a-carboxylate were obtained in the form of an orangey-yellow oil, used as in the following stage, the characteristic of which was as follows:

mass spectrum (EI): M/Z=465 (M$^+$).

Stage B

By carrying out the reaction as in Stage E of Example 1, but from 1.56 g of methyl (3aRS,4SR,9SR,9aRS)-2-benzyl-9-(2,3-dihydrobenzofuran-5-yl)-4,9-ethano-2,3,3a,4,9,9a-hexahydro-1H-benzo[f]isoindole-3a-carboxylate, from 0.63 g of ammonium formate and from 0.2 g of 10% (w/w) palladium-on-charcoal in 30 cm$^3$ of methanol at reflux for 5 hours, 0.995 g of impure methyl (3aRS,4SR,9SR,9aRS)-9-(2,3-dihydrobenzofuran-5-yl)-4,9-ethano-2,3,3a,4,9,9a-hexahydro- 1H-benzo[f]isoindole-3a-carboxylate was obtained in the form of an orange-coloured lacquer, which was used in the following stage, the characteristic of which was as follows:

mass spectrum (DCI): M/Z=376 (M+H$^+$).

Stage C

By carrying out the reaction as in Stage G of Example 1, but from a solution of 0.45 g of 2-(2-methoxyphenyl)propenoic acid in 20 cm$^3$ of dichloromethane containing 4 drops of N,N-dimethylformamide and from 0.54 cm$^3$ of oxalyl chloride, after one night at a temperature in the region of 20° C., by evaporating to dryness and by taking up the residue in 20 cm$^3$ of dichloromethane; by then pouring this solution onto a solution of 0.99 g of methyl (3aRS,4SR,9SR,9aRS)-9-(2,3-dihydrobenzofuran-5-yl)-4,9-ethano-2,3,3a,4,9,9a-hexahydro-1H-benzo[f]isoindole-3a-carboxylate, obtained in the preceding stage, with 0.31 cm$^3$ of triethylamine added, in 20 cm$^3$ of dichloromethane, 39 mg of methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate were obtained in the form of a beige solid, the characteristics of which were as follows:

melting point=200° C. (dec);
mass spectrum (EI): M/Z=535 (M$^+$).

EXAMPLE 62

Preparation of (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylic Acid By carrying out the reaction as in Example 2, but from 7.21 g of methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H- benzo[f]isoindole-3a-carboxylate, prepared in the preceding example, from 50 cm³ of a normal aqueous sodium hydroxide solution and from 100 cm³ of dioxane for three hours at reflux, 3.44 g of (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylic acid were obtained, after crystallization from 80 cm³ of an ethanol/water (75/25 by volume) mixture, in the form of a white crystalline powder, the characteristics of which were as follows:

melting point=241° C.;

mass spectrum (EI): M/Z=521 (M⁺).

EXAMPLE 63

Preparation of (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-N-(3-pyridylmethyl) carboxamide By carrying out the reaction as in Example 42, but from 522 mg of (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylic acid, from 0.122 cm³ of 3-(aminomethyl)pyridine, from 0.23 g of 1-ethyl-3-[3-(dimethylamino)propyl]carbodiimide hydrochloride and from 80 mg of N-1-hydroxybenzotriazole hydrate in 15 cm³ of dichloromethane, 462 mg of (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide were obtained in the form of a white powder, the characteristics of which were as follows:

melting point=238° C. (dec);

mass spectrum (EI): M/Z=611 (M⁺).

¹H N.M.R. spectrum (400 MHz, (CD₃)₂SO, at a temperature of 383 K, δ in ppm): 1.40, 1.60, 199 and 2.14 (4 mts, each 1H, CH₂CH₂), 3.29 and 3.41 (respectively dd and d (broad), J=12 and 9 Hz and J=12 Hz, each 1H, CH₂ at 1), 3.26 (broad t, J=8.5 Hz, 2H, ArCH₂ of the 2,3-dihydrobenzofuran), 3.47 and 4.17 (2d, J=12.5 Hz, each 1H, CH₂ at 3), 3.53 (mt, 1H, CH at 9a), 3.56 (broad s, 1H, CH at 4), 3.70 (s, 3H, ArOCH₃), 4.22 (AB, J=15 and 6 Hz, 2H, NCH₂Ar), 4.60 (t, J=8.5 Hz, 2H, CH₂O of the 2,3-dihydrobenzofuran), 5.52 and 5.68 (2 s, each 1H, =CH₂), 6.48 (mt, 1H, H at 8), from 6.75 to 7.50 (mt, 12H, H at 5, H at 6, H at 7, aromatic H of the 2-methoxyphenyl, aromatic H of the 2,3-dihydrobenzofuran, H at the 4 position of the pyridyl and H at the 3 position of the pyridyl), 7.96 (mt, 1H, CONH), 8.38 (broad s, 1H, H at 2 of the pyridyl), 8.44 (broad d, J=5 and 1.5 Hz, 1H, H at 6 of the pyridyl).

EXAMPLE 64

Preparation of methyl (3aRS,4SR,9SR,9aRS)-4,9-ethano-9-(4-fluorophenyl)-2-[2-(2-methoxyphenyl) propenoyl]-2,3,3a,4,9,9a-hexahydro-1H-benzo[f] isoindole-3a-carboxylate Stage A By carrying out the reaction as in Stage A of Example 39, but from 2.8 g of 4-fluorobromobenzene, from 0.4 g of magnesium turnings in 20 cm³ of diethylether and from 2.9 g of methyl (3aRS,4SR,9SR,9aRS)-2-benzyl-7-oxo-4-phenyloctahydroisoindole-3a-carboxylate in 20 cm³ of diethyl ether, 1.2 g of methyl (3aRS,4SR,7RS,7aRS)-2-benzyl-7-(4-fluorophenyl)-7-hydroxy-4-phenyloctahydroisoindole-3a-carboxylate were obtained, after crystallization from 40 cm³ of an isopropanol/diisopropyl ether (50/50 by volume) mixture, in the form of a white solid, the characteristic of which was as follows:

melting point=130° C.

The purification of this filtrate by flash chromatography on silica gel (230–400 mesh), elution being carried out with a cyclohexane/ethyl acetate (80/20 by volume) mixture, made it possible to obtain an additional 1.2 g.

Stage B

By carrying out the reaction as in Stage C of Example 38, but from 2.2 g of methyl (3aRS,4SR)-2-benzyl-7-(4-fluorophenyl)-7-hydroxy-4-phenyl-2,3,3a,4,5,6-hexahydroisoindole-3a-carboxylate, from 6.3 cm³ of trifluoromethanesulphonic acid and from 21 cm³ of dichloromethane, 1.0 g of methyl (3aRS,4SR,9SR,9aRS)-2-benzyl-4,9-ethano-9-(4-fluorophenyl)-2,3,3a,4,9,9a-hexahydro-1H-benzo[f]isoindole-3a-carboxylate was obtained, after recrystallization from 24 cm³ of diisopropyl ether, in the form of a white solid, the characteristic of which was as follows:

melting point=135° C.

By concentrating the filtrate and crystallization from 25 cm³ of petroleum ether, an additional 0.75 g was obtained.

Stage C

By carrying out the reaction as in Stage E of Example 1, but from 1.5 g of methyl (3aRS,4SR,9SR,9aRS)-2-benzyl-4,9-ethano-9-(4-fluorophenyl)-2,3,3a,4,9,9a-hexahydro-1H-benzo[f]isoindole-3a-carboxylate, from 0.64 g of ammonium formate and from 0.2 g of 10% (w/w) palladium-on-charcoal, 1.0 g of methyl (3aRS,4SR,9SR,9aRS)-4,9-ethano-9-(4-fluorophenyl)-2,3,3a,4,9,9a-hexahydro-1H-benzo[f]isoindole-3a-carboxylate was obtained in the form of a white solid, the characteristic of which was as follows:

melting point=145° C.

Stage D

By carrying out the reaction as in Stage G of Example 1, but from 1.0 g of methyl (3aRS,4SR,9SR,9aRS)-4,9-ethano-9-(4-fluorophenyl)-2,3,3a,4,9,9a-hexahydro-1H-benzo[f]isoindole-3a-carboxylate, from 0.51 g of 2-(2-methoxyphenyl)propenoic acid, from 0.24 cm³ of oxalyl chloride and from 0.79 cm³ of triethylamine, 0.7 g of methyl (3aRS,4SR,9SR,9aRS)-4,9-ethano-9-(4-fluorophenyl)-2-[2-(2-methoxyphenyl)propenoyl]-2,3,3a,4,9,9a-hexahydro-1H-benzo[f]isoindole-3a-carboxylate was obtained, after crystallization from 16 cm³ of isopropanol, in the form of a white solid, the characteristic of which was as follows:

melting point=165° C.

EXAMPLE 65

Preparation of (3aRS,4SR,9SR,9aRS)-4,9-ethano-9-(4-fluorophenyl-2-[2-(2-methoxyphenyl)propenoyl]-2,3,3a,4,9,9a-hexahydro-1H-benzo[f]isoindole-3a-carboxylic Acid By carrying out the reaction as in Example 2, but from 0.85 g of methyl (3aRS,4SR,9SR,9aRS)-4,9-ethano-9-(4-fluorophenyl)-2-[2-( 2-methoxyphenyl)propenoyl]-2,3,3a,4,9,9a-hexahydro-1H-benzo[f]isoindole-3a-carboxylate, from 8.5 cm³ of a normal aqueous sodium hydroxide solution and from 15 cm³ of methanol, 0.65 g of (3aRS,4SR,9SR,9aRS)-4,9-ethano-9-(4-fluorophenyl)-2-[2-(2-methoxyphenyl) propenoyl]-2,3,3a,4,9,9a-hexahydro-1H-benzo[f]isoindole-3a-carboxylic acid was obtained, after crystallization from aqueous acidic medium, the characteristic of which compound was as follows:

melting point=170° C.

EXAMPLE 66

Preparation of methyl (3aRS,4SR,9SR,9aRS)-9-(4-chloro-3-fluorophenyl)-4,9-ethano-2-[2-(2-methoxyphenyl)-propenoyl]-2,3,3a,4,9,9a-hexahydro-1H-benzo[f]isoindole-3a-carboxylate Stage A By carrying out the reaction as in Stage C of Example 1, but from 6.3 g of 4-chloro-3-fluorobromobenzene, from 0.73 g of magnesium turnings and from 5.45 g of methyl (3aRS,4SR,7aRS)-2-benzyl-7-oxo-4-phenyloctahydroisoindole-3a-carboxylate, 4.8 g of methyl (3aRS,4SR,7RS,7aRS)-2-benzyl-7-(4-chloro-3-fluorophenyl)-7-hydroxy-4-phenyloctahydroisoindole-3a-carboxylate were obtained, after flash chromatography on silica gel (230–400 mesh), elution being carried out with a cyclohexane/ethyl acetate (95/5 by volume) mixture, and recrystallization from 75 cm$^3$ of isopropanol, in the form of a white solid, the characteristic of which was as follows:

melting point=175° C.

Stage B

By carrying out the reaction as in Stage D of Example 1, but from 4.6 g of methyl (3aRS,4SR,7RS,7aRS)-2-benzyl-7-(4-chloro-3-fluorophenyl)-7-hydroxy-4-phenyloctahydroisoindole-3a-carboxylate, from 12.4 cm$^3$ of trifluoromethanesulphonic acid and from 50 cm$^3$ of dichloromethane, 3 g of methyl (3aRS,4SR,9SR,9aRS)-2-benzyl-9-(4-chloro-3-fluorophenyl)-4,9-ethano-2,3,3a,4,9,9a-hexahydro-1H-benzo[f]isoindole-3a-carboxylate were obtained, after crystallization from 25 cm$^3$ of isopropanol, in the form of a white solid, the characteristic of which was as follows:

melting point=136° C.

Stage C

By carrying out the reaction as in Stage C of Example 51, but from 2.8 g of methyl (3aRS,4SR,9SR,9aRS)-2-benzyl-9-(4-chloro-3-fluorophenyl)-4,9-ethano-2,3,3a,4,9,9a-hexahydro-1H-benzo[f]isoindole-3a-carboxylate and from 1.95 cm$^3$ of vinyl chloroformate in 40 cm$^3$ of dichloromethane, and by then treating the intermediate, dissolved in 40 cm$^3$ of methanol, with 59 cm$^3$ of a normal solution of hydrogen chloride gas in diethyl ether, 1 g of methyl (3aRS,4SR,9SR,9aRS)-9-(4-chloro-3-fluorophenyl)-4,9-ethano-2,3,3a,4,9,9a-hexahydro-1H-benzo[f]isoindole- 3a-carboxylate was obtained, after flash chromatography on silica gel (230–400 mesh), elution being carried out with a dichloromethane/methanol (97.5/2.5 by volume) mixture, in the form of a yellow foam, used in the subsequent syntheses.

Stage D

By carrying out the reaction as in Stage G of Example 1, but from 1.4 g of methyl (3aRS,4SR,9SR,9aRS)-9-(4-chloro-3-fluorophenyl)-4,9-ethano-2,3,3a,4,9,9a-hexahydro-1H-benzo[f]isoindole-3a-carboxylate, from 0.67 g of 2-(2-methoxyphenyl)propenoic acid, from 0.33 cm$^3$ of oxalyl chloride and from 1.06 cm$^3$ of triethylamine, 1.5 g of methyl (3aRS,4SR,9SR,9aRS)-9-(4-chloro-3-fluorophenyl)-4,9-ethano-2-[2-(2-methoxyphenyl)propenoyl]-2,3,3a,4,9,9a-hexahydro-1H-benzo[f]isoindole-3a-carboxylate were obtained, after flash chromatography on silica gel (230–400 mesh), elution being carried out with a cyclohexane/ethyl acetate (70/30 by volume) mixture, and recrystallization from an isopropanol/diisopropyl ether (1/1 by volume) mixture, the characteristic of which compound was as follows:

melting point=173° C.

EXAMPLE 67

Preparation of (3aRS,4SR,9SR,9aRS)-9-(4-chloro-3-fluorophenyl)-4,9-ethano-2-[2-(2-methoxyphenyl) propenoyl]-2,3,3a,4,9,9a-hexahydro-1H-benzo[f] isoindole-3a-carboxylic Acid By carrying out the reaction as in Example 2, but from 1.2 g of methyl (3aRS,4SR,9SR,9aRS)-9-(4-chloro-3-fluorophenyl)-4,9-ethano-2-[2-(2-methoxyphenyl) propenoyl]-2,3,3a,4,9,9a-hexahydro-1H-benzo[f]isoindole-3a-carboxylate, from 3.3 cm$^3$ of a normal aqueous sodium hydroxide solution and from 20 cm$^3$ of ethanol, 1.15 g of (3aRS,4SR,9SR,9aRS)-9-(4-chloro-3-fluorophenyl)-4,9-ethano-2-[2-(2-methoxyphenyl)propenoyl]-2,3,3a,4,9,9a-hexahydro-1H-benzo[f]isoindole-3a-carboxylic acid were obtained, after recrystallization from 5 cm$^3$ of isopropanol, the characteristic of which compound was as follows:

melting point=170° C.

EXAMPLE 68

Preparation of methyl (3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f] isoindole-3a-carboxylate Stage A By carrying out the reaction as in Stage C of Example 1, but from 3.68 cm$^3$ of 3-bromotoluene, from 0.73 g of magnesium turnings and from 5.45 g of methyl (3aRS,4SR,7aRS)-2-benzyl-7-oxo-4-phenyloctahydroisoindole-3a-carboxylate, 4.2 g of methyl (3aRS,4SR,7RS,7aRS)-2-benzyl-7-hydroxy-7-(3-methylphenyl)-4-phenyloctahydroisoindole-3a-carboxylate were obtained, after flash chromatography on silica gel (230–400 mesh), elution being carried out with a cyclohexane/ethyl acetate (95/5 by volume) mixture, and recrystallization from 75 cm$^3$ of isopropanol, in the form of an orangey-yellow foam, used in the subsequent syntheses.

Stage B

By carrying out the reaction as in Stage C of Example 38, but from 4.2 g of methyl (3aRS,4SR,7RS,7aRS)-2-benzyl-7-hydroxy-7-(3-methylphenyl)-4-phenyloctahydroisoindole-3a-carboxylate, from 12.4 cm$^3$ of trifluoromethanesulphonic acid and from 42 cm$^3$ of dichloromethane, 4 g of methyl (3aRS,4SR,9SR,9aRS)-2-benzyl-4,9-ethano-9-(3-methylphenyl)-2,3,3a,4,9,9a-hexahydro-1H-benzo[f]isoindole-3a-carboxylate were obtained in the form of an orange-coloured foam, used as is in the subsequent syntheses.

Stage C

By carrying out the reaction as in Stage E of Example 1, but from 4 g of methyl (3aRS,4SR,9SR,9aRS)-2-benzyl-4,9-ethano-9-(3-methylphenyl)-2,3,3a,4,9,9a-hexahydro-1H-benzo[f]isoindole-3a-carboxylate, from 1.73 g of ammonium formate and from 0.75 g of 10% (w/w) palladium-on-charcoal, 3 g of methyl (3aRS,4SR,9SR,9aRS)-4,9-ethano-9-(3-methylphenyl)-2,3,3a,4,9,9a-hexahydro-1H-benzo[f] isoindole-3a-carboxylate were obtained in the form of a yellow oil, used in the subsequent syntheses.

Stage D

By carrying out the reaction as in Stage G of Example 1, but from 3 g of methyl (3aRS,4SR,9SR,9aRS)-4,9-ethano-9-(3-methylphenyl)-2,3,3a, 4,9,9a-hexahydro-1H-benzo[f] isoindole-3a-carboxylate, from 1.54 g of 2-(2-methoxyphenyl)propenoic acid, from 0.74 cm$^3$ of oxalyl chloride and from 2.45 cm$^3$ of triethylamine, 2.5 g of methyl (3aRS,4SR,9SR,9aRS)-4,9-ethano-2-[2-(2-methoxyphenyl)

propenoyl]-9-(3-methylphenyl)-2,3,3a,4,9,9a-hexahydro-1H-benzo[f]isoindole-3a-carboxylate were obtained, after flash chromatography on silica gel (230–400 mesh), elution being carried out with a cyclohexane/ethyl acetate (50/50 by volume) mixture, and recrystallization from 10 cm$^3$ of isopropanol, the characteristic of which compound was as follows:

melting point=142° C.

EXAMPLE 69

Preparation of (3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f]isoindole-3a-carboxylic Acid By carrying out the reaction as in Example 2, but from 2.2 g of methyl (3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f]isoindole-3a-carboxylate, from 8.7 cm$^3$ of a normal aqueous sodium hydroxide solution and from 22 cm$^3$ of ethanol, 1.75 g of (3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f]isoindole-3a-carboxylic acid were obtained, after recrystallization from 50 cm$^3$ of isopropanol, the characteristic of which compound was as follows:

melting point=252° C.

EXAMPLE 70

Preparation of (3aRS,4SR,9SR,9aRS)-9-(1,3-benzodioxol-5-yl)-4,9-ethano-2-[2-(2-methoxyphenyl)propenoyl]-2,3,3a,4,9,9a-hexahydro-1H-benzo[f]isoindole-3a-carboxylic Acid Stage A By carrying out the reaction as in Stage A of Example 31, but from 5.9 g of methyl (3aRS,4SR,7aRS)-2-benzyl-7-oxo-4-phenyloctahydroisoindole-3a-carboxylate, from 2.5 cm$^3$ of veratrole and from 6.3 cm$^3$ of trifluoromethanesulfonic acid in 26 cm$^3$ of dichloromethane, 1.8 g of methyl (3aRS,4SR,9SR,9aRS)-2-benzyl-9-(3,4-dimethoxyphenyl)-4,9-ethano-2,3,3a,4,9,9a-hexahydro-1H-benzo[f]isoindole-3a-carboxylate were obtained, after purification by flash chromatography on silica gel (230–400 mesh), elution being carried out with a cyclohexane/ethyl acetate (90/10 by volume) mixture, in the form of a colourless oil, used in the subsequent syntheses.

Stage B

A solution of 1.8 g of methyl (3aRS,4SR,9SR,9aRS)-2-benzyl-9-(3,4-dimethoxyphenyl)-4,9-ethano-2,3,3a,4,9,9a-hexahydro-1H-benzo[f]isoindole-3a-carboxylate in 20 cm$^3$ of dichloromethane was added to 22.3 cm$^3$ of boron tribromide cooled to a temperature in the region of −50° C. The reaction mixture was stirred for one hour at a temperature in the region of −50° C. and then 75 cm$^3$ of a saturated aqueous sodium hydrogencarbonate solution were added. The aqueous phase was separated by settling and extracted with two times 25 cm$^3$ of dichloromethane. The organic phases were combined, washed with three times 15 cm$^3$ of distilled water, dried over magnesium sulphate and concentrated under reduced pressure. The residue was purified by flash chromatography on silica gel (230–400 mesh), elution being carried out with a dichloromethane/methanol (97.5/2.5 by volume) mixture. 0.8 g of methyl (3aRS,4SR,9SR,9aRS)-2-benzyl-9-(3,4-dihydroxyphenyl)-4,9-ethano-2,3,3a,4,9,9a-hexahydro-1H-benzo[f]isoindole-3a-carboxylate, in the form of an orange oil used as is in the subsequent syntheses, and 1.0 g of a mixture of methyl (3aRS,4SR,9SR,9aRS)-2-benzyl-4,9-ethano-9-(3-hydroxy-4-methoxyphenyl)-2,3,3a,4,9,9a-hexahydro-1H-benzo[f]isoindole-3a-carboxylate and of methyl (3aRS,4SR,9SR,9aRS)-2-benzyl-4,9-ethano-9-(4-hydroxy-3-methoxyphenyl)-2,3,3a,4,9,9a-hexahydro-1H-benzo[f]isoindole-3a-carboxylate, in the form of an orange oil used as is in the subsequent syntheses, were thus obtained.

Stage C

A solution of 1.8 g of potassium carbonate in 4 cm$^3$ of distilled water and then 60 mg of Adogen 464 are added to a solution of 0.58 g of methyl (3aRS,4SR,9SR,9aRS)-2-benzyl-9-(3,4-dihydroxyphenyl)-4,9-ethano-2,3,3a, 4,9,9a-hexahydro-1H-benzo[f]isoindole-3a-carboxylate in 4 cm$^3$ of dibromomethane. The reaction mixture was heated at reflux with stirring for 90 minutes, then cooled to a temperature in the region of 20° C. and diluted with 25 cm$^3$ of dichloromethane. The aqueous phase was separated by settling and extracted with two times 15 cm$^3$ of dichloromethane. The organic phases were combined, washed with three times 15 cm$^3$ of distilled water, dried over magnesium sulphate and concentrated under reduced pressure. 0.8 g of a crude product was thus obtained, which product was combined with a second batch of 0.4 g originating from another experiment. The purification of this mixture by flash chromatography on silica gel (230–400 mesh), elution being carried out with a cyclohexane/ethyl acetate (90/10 by volume) mixture, provided 0.45 g of methyl (3aRS,4SR,9SR,9aRS)-9-(1,3-benzodioxol-5-yl)-2-benzyl-4,9-ethano-2,3,3a,4,9,9a-hexahydro-1H-benzo[f]isoindole-3a-carboxylate in the form of a white foam, used in the subsequent syntheses, the characteristics of which were as follows:

$^1$H N.M.R. spectrum (400 MHz, CDCl$_3$, at a temperature of 333 K, δ in ppm): 1.43, 1.65 and 2.47 (3 mts, respectively 1H, 1H and 2H, CH$_2$CH$_2$), from 2.25 to 2.40 (mt, 1H, 1H of the CH$_2$ at 1), 2.36 (d, J=10 Hz, 1H, 1H of the CH$_2$ at 3), 2.77 (broad d, J=9.5 Hz, 1H, the other H of the CH$_2$ at 1), from 3.15 to 3.25 (mt, 1H, CH at 9a), 3.21 (d, J=10 Hz, 1H, the other H of the CH$_2$ at 3), 3.39 (broad s, 1H, CH at 4), 3.43 and 3.67 (2 d, J=13 Hz, each 1H, NCH$_2$Ar), 3.55 (s, 3H, COOCH$_3$), 5.98 (limit AB, 2H, OCH$_2$O), 6.63 (broad d, J=7.5 Hz, 1H, H at 8), 6.85 and 6.91 (2 broad d, J=8.5 Hz, each 1H, H at 6 and H at 7 of the 1,3-benzodioxol), 6.96 (broad s, 1H, H at 4 of the 1,3-benzodioxol), from 7.00 to 7.35 (mt, 8H, H at 5, H at 6, H at 7 and aromatic H of the benzyl).

Stage D

By carrying out the reaction as in Stage E of Example 1 but from 0.5 g of methyl (3aRS,4SR,9SR,9aRS)-9-(1,3-benzodioxol-5-yl)-2-benzyl-4,9-ethano-2,3,3a,4,9,9a-hexahydro-1H-benzo[f]isoindole-3a-carboxylate, from 0.21 g of ammonium formate and from 70 mg of 10% (w/w) palladium-on-charcoal, 0.25 g of methyl (3aRS,4SR,9SR, 9aRS)-9-(1,3-benzodioxol-5-yl)-4,9-ethano-2,3,3a,4,9,9a-hexahydro-1H-benzo[f]isoindole-3a-carboxylate was obtained in the form of a white solid, used in the subsequent syntheses.

Stage E

By carrying out the reaction as in Stage G of Example 1, but from 0.25 g of methyl (3aRS,4SR,9SR,9aRS)-9-(1,3-benzodioxol-5-yl)-4,9-ethano-2,3,3a,4,9,9a-hexahydro-1H-benzo[f]isoindole-3a-carboxylate, from 0.12 g of 2-(2-methoxyphenyl)-propenoic acid, from 0.06 cm$^3$ of oxalyl chloride and from 0.19 cm$^3$ of triethylamine, 0.26 g of methyl (3aRS,4SR,9SR,9aRS)-9-(1,3-benzodioxol-5-yl)-4, 9-ethano-2-[2-(2-methoxyphenyl)propenoyl]-2,3,3a,4,9,9a- hexahydro-1H-benzo[f]isoindole-3a-carboxylate was obtained, after flash chromatography on silica gel (230–400 mesh), elution being carried out with a dichloromethane/methanol (97.5/2.5 by volume) mixture, in the form of a white foam, used in the subsequent syntheses.

Stage F

By carrying out the reaction as in Example 2, but from 0.26 g of (3aRS,4SR,9SR,9aRS)-9-(1,3-benzodioxol-5-yl)-4,9-ethano-2-[2-(2-methoxyphenyl)propenoyl]-2,3,3a,4,9,9a-hexahydro-1H-benzo[f]isoindole-3a-carboxylate, from 2.4 cm$^3$ of a normal aqueous sodium hydroxide solution and from 5 cm$^3$ of methanol, 80 mg of (3aRS,4SR,9SR,9aRS)-9-(1,3-benzodioxol-5-yl)-4,9-ethano-2-[2-(2-methoxyphenyl)propenoyl]-2,3,3a,4,9,9a-hexahydro-1H-benzo[f]isoindole-3a-carboxylic acid were obtained, after purification by flash chromatography on silica gel (230–400 mesh), elution being carried out with a dichloromethane/methanol (97.5/2.5 by volume) mixture, and crystallization from 2.5 cm$^3$ of diisopropyl ether, the characteristic of which compound was as follows:

melting point=204° C.

EXAMPLE 71

Preparation of methyl (3aRS,4SR,9SR,9aRS)-9-(3,4-dimethylphenyl)-4,9-ethano-2-[2-(2-methoxyphenyl)propenoyl]-2,3,3a,4,9,9a-hexahydro-1H-benzo[f]isoindole-3a-carboxylate Stage A By carrying out the reaction as in Stage A of Example 31, but from 10.34 g of methyl (3aRS,4SR,7aRS)-2-benzyl-7-oxo-4-phenyloctahydroisoindole-3a-carboxylate in 40 cm$^3$ of dichloromethane, from 50 cm$^3$ of ortho-xylene, from 24 cm$^3$ of 99% trifluoromethanesulphonic acid and from 6.5 cm$^3$ of trifluoromethanesulphonic anhydride under an argon atmosphere for 23 hours at a temperature in the region of 20° C., 7.27 g of impure methyl (3aRS,4SR,9SR,9aRS)-2-benzyl-9-(3,4-dimethylphenyl)-4,9-ethano-2,3,3a,4,9,9a-hexahydro-1H-benzo[f]isoindole-3a-carboxylate were obtained in the form of a colourless oil, which was used in the following stage, the characteristic of which was as follows:

mass spectrum (DCI): M/Z=452 (M+H$^+$).

Stage B

By carrying out the reaction as in Stage E of Example 1, but from 9.51 g of methyl (3aRS,4SR,9SR,9aRS)-2-benzyl-9-(3,4-dimethylphenyl)-4,9-ethano-2,3,3a,4,9,9a-hexahydro-1H-benzo[f]isoindole-3a-carboxylate, obtained as in the preceding stage, from 4 g of ammonium formate, from 0.5 g of 10% (w/w) palladium-on-charcoal in 150 cm$^3$ of methanol and from 100 cm$^3$ of dioxane at a temperature in the region of 50° C. for six hours, after flash chromatography on 500 g of silica gel, elution being carried out successively with one dm$^3$ of pure dichloromethane, then one dm$^3$ of the dichloromethane/ethanol (98/2 by volume) mixture, then one dm$^3$ of the dichloromethane/ethanol (95/5 by volume) mixture, then with the dichloromethane/ethanol (90/10 by volume) mixture and then the dichloromethane/ethanol (80/20 by volume) mixture, 5.79 g of methyl (3aRS,4SR,9SR,9aRS)-9-(3,4-dimethylphenyl)-4,9-ethano-2,3,3a,4,9,9a-hexahydro-1H-benzo[f]isoindole-3a-carboxylate were obtained in the form of a slightly foamy colourless lacquer, used in the following stage, the characteristic of which was as follows:

mass spectrum (DCI): M/Z=361 (M$^+$).

Stage C

By carrying out the reaction as in Stage G of Example 1, but from a solution of 2.67 g of 2-(2-methoxyphenyl)propenoic acid in 50 cm$^3$ of dichloromethane containing 2 drops of N,N-dimethylformamide, from 1.31 cm$^3$ of oxalyl chloride, for 2 hours, and from a solution of 5.075 g of (3aRS,4SR,9SR,9aRS)-9-(3,4-dimethylphenyl)-4,9-ethano-2,3,3a,4,9,9a-hexahydro-1H-benzo[f]isoindole-3a-carboxylate, obtained in the preceding stage, and from 4.4 cm$^3$ of triethylamine in 100 cm$^3$ of dichloromethane, and then running in 100 cm$^3$ of water after 1 hour, 3.4 g of methyl (3aRS,4SR,9SR,9aRS)-9-(3,4-dimethylphenyl)-4,9-ethano-2-[2-(2-methoxyphenyl)propenoyl]-2,3,3a,4,9,9a-hexahydro-1H-benzo[f]isoindole-3a-carboxylate were obtained in the form of a white powder, the characteristics of which were as follows:

melting point=163° C. (dec);

mass spectrum (EI): M/Z=521 (M$^+$).

EXAMPLE 72

Preparation of (3aRS,4SR,9SR,9aRS)-9-(3,4-dimethylphenyl)-4,9-ethano-2-[2-(2-methoxyphenyl)propenoyl]-2,3,3a,4,9,9a-hexahydro-1H-benzo[f]isoindole-3a-carboxylic Acid By carrying out the reaction as in Example 2, but from 4.736 g of methyl (3aRS,4SR,9SR,9aRS)-9-(3,4-dimethylphenyl)-4,9-ethano-2-[2-(2-methoxyphenyl)propenoyl]-2,3,3a,4,9,9a-hexahydro-1H-benzo[f]isoindole-3a-carboxylate, obtained in the preceding stage, and from 36 cm$^3$ of a normal aqueous sodium hydroxide solution in 50 cm$^3$ of ethanol and 100 cm$^3$ of dioxane for sixteen hours at a temperature in the region of 70° C., 3.375 g of (3aRS,4SR,9SR,9aRS)-9-(3,4-dimethylphenyl)-4,9-ethano-2-[2-(2-methoxyphenyl)propenoyl]-2,3,3a,4,9,9a-hexahydro-1H-benzo[f]isoindole-3a-carboxylic acid were obtained in the form of a white powder, the characteristics of which were as follows:

melting point=200° C., then 245° C.;

N.M.R. spectrum No. 127748;

mass spectrum (EI): M/Z=507 (M$^+$).

EXAMPLE 73

Preparation of methyl (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylate Stage A By carrying out the reaction as in Stage A of Example 31, but from 11.5 g of methyl (3aRS,4SR,7aRS)-2-benzyl-7-oxo-4-phenyloctahydroisoindole-3a-carboxylate, from 13.1 cm$^3$ of anisole and from 21.2 cm$^3$ of trifluoromethanesulphonic acid in 120 cm$^3$ of dichloromethane, 12 g of methyl (3aRS,4SR,9SR,9aRS)-2-benzyl-4,9-ethano-9-(4-methoxyphenyl)-2,3,3a,4,9,9a-hexahydro-1H-benzo[f]isoindole-3a-carboxylate were obtained, after purification by flash chromatography on silica gel (230–400 mesh), elution being carried out with a cyclohexane/ethyl acetate (70/30 by volume) mixture, the characteristic of which compound was as follows:

melting point=150° C.

Stage B

By carrying out the reaction as in Stage E of Example 1, but from 11.4 g of methyl (3aRS,4SR,9SR,9aRS)-2-benzyl-4,9-ethano-9-(4-methoxyphenyl)-2,3,3a,4,9,9a-hexahydro-1H-benzo[f]isoindole-3a-carboxylate, from 4.76 g of ammonium formate and from 1 g of 10% (w/w) palladium-on-charcoal, 9 g of methyl (3aRS,4SR,9SR,9aRS)-4,9-ethano-9-(4-methoxyphenyl)-2,3,3a,4,9,9a-hexahydro-1H-benzo

[f]isoindole-3a-carboxylate were obtained, which product was used in the subsequent syntheses.

Stage C

By carrying out the reaction as in Stage G of Example 1, but from 8.9 g of methyl (3aRS,4SR,9SR,9aRS)-4,9-ethano-9-(4-methoxyphenyl)-2,3,3a,4,9,9a-hexahydro-1H-benzo[f]isoindole-3a-carboxylate, from 4.36 g of 2-(2-methoxyphenyl)propanoic acid, from 2.1 cm³ of oxalyl chloride and from 6.9 cm³ of triethylamine, 0.47 g of methyl (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylate was obtained, after purification by flash chromatography on silica gel (230–400 mesh), eluting being carried out with a cyclohexane/ethyl acetate (50/50 by volume) mixture, in the form of a white foam, the characteristic of which was as follows:

melting point=90° C.

EXAMPLE 74

Preparation of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic Acid By carrying out the reaction as in Example 2, but from 11 g of methyl (3aRS,4SR,9SR,9aRS)-4,9-ethano-9-(4-methoxyphenyl)-2-[2-( 2-methoxyphenyl)propenoyl]-2,3,3a,4,9,9a-hexahydro-1H-benzo[f]isoindole-3a-carboxylate, from 42 cm³ of a normal aqueous sodium hydroxide solution and from 100 cm³ of methanol, 2.15 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid were obtained, after purification by flash chromatography on silica gel (230–400 mesh), elution being carried out with dichloromethane/methanol (100/0 to 98/2 by volume) mixtures, the characteristic of which compound was as follows:

melting point=165° C.

EXAMPLE 75

Isolation of the Dextrorotatory Enantiomer of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic Acid 9.2 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid, obtained in Example 74, were resolved, on a chiral silica column carrying N-(3,5-dinitrobenzoyl)-(R)-phenylalanine grafts, in 5 successive injections and by eluting with an n-heptane/dichloromethane/methanol (50/50/3 by volume) mixture. On collecting the first fractions eluted (retention time 42 min), 3.51 g of the dextrorotatory enantiomer of (3aRS,4SR,9SR,9aRS)-4,9-ethano- 9-(4-methoxyphenyl)-2-[2-(2-methoxyphenyl)propenoyl]-2,3,3a,4,9,9a-hexahydro-1H-benzo[f]isoindole-3a-carboxylic acid were obtained, after concentrating the solvent under reduced pressure, in the form of a white powder, the characteristics of which were as follows:

melting point=203° C.;

mass spectrum (EI): M/Z=509 (M⁺);

optical rotation: $[\alpha]_{365}^{20}$=+71.7+/−1.2° (c=0.5, methanol).

EXAMPLE 76

Preparation of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N-(3-pyridylmethyl)carboxamide By carrying out the reaction as in Example 42, but from 1 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid, 0.24 cm³ of 3-(aminomethyl)pyridine, 0.46 g of 1-ethyl-3-[3-(dimethylamino)propyl]carbodiimide hydrochloride and 0.16 g of N-1-hydroxybenzotriazole hydrate, 0.72 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N-(3-pyridylmethyl)carboxamide was obtained, after crystallization from 11 cm³ of an isopropanol/diisopropyl ether (10/90 by volume) mixture, the characteristic of which compound was as follows:

melting point=121° C.

EXAMPLE 77

Preparation of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N'-phenylcarbohydrazide By carrying out the reaction as in Example 27, but from 1 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid, 0.25 cm³ of N-phenylhydrazine, 0.45 g of 1-ethyl-3-[3-(dimethylamino)propyl]carbodiimide hydrochloride and 0.16 g of N-1-hydroxybenzotriazole hydrate, 0.9 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N'-phenylcarbohydrazide was obtained, after crystallization from 11 cm³ of an isopropanol/diisopropyl ether (10/90 by volume) mixture, the characteristic of which compound was as follows:

melting point=180° C.

EXAMPLE 78

Preparation of (3aRS,4SR,9SR,9aRS)-4,9-ethano-9-(4-methoxyphenyl)-2-[2-(2-methogyphenyl)propenoyl]-2,3,3a,4,9,9a-hexahydro-1H-benzo[f]isoindole-3a-hydroxamic Acid Stage A A solution of 0.83 g of O-benzylhydroxylamine and of 0.73 cm³ of triethylamine in 10 cm³ of dichloromethane was added to a solution of 2.2 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid, of 1 g of 1-ethyl-3-[3-(dimethylamino)propyl]carbodiimide hydrochloride and of 0.35 g of N-1-hydroxybenzotriazole hydrate in 10 cm³ of dichloromethane. The reaction mixture was stirred for twenty-four hours at a temperature in the region of 20° C. and then 15 cm³ of distilled water were added. The organic phase was separated by settling, washed with 20 cm³ of distilled water, dried over magnesium sulphate and concentrated under reduced pressure. The residue was crystallized from 25 cm³ of an isopropanol/diisopropyl ether (20/80 by volume) mixture. 2.03 g of benzyl (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3-hydroxamate were thus obtained in the form of a white solid, the characteristic of which was as follows:

melting point=201° C.

Stage B

By carrying out the reaction as in Example 16, but from 1.84 g of benzyl (3aRS,4SR,9SR,9aRS)-4,9-ethano-9-(4-methoxyphenyl)-2-[2-(2-methoxyphenyl)propenoyl]-2,3, 3a,4,9,9a-hexahydro-1H-benzo[f]isoindole-3-hydroxamate, from 1 g of aluminium chloride and from 0.98 cm³ of anisole, 0.5 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-hydroxamic acid was obtained, after flash chromatography on silica gel (230–400 mesh), elution being carried out with a dichloromethane/methanol (90/10 by volume) mixture, in the form of an ecru solid, the characteristic of which was as follows:

melting point=165° C.

EXAMPLE 79

Preparation of (3aRS,4SR,9SR,9aRS)-4,9-ethano-9-(4-methoxyphenyl)-2-[2-(2-methoxyphenyl) propenoyl]-2,3,3a,4,9,9a-hexahydro-1H-benzo[f] isoindole-3a-N'-(3-pyridyl)carbohydrazide By carrying out the reaction as in Example 27, but from 1 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid, 0.26 g of N-(3-pyridyl)hydrazine, 0.45 g of 1-ethyl-3-[3-(dimethylamino)propyl]carbodiimide hydrochloride and 0.16 g of N-1-hydroxybenzotriazole hydrate, 0.6 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N'-(3-pyridyl)carbohydrazide was obtained, after purification by flash chromatography on silica gel (230–400 mesh), elution being carried out with dichloromethane/methanol (95/5, then 90/10, by volume) mixtures, and recrystallization from isopropanol, the characteristic of which compound was as follows:

melting point=180° C.

EXAMPLE 80

Preparation of (3aRS,4SR,9SR,9aRS)-4,9-ethano-9-(4-methogyphenyl)-2-[2-(2-methoxyphenyl) propenoyl]-2,3,3a,4,9,9a-hexahydro-1H-benzo[f] isoindole-3a-N-(3-thienylmethyl)carboxamide By carrying out the reaction as in Example 42, but from 1 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid, 0.2 g of 3-aminomethylthiophene, 0.45 g of 1-ethyl-3-[3-(dimethylamino)propyl]carbodimide hydrochloride and 0.16 g of N-1-hydroxybenzotriazole hydrate, 1 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole- 3a-N-(3-thienylmethyl)carboxamide was obtained, after recrystallization from 11 cm³ of an isopropanol/diisopropyl ether (10/90 by volume) mixture, the characteristic of which compound was as follows:

melting point=130° C.

EXAMPLE 81

Preparation of (RS)- and (SR)-2-{(3aRS,4SR,9SR, 9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carbonylamino}phenylacetic Acids Stage A By carrying out the reaction as in Example 42, but from 1.27 g of (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid, 0.61 g of methyl phenylglycinate hydrochloride, 0.59 g of 1-ethyl-3-[3-(dimethylamino)propyl]carbodiimide hydrochloride, 0.42 cm³ of triethylamine and 0.2 g of N-1-hydroxybenzotriazole hydrate, 1 g of a mixture of methyl (RS)- and (SR)-2-{(3aRS,4SR,9SR,9aRS)-4,9-ethano-9-(4-methoxyphenyl)-2-[2-(2-methoxyphenyl) propenoyl]-2,3,3a,4,9,9a-hexahydro-1H-benzo[f]isoindole-3a-carbonylamino}phenylacetates was obtained, after flash chromatography on silica gel (230–400 mesh), elution being carried out with a dichloromethane/methanol (99/1 by volume) mixture, in the form of a foam, used in the subsequent syntheses.

Stage B

By carrying out the reaction as in Example 2, but from 0.6 g of a mixture of methyl (RS)- and (SR)-2-{(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carbonylamino}phenylacetates in 1.83 cm³ of a normal aqueous sodium hydroxide solution and 20 cm³ of ethanol, 0.5 g of crude product was obtained, which was combined with a second batch of 0.65 g originating from another experiment. The purification of this mixture, by recrystallization from 50 cm³ of an isopropanol/diisopropyl ether (50/50 by volume) mixture, provided 1.05 g of an equimolar mixture of (RS)- and (SR)-2-{(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carbonylamino}phenylacetic acids, the characteristics of which were as follows:

melting point=196° C.

¹H N.M.R. spectrum (250 MHz, (CD$_3$)$_2$SO, at a temperature of 383 K, δ in ppm). The mixture of the two diastereoisomers was observed in the proportions 50/50.

1.38, 1.60, 1.98 and 2.14 (4 mts, each 1H, CH$_2$CH$_2$), from 3.15 to 3.80 (mt, 5H, CH$_2$ at 1, 1H of the CH$_2$ at 3, CH at 9a and CH at 4), 3.64, 3.71 and 3.84 (3 s, 6H in all, the 2 ArOCH$_3$), from 4.20 to 4.45 (mt, 1H, the other H of the CH$_2$ at 3), 5.19 (mt, 1H, NCHAr), 5.47, 5.51, 5.66 and 5.69 (4 broad s, 2H in all, =CH$_2$), 6.42 (mt, 1H, H at 8), from 6.80 to 7.50 (mt, 16H, H at 5, H at 6, H at 7, aromatic H of the 4-methoxyphenyl, aromatic H at the 2-methoxyphenyl and aromatic H of the phenyl), 7.98 and 8.02 (2 broad s, 1H in all, CONH).

EXAMPLE 82

Preparation of (3aRS,4SR,9SR,9aRS)-4,9-ethano-2-[2-(2-methoxyphenyl)propenoyl]-9-(4-trifluoromethoxyphenyl)-2,3,3a,4,9,9a-hexahydro-1H-benzo[f]isoindole-3a-carboxylic Acid Stage A By carrying out the reaction as in Stage C of Example 45, but from 1.51 g of methyl (3aRS,4SR,7aRS)-2-benzyl-7-iodo-4-phenyl-2,3,3a,4,5,7a-hexahydro-1H-isoindole-3a-carboxylate, from 0.17 g of tetrakis(triphenylphosphine) palladium, from 0.73 g of 4-trifluoromethoxyphenylboronic acid, obtained in trimeric anhydride form by carrying out the reaction as in Patent D.E. 4,218,614, and from 1.5 g of sodium carbonate at reflux for two hours in 15 cm³ of toluene and 13 cm³ of methanol, 1.2 g (79%) of methyl (3aRS,4SR,7aRS)-2-benzyl-4-phenyl-7-(4-trifluoromethoxyphenyl)-2,3,3a,4,5,7a-hexahydro-1H-isoindole-3a-carboxylate were obtained, after purification by flash chromatography on silica gel (230–400 mesh), elution being carried out with a mixture of cyclohexane and ethyl acetate (80/20 by volume), in the form of a pale-yellow oil, the characteristic of which was as follows:

mass spectrum (EI): M/Z=507 (M⁺).

Stage B

By carrying out the reaction as in Stage C of Example 38, but from 0.48 g of methyl (3aRS,4SR,7aRS)-2-benzyl-4-phenyl-7-(4-trifluoromethoxyphenyl)-2,3,3a,4,5,7a-hexahydro-1H-isoindole-3a-carboxylate and from 1.18 cm³ of trifluoromethanesulphonic acid in 2 cm³ of dichloromethane for two hours at room temperature, 0.43 g (89%) of methyl (3aRS,4SR,9SR,9aRS)-2-benzyl-4,9-ethano-9-(4-trifluoromethoxyphenyl)-2,3,3a,4,9,9a-hexahydro-1H-benzo[f]isoindole-3a-carboxylate was obtained, after purification by flash chromatography on silica gel (230–400 mesh), elution being carried out with a mixture of cyclohexane and ethyl acetate (90/10 by volume), in the form of a beige paste, used in the following stage, the characteristic of which was as follows:

mass spectrum (EI): M/Z=507 (M⁺).

Stage C

By carrying out the reaction as in Stage B of Example 47, but from 0.83 g of methyl (3aRS,4SR,9SR,9aRS)-2-benzyl-4,9-ethano-9-(4-trifluoromethoxyphenyl)-2,3,3a,4,9,9a-hexahydro-1H-benzo[f]isoindole-3a-carboxylate and from 0.29 cm³ of vinyl chloroformate for eighteen hours at room temperature in 10 cm³ of dichloromethane, and by then taking the concentrate up in 20 cm³ of a normal solution of hydrogen chloride gas in isopropanol at reflux for one hour, 0.59 g (75%) of methyl (3aRS,4SR,9SR,9aRS)-4,9-ethano-9-(4-trifluoromethoxyphenyl)-2,3,3,a,4,9,9a-hexahydro-1H-benzo[f]isoindole-3a-carboxylate was obtained, after neutralization with a normal aqueous sodium hydroxide solution and then extraction with dichloromethane and concentration of the solvent under reduced pressure, in the form of a white foam, used in the following stage, the characteristic of which was as follows:

mass spectrum (EI): M/Z=417 (M⁺).

Stage D

By carrying out the reaction as in Stage E of Example 5, but from 0.59 g of methyl (3aRS,4SR,9SR,9aRS)-4,9-ethano-9-(4-trifluoromethoxyphenyl)-2,3,3a,4,9,9a-hexahydro-1H-benzo[f]isoindole-3a-carboxylate, from 0.25 g of 2-(2-methoxyphenyl)propanoic acid, from 0.2 g of 1-ethyl-3-[3-(dimethylamino)propyl]carbodiimide hydrochloride and from 27 mg of N-1-hydroxybenzotriazole hydrate in 15 cm³ of dichloromethane for eighteen hours at room temperature, 0.41 g (53%) of methyl (3aRS,4SR,9SR,9aRS)-4,9-ethano-2-[2-(2-methoxyphenyl)propenoyl]-9-(4-trifluoromethoxyphenyl)-2,3,3a,4,9,9a-hexahydro-1H-benzo[f]isoindole-3a-carboxylate was obtained, after purification by flash chromatography on silica gel (230–400 mesh), elution being carried out with a mixture of cyclohexane and ethyl acetate (60/40 by volume), in the form of a light-beige powder, the characteristics of which were as follows:

melting point=86° C.;
mass spectrum (EI): M/Z=577 (M⁺).

Stage E

By carrying out the reaction as in Example 2, but from 0.38 g of methyl (3aRS,4SR,9SR,9aRS)-4,9-ethano-2-[2-(2-methoxyphenyl)propenoyl]-9-(4-trifluoromethoxyphenyl)-2,3,3a,4,9,9a-hexahydro-1H-benzo[f]isoindole-3a-carboxylate at reflux for four hours in 13 cm³ of a decinormal aqueous sodium hydroxide solution and 13 cm³ of methanol, 200 mg (54%) of (3aRS,4SR,9SR,9aRS)-4,9-ethano-2-[2-(2-methoxyphenyl)propenoyl]-9-(4-trifluoromethoxyphenyl)-2,3,3a,4,9,9a-hexahydro-1H-benzo[f]isoindole-3a-carboxylic acid were obtained, after purification by recrystallization from pentane, in the form of a white solid, the characteristics of which were as follows:

melting point=160° C.;
mass spectrum (EI): M/Z=563 (M⁺).

EXAMPLE 83

Preparation of methyl (3aRS,4SR,9SR,9aRS)-9-(3-bromophenyl)-4,9-ethano-2-[2-(2-methoxyphenyl)propenoyl]-2,3,3a,4,9,9a-hexahydro-1H-benzo[f]isoindole-3a-carboxylate Stage A By carrying out the reaction as in Stage C of Example 45, but from 11.61 g of methyl (3aRS,4SR,7aRS)-2-benzyl-7-iodo-4-phenyl-2,3,3a,4,5,7a-hexahydro-1H-isoindole-3a-carboxylate, from 1.33 g of tetrakis(triphenylphosphine)palladium, from 5.46 g of 3-bromophenylboronic acid, obtained in the trimeric anhydride form, and from 11.5 g of sodium carbonate at reflux for two hours in 70 cm³ of toluene and 50 cm³ of methanol, 8.5 g (75%) of methyl (3aRS,4SR,7aRS)-2-benzyl-7-(3-bromophenyl)-4-phenyl-2,3,3a,4,5,7a-hexahydro-1H-isoindole-3a-carboxylate were obtained, after purification by flash chromatography on silica gel (230–400 mesh), elution being carried out with a mixture of cyclohexane and of ethyl acetate (80/20 by volume), in the form of a pale-yellow oil, the characteristic of which was as follows:

mass spectrum (EI): M/Z=502 (M⁺).

Stage B

By carrying out the reaction as in Stage C of Example 38, but from 8.6 g of methyl (3aRS,4SR,7aRS)-2-benzyl-7-(3-bromophenyl)-4-phenyl-2,3,3a,4,5,7a-hexahydro-1H-isoindole-3a-carboxylate and from 25 cm³ of trifluoromethanesulphonic acid in 25 cm³ of dichloromethane for two hours at room temperature, 4.58 g (64%) of methyl (3aRS,4SR,9SR,9aRS)-2-benzyl-9-(3-bromophenyl)-4,9-ethano-2,3,3a,4,9,9a-hexahydro-1H-benzo[f]isoindole-3a-carboxylate were obtained, after purification by flash chromatography on silica gel (230–400 mesh), elution being carried out with a mixture of cyclohexane and of ethyl acetate (90/10 by volume), in the form of a beige powder, the characteristics of which were as follows:

melting point=74° C.;
mass spectrum (EI): M/Z=502 (M⁺).

Stage C

By carrying out the reaction as in Stage B of Example 47, but from 1.88 g of methyl (3aRS,4SR,9SR,9aRS)-2-benzyl-9-(3-bromophenyl)-4,9-ethano-2,3,3a,4,9,9a-hexahydro-1H-benzo[f]isoindole-3a-carboxylate and from 0.6 cm³ of vinyl chloroformate for two hours at room temperature in 15 cm³ of dichloromethane, and by then taking the concentrate up in 30 cm³ of a 2M solution of hydrogen chloride gas in methanol at reflux for three hours, 1.72 g (76%) of methyl (3aRS,4SR,9SR,9aRS)-9-(3-bromophenyl)-4,9-ethano-2,3,3a,4,9,9a-hexahydro-1H-benzo[f]isoindole-3a-carboxylate hydrochloride were obtained, after crystallization from diisopropyl ether, in the form of white crystals, the characteristic of which was as follows:

mass spectrum (EI): M/Z=412 (M⁺).

Stage D

By carrying out the reaction as in Stage E of Example 5, but from 1.72 g of methyl (3aRS,4SR,9SR,9aRS)-9-(3-bromophenyl)-4,9-ethano-2,3,3a,4,9,9a-hexahydro-1H-benzo[f]isoindole-3a-carboxylate hydrochloride, from 0.68 g of 2-(2-methoxyphenyl)propenoic acid, from 0.73 g of 1-ethyl-3-[3-(dimethylamino)propyl]carbodiimide hydrochloride, from 50 mg of N-1-hydroxybenzotriazole hydrate and from 0.54 cm³ of triethylamine in 15 cm³ of dichloromethane for eighteen hours at room temperature, 0.58 g (27%) of methyl (3aRS,4SR,9SR,9aRS)-9-(3- bromophenyl)-4,9-ethano-2-[2-(2-methoxyphenyl)
propenoyl]-2,3,3a,4,9,9a-hexahydro-1H-benzo[f]isoindole-
3a-carboxylate was obtained, after purification on silica gel
(230–400 mesh), elution being carried out with a mixture of
cyclohexane and of ethyl acetate (70/30 by volume), in the
form of a light-beige powder, the characteristics of which
were as follows:

melting point=184–5° C.;
mass spectrum (EI): M/Z=572 (M$^+$).

EXAMPLE 84

Preparation of (3aRS,4SR,9SR,9aRS)-9-(3-
bromophenyl)-4,9-ethano-2-[2-(2-methoxyphenyl)
propenoyl]-2,3,3a,4,9,9a-hexahydro-1H-benzo[f]
isoindole-3a-carboxylic Acid By carrying out the reaction as in Example 2, but from
0.50 g of methyl (3aRS,4SR,9SR,9aRS)-9-(3-
bromophenyl)-4,9-ethano-2-[2-(2-methoxyphenyl)
propenoyl]-2,3,3a,4,9,9a-hexahydro-1H-benzo[f]isoindole-
3a-carboxylate at reflux for four hours in 70 cm$^3$ of a
decinormal aqueous sodium hydroxide solution and 70 cm$^3$
of methanol, 170 mg (35%) of (3aRS,4SR,9SR,9aRS)-9-(3-
bromophenyl)-4,9-ethano-2-[2-(2-methoxyphenyl)
propenoyl]-2,3,3a,4,9,9a-hexahydro-1H-benzo[f]isoindole-
3a-carboxylic acid were obtained, after purification by
recrystallization from a mixture of water and of ethanol
(90/10 by volume), in the form of a white solid, the
characteristics of which were as follows:

melting point: 164° C.;
mass spectrum (EI): M/Z=558 (M$^+$).

EXAMPLE 85

Preparation of methyl (3aRS,4SR,9SR,9aRS)-4,9-
ethano-9-(3-fluorophenyl)-2-[2-(2-methoxyphenyl)
propenoyl]-2,3,3a,4,9,9a-hexahydro-1H-benzo[f]
isoindole-3a-carboxylate Stage A By carrying out the reaction as in Stage C of Example 1,
but from 2 g of magnesium turnings, from 9.1 cm$^3$ of
3-fluorobromobenzene, in 60 cm$^3$ of diethyl ether, then in 20
cm$^3$ of toluene, and then from 15 g of methyl (3aRS,4SR,
7aRS)-2-benzyl-7-oxo-4-phenyloctahydroisoindole-3a-
carboxylate in 60 cm$^3$ of toluene, 21.29 g of impure methyl
(3aRS,4SR,7RS,7aRS)-2-benzyl-7-(3-fluorophenyl)-7-
hydroxy-4-phenyloctahydroisoindole-3a-carboxylate were
obtained in the form of a brown oil, used in the following
stage, the characteristic of which was as follows:

mass spectrum (DCI): M/Z=460 (M+H$^+$).

Stage B

By carrying out the reaction as in Stage D of Example 1,
but from 21.29 g of methyl (3aRS,4SR,7RS,7aRS)-2-
benzyl-7-(3-fluorophenyl)-7-hydroxy-
4-phenyloctahydroisoindole-3a-carboxylate and from 40
cm$^3$ of 99% trifluoromethanesulphonic acid in 300 cm$^3$ of
dichloromethane under an argon atmosphere for forty-three
hours at a temperature in the region of 20° C., 14.38 g of
impure methyl (3aRS,4SR,9SR,9aRS)-2-benzyl-4,9-ethano-
9-(3-fluorophenyl)-2,3,3a,4,9,9a-hexahydro-1H-benzo[f]
isoindole-3a-carboxylate were obtained in the form of a
brown oil, used as was in the following stage, the charac-
teristic of which was as follows:

mass spectrum (EI): M/Z=441 (M$^+$).

Stage C

By carrying out the reaction as in Stage E of Example 1,
but from 14.38 g of methyl (3aRS,4SR,9SR,9aRS)-2-
benzyl-4,9-ethano-9-(3-fluorophenyl)-2,3,3a,4,9,9a-
hexahydro-1H-benzo[f]isoindole-3a-carboxylate, from 5.53
g of ammonium formate and from 1.8 g of 10% (w/w)
palladium-on-charcoal in 200 cm$^3$ of methanol for sixteen
hours at reflux, 10.36 g of impure methyl (3aRS,4SR,9SR,
9aRS)-4,9-ethano-9-(3-fluorophenyl)-2,3,3a,4,9,9a-
hexahydro-1H-benzo[f]isoindole-3a-carboxylate were
obtained in the form of a brown oil, used in the following
stage, the characteristic of which was as follows:

mass spectrum (EI): M/Z=351 (M$^+$).

Stage D

By carrying out the reaction as in Stage G of Example 1,
but from a solution of 5.66 g of 2-(2-methoxyphenyl)
propenoic acid in 50 cm$^3$ of dichloromethane containing 2
drops of N,N-dimethylformamide, from 2.75 cm$^3$ of oxalyl
chloride, for two hours, from a solution of 10.36 g of methyl
(3aRS,4SR,9SR,9aRS)-4,9-ethano-9-(3-fluorophenyl)-2,3,
3a,4,9,9a-hexahydro-1H-benzo[f]isoindole-3a-carboxylate,
obtained in the preceding stage, and from 7.3 cm$^3$ of
triethylamine in 100 cm$^3$ of dichloromethane, 3.59 g of
methyl (3aRS,4SR,9SR,9aRS)-4,9-ethano-9-(3-
fluorophenyl)-2-[2-(2-methoxyphenyl)propenoyl]-2,3,3a,4,
9,9a-hexahydro-1H-benzo[f]isoindole-3a-carboxylate were
then obtained, after crystallization from petroleum ether
(40–60° C.), in the form of a beige powder, the character-
istics of which were as follows:

melting point=151° C.;
mass spectrum (EI): M/Z=511 (M$^+$).

EXAMPLE 86

Preparation of (3aRS,4SR,9SR,9aRS)-4,9-ethano-9-
(3-fluorophenyl)-2-[2-(2-methoxyphenyl)
propenoyl]-2,3,3a,4,9,9a-hexahydro-1H-benzo[f]
isoindole-3a-carboxylic Acid By carrying out the reaction as in Example 2, but from
1.02 g of methyl (3aRS,4SR,9SR,9aRS)-4,9-ethano-9-(3-
fluorophenyl)-2-[2-(2-methoxyphenyl)propenoyl]-2,3,3a,4,
9,9a-hexahydro-1H-benzo[f]isoindole-3a-carboxylate,
obtained as in the preceding stage, and from 24 cm$^3$ of a
normal aqueous sodium hydroxide solution in 30 cm$^3$ of
dioxane for eighteen hours at reflux, 0.71 g of (3aRS,4SR,
9SR,9aRS)-4,9-ethano-9-(3-fluorophenyl)-2-[2-(2-
methoxyphenyl)propenoyl]-2,3,3a,4,9,9a-hexahydro-1H-
benzo[f]isoindole-3a-carboxylic acid was obtained in the
form of a white powder, the characteristics of which were as
follows:

melting point=161° C.;
mass spectrum (EI): M/Z=497 (M$^+$).

EXAMPLE 87

Preparation of (3aRS,4SR,9SR,9aRS)-4,9-ethano-9-
(3-fluorophenyl)-2-[2-(2-methoxyphenyl)
propenoyl]-2,3,3a,4,9,9a-hexahydro-1H-benzo[f]
isoindole-3a-N-(3-pyridylmethyl)carboxamide By carrying out the reaction as in Example 42, but from
0.52 g of (3aRS,4SR,9SR,9aRS)-4,9-ethano-9-(3-
fluorophenyl)-2-[2-(2-methoxyphenyl)propenoyl]-2,3,3a,4,
9,9a-hexahydro-1H-benzo[f]isoindole-3a-carboxylic acid,
from 0.128 cm$^3$ of 3-(aminomethyl)pyridine, from 0.24 g of
1-ethyl-3-[3-(dimethylamino)propyl]carbodiimide hydro-
chloride and from 85 mg of N-1-hydroxybenzotriazole
hydrate in 30 cm$^3$ of dichloromethane, 183.6 mg of (3aRS,
4SR,9SR,9aRS)-4,9-ethano-9-(3-fluorophenyl)-2-[2-(2-
methoxyphenyl)propenoyl]-2,3,3a,4,9,9a-hexahydro-1H- benzo[f]isoindole-3a-N-(3-pyridylmethyl)carboxamide were obtained, after sixteen hours at a temperature in the region of 20° C., in the form of an ecru powder, the characteristics of which were as follows:

melting point=223° C.;

mass spectrum (EI): M/Z=587 (M⁺).

EXAMPLE 88

Preparation of methyl (3aRS,4SR,9SR,9aRS)-9-(3-chlorophenyl)-4,9-ethano-2-[2-(2-methoxyphenyl) propenoyl]-2,3,3a,4,9,9a-hexahydro-1H-benzo[f] isoindole-3a-carboxylate Stage A By carrying out the reaction as in Stage C of Example 1, but from 2 g of magnesium turnings, from 9.75 cm³ of 3-chlorobromobenzene, in 60 cm³ of diethyl ether, then in 20 cm³ of toluene, and then from 15 g of methyl (3aRs, 4SR,7aRS)-2-benzyl-7-oxo-4-phenyloctahydroisoindole-3a-carboxylate in 60 cm³ of toluene, 31.2 g of impure methyl (3aRS,4SR,7RS,7aRS)-2-benzyl-7-(3-chlorophenyl)-7-hydroxy-4-phenyloctahydroisoindole-3a-carboxylate, which were used in the following stage, were obtained in the form of an orange-coloured oil, the characteristic of which was as follows:

mass spectrum (DCI): M/Z=476 (M+H⁺).

Stage B

By carrying out the reaction as in Stage D of Example 1, but from 31.2 g of methyl (3aRS,4SR,7RS,7aRS)-2-benzyl-7-(3-chlorophenyl)-7-hydroxy-4-phenyloctahydroisoindole-3a-carboxylate, obtained in the preceding stage, and from 40 cm³ of 99% trifluoromethanesulphonic acid in 300 cm³ of dichloromethane under an argon atmosphere for four days at a temperature in the region of 20° C., 23.88 g of impure methyl (3aRS,4SR,9SR,9aRS)-2-benzyl-9-(3-chlorophenyl)-4,9-ethano-2,3,3a,4,9,9a-hexahydro-1H-benzo[f]isoindole-3a-carboxylate were obtained in the form of an oil, used in the following stage, the characteristic of which was as follows:

mass spectrum (EI): M/Z=457 (M⁺).

Stage C

By carrying out the reaction as in Stage B of Example 47, but from 23.88 g of impure methyl (3aRS,4SR,9SR,9aRS)-2-benzyl-9-(3-chlorophenyl)-4,9-ethano-2,3,3a,4,9,9a-hexahydro-1H-benzo[f]isoindole-3a-carboxylate, from 5.4 cm³ of vinyl chloroformate and from 11.5 g of potassium carbonate in 200 cm³ of dichloromethane for sixteen hours at a temperature in the region of 20° C., 24.4 g of impure methyl (3aRS,4SR,9SR,9aRS)-9-(3-chlorophenyl)-4,9-ethano-2-vinyloxycarbonyl-2,3,3a,4,9,9a-hexahydro-1H-benzo[f]isoindole-3a-carboxylate were obtained in the form of a brown oil, used in the following stage, the characteristic of which was as follows:

mass spectrum (EI): M/Z=437 (M⁺).

After taking this oil up again for eighteen hours in a 6N solution of hydrogen chloride gas in dioxane, 18.28 g of impure methyl (3aRS,4SR,9SR,9aRS)-9-(3-chlorophenyl)-4,9-ethano-2,3,3a,4,9,9a-hexahydro-1H-benzo[f]isoindole-3a-carboxylate hydrochloride were obtained in the form of a thick brown oil, used in the following stage, the characteristic of which was as follows:

mass spectrum (EI): M/Z=368 (M⁺).

Stage D

By carrying out the reaction as in Stage G of Example 1, but from a solution of 8.76 g of 2-(2-methoxyphenyl) propenoic acid in 50 cm³ of dichloromethane containing 2 drops of N,N-dimethylformamide, from 4.21 cm³ of oxalyl chloride, for two hours thirty minutes, then from a solution of 18.5 g of methyl (3aRS,4SR,9SR,9aRS)-9-(3-chlorophenyl)-4,9-ethano-2,3,3a,4,9,9a-hexahydro-1H-benzo[f]isoindole-3a-carboxylate hydrochloride, obtained in the preceding stage, and from 11.5 cm³ of triethylamine in 100 cm³ of dichloromethane, then running in 100 cm³ of water after forty-two hours, 0.95 g of methyl (3aRS,4SR, 9SR,9aRS)-9-(3-chlorophenyl)-4,9-ethano-2-[2-(2-methoxyphenyl)propenoyl]-2,3,3a,4,9,9a-hexahydro-1H-benzo[f]isoindole-3a-carboxylate was obtained in the form of a beige powder, the characteristics of which were as follows:

melting point=159° C.;

mass spectrum (EI): M/Z=527 (M⁺).

EXAMPLE 89

Preparation of (3aRS,4SR,9SR,9aRS)-9-(3-chlorophenyl)-4,9-ethano-2-[2-(2-methoxyphenyl) propenoyl]-2,3,3a,4,9,9a-hexahydro-1H-benzo[f] isoindole-3a-carboxylic Acid By carrying out the reaction as in Example 2, but from 795 mg of methyl (3aRS,4SR,9SR,9aRS)-9-(3-chlorophenyl)-4,9-ethano-2-[2-(2-methoxyphenyl) propenoyl]-2,3,3a,4,9,9a-hexahydro-1H-benzo[f]isoindole-3a-carboxylate, obtained as in the preceding stage, and from 30 cm³ of a normal aqueous sodium hydroxide solution in 30 cm³ of dioxane for eighteen hours at reflux, 0.77 g of (3aRS,4SR,9SR,9aRS)-9-(3-chlorophenyl)-4,9-ethano-2-[2-(2-methoxyphenyl)propenoyl]-2,3,3a,4,9,9a-hexahydro-1H-benzo[f]isoindole-3a-carboxylic acid was obtained in the form of a white powder, the characteristics of which were as follows:

melting point=170° C.;

mass spectrum (EI): M/Z=513 (M⁺).

EXAMPLE 90

Preparation of (3aRS,4SR,9SR,9aRS)-9-(3-chlorophenyl)-4,9-ethano-2-[2-(2-methoxyphenyl) propenoyl]-2,3,3a,4,9,9a-hexahydro-1H-benzo[f] isoindole-3a-N-(3-pyridylmethyl)carboxamide By carrying out the reaction as in Example 42, but from 0.46 g of (3aRS,4SR,9SR,9aRS)-9-(3-chlorophenyl)-4,9-ethano-2-[2-( 2-methoxyphenyl)propenoyl]-2,3,3a,4,9,9a-hexahydro-1H-benzo[f]isoindole-3a-carboxylic acid, from 0.11 cm³ of 3-(aminomethyl)pyridine, from 0.21 g of 1-ethyl-3-[3-(dimethylamino)propyl]carbodiimide hydrochloride and from 70 mg of N-1-hydroxybenzotriazole hydrate in 30 cm³ of dichloromethane, 269.8 mg of (3aRS, 4SR,9SR,9aRS)-9-(3-chlorophenyl)-4,9-ethano-2-[2-(2-methoxyphenyl)propenoyl]-2,3,3a,4,9,9a-hexahydro-1H-benzo[f]isoindole-3a-N-(3-pyridylmethyl)carboxamide were obtained, after sixteen hours at a temperature in the region of 20° C., in the form of an off-white powder, the characteristics of which were as follows:

melting point=244° C.;

mass spectrum (EI): M/Z=603 (M⁺).

EXAMPLE 91

Preparation of methyl (3aRS,4SR,9SR,9aRS)-9-(3-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylate Stage A By carrying out the reaction as in Stage C of Example 45, but from 2.5 g of methyl (3aRS,4SR,7aRS)-2-benzyl-7-iodo-4-phenyl-2,3,3a,4,5,7a-hexahydro-1H-isoindole-3a-carboxylate, from 0.30 g of tetrakis(triphenylphosphine)palladium, from 0.77 g of 3-N,N-dimethylaminophenylboronic acid, obtained in the trimeric anhydride form, and from 20 cm³ of a 2M aqueous sodium carbonate solution at reflux for seven hours in 20 cm³ of toluene and 10 cm³ of methanol, 2.09 g (85%) of methyl (3aRS,4SR,7aRS)-2-benzyl-7-(3-N N-dimethylaminophenyl)-4-phenyl-2,3,3a,4,5,7a-hexahydro-1H-isoindole-3a-carboxylate were obtained, after purification by flash chromatography on silica gel (230–400 mesh), elution being carried out with a mixture of cyclohexane and of ethyl acetate (90/10 by volume), in the form of an orange-coloured pasty solid, used in the following stage, the characteristic of which was as follows:

mass spectrum (EI): M/Z=466 (M⁺).

Stage B

The reaction was carried out as in Stage B of Example 39, but from 2.09 g of methyl (3aRS,4SR,7aRS)-2-benzyl-7-(3-N,N-dimethylaminophenyl)-4-phenyl-2,3,3a,4,5,7a-hexahydro-1H-isoindole-3a-carboxylate and from 20 cm³ of pure trifluoromethanesulphonic acid for four days at room temperature. After neutralization with a 30% aqueous sodium hydroxide solution in the presence of dichloromethane, the organic phase was separated by settling, then washed with water and dried over magnesium sulphate, and then stirred for one hour with 20 g of silica gel (230–400 mesh). After concentrating the solvent under reduced pressure, 1.74 g (83%) of methyl (3aRS,4SR,9SR,9aRS)-2-benzyl-9-(3-N,N-dimethylaminophenyl)-4,9-ethano-2,3,3a,4,9,9a-hexahydro-1H-benzo[f]isoindole-3a-carboxylate were then obtained in the form of a yellow pasty solid, used in the following stage, the characteristic of which was as follows:

mass spectrum (EI): M/Z=466 (M⁺).

Stage C

The reaction was carried out as in Stage B of Example 47, but from 2.21 g of methyl (3aRS,4SR,9SR,9aRS)-2-benzyl-9-(3-N,N-dimethylaminophenyl)-4,9-ethano-2,3,3a,4,9,9a-hexahydro-1H-benzo[f]isoindole-3a-carboxylate, from 3 cm³ of vinyl chloroformate and from 4.6 cm³ of triethylamine for seven hours at room temperature in 20 cm³ of dichloromethane. After hydrolysis, the organic phase was separated by settling and then concentrated under reduced pressure. After purification by flash chromatography on silica gel (230–400 mesh), elution being carried out with a mixture of cyclohexane and of ethyl acetate (85/15 by volume), 0.27 g (27%) of methyl (3aRS,4SR,7aRS)-9-(3-N,N-dimethylaminophenyl)-4,9-ethano-2-vinyloxycarbonyl-2,3,3a,4,9,9a-hexahydro-1H-benzo[f]isoindole-3a-carboxylate was then obtained, which product was dissolved in methanol and heated at reflux for five hours in the presence of 5 cm³ of a 5M solution of hydrogen chloride gas in dioxane. After crystallization from diisopropyl ether, 0.68 g (98%) of methyl (3aRS,4SR,9SR,9aRS)-9-(3-N,N-dimethylaminophenyl)-4,9-ethano-2,3,3a,4,9,9a-hexahydro-1H-benzo[f]isoindole-3a-carboxylate dihydrochloride was thus obtained in the form of a white solid, the characteristic of which was as follows:

mass spectrum (EI): M/Z=376 (M⁺).

Stage D

By carrying out the reaction as in Stage E of Example 5, but from 0.68 g of methyl (3aRS,4SR,9SR,9aRS)-9-(3-N,N-dimethylaminophenyl)-4,9-ethano-2,3,3a,4,9,9a-hexahydro-1H-benzo[f]isoindole-3a-carboxylate dihydrochloride, from 0.29 g of 2-(2-methoxyphenyl)propenoic acid, from 0.38 g of 1-ethyl-3-[3-(dimethylamino)propyl]carbodiimide hydrochloride, from 20 mg of N-1-hydroxybenzotriazole hydrate and from 0.42 cm³ of triethylamine in 15 cm³ of dichloromethane for twenty-four hours at room temperature, 0.27 g (33%) of methyl (3aRS,4SR,9SR,9aRS)-9-(3-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylate was obtained, after purification by flash chromatography on silica gel (230–400 mesh), elution being carried out with a mixture of cyclohexane and of ethyl acetate (70/30 by volume), and then recrystallization from pentane, in the form of a white powder, the characteristics of which were as follows:

melting point=95° C.;
mass spectrum (EI): M/Z=536 (M⁺).

EXAMPLE 92

Preparation of (3aRS,4SR,9SR,9aRS)-9-(3-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylic Acid By carrying out the reaction as in Example 2, but from 0.23 g of methyl (3aRS,4SR,9SR,9aRS)-9-(3-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylate at reflux for five hours in 2 cm³ of a normal aqueous sodium hydroxide solution and 5 cm³ of ethanol, 120 mg (55%) of (3aRS,4SR,9SR,9aRS)-9-(3-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylic acid were obtained, after purification by recrystallization from a mixture of dichloromethane and of pentane (50/50 by volume), in the form of a white solid, the characteristics of which were as follows:

melting point=194° C.;
mass spectrum (EI): M/Z=522 (M⁺).

EXAMPLE 93

Preparation of methyl (3aRS,4SR,9SR,9aRS)-9-(3-aminophenyl)-4,9-ethano-2-[2-(2-methoxyphenyl)propenoyl]-2,3,3a,4,9,9a-hexahydro-1H-benzo[f]isoindole-3a-carboxylate hydrochloride Stage A By carrying out the reaction as in Stage C of Example 45, but from 2.5 g of methyl (3aRS,4SR,7RS)-2-benzyl-7-iodo-4-phenyl-2,3,3a,4,5,7a-hexahydro-1H-isoindole-3a-carboxylate, from 0.30 g of tetrakis(triphenylphosphine)palladium, from 0.72 g of 3-aminophenylboronic acid and from 20 cm³ of a 2M aqueous sodium carbonate solution at reflux for seven hours in 20 cm³ of toluene and 10 cm³ of methanol, 1.60 g (70%) of methyl (3aRS,4SR,7aRS)-7-(3-aminophenyl)-2-benzyl-4-phenyl-2,3,3a,4,5,7a-hexahydro-1H-isoindole-3a-carboxylate were obtained, after purification by flash chromatography on silica gel (230–400 mesh), elution being carried out with a mixture of cyclohexane and ethyl acetate (80/20 by volume), in the form of an orange-coloured solid, used in the following stage, the characteristic of which was as follows:

mass spectrum (EI): M/Z=438 (M⁺).

Stage B

The reaction is carried out as in Stage B of Example 39, but from 0.20 g (0.4 mmol) of methyl (3aRS,4SR,7aRS)-7-(3-aminophenyl)-2-benzyl-4-phenyl-2,3,3a,4,5,7a-hexahydro-1H-isoindole-3a-carboxylate and from 5 cm³ of pure trifluoromethanesulphonic acid for three days at room temperature. After neutralization with a 30% aqueous sodium hydroxide solution in the presence of dichloromethane, the organic phase was separated by settling, then washed with water and dried over magnesium sulphate, and then stirred for one hour with 20 g of silica gel (230–400 mesh). After concentrating the solvent under reduced pressure, 0.16 g (80%) of methyl (3aRS,4SR,9SR,9aRS)-9-(3-aminophenyl)-2-benzyl-4,9-ethano-2,3,3a,4,9,9a-hexahydro-1H-benzo[f]isoindole-3a-carboxylate was then obtained in the form of a brown oil, used in the following stage, the characteristic of which was as follows:

mass spectrum (EI): M/Z=438 (M⁺).

Stage C

By carrying out the reaction as in Stage E of Example 45, but from 1.5 g of methyl (3aRS,4SR,9SR,9aRS)-9-(3-aminophenyl)-2-benzyl-4,9-ethano-2,3,3a,4,9,9a-hexahydro-1H-benzo[f]isoindole-3a-carboxylate and from 0.6 g of 10% (w/w) palladium-on-charcoal in 100 cm³ of methanol and 3.5 cm³ of hydrogen chloride gas as a 1M solution in methanol for eight hours at 50° C. under a hydrogen atmosphere, 1.27 g (79%) of methyl (3aRS,4SR,9SR,9aRS)-9-(3-aminophenyl)-4,9-ethano-2,3,3a,4,9,9a-hexahydro-1H-benzo[f]isoindole-3a-carboxylate dihydrochloride were obtained, after crystallization from diisopropyl ether, in the form of a white solid, the characteristics of which were as follows:

mass spectrum (EI): M/Z=348 (M⁺).

Stage D

By carrying out the reaction as in Stage G of Example 1, but from 0.74 g of methyl (3aRS,4SR,9SR,9aRS)-9-(3-aminophenyl)-4,9-ethano-2,3,3a,4,9,9a-hexahydro-1H-benzo[f]isoindole-3a-carboxylate dihydrochloride, from 0.41 g of 2-(2-methoxyphenyl)propenoic acid, from 0.22 cm³ of oxalyl chloride and from 0.76 cm³ of triethylamine in 10 cm³ of dichloromethane for twenty hours at room temperature, 0.20 g (21%) of methyl (3aRS,4SR,9SR,9aRS)-9-(3-aminophenyl)-4,9-ethano-2-[2-(2-methoxyphenyl)propenoyl]-2,3,3a,4,9,9a-hexahydro-1H-benzo[f]isoindole-3a-carboxylate hydrochloride were obtained, after purification by flash chromatography on silica gel (230–400 mesh), elution being carried out with a mixture of cyclohexane and of ethyl acetate (50/50 by volume), and then recrystallization from diisopropyl ether, in the form of a white powder, the characteristics of which were as follows:

melting point=186° C.;
mass spectrum (EI): M/Z=508 (M⁺).

EXAMPLE 94

Preparation of methyl (3aRS,4SR,9SR,9aRS)-9-(4-N,N-dimethylaminophenyl)-4,9-ethano-2-[2-(2-methoxyphenyl)propenoyl]-2,3,3a,4,9,9a-hexahydro-1H-benzo[f]-isoindole-3a-carboxylate Stage A By carrying out the reaction as in Stage C of Example 45, but from 1.15 g of methyl (3aRS,4SR,7aRS)-2-benzyl-7-iodo-4-phenyl-2,3,3a,4,5,7a-hexahydro-1H-isoindole-3a-carboxylate, from 0.12 g of tetrakis(triphenylphosphine)palladium, from 0.44 g of 4-N,N-dimethylaminophenylboronic acid and from 15 cm³ of a 2M aqueous sodium carbonate solution at reflux for four hours in 20 cm³ of toluene and 10 cm³ of methanol, 0.93 g (82%) of methyl (3aRs,4SR,7aRS)-2-benzyl-7-(4-N,N-dimethylaminophenyl)-4-phenyl-2,3,3a,4,5,7a-hexahydro-1H-isoindole-3a-carboxylate was obtained, after purification by flash chromatography on silica gel (230–400 mesh), elution being carried out with a mixture of cyclohexane and of ethyl acetate (80/20 by volume), in the form of an orange-coloured oil, used in the following stage, the characteristic of which was as follows:

mass spectrum (EI): M/Z=466 (M⁺).

Stage B

The reaction is carried out as in Stage B of Example 39, but from 0.53 g of methyl (3aRs,4SR,7aRS)-2-benzyl-7-(4-N,N-dimethylaminophenyl)-4-phenyl-2,3,3,a,4,5,7a-hexahydro-1H-isoindole-3a-carboxylate and from 10 cm³ of pure trifluoromethanesulphonic acid for two days at room temperature. After neutralization with a 30% aqueous sodium hydroxide solution in the presence of dichloromethane, the organic phase was separated by settling, then washed with water and dried over magnesium sulphate. After concentrating the solvent under reduced pressure, the residue was purified by flash chromatography on silica gel (230–400 mesh), elution being carried out with a mixture of cyclohexane and of ethyl acetate (90/10 by volume). 0.34 g (64%) of methyl (3aRS,4SR,9SR,9aRS)-2-benzyl-9-(4-N,N-dimethylaminophenyl)-4,9-ethano-2,3,3a,4,9,9a-hexahydro-1H-benzo[f]isoindole-3a-carboxylate was then obtained in the form of a colourless oil, the characteristic of which was as follows:

mass spectrum (EI): M/Z=466 (M⁺).

Stage C By carrying out the reaction as in Stage E of Example 45, but from 0.34 g of methyl (3aRS,4SR,9SR,9aRS)-2-benzyl-9-(4-N,N-dimethylaminophenyl)-4,9-ethano-2,3,3a,4,9,9a-hexahydro-1H-benzo[f]isoindole-3a-carboxylate and from 0.15 g of 10% (w/w) palladium-on-charcoal in 20 cm³ of methanol, 10 cm³ of chloroform and 1.5 cm³ of a 1M solution of hydrogen chloride gas in methanol for 5 hours at 40° C. under a hydrogen atmosphere, 0.31 g (96%) of methyl (3aRS,4SR,9SR,9aRS)-9-(4-N,N-dimethylaminophenyl)-4,9-ethano-2,3,3a,4,9,9a-hexahydro-1H-benzo[f]isoindole-3a-carboxylate dihydrochloride was obtained, after crystallization from diisopropyl ether, in the form of a light-green solid, the characteristic of which was as follows:

mass spectrum (EI): M/Z=376 (M⁺).

Stage D

By carrying out the reaction as in Stage G of Example 1, but from 0.30 g of methyl (3aRS,4SR,9SR,9aRS)-9-(4-N,N-dimethylaminophenyl)-4,9-ethano-2,3,3a,4,9,9a-hexahydro-1H-benzo[f]isoindole-3a-carboxylate dihydrochloride, from 00.13 g of 2-(2-methoxyphenyl)propenoic acid, from 0.07 cm³ of oxalyl chloride and from 0.3 cm³ of triethylamine in 5 cm³ of dichloromethane for eighteen hours at room temperature, 0.18 g (50%) of methyl (3aRS,4SR,9SR,9aRS)-9-(4-N,N-dimethylaminophenyl)-4,9-ethano-2-[2-(2-methoxyphenyl)propenoyl]-2,3,3a,4,9,9a-hexahydro-1H-benzo[f]isoindole-3a-carboxylate was obtained, after purification on silica gel (230–400 mesh), elution being carried out with a mixture of cyclohexane and of ethyl acetate and of a 28% ammonia solution (60/40/0.2 by volume), in the form of a white powder, the characteristics of which were as follows:

EXAMPLE 95

Preparation of (3aRS,4SR,9SR,9aRS)-9-(4-cyanophenyl)-4,9-ethano-2-[2-(2-methoxyphenyl) propenoyl]-2,3,3a,4,9,9a-hexahydro-1H-benzo[f] isoindole-3a-carboxylic Acid Stage A 1.15 g of tetrakis(triphenylphosphine)palladium and 5.84 g of zinc cyanide are added to a solution, maintained under an argon atmosphere, of 5.02 g of methyl (3aRS,4SR,9SR, 9aRS)-2-benzyl-9-(4-bromophenyl)-4,9-ethano-2,3,3a,4,9, 9a-hexahydro-1H-benzo[f]isoindole-3a-carboxylate, obtained in Stage B of Example 49, in 50 cm$^3$ of dimethylformamide, the mixture was brought to reflux for five hours and was then stirred for an additional eighteen hours at room temperature, still under an argon atmosphere. After addition of water and of ethyl acetate, the organic phase was separated by settling, washed with water, dried over magnesium sulphate and concentrated under reduced pressure. The residue was purified by flash chromatography on silica gel (230–400 mesh), elution being carried out with a mixture of cyclohexane and of ethyl acetate (95/5 by volume). 3.09 g (69%) of methyl (3aRS,4SR,9SR,9aRS)-2-benzyl-9-(4-cyanophenyl)-4,9-ethano-2,3,3a,4,9,9a-hexahydro-1H-benzo[f]isoindole-3a-carboxylate were thus obtained in the form of a white powder, the characteristics of which were as follows:

melting point=158° C.

$^1$H N.M.R. spectrum (300 MHz, CDCl$_3$, δ in ppm): 1.46, 1.70 and 2.49 (3 mts, respectively 1H, 1H and 2H, CH$_2$CH$_2$), from 2.25 to 2.40 and 2.63 (respectively mt and d, J=10 Hz, each 1H, CH$_2$ at 1), 2.31 and 3.21 (2 d, J=10 Hz, each 1H, CH$_2$ at 3), 3.23 (mt, 1H, CH at 9a), 3.41 and 3.63 (2 d, J=12.5 Hz, each 1H, NCH$_2$Ar), 3.45 (broad s, 1H, CH at 4), 3.55 (s, 3H, COOCH$_3$), 6.43 (d, J=7.5 Hz, 1H, H at 8), from 6.95 to 7.80 (mts, 12H, H at 5, H at 6, H at 7, aromatic H of the 4-cyanophenyl and aromatic H of the benzyl).

mass spectrum (EI): M/Z=448 (M$^+$).

Stage B

The reaction was carried out as in Stage B of Example 47, but from 0.80 g of methyl (3aRS,4SR,9SR,9aRS)-2-benzyl-9-(4-cyanophenyl)-4,9-ethano-2,3,3a,4,9,9a-hexahydro-1H-benzo[f]isoindole-3a-carboxylate and from 1 cm$^3$ of vinyl chloroformate for twenty-four hours at room temperature in 20 cm$^3$ of dichloromethane. After hydrolysis, the organic phase was separated by settling and then concentrated under reduced pressure. After purification by flash chromatography on silica gel (230–400 mesh), elution being carried out with a mixture of cyclohexane and of ethyl acetate (90/10 by volume), 0.69 g (91%) of methyl (3aRS,4SR,9SR,9aRS)-9-(4-cyanophenyl)-4,9-ethano-2-vinyloxycarbonyl-2,3,3a,4,9, 9a-hexahydro-1H-benzo[f]isoindole-3a-carboxylate is then obtained, which compound is dissolved in 20 cm$^3$ of methanol and heated at reflux for five hours in the presence of 5 cm$^3$ of a 5M solution of hydrogen chloride gas in dioxane. After crystallization from diisopropyl ether, 0.62 g (98%) of methyl (3aRS,4SR,9SR,9aRS)-9-(4-cyanophenyl)-4,9-ethano-2,3,3a,4,9,9a-hexahydro-1H-benzo[f]isoindole-3a-carboxylate hydrochloride was thus obtained in the form of a white solid, the characteristic of which was as follows:

mass spectrum (EI): M/Z=358 (M$^+$).

Stage C

By carrying out the reaction as in Stage G of Example 1, but from 0.72 g of methyl (3aRS,4SR,9SR,9aRS)-9-(4-cyanophenyl)-4,9-ethano-2,3,3a,4,9,9a-hexahydro-1H-benzo[f]isoindole-3a-carboxylate hydrochloride, from 0.32 g of 2-(2-methoxyphenyl)propenoic acid, from 0.175 cm$^3$ of oxalyl chloride and from 0.55 cm$^3$ of triethylamine in 20 cm$^3$ of dichloromethane for eighteen hours at room temperature, 0.52 g (55%) of methyl (3aRS,4SR,9SR, 9aRS)-9-(4-cyanophenyl)-4,9-ethano-2-[2-(2-methoxyphenyl)propenoyl]-2,3,3a,4,9,9a-hexahydro-1H-benzo[f]isoindole-3a-carboxylate was obtained, after purification on silica gel (230–400 mesh), elution being carried out with a mixture of cyclohexane and of ethyl acetate (70/30 by volume), in the form of a white powder, the characteristics of which were as follows:

melting point=90–2° C.;

mass spectrum (EI): M/Z=518 (M$^+$).

Stage D

By carrying out the reaction as in Example 2, but from 0.50 g of methyl (3aRS,4SR,9SR,9aRS)-9-(4-cyanophenyl)-4,9-ethano-2-[2-( 2-methoxyphenyl)propenoyl]-2,3,3a,4,9, 9a-hexahydro-1H-benzo[f]isoindole-3a-carboxylate at reflux for five hours in 1.1 cm$^3$ of a normal aqueous sodium hydroxide solution and 20 cm$^3$ of ethanol, 220 mg (45%) of (3aRS,4SR,9SR,9aRS)-9-(4-cyanophenyl)-4,9-ethano-2-[2-(2-methoxyphenyl)propenoyl]-2,3,3a,4,9,9a-hexahydro-1H-benzo[f]isoindole-3a-carboxylic acid were obtained, after purification by flash chromatography on silica gel, elution being carried out with a gradient of mixtures of cyclohexane and of ethyl acetate (from 95/5 to 50/50 by volume), in the form of a white solid, the characteristics of which were as follows:

melting point=182° C.;

mass spectrum (EI): M/Z=504 (M$^+$).

EXAMPLE 96

Preparation of methyl (3aRS,4SR,9SR,9aRS)-9-(3-cyanophenyl)-4,9-ethano-2-[2-(2-methoxyphenyl) propenoyl]-2,3,3a,4,9,9a-hexahydro-1H-benzo[f] isoindole-3a-carboxylate Stage A By carrying out the reaction as in Stage A of Example 95, but from 2.69 g of methyl (3aRS,4SR,9SR,9aRS)-2-benzyl-9-(3-bromophenyl)-4,9-ethano-2,3,3a,4,9,9a-hexahydro-1H-benzo[f]isoindole-3a-carboxylate, obtained in Stage B of Example 83, from 0.62 g of tetrakis(triphenylphosphine) palladium and from 3.14 g of zinc cyanide in 50 cm$^3$ of dimethylformamide at reflux for five hours and then for an additional eighteen hours at room temperature under an argon atmosphere, 2.0 g (83%) of methyl (3aRS,4SR,9SR, 9aRS)-2-benzyl-9-(3-cyanophenyl)-4,9-ethano-2,3,3a,4,9, 9a-hexahydro-1H-benzo[f]isoindole-3a-carboxylate were obtained, after purification by flash chromatography on silica gel (230–400 mesh), elution being carried out with a mixture of cyclohexane and ethyl acetate (90/10 by volume), in the form of a white powder, the characteristics of which were as follows:

melting point=88° C.;

mass spectrum (EI): M/Z=448 (M$^+$).

Stage B

By carrying out the reaction as in Stage B of Example 47, but from 2.0 g of methyl (3aRS,4SR,9SR,9aRS)-2-benzyl-9-(3-cyanophenyl)-4,9-ethano-2,3,3a,4,9,9a-hexahydro-1H-benzo[f]isoindole-3a-carboxylate and from 0.6 cm$^3$ of vinyl chloroformate for 4 hours at room temperature in 20 cm$^3$ of dichloromethane, and by then taking the concentrate up in 20 cm$^3$ of methanol and 10 cm$^3$ of a normal solution of hydrogen chloride gas in isopropanol at reflux for 2 hours, 1.22 g (77%) of methyl (3aRS,4SR,9SR,9aRS)-9-(3-cyanophenyl)-4,9-ethano-2,3,3a,4,9,9a-hexahydro-1H- benzo[f]isoindole-3a-carboxylate were obtained, after neutralization with a 5N aqueous sodium hydroxide solution and extraction with diethyl ether, in the form of a white foam, used in the following stage, the characteristic of which was as follows:

mass spectrum (EI): M/Z=358 (M$^+$).

Stage C

By carrying out the reaction as in Stage G of Example 1, but from 1.22 g of methyl (3aRS,4SR,9SR,9aRS)-9-(3-cyanophenyl)-4,9-ethano-2,3,3a,4,9,9a-hexahydro-1H-benzo[f]isoindole-3a-carboxylate hydrochloride, from 0.61 g of 2-(2-methoxyphenyl)propenoic acid, from 0.3 cm$^3$ of oxalyl chloride and from 0.96 cm$^3$ of triethylamine in 25 cm$^3$ of dichloromethane for 2 hours at room temperature, 0.75 g (48%) of methyl (3aRS,4SR,9SR,9aRS)-9-(3-cyanophenyl)-4,9-ethano-2-[2-(2-methoxyphenyl)propenoyl]-2,3,3a,4,9,9a-hexahydro-1H-benzo[f]isoindole-3a-carboxylate was obtained, after purification on silica gel (230–400 mesh), elution being carried out with mixtures of cyclohexane and of ethyl acetate (95/5, then 80/20, by volume), in the form of a white powder, the characteristics of which were as follows:

melting point=176–8° C.;
mass spectrum (EI): M/Z=518 (M$^+$).

EXAMPLE 97

Preparation of (3aRS,4SR,9SR,9aRS)-4,9-ethano-9-(3-hydroxy-4-methoxyphenyl)-2-[2-(2-methoxyphenyl)propenoyl]-2,3,3a,4,9,9a-hexahydro-1H-benzo[f]isoindole-3a-carboxylic Acid Stage A By carrying out the reaction as in Stage E of Example 1, but from 3.1 g of a mixture of methyl (3aRS,4SR,9SR,9aRS)-2-benzyl-4,9-ethano-9-(3-hydroxy-4-methoxyphenyl)-2,3,3a,4,9,9a-hexahydro-1H-benzo[f]isoindole-3a-carboxylate and of methyl (3aRS,4SR,9SR,9aRS)-2-benzyl-4,9-ethano-9-(4-hydroxy-3-methoxyphenyl)-2,3,3a,4,9,9a-hexahydro-1H-benzo[f]isoindole-3a-carboxylate, obtained in Stage B of Example 70, from 1.25 g of ammonium formate and from 0.4 g of 10% (w/w) palladium-on-charcoal, 2.1 g of a mixture of methyl (3aRS,4SR,9SR,9aRS)-4,9-ethano-9-(3-hydroxy-4-methoxyphenyl)-2,3,3a,4,9,9a-hexahydro-1H-benzo[f]isoindole-3a-carboxylate and of methyl (3aRS,4SR,9SR,9aRS)-4,9-ethano-9-(4-hydroxy-3-methoxyphenyl)-2,3,3a,4,9,9a-hexahydro-1H-benzo[f]isoindole-3a-carboxylate were obtained in the form of a colourless oil, used in the subsequent syntheses.

Stage B

By carrying out the reaction as in Stage G of Example 1, but from 2.1 g of a mixture of methyl (3aRS,4SR,9SR,9aRS)-4,9-ethano-9-(3-hydroxy-4-methoxyphenyl)-2,3,3a,4,9,9a-hexahydro-1H-benzo[f]isoindole-3a-carboxylate and of methyl (3aRS,4SR,9SR,9aRS)-4,9-ethano-9-(4-hydroxy-3-methoxyphenyl)-2,3,3a,4,9,9a-hexahydro-1H-benzo[f]isoindole-3a-carboxylate, from 1.0 g of 2-(2-methoxyphenyl)propenoic acid, from 0.47 cm$^3$ of oxalyl chloride and from 1.5 cm$^3$ of triethylamine, 0.4 g of methyl (3aRS,4SR,9SR,9aRS)-4,9-ethano-9-(3-hydroxy-4-methoxyphenyl)-2-[2-(2-methoxyphenyl)propenoyl]-2,3,3a,4,9,9a-hexahydro-1H-benzo[f]isoindole-3a-carboxylate, containing 5% of methyl (3aRS,4SR,9SR,9aRS)-4,9-ethano-9-(4-hydroxy-3-methoxyphenyl)-2-[2-(2-methoxyphenyl)propenoyl]-2,3,3a,4,9,9a-hexahydro-1H-benzo[f]isoindole-3a-carboxylate, was obtained, after three flash chromatography operations on silica gel (230–400 mesh), elution being carried out with a dichloromethane/methanol (96.5/3.5 by volume) mixture for the first, a dichloromethane/methanol (99/1 by volume) mixture for the second and a dichloromethane/methanol (99.5/0.5 by volume) mixture for the third, and after recrystallization from 25 cm$^3$ of acetonitrile, the characteristic of which compound was as follows:

melting point=242° C.

Stage C

By carrying out the reaction as in Example 2, but from 0.35 g of methyl (3aRS,4SR,9SR,9aRS)-4,9-ethano-9-(3-hydroxy-4-methoxyphenyl)-2-[2-(2-methoxyphenyl)propenoyl]-2,3,3a,4,9,9a-hexahydro-1H-benzo[f]isoindole-3a-carboxylate, from 3.25 cm$^3$ of a normal aqueous sodium hydroxide solution and from 5 cm$^3$ of methanol, 0.24 g of (3aRS,4SR,9SR,9aRS)-4,9-ethano-9-(3-hydroxy-4-methoxyphenyl)-2-[2-(2-methoxyphenyl)propenoyl]-2,3,3a,4,9,9a-hexahydro-1H-benzo[f]isoindole-3a-carboxylic acid was obtained, after recrystallization from 6 cm$^3$ of isopropanol, the characteristics of which compound were as follows:

melting point=278° C.

$^1$H N.M.R. spectrum (250 MHz, (CD$_3$)$_2$SO, at a temperature of 383 K, δ in ppm): 1.38, 1.56, 1.96 and 2.12 (4 mts, each 1H, CH$_2$CH$_2$), from 3.20 to 3.50 (mt, 3H, CH$_2$ at 1 and CH at 9a), 3.42 (mt, 1H: CH at 4), 3.59 and 4.06 (respectively d and d (broad), J=12.5 Hz, each 1H, CH$_2$ at 3), 3.73 and 3.86 (2 s, each 3H, the two ArOCH$_3$, 5.54 and 5.69 (respectively d and s (broad), J=1 Hz, each 1H, =CH$_2$), 6.52 (broad d, J=7.5 Hz, 1H, H at 8), 6.73 (dd, J=8 and 2 Hz, 1H, H at the 6 position of the 3-hydroxy-4-methoxyphenyl), 6.86 (d, J=2 Hz, 1H, H at the 2 position of the 3-hydroxy-4-methoxyphenyl), from 6.90 to 7.40 (mt, 8H, H at 5, H at 6, H at 7, H at the 5 position of the 3-hydroxy-4-methoxyphenyl and aromatic H of the 2-methoxyphenyl), from 8.20 to 8.90 (broad unresolved peak, 1H, ArOH).

EXAMPLE 98

Preparation of methyl (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylate Stage A 77.5 g (1.1 mol) of methyl vinyl ketone and 1.1 dm$^3$ of a normal aqueous sodium hydroxide solution were successively added to a solution, cooled to 0° C., of 178 g (0.917 mol) of (2-methoxyphenyl)pyruvic acid, which was obtained according to Org. Synth., 1939, 19, 1–3, in 970 cm$^3$ of methanol and then the mixture was stirred at a temperature in the region of 20° C. for two hours. After neutralization with 1.1 dm$^3$ of a normal aqueous hydrochloric acid solution and concentration of the methanol, the precipitate formed was filtered off, washed with water and then dried at 20° C. 189.7 g (78%) of 1-hydroxy-6-(2-methoxyphenyl)-3-oxocyclohexane-1-carboxylic acid were thus obtained in the form of a yellow powder, the characteristics of which were as follows:

melting point=204° C.

$^1$H N.M.R. spectrum (250 MHz, CDCl$_3$, δ in ppm): 1.20 (t, J=7 Hz, 3H, CH$_3$ of the ethyl), 1.47 (d, J=7 Hz, 3H, CH$_3$), 4.17 (q, J=7 Hz, 2H, OCH$_2$ of the ethyl), 4.49 (q, J=7 Hz, 1H, ArCH), from 7.15 to 7.45 (mt, 5H, aromatic H).

Stage B 396.7 g (1.5 mol) of 1-hydroxy-6-(2-methoxyphenyl)-3-oxocyclohexane-1-carboxylic acid were heated at reflux for two hours in 13.3 dm$^3$ of toluene in the presence of 39.7 g of para-toluenesulphonic acid. The reaction mixture was subsequently concentrated under reduced pressure and the precipitate formed was filtered off, washed with isopropyl ether and then dried at 50° C. 288 g (78%) of (RS)-6-(2-methoxyphenyl)-3-oxocyclohexene-1-carboxylic acid were thus obtained in the form of a brown solid, the characteristics of which were as follows:

melting point=177° C.;
mass spectrum (EI): M/Z=246 (M⁺).
$^1$H N.M.R. spectrum (300 MHz, CDCl$_3$, δ in ppm): from 2.10 to 2.50 (mt, 4H, CH$_2$CH$_2$), 3.70 (s, 3H, COOCH$_3$), 3.90 (s, 3H, ArOCH$_3$), 4.61 (mt, 1H, ArCH), from 6.80 to 7.00 and 7.25 (2 mts, 5H in whole, =CH and aromatic H).

Stage C 235 g (1.66 mol) of methyl iodide and 212 g (1.39 mol) of 1,8-diazabicyclo[5.4.0]undec-7-ene, dropwise, were successively added to a solution of 288 g (1.17 mol) of (RS)-6-(2-methoxyphenyl)-3-oxocyclohexene-1-carboxylic acid in 2.5 dm$^3$ of acetone and then the mixture was brought to reflux for one hour. The acetone was subsequently concentrated and then the residue was stirred with 1 dm$^3$ of water. After cooling to 10° C., the precipitate formed was filtered off, washed with petroleum ether and then dried at 50° C. 289 g (95%) of methyl (RS)-6-(2-methoxyphenyl)-3-oxocyclohexene-1-carboxylate were thus obtained in the form of a mustard-coloured powder, the characteristics of which were as follows:

melting point=76° C.;
mass spectrum (EI): M/Z=260 (M⁺).

Stage D

A solution of 6 g (0.023 mol) of methyl (RS)-6-(2-methoxyphenyl)-3-oxocyclohexene-1-carboxylate and of 0.3 cm$^3$ of trifluoroacetic acid in 185 cm$^3$ of dichloromethane was brought to reflux. 7.7 g (0.0275 mol) of N-n-butoxymethyl-N-(trimethylsilylmethyl)benzylamine, which was obtained according to Chem. Pharm. Bull., 1985, 276, were then added dropwise and the mixture was brought to reflux for three hours. The reaction mixture was then cooled to 20° C. After stirring for one hour with approximately 5 g of potassium carbonate, the organic phase was concentrated and the yellow oil obtained was purified by chromatography on silica gel (230–400 mesh), elution being carried out with a cyclohexane/ethyl acetate (95/05 by volume) mixture. 6.1 g (68%) of methyl (3aRS,4SR,7aRS)-2-benzyl-4-(2-methoxyphenyl)-7-oxooctahydroisoindole-3a-carboxylate were then obtained in the form of a yellow oil, the characteristics of which were as follows:

mass spectrum (EI): M/Z=393 (M⁺).

Stage E

A solution of 166.6 g (0.424 mol) of methyl (3aRS,4SR,7aRS)-2-benzyl-4-(2-methoxyphenyl)-7-oxo-octahydroisoindole-3a-carboxylate and of 84.5 g (1.69 mol) of hydrazine hydrate in 2.8 dm$^3$ of methanol is brought to reflux for two hours. After concentrating the methanol under reduced pressure, the residue was taken up in 2 dm$^3$ of dichloromethane, washed with four times 1 dm$^3$ of distilled water, dried over magnesium sulphate and concentrated under reduced pressure. 175.2 g of methyl (3aRS,4SR,7aRS)-2-benzyl-7-hydrazono-4-(2-methoxyphenyl) octahydroisoindole-3a-carboxylate were thus obtained in the form of a yellow oil, the characteristics of which were as follows:

mass spectrum (EI): M/Z=407 (M⁺).

Stage F 106.1 g (0.418 mol) of iodine in 1.1 dm$^3$ of tetrahydrofuran were added dropwise to a solution of 85 g (0.209 mol) of methyl (3aRS,4SR,7aRS)-2-benzyl-7-hydrazono-4-(2-methoxyphenyl)octahydroisoindole-3a-carboxylate in 2 dm$^3$ of tetrahydrofuran. After addition of 2 dm$^3$ of ethyl acetate, the organic phases were washed with two times 1 dm$^3$ of a saturated aqueous sodium hydrogencarbonate solution, washed with two times 1 dm$^3$ of a saturated aqueous sodium thiosulphate solution, then dried over magnesium sulphate and concentrated under reduced pressure. After purification by chromatography on silica gel (230–400 mesh), elution being carried out with a cyclohexane/ethyl acetate (95/05 by volume) mixture, 51 g (48%) of methyl (3aRS,4SR,7aRS)-2-benzyl-7-iodo-4-(2-methoxyphenyl)-2,3,3a,4,5,7a-hexahydro-1H-isoindole-3a-carboxylate were obtained in the form of a brown oil, the characteristics of which were as follows:

mass spectrum (EI): M/Z=503 (M⁺).

Stage G

A solution of 0.41 g (2.99 mmol) of 4-methylphenylboronic acid in 13 cm$^3$ of methanol and 30 cm$^3$ of a 2N aqueous sodium carbonate solution were successively added to a solution of 1.37 g (2.7 mmol) of methyl (3aRS,4SR,7aRS)-2-benzyl-7-iodo-4-(2-methoxyphenyl)-2,3,3a,4,5,7a-hexahydro-1H-isoindole-3a-carboxylate and of 0.15 g (0.13 mmol) of tetrakis (triphenylphosphine)palladium in 30 cm$^3$ of toluene and then the mixture was brought to reflux for two hours. After returning to a temperature in the region of 20° C., the reaction mixture was extracted with 100 cm$^3$ of ethyl acetate, washed with two times 50 cm$^3$ of distilled water, dried over magnesium sulphate and then concentrated under reduced pressure. The brown residue obtained was purified by flash chromatography on silica gel (230–400 mesh), elution being carried out with a cyclohexane/ethyl acetate (95/05 by volume) mixture. 1.2 g (93%) of methyl (3aRS, 4SR,7aRS)-2-benzyl-4-(2-methoxyphenyl)-7-(4-methylphenyl)-2,3,3a,4,5,7a-hexahydro-1H-isoindole-3a-carboxylate were thus obtained in the form of a yellow oil, the characteristics of which were as follows:

mass spectrum (EI): M/Z=467 (M⁺).

Stage H 94 cm$^3$ of trifluoromethanesulphonic acid were added dropwise to a solution of 66.4 g (0.142 mol) of methyl (3aRS,4SR,7aRS)-2-benzyl-4-(2-methoxyphenyl)-7-(4-methylphenyl)-2,3,3a,4,5,7a-hexahydro-1H-isoindole-3a-carboxylate in 750 cm$^3$ of dichloromethane maintained at a temperature in the region of 0° C. The reaction mixture was stirred for three hours at a temperature in the region of 20° C. and then cooled to a temperature in the region of 0° C. 700 cm$^3$ of a saturated aqueous potassium carbonate solution were then added. The organic phase was separated by settling, washed successively with three times 150 cm$^3$ of distilled water and with two times 100 cm$^3$ of a saturated aqueous sodium chloride solution, dried over magnesium sulphate and concentrated under reduced pressure. After washing with diisopropyl ether, 54.9 g (82%) of methyl (3aRS,4SR,9SR,9aRS)-2-benzyl- 4,9-ethano-5-methoxy-9-(4-methylphenyl)-2,3,3a,4,9,9a-hexahydro-1H-benzo[f] isoindole-3a-carboxylate were thus obtained in the form of an off-white solid, the characteristics of which were as follows:

melting point=129° C.
$^1$H N.M.R. spectrum (250 MHz, CDCl$_3$, δ in ppm): 1.41, 1.73 and from 2.40 to 2.60 (3 mts, respectively 1H, 1H and 2H, CH$_2$CH$_2$), from 2.30 to 2.40 (mt, 2H, 1H of the CH$_2$ at 1 and 1H of the CH$_2$ at 3), 2.39 (s, 3H, ArCH$_3$), 2.75 (broad d, J=10 Hz, 1H, the other H of the CH$_2$ at 1), 3.23 (d, J=9.5 Hz, 1H, the other H of the CH$_2$ at 3), 3.26 (mt, 1H, CH at 9a), 3.41 and 3.65 (2 d, J=12.5 Hz, each 1H, NCH$_2$Ar), 3.55 (s, 3H, COOCH$_3$), 3.81 (s, 3H, ArOCH$_3$), 3.96 (mt, 1H, CH at 4), 6.21 (d, J=7.5 Hz, 1H, H at 8), 6.71 (d, J=7.5 Hz, 1H, H at 6), 6.99 (t, J=7.5 Hz, 1H, H at 7), from 7.15 to 7.40 (mt, 9H, aromatic H of the 4-methylphenyl and aromatic H of the benzyl).

Stage I

From 0.54 g (1.1 mmol) of methyl (3aRS,4SR,9SR,9aRS)-2-benzyl-4,9-ethano-5-methoxy-9-(4-methylphenyl)-2,3,3a,4,9,9a-hexahydro-1H-benzo[f]isoindole-3a-carboxylate in solution in 100 cm³ of methanol and in the presence of 54 mg of 10% (w/w) palladium-on-charcoal, 0.5 g of methyl (3aRS,4SR,9SR,9aRS)-4,9-ethano-5-methoxy-9-(4-methylphenyl)-2,3,3a,4,9,9a-hexahydro-1H-benzo[f]isoindole-3a-carboxylate hydrochloride was obtained, after stirring for one hour under hydrogen at atmospheric pressure and at 40° C., filtering off the catalyst and concentrating to dryness under reduced pressure, in the form of a beige solid, the characteristics of which were as follows:

melting point>260° C.;
IR spectrum (KBr):

| | |
|---|---|
| 3050-2250 cm⁻¹ | ν N⁺H + ν CH, aromatic and aliphatic |
| 2833 cm⁻¹ | ν CH, OCH₃ |
| 1738 cm⁻¹ | ν C=O, methyl ester |
| 1603, 1584, 1514, 1477 cm⁻¹ | breathing of the aromatic nuclei |
| 1258 cm⁻¹ | ν O—C=O, methyl ester, + νₐ C—O, ether |
| 824 cm⁻¹ | γ CH, para-disubstituted phenyl aromatic |
| 776, 755 cm⁻¹ | γ CH, trisubstituted phenyl aromatic |

Stage J

A solution of 0.058 cm³ of oxalyl chloride in 5 cm³ of dichloromethane was added dropwise to a solution of 0.12 g of 2-(2-methoxyphenyl)propenoic acid in 5 cm³ of dichloromethane containing 3 drops of N,N-dimethylformamide. The reaction mixture was stirred for a further two hours at a temperature in the region of 20° C., then cooled to a temperature in the region of 0° C. and run dropwise into a solution of 0.25 g of methyl (3aRS,4SR,9SR,9aRS)-4,9-ethano-5-methoxy-9-(4-methylphenyl)-2,3,3a,4,9,9a-hexahydro-1H-benzo[f]isoindole-3a-carboxylate hydrochloride in 7 cm³ of dichloromethane and 0.19 cm³ of triethylamine, the temperature being maintained in the region of 0° C. The reaction mixture was stirred for a further one hour at a temperature in the region of 0° C. and then at 20° C. overnight, and poured into 15 cm³ of distilled water. The organic phase was separated by settling, washed with two times 15 cm³ of distilled water and then 15 cm³ of a saturated aqueous sodium chloride solution, dried over magnesium sulphate and concentrated under reduced pressure. After purification by flash chromatography on silica gel (230–400 mesh), elution being carried out with a cyclohexane/ethyl acetate (70/30 by volume) mixture, 0.17 g of methyl (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylate was obtained in the form of a white solid, the characteristics of which were as follows:

melting point=185° C.;
mass spectrum (EI): M/Z=537 (M⁺).

EXAMPLE 99

Preparation of (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic Acid 0.365 g of methyl (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylate was heated at reflux for three hours in 30 cm³ of ethanol in the presence of 0.82 cm³ of a normal aqueous sodium hydroxide solution. The reaction mixture was subsequently concentrated under reduced pressure and the residue dissolved in 10 cm³ of distilled water. The aqueous phase was washed with two times 10 cm³ of dichloromethane, acidified with a normal aqueous hydrochloric acid solution to a pH in the region of 2, extracted with 30 cm³ of dichloromethane, washed with distilled water, dried over magnesium sulphate and then concentrated under reduced pressure. The orange solid obtained was purified by flash chromatography on silica gel (230–400 mesh), elution being carried out with a dichloromethane/methanol/acetic acid (98/1.5/0.5 by volume) mixture. 0.09 g (26%) of (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid was thus obtained in the form of a white solid, the characteristics of which were as follows:

melting point>260° C.

¹H N.M.R. spectrum (250 MHz, (CD₃)₂SO, at a temperature of 383 K, δ in ppm): 1.32, 1.60 and from 1.85 to 2.20 (3 mts, respectively 1H, 1H and 2H, CH₂CH₂), 2.38 (s, 3H, ArCH₃), 3.34 (mt, 3H, CH₂ at 1 and CH at 9a), 3.62 and 4.04 (2 d, J=12.5 Hz, each 1H, CH₂ at 3), 3.72 and 3.81 (2 s, each 3H, ArOCH₃), 3.93 (mt, 1H, CH at 4), 5.52 and 5.66 (2 broad s, each 1H, =CH₂), 6.06 (d, J=7.5 Hz, 1H, H at 8), 6.82 (d, J=7.5 Hz, 1H, H at 6), from 6.90 to 7.10 (mt, 3H, H at 7 and 2 aromatic H of the 2-methoxyphenyl), from 7.20 to 7.40 (mt, 6H, 2 aromatic H of the 2-methoxyphenyl and aromatic H of the 4-methoxyphenyl).

EXAMPLE 100

Isolation of the Dextrorotatory Enantiomer of (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic Acid 6.5 g of (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid, obtained in Example 99, were resolved, on a chiral silica column carrying N-(3,5-dinitrobenzoyl)-(R)-phenylalanine grafts, in 4 successive injections and by eluting with an n-heptane/dichloromethane/ethanol (50/50/1 by volume) mixture. On collecting the first fractions eluted (retention time 30 min), 2.81 g of the dextrorotatory enantiomer of (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid were obtained, after concentrating the solvent under reduced pressure, in the form of a white powder, the characteristics of which were as follows:

mass spectrum (EI): M/Z=523 (M⁺);

optical rotation: $[\alpha]_{365}^{20}$=+36.5+/−1° (c=0.5, dichloromethane).

EXAMPLE 101

Preparation of (3aRS,4SR,9SR,9aRS)-4,9-ethano-2-[2-(2-methoxyphenyl)propenoyl]-9-(4-methoxyphenyl)-4-methyl-2,3,3a,4,9,9a-hexahydro-1H-benzo[f]isoindole-3a-carboxylic Acid Stage A A 1.6 N solution of n-butyllithium in hexane was run dropwise into a solution, cooled to the region of −70° C., of 33 g (0.220 mol) of (RS)-2-phenylpropionic acid in 220 cm$^3$ of tetrahydrofuran and of 44 cm$^3$ of N,N'-tetramethylethylenediamine. After having stirred the reaction mixture for three hours at −70° C., the reaction mixture was returned to a temperature in the region of 20° C. and the solution obtained was run into a solution of 75 cm$^3$ (0.55 mol) of ethyl oxalate in 110 cm$^3$ of tetrahydrofuran, the temperature being maintained at −75° C., for 1 hour. The reaction mixture was hydrolysed with 800 cm$^3$ of a saturated aqueous sodium hydrogencarbonate solution, extracted with three times 100 cm$^3$ of ethyl acetate, washed with three times 50 cm$^3$ of a normal aqueous hydrochloric acid solution, dried over sodium sulphate and concentrated under reduced pressure. 44 g (97%) of ethyl (RS)-2-oxo-3-phenylbutyrate were then obtained in the form of an orange oil, the characteristics of which were as follows:

$^1$H N.M.R. spectrum (250 MHz, CDCl$_3$, δ in ppm): 1.20 (t, J=7 Hz, 3H, CH$_3$ of the ethyl), 1.47 (d, J=7 Hz, 3H, CH$_3$), 4.17 (q, J=7 Hz, 2H, OCH$_2$ of the ethyl), 4.49 (q, J=7 Hz, 1H, ArCH), from 7.15 to 7.45 (mt, 5H, aromatic H).

Stage B 3.5 cm$^3$ (39 mmol) of methyl vinyl ketone and 72 cm$^3$ (71.5 mmol) of a normal aqueous sodium hydroxide solution were successively added to a solution, cooled to the region of 7° C., of 6.7 g (32.5 mmol) of ethyl (RS)-2-oxo-3-phenylbutyrate in 68 cm$^3$ of ethanol and then the reaction mixture was stirred at a temperature in the region of 20° C. for two hours. The reaction mixture was cooled to 15° C. and 72 cm$^3$ of a normal aqueous hydrochloric acid solution were added. After concentrating the ethanol, the precipitate formed was filtered off, washed with water and then dried at 50° C. 4.4 g (50%) of (1RS,2RS)-1-hydroxy-2-methyl-5-oxo-2-phenylcyclohexane-1-carboxylic acid were thus obtained in the form of a beige powder, the characteristics of which were as follows:

$^1$H N.M.R. spectrum (300 MHz, CDCl$_3$, δ in ppm): 1.79 (s, 3H, CH$_3$), from 2.00 to 2.25 and from 2.25 to 2.55 (2 mts, each 2H, CH$_2$CH$_2$), 3.59 (s, 3H, COOCH$_3$), 6.72 (s, 1H, =CH), from 7.15 to 7.35 (mt, 5H, aromatic H).

Stage C 4.4 g (17.6 mmol) of (1RS,2RS)-1-hydroxy-2-methyl-5-oxo-2-phenylcyclohexane-1-carboxylic acid were heated at reflux for one hour in 100 cm$^3$ of toluene in the presence of 0.34 g of para-toluenesulphonic acid. The reaction mixture was cooled to 0° C. and the precipitate formed was filtered off, washed with ethyl ether and then dried at 50° C. 2.8 g (69%) of (RS)-2-methyl-5-oxo-2-phenylcyclohexene-1-carboxylic acid were thus obtained in the form of a pink solid, the characteristics of which were as follows:

melting point=206° C.;
mass spectrum (EI): M/Z=230 (M$^+$).

Stage D 0.88 cm$^3$ (14 mmol) of methyl iodide and 1.8 cm$^3$ (12 mmol) of 1,8-diazabicyclo[5.4.0]undec-7-ene, dropwise, were successively added to a solution of 2.3 g (10 mmol) of (RS)-2-methyl-5-oxo-2-phenylcyclohexene-1-carboxylic acid in 20 cm$^3$ of acetone. The reaction mixture was subsequently heated at reflux for two hours. The acetone was subsequently concentrated, the residue was then stirred with 100 cm$^3$ of water and then extracted with three times 30 cm$^3$ of ethyl acetate. After drying over magnesium sulphate and concentrating under reduced pressure, 2.3 g (94%) of methyl (RS)-2-methyl-5-oxo-2-phenylcyclohexene-1-carboxylate were obtained in the form of an orange oil, the characteristic of which was as follows:

mass spectrum (EI): M/Z=244 (M$^+$).

Stage E

A solution of 18.3 g (0.075 mol) of methyl (RS)-2-methyl-5-oxo-2-phenylcyclohexene-1-carboxylate and of 0.57 cm$^3$ of trifluoroacetic acid in 145 cm$^3$ of dichloromethane was brought to reflux. 31.4 g (0.112 mol) of N-n-butoxymethyl-N-(trimethylsilylmethyl)benzylamine, which was obtained according to Chem. Pharm. Bull., 1985, 276, were then added dropwise and the reaction mixture was brought to reflux for four hours. The reaction mixture was then cooled to 20° C. After stirring for one hour with approximately 15 g of potassium carbonate, the organic phase was concentrated and the oil obtained was crystallized from pentane. After filtration, 19 g (67%) of methyl (3aRS,4SR,7aRS)-2-benzyl-4-methyl-7-oxo-4-phenyloctahydroisoindole-3a-carboxylate were obtained in the form of a yellow solid, the characteristics of which were as follows:

melting point=115° C.;
mass spectrum (EI): M/Z=377 (M$^+$).

Stage F

A solution of 3 g (7.95 mmol) of methyl (3aRS,4SR,7aRS)-2-benzyl-4-methyl-7-oxo-4-phenyloctahydroisoindole-3a-carboxylate and of 1.55 cm$^3$ (31.8 mmol) of hydrazine hydrate in 30 cm$^3$ of methanol was brought to reflux for two hours. After concentrating the methanol under reduced pressure, the residue was taken up in dichloromethane, washed with three times 30 cm$^3$ of distilled water, dried over magnesium sulphate and concentrated under reduced pressure. 2.8 g (89%) of methyl (3aRS,4SR,7aRS)-2-benzyl-7-hydrazono-4-methyl-4-phenyloctahydroisoindole-3a-carboxylate were thus obtained in the form of a brown oil, the characteristics of which were as follows:

$^1$H N.M.R. spectrum (300 MHz, CDCl$_3$, δ in ppm): 1.33 (s, 3H, CH$_3$), 1.86, 2.24, 2.48 and 2.84 (4 mts, each 1H, CH$_2$ at 5 and CH$_2$ at 6), 2.43 and 3.47 (2 d, J=9 Hz, each 1H, CH$_2$ at 3), 2.67 and 3.19 (2 t, J=8.5 Hz, each 1), 3.10 (s, 3H, COOCH$_3$), 3.53 and 3.71 (2 d, J=13 Hz, each 1H, NCH$_2$Ar), 3.78 (t, J=8.5 Hz, 1H, H at 7a), 4.98 (broad s, 2H, NH$_2$), from 7.10 to 7.35 (mt, 10H, aromatic H of the phenyl and aromatic H of the benzyl).

Stage G 2.95 cm$^3$ of triethylamine were added to a solution of 2.8 g (7 mmol) of methyl (3aRS,4SR,7aRS)-2-benzyl-7-hydrazono-4-methyl-4-phenyloctahydroisoindole-3a-carboxylate in 80 cm$^3$ of tetrahydrofuran and a solution of 3.6 g (14.1 mmol) of iodine in 40 cm$^3$ of tetrahydrofuran was run in dropwise. After addition of ethyl acetate, the organic phases were washed with two times 50 cm$^3$ of a saturated aqueous sodium hydrogencarbonate solution, washed with two times 50 cm$^3$ of a saturated aqueous sodium thiosulphate solution, then dried over magnesium sulphate and concentrated under reduced pressure. After purification by chromatography on silica gel (230–400 mesh), elution being carried out with a cyclohexane/ethyl acetate (85/15 by volume) mixture, 2.4 g (69%) of methyl (3aRS,4SR,7aRS)-2-benzyl-7-iodo-4-methyl-4-phenyl-2,3,3a,4,5,7a-hexahydro-1H-isoindole-3a-carboxylate were obtained in the form of a yellow oil, the characteristic of which was as follows:

mass spectrum (EI): M/Z=487 (M⁺).

Stage H

A solution of 20.1 g (0.132 mol) of 4-methoxyphenylboronic acid in 580 cm³ of methanol and 1170 cm³ of a 2N aqueous sodium carbonate solution were successively added to a solution of 58.6 g (0.12 mol) of methyl (3aRS,4SR,7aRS)-2-benzyl-7-iodo-4-methyl-4-phenyl-2,3,3a,4,5,7a-hexahydro-1H-isoindole-3a-carboxylate and of 7 g of tetrakis(triphenylphosphine) palladium in 30 cm³ of toluene and then the mixture was brought to reflux for twenty-four hours. After returning to a temperature in the region of 20° C., the reaction mixture was extracted with ethyl acetate, washed with distilled water, dried over magnesium sulphate and then concentrated under reduced pressure. The residue obtained was purified by flash chromatography on silica gel (230–400 mesh), elution being carried out with a cyclohexane/ethyl acetate (98/02 by volume) mixture. 29 g (52%) of methyl (3aRS,4SR,7aRS)-2-benzyl-7-(4-methoxyphenyl)-4-methyl-4-phenyl-2,3,3a,4,5,7a-hexahydro-1H-isoindole-3a-carboxylate were thus obtained in the form of a brown powder, the characteristics of which were as follows:

melting point=132° C.

$^1$H N.M.R. spectrum (250 MHz, CDCl$_3$, δ in ppm): 1.60 (s, 3H, CH$_3$ at 4), 2.03 (dd, J=9 and 5 Hz, 1H, 1H of the CH$_2$ at 5), from 2.40 to 2.90 (mt, 1H, the other H of the CH$_2$ at 5), 3.56 (s, 3H, COOCH$_3$), from 3.40 to 3.95 (mt, 2H, NCH$_2$Ar), 3.79 (mt, 1H, CH at 7a), 3.83 (s, 3H, ArOCH$_3$), 6.08 (mt, 1H, =CH at 6), from 6.75 to 7.45 (mt, 14H, aromatic H of the 4-methoxyphenyl, aromatic H of the benzyl and aromatic H of the phenyl).

Stage I 105 cm³ of trifluoromethanesulphonic acid were added dropwise to a solution of 54.7 g (0.117 mol) of methyl (3aRS,4SR,7aRS)-2-benzyl-7-(4-methoxyphenyl)-4-methyl-4-phenyl-2,3,3a,4,5,7a-hexahydro-1H-isoindole-3a-carboxylate in 700 cm³ of dichloromethane maintained at a temperature in the region of 5° C. The reaction mixture was stirred for three hours at a temperature in the region of 20° C. and then cooled to a temperature in the region of 0° C. 100 cm³ of a 10N aqueous sodium hydroxide solution were then added. The organic phase was separated, washed successively with three times 100 cm³ of distilled water, dried over magnesium sulphate and concentrated under reduced pressure. After washing in petroleum ether, 50 g (92%) of methyl (3aRS,4SR,9SR,9aRS)-2-benzyl-4,9-ethano-9-(4-methoxyphenyl)-4-methyl-2,3,3a,4,9,9a-hexahydro-1H-benzo[f]isoindole-3a-carboxylate were thus obtained in the form of a grey solid, the characteristics of which were as follows:

melting point=143° C.

$^1$H N.M.R. spectrum (400 MHz, CDCl$_3$, δ in ppm): 1.21, 1.79, 2.36 and 2.53 (4 mts, each 1H, CH$_2$CH$_2$), 1.41 (s, 3H, CH$_3$), 2.37 and 2.55 (2 mts, each 1H, CH$_2$ at 1), 2.74 and 3.14 (2 d, J=10 Hz, each 1H, CH$_2$ at 3), 3.19 (mt, 1H, CH at 9a), 3.44 (s, 3H, COOCH$_3$), 3.47 and 3.61 (2 d, J=13 Hz, each 1H, NCH$_2$Ar), 3.86 (s, 3H, ArOCH$_3$), 6.59 (d, J=7.5 Hz, 1H, H at 8), 6.96 (broad d, J=7.5 Hz, 2H, aromatic H at the ortho positions with respect to the OCH$_3$), from 7.05 to 7.25 (mt, 3H, H at 5, H at 6 and H at 7), from 7.25 to 7.45 (mt, 7H, aromatic H at the meta positions with respect to the OCH$_3$ and aromatic H of the benzyl).

Stage J

From 13 g (0.028 mol) of methyl (3aRS,4SR,9SR,9aRS)-2-benzyl-4,9-ethano-9-(4-methoxyphenyl)-4-methyl-2,3,3a, 4,9,9a-hexahydro-1H-benzo[f]isoindole-3a-carboxylate in solution in 260 cm³ of methanol, and in the presence of 1.7 g of 10% (w/w) palladium-on-charcoal, 10.2 g (97%) of methyl (3aRS,4SR,9SR,9aRS)-4,9-ethano-9-(4-methoxyphenyl)-4-methyl-2,3,3a,4,9,9a-hexahydro-1H-benzo[f]isoindole-3a-carboxylate hydrochloride were obtained, after stirring for four hours under hydrogen at atmospheric pressure and at 40° C., filtering off the catalyst and concentrating to dryness under reduced pressure, in the form of a yellow solid, the characteristics of which were as follows:

IR spectrum (KBr).

| | |
|---|---|
| 3050-2250 cm⁻¹ | ν N⁺H + ν CH, aromatic and aliphatic |
| 2842 cm⁻¹ | ν CH, OCH$_3$ |
| 1737 cm⁻¹ | ν C=O, methyl ester |
| 1611, 1571, 1516, 1460 cm⁻¹ | breathing of the aromatic nuclei |
| 1253 cm⁻¹ | ν O—C=O, methyl ester, + ν$_a$ C—O, ether |
| 825 cm⁻¹ | γ CH, para-disubstituted phenyl aromatic |
| 768 cm⁻¹ | γ CH, ortho-disubstituted phenyl aromatic |

Stage K

A solution of 3.1 cm³ of oxalyl chloride in 50 cm³ of dichloromethane was added dropwise to a solution of 4.62 g (0.026 mol) of 2-(2-methoxyphenyl)propenoic acid in 100 cm³ of dichloromethane containing 2 drops of N,N-dimethylformamide. The reaction mixture was stirred for a further two hours at a temperature in the region of 20° C., then cooled to a temperature in the region of 0° C. and run dropwise into a solution of 8.3 g (0.024 mol) of methyl (3aRS,4SR,9SR,9aRS)-4,9-ethano-9-(4-methoxyphenyl)-4-methyl-2,3,3a,4,9,9a-hexahydro-1H-benzo[f]isoindole-3a-carboxylate hydrochloride in 100 cm³ of dichloromethane and 6.1 cm³ of triethylamine, the temperature being maintained in the region of 0° C. The reaction mixture was stirred for a further one hour at a temperature in the region of 0° C. and then overnight at 20° C. After washing with two times 100 cm³ of distilled water, the organic phase was separated by settling, washed successively with two times 100 cm³ of a normal aqueous hydrochloric acid solution and with two times 100 cm³ of a normal aqueous sodium hydroxide solution, dried over magnesium sulphate and concentrated under reduced pressure. After purification by flash chromatography on silica gel (230–400 mesh), elution being carried out with a cyclohexane/ethyl acetate (70/30 by volume) mixture, 9.1 g of methyl (3aRS,4SR,9SR,9aRS)-4,9-ethano-2-[2-(2-methoxyphenyl)propenoyl]-4-methyl-9-(4-methoxyphenyl)-2,3,3a,4,9,9a-hexahydro-1H-benzo[f]isoindole-3a-carboxylate were obtained in the form of an orange-coloured solid, the characteristics of which were as follows:

melting point=141° C.

$^1$H N.M.R. spectrum (300 MHz, (CD$_3$)$_2$SO, δ in ppm): from 0.95 to 1.25 and from 1.55 to 2.10 (2 mts, 4H in all, CH$_2$CH$_2$), 1.38 and 1.46 (2 s, 3H in all, CH$_3$), from 3.05 to 3.35 (mt, 3H, CH$_2$ at 1 and CH at 9a), from 3.30 to 3.40 and 3.41 (respectively mt and s, 3H in all, COOCH$_3$), 3.62, 3.72, 3.80 and 3.83 (4 s, 6H in all, ArOCH$_3$), from 3.80 to 4.20 (mt, 2H, CH$_2$ at 3), 5.43, 5.56, 5.60 and 5.78 (4 s, 2H in all, =CH$_2$), 6.39 and 6.42 (2 d, J=7.5 Hz, 1H in all, H at 8), from 6.85 to 7.45 (mts, 11H, H at 5, H at 6, H at 7, aromatic H of the 4-methoxyphenyl and aromatic H of the 2-methoxyphenyl).

Stage L 13.4 g (0.025 mol) of methyl (3aRS,4SR,9SR,9aRS)-4, 9-ethano-2-[2-(2-methoxyphenyl)propenoyl]-4-methyl-9-(4-methoxyphenyl)-2,3,3a,4,9,9a-hexahydro-1H-benzo[f] isoindole-3a-carboxylate were heated at reflux for three hours in 250 cm³ of ethanol in the presence of 52 cm³ of a normal aqueous sodium hydroxide solution. The reaction mixture was subsequently concentrated under reduced pressure and the residue was dissolved in 250 cm³ of distilled water. The aqueous phase was washed with two times 100 cm³ of ethyl ether, acidified with 60 cm³ of a normal aqueous hydrochloric acid solution, extracted with two times 150 cm³ of dichloromethane, dried over magnesium sulphate and then concentrated under reduced pressure. The white solid obtained was purified by washing in 100 cm³ of pentane. 10.8 g (83%) of (3aRS,4SR,9SR,9aRS)-4,9-ethano-2-[2-(2-methoxyphenyl)propenoyl]-9-(4-methoxyphenyl)-4-methyl-2,3,3a,4,9,9a-hexahydro-1H-benzo[f]isoindole-3a-carboxylic acid were thus obtained in the form of a white solid, the characteristics of which were as follows:

melting point=157° C.;
mass spectrum (EI): M/Z=523 (M⁺).

Isolation of the Dextrorotatory Eantiomer of (3aRS, 4SR,9SR,9aRS)-4,9-ethano-2-[2-(2-methoxyphenyl) propenoyl]-9-(4-methoxyphenyl)-4-methyl-2,3,3a,4, 9,9a-hexahydro-1H-benzo[f]isoindole-3a-carboxylic Acid 17.6 g of (3aRS,4SR,9SR,9aRS)-4,9-ethano-2-[2-(2-methoxyphenyl)propenoyl]-9-(4-methoxyphenyl)-4-methyl-2,3,3a,4,9,9a-hexahydro-1H-benzo[f]isoindole-3a-carboxylic acid were resolved, in 4 injections, on a Whelk 01 (SS) chiral silica column, elution being carried out with an n-heptane/dichloromethane/propanol (50/48/2 by volume) mixture containing 0.05% of trifluoroacetic acid. On collecting the first fraction eluted (retention time 38 min), 7.01 g of the dextrorotatory enantiomer of (3aRS,4SR,9SR, 9aRS)-4,9-ethano-2-[2-(2-methoxyphenyl)propenoyl]-9-(4-methoxyphenyl)-4-methyl-2,3,3a,4,9,9a-hexahydro-1H-benzo[f]isoindole-3a-carboxylic acid were obtained, after concentrating under reduced pressure, in the form of a white powder, the characteristics of which were as follows:

melting point=238° C.;
mass spectrum (EI): M/Z=523 (M⁺);
optical rotation: $[\alpha]_{365}^{20}$=+74.4+/−1.3° (c=0.5, methanol).

EXAMPLE 102

Evaluation of the Farnesyl Transferase Activity of Compounds According to the Invention The farnesyl transferase activity was measured by the amount farnesylated of K-ras substrate or of substrate derived from the peptide corresponding to its C-terminal part, the farnesyl group being introduced by farnesyl pyrophosphate (FPP).

Specifically, the biotinylated substrate used, representative of K-ras: BIOT-(βA)₃-S-K-D-G-(K)₆-S-K-T-K-C-V-I-M, is [³H]-farnesylated on its cysteine C by farnesyl transferase in the presence of [³H]-FPP. It was then brought into contact with PVT-streptavidin (Amersham)® beads and was quantified by proximity scintillation (SPA assay) between the tritium and the PVT beads, by virtue of the streptavidin/biotin interaction.

Experimentally, farnesyl transferase purified according to the appended protocol was diluted, for this assay, to a concentration such that a consumption of substrates of less than 30% was obtained. The final molar concentrations of each substrate were adjusted to their respective Km: 50 nM for the biotinylated K ras peptide and 120 nM for FPP, introduced at 20 μl into a final volume of 100 μl of the reaction mixture based on 50 mM pH 7.5 Hepes buffer, 5 mM MgCl₂, 40 mM KCl, 5 mM dithiothreitol, 0.01% Triton X100.

The inhibitors that were tested, initially dissolved at 1 mM in an appropriate solvent (DMF or DMSO), were diluted in the assay buffer and were added in the form of 10 μl, in triplicate, to the reaction mixture at a concentration 10 times greater than their final concentration.

The reaction, carried out in Optiplates 96° microtitration plates, was initiated by the enzyme and lasted sixty minutes at 37° C. It was stopped by addition of 150 μl of mixture of a blocking buffer at pH 4 composed of 0.2M H₃PO₄, 1.5 mM MgCl₂, 0.5% (w/v) BSA, 0.05% (w/v) sodium azide containing 200 μg of PVT-streptavidin beads.

After slow agitation for thirty minutes (in order to remove the chemiluminescence), the plates were read as [³H]CPM in a Top Count® (Packard) scintillation counter for microplates, where they were converted into [³H]DPM from a range of coloured agent attenuating the scintillation (quenching).

The percentages of inhibition were calculated with respect to an inhibitor-free control after subtraction from all the values of that of a blank which only contained the substrates and the buffer.

The IC₅₀ values were calculated or measured, from the inhibitions obtained at nine different concentrations, with Enzfitter® or Grafit® software. The IC₅₀ values which appear in the results are the mean of measurements and calculations of two IC₅₀ values. By way of illustration and without implied limitation, some results obtained are collated in Table I.

TABLE I

| Product | In vitro inhibitory activity (K-Ras) IC₅₀ (μM) |
|---|---|
| Example 1 | 0.305 |
| Example 2 | 0.045 |
| Example 3 | 0.028 |
| Example 4 | 1.80 |
| Example 5 | 0.050 |
| Example 6 | 0.0575 |
| Example 7 | 0.050 |
| Example 8 | 0.100 |
| Example 9 | 0.055 |
| Example 10 | 0.160 |
| Example 11 | 0.345 |
| Example 12 | 0.045 |
| Example 13 | 0.140 |
| Example 14 | 0.210 |
| Example 15 | 0.170 |
| Example 16 | 0.360 |
| Example 17 | 0.235 |
| Example 18 | 0.050 |
| Example 19 | 0.181 |
| Example 20 | 0.140 |
| Example 21 | 0.111 |
| Example 22 | 0.131 |
| Example 23 | 0.277 |
| Example 24 | 0.084 |
| Example 25 | 0.193 |
| Example 26 | 0.145 |
| Example 27 | 0.009 |
| Example 28 | 0.054 |
| Example 29 | 0.140 |
| Example 30 | 0.074 |
| Example 31 | 0.101 |
| Example 32 | 0.106 |
| Example 33 | 0.242 |
| Example 34 | <0.02 |

TABLE I-continued

| Product | In vitro inhibitory activity (K-Ras) IC$_{50}$ ($\mu$M) |
|---|---|
| Example 35 | 0.084 |
| Example 36 | 0.120 |
| Example 37 | 0.088 |
| Example 38 | 0.099 |
| Example 39 | 0.273 |
| Example 40 | 0.083 |
| Example 41 | 0.009 |
| Example 42 | 0.083 |
| Example 43 | 0.590 |
| Example 44 | 0.369 |
| Example 45 | 0.181 |
| Example 46 | 0.132 |
| Example 47 | 0.207 |
| Example 48 | 0.095 |
| Example 49 | 0.229 |
| Example 50 | 0.059 |
| Example 51 | 0.068 |
| Example 52 | 0.181 |
| Example 53 | 0.020 |
| Example 54 | 0.078 |
| Example 55 | 0.558 |
| Example 56 | 0.589 |
| Example 57 | 0.280 |
| Example 58 | 0.138 |
| Example 59 | 0.408 |
| Example 60 | 0.124 |
| Example 61 | 0.178 |
| Example 62 | 0.036 |
| Example 63 | <0.020 |
| Example 64 | 0.325 |
| Example 65 | 0.040 |
| Example 66 | 0.379 |
| Example 67 | 0.101 |
| Example 68 | 0.431 |
| Example 69 | 0.053 |
| Example 70 | 0.067 |
| Example 71 | 0.335 |
| Example 72 | 0.098 |
| Example 73 | 0.460 |
| Example 74 | 0.048 |
| Example 75 | 0.008 |
| Example 76 | 0.244 |
| Example 77 | 0.204 |
| Example 78 | 0.048 |
| Example 79 | 0.045 |
| Example 80 | 0.067 |
| Example 81 | 0.018 |
| Example 82 | 0.097 |
| Example 83 | 0.319 |
| Example 84 | 0.008 |
| Example 85 | 0.508 |
| Example 86 | 0.005 |
| Example 87 | 0.064 |
| Example 88 | 0.404 |
| Example 89 | 0.005 |
| Example 90 | 0.068 |
| Example 91 | 0.183 |
| Example 92 | 0.028 |
| Example 93 | 0.786 |
| Example 94 | 0.557 |
| Example 95 | 0.177 |
| Example 96 | 0.955 |
| Example 97 | 0.040 |
| Example 98 | 0.663 |
| Example 99 | 0.018 |
| Example 100 | <0.019 |
| Example 101 | <0.019 |

Other compounds of formula (I) were tested and exhibited IC$_{50}$ values <50 $\mu$M, and most of the compounds tested exhibited IC$_{50}$ values <10 $\mu$M.

EXAMPLE 103

The activity of the compounds according to the invention were also evaluated by the ability of the said compounds to inhibit the growth in agar of clones resulting from human tumour lines. For example, cells from the HCT116 human colic carcinoma line, supplied by the ATCC, were grown as a monolayer in a culture medium, Dulbecco's modified Eagle, containing 2 mM of L-glutamine, 200 U/ml of penicillin, 200 $\mu$g/ml of streptomycin complemented by 10% by volume of heat inactivated foetal calf serum. The cells in exponential growth were trypsinized, washed with PBS and diluted to a final concentration of 5000 cells/ml in the complete culture medium. The inhibitors that were tested, or the control solvent, were then added, at a volume of 50 $\mu$l, to 2.5 ml of cell suspension, prepared above. 0.4 ml of an agar solution, Noble Difco, maintained at 45° C., was subsequently added and mixing was then carried out. The medium thus obtained was immediately placed in Petri dishes, maintained for five minutes at 4° C. and then incubated at 37° C. under an atmosphere containing 5% of CO$_2$. The number of cell clones (>50 cells) was counted after incubating for twelve days at 37° C. under an atmosphere containing 5% of CO$_2$. Each inhibitor was tested in duplicate at the final concentrations in agar of 10, 1, 0.1, 0.01 and 0.001 $\mu$g/ml. The results were expressed as percentage of inhibition of clonogenicity with respect to the untreated controls. The inhibitory doses IC$_{50}$ were determined graphically from the semi-logarithmic means of the values obtained for each concentration.

The products according to the invention inhibit farnesylation of the Ras protein by 50% at concentrations of between 0.1 nM and 100 $\mu$M.

EXAMPLE 104

The antitumour activity of the compounds according to the invention was demonstrated by an in vivo test in mice, according to the tests and methodologies conventionally used (Corbett et al., Cancer Research 42, 1707–1715 (1982), Corbett et al., Cancer Treatment Report, 66, 1187–1200 (1982), Corbett et al., 40, 2660–2680 (1977)).

The influence of the compounds according to the invention, administered to mice, on the growth of carcinomas of human origin grafted subcutaneously into these mice was studied.

On day 0 of the experiment, the mice received a tumour fragment (30–60 mg) bilaterally under the skin using a trocar. The bilateral implantation of the tumours ensured a more uniform tumour weight per mouse and thus made it possible to reduce the number of animals per group. The mice were then divided into the different treated and untreated groups.

The product was suspended in an aqueous solution at concentrations that ranged from 0.01 to 1200 mg/ml, corresponding to doses of 0.1 to 10,000 mg/kg.

The treatments or their possible excipient were administered every day orally, at a maximum volume of 0.2 ml, the duration of administration depending on the doubling time of the tumour.

The tumours were measured 2 to 3 times per week, using a calliper rule, according to two measurements in mm, which were subsequently converted into tumour weight according to the following formula:

tumour weight (mg)=Length (mm)×width$^2$ (mm$^2$)/2

An active product was a product which made it possible to limit the growth of the tumour after it had been administered.

The following example may be mentioned by way of illustration and without implied limitation of the present invention:

Tumour stabilization was obtained at a dose of 400 mg/kg/adm. of the product of Example 3, administered orally to mice grafted subcutaneously with the HCT116 human colic carcinoma line supplied by the ATCC (Brattain et al., Cancer Research, 41, 1751–1756 (1981)).

EXAMPLE 105

EXAMPLE A

Hard gelatin capsules containing 50 mg of active product were prepared, according to the usual technique, which had the following composition:

| | |
|---|---|
| Active product | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50 mg of active product were prepared, according to the usual technique, which had the following composition:

| | |
|---|---|
| Active product | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose glycerol and titanium oxide (72/3.5/24.5) q.s. for 1 coated tablet completed to | 245 mg |

EXAMPLE C

An injectable solution containing 50 mg of active product was prepared which had the following composition:

| | | |
|---|---|---|
| Active product | | 50 mg |
| Benzoic acid | | 80 mg |
| Benzyl alcohol | | 0.06 ml |
| Sodium benzoate | | 80 mg |
| 95% Ethanol | | 0.4 ml |
| Sodium hydroxide | | 24 mg |
| Propylene glycol | | 1.6 ml |
| Water | q.s. for | 4 ml |

What is claimed is:

1. A composition comprising at least one farnesyl transferase inhibitor and at least one epipodophyllotoxin, wherein said at least one farnesyl transferase inhibitor is chosen from a compound of formula (I) or its pharmaceutically acceptable salt:

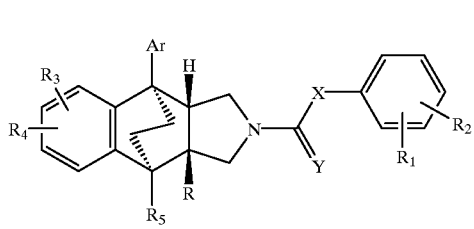

in which:
Ar represents
a phenyl radical substituted by one or more atoms or radicals, which are identical or different and are selected from halogen atoms and the radicals: alkyl, alkenyl containing 2 to 4 carbon atoms, hydroxyl, mercapto, alkylthio, alkylsulphonyl, alkylsulphinyl, amino, alkylamino, dialkylamino, formyl, alkylcarbonyl, carboxyl, alkyloxycarbonyl, carbamoyl, alkylcarbamoyl, dialkylcarbamoyl, cyano, and alkyloxy, the alkyl portions and radicals being optionally perhalogenated, or
a phenyl radical condensed with a 4- to 7-membered nonaromatic heterocycle containing one or more heteroatoms selected from oxygen, nitrogen and sulphur atoms, or
a polycyclic aromatic radical, wherein said polycylic aromatic radical can optionally contains at least one cycle that is saturated or only partially unsaturated but at least one cycle thereof must be aromatic, or
a monocyclic 5- to 12-membered heterocyclic aromatic radical incorporating
one or more heteroatoms selected from oxygen, nitrogen and sulphur atoms, said heterocyclic aromatic radical being bonded to the condensed ring via a carbon—carbon bond and optionally being substituted by one or more atoms or radicals, which are identical or different and are selected from halogen atoms and the radicals: alkyl, alkenyl containing 2 to 4 carbon atoms, hydroxyl, alkyloxy, mercapto, alkylthio, alkylsulphonyl, alkylsulphinyl, amino, alkylamino, dialkylamino, formyl, alkylcarbonyl, carboxyl, alkyloxycarbonyl, carbamoyl, alkylcarbamoyl, dialkylcarbamoyl, cyano, and trifluoromethyl, wherein each of the alkyl portions and radicals in the definition of Ar contains 1 to 4 carbon atoms;
R represents
a radical of formula: $-(CH_2)_m-X_1-(CH_2)_n-Z$
in which $X_1$ represents a single bond or an oxygen or sulphur atom,
m represents an integer equal to 0 or 1, and
n represents an integer equal to 0, 1 or 2;
wherein one or more methylene radicals in said R radical is optionally substituted by a carboxyl, alkyloxycarbonyl, carbamoyl, alkylcarbamoyl, dialkylcarbamoyl, amino, alkylamino or dialkylamino radical, wherein each of the alkyl portions and radicals in the definition of R contains 1 to 4 carbon atoms;
Z represents
a carboxyl radical, or
a $COOR_6$ radical, in which $R_6$ represents a straight or branched alkyl radical containing 1 to 3 carbon atoms, or
a radical of formula $CON(R_7)(R_8)$ in which
$R_7$ represents a hydrogen atom or a straight or branched alkyl radical containing 1 to 6 carbon atoms, and $R_8$ represents
- a hydrogen atom, or
- a hydroxyl radical, or
- an arylsulphonyl radical, optionally substituted by one or more atoms or radicals, which are identical or different and are selected from halogen atoms and alkyl and alkyloxy radicals, or
- a 5- to 7-membered heterocycle incorporating one or more heteroatoms selected from nitrogen, oxygen and sulphur atoms, it being possible for said heterocycle to be bonded to the N in said $CON(R_7)(R_8)$ radical via a heteroatom, or
- an amino radical optionally substituted by one or two radicals, which are identical or different and are selected from the radicals:
  - alkyl,
  - carbocyclic aryl, optionally substituted by one or more radicals, which are identical or different and are selected from alkyl and alkyloxy radicals,
  - 5- to 7-membered heterocyclyl containing one or more heteroatoms selected from nitrogen, oxygen and sulphur atoms,
  - arylcarbonyl, optionally substituted by one or more radicals, which are identical or different and are selected from alkyl and alkyloxy radicals,
- or $R_8$ represents an alkyloxy radical containing 1 to 6 straight- or branched-chain carbon atoms optionally substituted by a phenyl radical, or
- a straight or branched alkyl radical containing 1 to 6 carbon atoms, optionally substituted by at least one radical selected from amino, alkylamino, dialkylamino, hydroxyl, alkyloxy, mercapto, alkylthio, alkyloxycarbonyl, carboxyl, cyano, and optionally substituted mono- and polycyclic aromatic having from 5 to 12 ring members which may or may not incorporate one or more heteroatoms selected from oxygen, nitrogen and sulphur atoms, it being possible for said mono- and polycyclic aromatic radicals incorporating one or more nitrogen heteroatoms to be in the form of the N-oxide, or Z represents
- a $PO(OR_9)_2$ radical in which $R_9$ represents a hydrogen atom or a straight or branched alkyl radical containing 1 to 6 carbon atoms, or
- an —NH—CO—T radical in which T represents a hydrogen atom or a straight or branched alkyl radical containing 1 to 6 carbon atoms, optionally substituted by an amino, carboxyl, alkyloxycarbonyl, hydroxyl, alkyloxy, mercapto, or alkylthio radical, or a

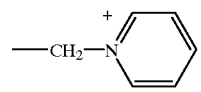

radical having an anion as a counterion,
wherein each of the alkyl portions and radicals provided in the definition of Z that is not of a specifically defined carbon length contains 1 to 4 carbon atoms;

$R_1$ and $R_2$, which are identical or different, are selected from a hydrogen atom, a halogen atom, an alkyl radical, and an alkyloxy radical, wherein each of said radicals may optionally be substituted by a dialkylamino radical, wherein the two alkyl portions of said dialkylamino radical may form, together with the nitrogen atom to which they are attached, a saturated heterocycle containing 5 or 6 ring members, and from an alkylthio radical and an alkyloxycarbonyl radical; or alternatively, situated at the ortho position with respect to one another, $R_1$ and $R_2$, together with the ring carbon atoms to which they are attached, form a saturated or unsaturated heterocycle containing 1 or 2 heteroatoms selected from nitrogen and oxygen, optionally substituted by a halogen atom or by an alkyl or alkyloxy radical, wherein the alkyl portions and radicals in the definition of $R_1$ and $R_2$ contain 1 to 4 carbon atoms;

$R_3$ and $R_4$, which are identical or different, are selected from a hydrogen atom, a halogen atom and a radical selected from alkyl, hydroxyl, alkyloxy, alkylcarbonyloxy, mercapto, alkylthio, alkylsulphonyl, alkylsulphinyl, amino, alkylamino, dialkylamino, alkyloxycarbonylamino, carboxyl, alkyloxycarbonyl, carbamoyl, alkylcarbamoyl, dialkylcarbamoyl, formyl, alkylcarbonyl, cyano, and trifluoromethyl, wherein the alkyl portions and radicals in the definition of $R_3$ and $R_4$ contain 1 to 4 carbon atoms;

$R_5$ represents a hydrogen atom or an alkyl or alkylthio radical, wherein for the definition of $R_5$, the alkyl portions and radicals contain 1 to 4 carbon atoms; X represents an oxygen or sulphur atom or one of the groups: —NH—, —CO—, methylene, alkene-1,1-diyl, or cycloalkane-1,1-diyl containing 3 to 6 carbon atoms;

and Y represents an oxygen or sulphur atom.

2. A composition according to claim 1, wherein said at least one epipodophyllotoxin is chosen from etoposide and teniposide.

* * * * *